US012594345B2

(12) United States Patent
Stark et al.

(10) Patent No.: US 12,594,345 B2
(45) Date of Patent: Apr. 7, 2026

(54) DEGRADABLE HYALURONIC ACID HYDROGELS

(71) Applicant: Ascendis Pharma A/S, Hellerup (DK)

(72) Inventors: Sebastian Stark, Heidelberg (DE); Burkhardt Laufer, Heidelberg (DE); Thomas Knappe, Heidelberg (DE); Tobias Voigt, Heidelberg (DE); Nicola Bisek, Heidelberg (DE)

(73) Assignee: ASCENDIS PHARMA A/S, Hellerup (DK)

(*) Notice: Subject to any disclaimer, the term of this patent is extended or adjusted under 35 U.S.C. 154(b) by 66 days.

(21) Appl. No.: 17/280,760

(22) PCT Filed: Sep. 25, 2019

(86) PCT No.: PCT/EP2019/075884

§ 371 (c)(1),
(2) Date: Mar. 26, 2021

(87) PCT Pub. No.: WO2020/064847

PCT Pub. Date: Apr. 2, 2020

(65) Prior Publication Data

US 2021/0338834 A1 Nov. 4, 2021

(30) Foreign Application Priority Data

Sep. 26, 2018 (EP) .................................... 18196869
Jan. 4, 2019 (EP) .................................... 19150398
Jun. 21, 2019 (EP) .................................... 19181815

(51) Int. Cl.
*A61K 47/69* (2017.01)
*A61K 47/61* (2017.01)

(52) U.S. Cl.
CPC .......... *A61K 47/6903* (2017.08); *A61K 47/61* (2017.08)

(58) Field of Classification Search
CPC ............................ A61K 47/61; A61K 47/6903
See application file for complete search history.

(56) References Cited

U.S. PATENT DOCUMENTS

| | | | |
|---|---|---|---|
| 5,510,418 | A | 4/1996 | Rhee et al. |
| 5,789,554 | A | 8/1998 | Leung et al. |
| 6,676,924 | B2 | 1/2004 | Hansen et al. |
| 7,109,304 | B2 | 9/2006 | Hansen et al. |
| 7,138,496 | B2 | 11/2006 | Hua et al. |
| 7,151,164 | B2 | 12/2006 | Hansen et al. |
| 7,238,785 | B2 | 7/2007 | Govindan et al. |
| 7,282,567 | B2 | 10/2007 | Goldenberg et al. |
| 7,300,655 | B2 | 11/2007 | Hansen et al. |
| 7,312,318 | B2 | 12/2007 | Hansen et al. |
| 7,387,772 | B1 | 6/2008 | Hansen et al. |
| 7,541,440 | B2 | 6/2009 | Goldenberg et al. |
| 7,585,837 | B2 | 9/2009 | Shechter et al. |
| 7,612,180 | B2 | 11/2009 | Goldenberg et al. |
| 8,287,865 | B2 | 10/2012 | Hansen et al. |
| 8,618,124 | B2 | 12/2013 | Greenwald et al. |
| 8,754,190 | B2 | 6/2014 | Ashley et al. |
| 8,907,065 | B2 | 12/2014 | Hermans et al. |
| 8,946,405 | B2 | 2/2015 | Ashley et al. |
| 9,441,043 | B2 | 9/2016 | Chang et al. |
| 10,072,075 | B2 | 9/2018 | Koenig et al. |
| 2009/0124540 | A1* | 5/2009 | Prestwich .............. A61L 27/54 514/56 |
| 2011/0236388 | A1 | 9/2011 | Baehner et al. |
| 2018/0042996 | A1 | 2/2018 | Rau et al. |

FOREIGN PATENT DOCUMENTS

| | | | | |
|---|---|---|---|---|
| EP | 1534334 B1 | 6/2014 | | |
| KR | 20170010651 A | 2/2017 | | |
| KR | 20170010651 A1 * | 2/2017 | ............ A61K 47/36 | |
| WO | WO-2002089789 A1 | 11/2002 | | |
| WO | WO-2005099768 A2 | 10/2005 | | |
| WO | WO-2006136586 A2 | 12/2006 | | |
| WO | WO-2008034122 A2 | 3/2008 | | |
| WO | WO-2009009712 A1 | 1/2009 | | |
| WO | WO-2009095479 A2 | 8/2009 | | |
| WO | WO-2009143412 A2 | 11/2009 | | |
| WO | WO-2011012722 A1 | 2/2011 | | |
| WO | WO-2011082368 A2 | 7/2011 | | |
| WO | WO-2011089214 A1 | 7/2011 | | |
| WO | WO-2011089215 A1 | 7/2011 | | |
| WO | WO-2011089216 A1 | 7/2011 | | |
| WO | WO-2013024052 A1 | 2/2013 | | |
| WO | WO-2013024053 A1 | 2/2013 | | |
| WO | WO-2013036857 A1 | 3/2013 | | |
| WO | WO-2013160340 A1 | 10/2013 | | |
| WO | WO-2016020373 A1 | 2/2016 | | |
| WO | WO-2016193371 A1 | 12/2016 | | |
| WO | WO-2017087588 A1 | 5/2017 | | |
| WO | WO-2017087589 A2 | 5/2017 | | |
| WO | WO-2018175788 A1 | 9/2018 | | |
| WO | WO/2020/064847 | 4/2020 | | |

OTHER PUBLICATIONS

Sharma et al. "Wound healing activity of curcumin conjugated to hyaluronic acid: in vitro and in vivo evaluation", Artificial Cells, Nanomedicine, and Biotechnology 2018, vol. 46, No. 5, 1009-1017, Published online: Jul. 28, 2017 (Year: 2017).*

(Continued)

*Primary Examiner* — James W Rogers

(74) *Attorney, Agent, or Firm* — Raphael Bellum PLLC

(57) ABSTRACT

The present invention relates to conjugates comprising crosslinked hyaluronic acid to which a plurality of drug moieties are covalently and reversibly conjugated, wherein the hyaluronic acid exhibits a certain degree of modification and comprises degradable crosslinked moieties. It also relates to their use as medicaments and their use in the diagnosis, prevention and treatment of diseases.

10 Claims, No Drawings

(56) References Cited

OTHER PUBLICATIONS

Ito et al. "Anti-inflammatory function of an in situ cross-linkable conjugate hydrogel of hyaluronic acid and dexamethasone", Biomaterials 28 (2007) 1778-1786 (Year: 2007).*
PCT/EP2019/075884, Sep. 25, 2019, Sebastian Stark.
Ellman, "Tissue sulfhydryl groups," Arch Biochem Biophys. (1959) 82(1):70-7.
Miedel et al., "The use of fluorescamine as a detection reagent in protein microcharacterization," J Biochem Biophys Methods. (1989) 18(1):37-52.
Molnár-Perl et al., "HPLC of amines as o-phthalaldehyde derivatives," Quantitation of Amino Acids and Amines by Chromatography: Methods and Protocols (vol. 70) (Journal of Chromatography Library, vol. 70). (2005) pp. 405-444.
Morales-Kastresana et al., "Combined immunostimulatory monoclonal antibodies extend survival in an aggressive transgenic hepatocellular carcinoma mouse model," Clin Cancer Res. (2013) 19(22):6151-62.
Van Der Neut Kolfschoten, Marijn et al., "Anti-inflammatory activity of human IgG4 antibodies by dynamic Fab arm exchange," Science. (2007) 317(5844): 1554-7.
Sasaki et al., "Development of lipophilic prodrugs of mitomycin C. III. Physicochemical and biological properties of newly synthesized alkoxycarbonyl derivatives," Chem Pharm Bull. 1983;31(11):4083-90.

* cited by examiner

DEGRADABLE HYALURONIC ACID HYDROGELS

CROSS-REFERENCE TO RELATED APPLICATIONS

The present application is a § 371 National Stage of PCT International Application No. PCT/EP2019/075884, filed Sep. 25, 2019, which claims the benefit of EP patent application Ser. No. 19/181,815.2, filed on Jun. 21, 2019; EP patent application Ser. No. 19/150,398.6, filed on Jan. 4, 2019; and EP patent application Ser. No. 18/196,869.4, filed on Sep. 26, 2018. The entirety of each application is incorporated herein by reference thereto.

The present invention relates to conjugates comprising crosslinked hyaluronic acid to which a plurality of drug moieties are covalently and reversibly conjugated, wherein the hyaluronic acid exhibits a certain degree of modification and comprises degradable crosslinker moieties.

It also relates to their use as medicaments and their use in the diagnosis, prevention and treatment of diseases.

Hydrogels are three-dimensional, hydrophilic or amphiphilic polymeric networks capable of taking up large quantities of water. These networks may be composed of various polymers and are insoluble due to the presence of covalent chemical and/or physical crosslinks.

Hydrogels can be used for many applications, such as for the sustained release of drug molecules. Such drug molecules may either be non-covalently embedded or covalently and reversibly attached to the hydrogel. Hyaluronic acid, an anionic, non-sulfated glycosaminoglycan, is a useful polymer for such hydrogels, because it occurs naturally in connective, epithelial and neural tissue and is thus well tolerated within the human body. Due to the widespread presence of hyaluronidases, hyaluronic acid is also biodegradable.

Depending on the drug to be conjugated to the hydrogel and the desired administration frequency high or low amounts of drug loading may be needed and such fine-tuning may be difficult to achieve. Derivatization of hyaluronic acid may interfere with its degradability by hyaluronidases, so the presence of degradable bonds is desirable.

Therefore, there is a need for degradable hyaluronic acid-based hydrogels that allow both a high or low degree of covalent drug loading.

It is an object of the present invention to at least partially overcome this shortcoming.

This object is achieved with a conjugate comprising crosslinked hyaluronic acid strands to which a plurality of drug moieties are covalently and reversibly conjugated, wherein the conjugate comprises a plurality of connected units selected from the group consisting of $Z^1$

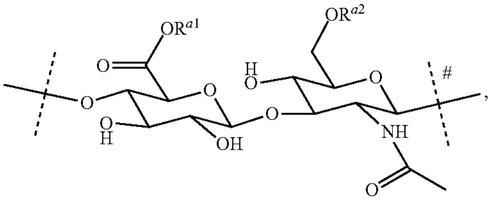

,

-continued $Z^2$

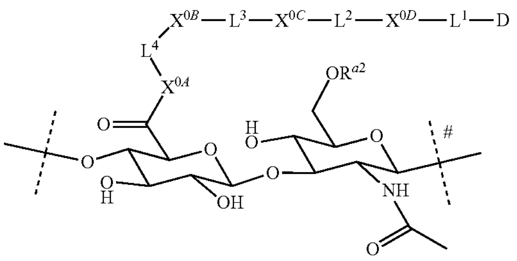

and $Z^3$

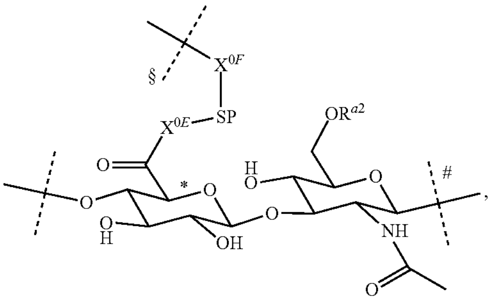

, wherein an unmarked dashed line indicates a point of attachment to an adjacent unit at a dashed line marked with #or to a hydrogen;

a dashed line marked with #indicates a point of attachment to an adjacent unit at an unmarked dashed line or to a hydroxyl;

a dashed line marked with § indicates a point of connection between at least two units $Z^3$ via a moiety —CL-;

each -D is independently a drug moiety;

each $-L^1-$ is independently a linker moiety to which -D is covalently and reversibly conjugated;

each $-L^2-$, $-L^3-$ and $-L^4-$ is independently either absent or a spacer moiety;

each —CL- is independently a moiety connecting at least two units $Z^3$ and wherein there is at least one degradable bond in the direct connection between any two carbon atoms marked with the * connected by a moiety —CL-;

each —SP— is independently absent or a spacer moiety;

each $—R^{a1}$ is independently selected from the group consisting of —H, $C_{1-4}$ alkyl, an ammonium ion, a tetrabutylammonium ion, a cetyl methylammonium ion, an alkali metal ion and an alkaline earth metal ion;

each $—R^{a2}$ is independently selected from the group consisting of —H and $C_{1-10}$ alkyl;

each $—X^{0A}—$, $—X^{0B}—$, $—X^{0C}—$, $—X^{0D}—$, $—X^{0E}—$ and $—X^{0F}—$ is independently either absent or a linkage;

optionally $—X^{0A}—$ and/or $—X^{0B}—$ form together with $-L^4-$ or parts of $-L^4-$ one or more ring structure selected from the group consisting of 4- to 7-membered heterocyclyl, 8- to 11-membered heterobicyclyl and adamantyl;

optionally $—X^{0B}—$ and/or $—X^{0C}—$ form together with $-L^3-$ or parts of $-L^3-$ one or more ring structure selected from the group consisting of 4- to 7-membered heterocyclyl, 8- to 11-membered heterobicyclyl and adamantyl;

optionally, $—X^{0C}—$ and/or $—X^{0D}—$ form together with $-L^2-$ or parts of $-L^2-$ one or more ring structure selected from the group consisting of 4- to 7-membered heterocyclyl, 8- to 11-membered heterobicyclyl and adamantyl;

optionally —$X^{0E}$— and/or —$X^{0F}$— form together with —SP— or parts of —SP— one or more ring structure selected from the group consisting of 4- to 7-membered heterocyclyl, 8- to 11-membered heterobicyclyl and adamantyl;

wherein all units $Z^1$ present in the conjugate may be the same or different;

all units $Z^2$ present in the conjugate may be the same or different;

all units $Z^3$ present in the conjugate may be the same or different;

at least one unit $Z^3$ is present per hyaluronic acid strand which is connected to at least one unit $Z^3$ on a different hyaluronic acid strand; and the conjugate comprises at least one moiety -$L^1$-D.

Within the present invention the terms are used having the meaning as follows.

As used herein, the terms "strand" or "hyaluronic acid strand" are used synonymously and refer to the linear chain of disaccharide units that are connected such that an unmarked dashed line indicates a point of attachment to an adjacent unit at a dashed line marked with #, wherein the unmarked dashed line of a first unit of such linear chain indicates attachment to a hydrogen and wherein the dashed line marked with # of the last unit of such linear chain indicates attachment to a hydroxyl.

As used herein the phrase "direct connection" between two particular atoms refers to the shortest moiety connecting said two particular atoms, wherein the "shortest moiety" is measured in the number of atoms that lie between these two particular atoms.

As used herein the term "spacer" refers to a moiety that connects at least two other moieties with each other.

As used herein the term "crosslinker" refers to a moiety, such as a spacer moiety, connecting at least two hyaluronic acid strands. If at least two hyaluronic acid strands are connected by a crosslinker moiety, such hyaluronic acid strands are "crosslinked".

As used herein, the term "water-insoluble" refers to a compound of which less than 1 g can be dissolved in one liter of water at 20° C. to form a homogeneous solution. Accordingly, the term "water-soluble" refers to a compound of which 1 g or more can be dissolved in one liter of water at 20° C. to form a homogeneous solution.

As used herein, the term "sustained release" refers to the property of a compound, such as the conjugates of the present invention, to release a drug, such as one or more antibiotic, with a release half-life of at least 1 day.

The term "drug" as used herein refers to a substance used in the treatment, cure, prevention, or diagnosis of a disease or used to otherwise enhance physical or mental well-being. If a drug is conjugated to another moiety, the part of the resulting product that originated from the drug is referred to as "drug moiety".

As used herein, the term "a π-electron-pair-donating heteroaromatic N-comprising moiety" refers to the moiety which after cleavage of the linkage between -D and -$L^1$- results in a drug D-H and wherein the drug moiety -D and analogously the corresponding D-H comprises at least one, such as one, two, three, four, five, six, seven, eight, nine or ten heteroaromatic nitrogen atoms that donate a π-electron pair to the aromatic π-system. Examples of chemical structures comprising such heteroaromatic nitrogens that donate a π-electron pair to the aromatic π-system include, but are not limited to, pyrrole, pyrazole, imidazole, isoindazole, indole, indazole, purine, tetrazole, triazole and carbazole. For example, in the imidazole ring below the heteroaromatic nitrogen which donates a π-electron pair to the aromatic π-system is marked with "#":

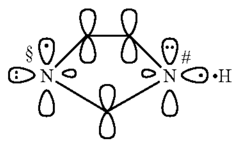

The π-electron-pair-donating heteroaromatic nitrogen atoms do not comprise heteroaromatic nitrogen atoms which only donate one electron (i.e. not a pair of π-electrons) to the aromatic π-system, such as for example the nitrogen that is marked with "§ " in the abovementioned imidazole ring structure. The drug D-H may exist in one or more tautomeric forms, such as with one hydrogen atom moving between at least two heteroaromatic nitrogen atoms. In all such cases, the linker moiety is covalently and reversibly attached at a heteroaromatic nitrogen that donates a π-electron pair to the aromatic π-system.

As used herein the term "prodrug" refers to a biologically active moiety reversibly and covalently connected to a specialized protective group through a reversible prodrug linker moiety which is a linker moiety comprising a reversible linkage with the biologically active moiety and wherein the specialized protective group alters or eliminates undesirable properties in the parent molecule. This also includes the enhancement of desirable properties in the drug and the suppression of undesirable properties. The specialized nontoxic protective group may also be referred to as "carrier". A prodrug releases the reversibly and covalently bound biologically active moiety in the form of its corresponding drug. In other words, a prodrug is a conjugate comprising a drug moiety, which is covalently and reversibly conjugated to a carrier moiety via a reversible prodrug linker moiety, which covalent and reversible conjugation of the carrier to the reversible prodrug linker moiety is either directly or through a spacer. Such conjugate preferably releases the formerly conjugated drug moiety in the form of a free drug, in which case the reversible linker or reversible prodrug linker is a traceless linker. The conjugates of the present invention are prodrugs.

As used herein, the term "free form" of a drug means the drug in its unmodified, pharmacologically active form.

As used herein, the term "reversible", "reversibly", "degradable" or "degradably" refers to a bond that is cleavable under physiological conditions, which are aqueous buffer at pH 7.4 and 37° C., with a half-life ranging from 12 hours to three months, such as from one day to 10 weeks, from two days to two months or from two days to one month. Cleavage is preferably non-enzymatically. Accordingly, the term "stable" with regard to the attachment of a first moiety to a second moiety means that the linkage that connects said first and second moiety exhibits a half-life of more than three months under physiological conditions.

As used herein, the term "reagent" means a chemical compound, which comprises at least one functional group for reaction with the functional group of another chemical compound or drug. It is understood that a drug comprising a functional group is also a reagent.

As used herein, the term "moiety" means a part of a molecule, which lacks one or more atoms compared to the corresponding reagent. If, for example, a reagent of the formula "H—X—H" reacts with another reagent and becomes part of the reaction product, the corresponding moiety of the reaction product has the structure "H—X—" or "—X—", whereas each indicates attachment to another moiety. Accordingly, a drug moiety is released from a reversible linkage as a drug.

It is understood that if the chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N($R^1$)—" can be attached to two moieties or interrupting a moiety either as "—C(O)N($R^1$)—" or as "—N($R^1$)C(O)—". Similarly, a moiety

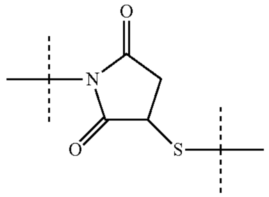

can be attached to two moieties or can interrupt a moiety either as

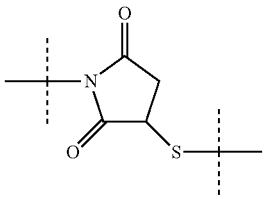

or as

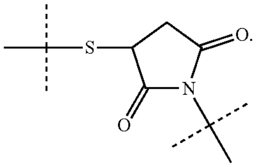

As used herein, the term "activation agent" refers for example to agents selected from the group consisting of N,N'-di cyclohexyl carbodiimide (DCC), 1-ethyl-3-(3-dimethylaminopropyl)carbodiimide (EDC), 2-(1H-benzotriazol-1-yl)-1,1,3,3-tetramethyluronium hexafluorophosphate (HBTU), 1(-[Bis(dimethylamino)methylene]-1H-1,2,3-triazole[4,5-b]pyridinium 3-oxid hexaflurophosphate (HATU), 1-cyano-2-ethoxy-2-oxoethylidenaminooxy)dimethyl-amino-morpholino-carbenium hexaflurophosphate (COMU), 2-(1H-benzotriazole-1-yl)-1,1,3,3-tetramethylaminium tetrafluoroborate (TBTU), 3-(diethoxyphosphoryloxy)-1,2,3-benzotriazin-4(3H)-one (DEPBT), benzotriazol-1-yl-oxytripyrrolidinophosphonium hexaflurophosphate (PyBOP), benzotriazol-1-yl-oxytris(dimethylamino)phosphonium hexaflurophosphate (BOP), bromotripyrrolidinophosphonium hexaflurophosphate (PyBrOP), tetramethylfluoroformamidinium hexaflurophosphate (TFFH), (7-azabenzotriazol-1-yloxy)tripyrrolidinophosphonium hexaflurophosphate (PyAOP), [ethyl eyano(hydroxyimino) acetate-$O^2$]tri-1-pyrrolidinylphosphonium hexaflurophosphate (PyOxim), 2-(6-chloro-1H-benzotriazol-1-yl)-1,1,3,3-tetramethylaminium hexaflurophosphate (HCTU), N-[(5-chloro-3-oxido-1H-benzotriazol-1-yl)-4-morpholinylmethylene]-N-methylmethanaminium hexaflurophosphate (HDMC), 1-[bis(dimethylamino)methylene]-1H-1,2,3-triazole[4,5-b]pyridinium tetrafluoroborate (TATU), 2-(1-oxy-pyridin-2-yl)-1,1,3,3-tetramethylisothiouronium tetrafluoroborate (TOTT), tetramethylfluoroformamidinium hexafluorophosphate (TFFH), N-ethoxycarbonyl-2-ethoxy-1,2-dihydroquinoline (EEDQ), 2-propanephosphonic acid anhydride (T3P), 4-(4,6-dimethoxy-1,3,5-triazin-2-yl)-4-methylmorpholinium salts (DMTMM), bis-trichloromethylcarbonate (BTC), 1,1'-carbonyldiimidazole (CDI) and dicyclohexylcarbodiimide (DIC).

As used herein, the "additive agent" is for example selected from the group consisting of hydroxybenzotriazole (HOBt), 1-hydroxy-7-azabenzotriazole (HOAt), hydroxy-3,4-dihydro-4-oxo-1,2,3-benzotriazine (HOOBt), ethyl 2-cyano-2-(hydroximino)acetate, carboxylic acid derivatives (such as those of formula (y-3')) 4,6-dimethoxy-1,3,5-triazin-2-ol, N-hydroxysuccinimide, 1-hydroxy-2,5-dioxopyrrolidine-3-sulfonic acid, 4-nitrophenol, 2,4-dinitrophenol and mono-, di-, tri-, tetra-, penta-flurophenol (such as shown in formula (y'-10)).

The term "substituted" as used herein means that one or more —H atom(s) of a molecule or moiety are replaced by a different atom or a group of atoms, which are referred to as "substituent".

As used herein, the term "substituent" refers in certain embodiments to a moiety selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more —R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$-, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more —R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —$R^{x2}$ is independently selected from the group consisting of halogen, —CN, oxo (=O), —$COOR^{x4}$, —$OR^{x4}$, —$C(O)R^{x4}$, —$C(O)N(R^{x4}R^{x4a})$, —$S(O)_2N(R^{x4}R^{x4a})$, —$S(O)N(R^{x4}R^{x4a})$, —$S(O)_2R^{x4}$, —$S(O)R^{x4}$, —$N(R^{x4})S(O)_2N(R^{x4a}R^{x4b})$, —$SR^{x4}$, —$N(R^{x4}R^{x4a})$, —$NO_2$, —$OC(O)R^{x4}$, —$N(R^{x4})C(O)R^{x4a}$, —$N(R^{x4})S(O)_2R^{x4a}$, —$N(R^{x4})S(O)R^{x4a}$, —$N(R^{x4})C(O)OR^{x4a}$, —$N(R^{x4})C(O)N(R^{x4a}R^{x4b})$, —$OC(O)N(R^{x4}R^{x4a})$, and $C_{1-6}$ alkyl; wherein $C_{1-6}$ alkyl is optionally substituted with one or more halogen, which are the same or different;

each —$R^{x3}$, —$R^{x3a}$, —$R^{x4}$, —$R^{x4a}$, —$R^{x4b}$ is independently selected from the group consisting of —H and $C_{1-6}$ alkyl; wherein $C_{1-6}$ alkyl is optionally substituted with one or more halogen, which are the same or different.

In certain embodiments a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

As used herein, the term "hydrogel" means a hydrophilic or amphiphilic polymeric network composed of homopolymers or copolymers, which is insoluble due to the presence of hydrophobic interactions, hydrogen bonds, ionic interactions and/or covalent chemical crosslinks. The crosslinks provide the network structure and physical integrity. It is understood that the conjugates of the present invention are hydrogels.

As used herein the term "about" in combination with a numerical value is used to indicate a range ranging from and including the numerical value plus and minus no more than 25% of said numerical value, more preferably no more than 20% of said numerical value and most preferably no more than 10% of said numerical value. For example, the phrase "about 200" is used to mean a range ranging from and including 200+/−25%, i.e. ranging from and including 150 to 250; preferably 200+/−20%, i.e. ranging from and including 160 to 240; even more preferably ranging from and including 200+/−10%, i.e. ranging from and including 180 to 220. It is understood that a percentage given as "about 50%" does not mean "50%+/−25%", i.e. ranging from and including 25 to 75%, but "about 50%" means ranging from and including 37.5 to 62.5%, i.e. plus and minus 25% of the numerical value which is 50.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. The monomers may be identical, in which case the polymer is a homopolymer, or may be different, in which case the polymer is a heteropolymer. A heteropolymer may also be referred to as a "copolymer" and includes for example alternating copolymers in which monomers of different types alternate; periodic copolymers in which monomers of different types of monomers are arranged in a repeating sequence; statistical copolymers in which monomers of different types are arranged randomly; block copolymers in which blocks of different homopolymers consisting of only one type of monomers are linked by a covalent bond; and gradient copolymers in which the composition of different monomers changes gradually along a polymer chain. It is understood that a polymer may also comprise one or more other moieties, such as, for example, one or more functional groups. Likewise, it is understood that also a peptide or protein is a polymer, even though the side chains of individual amino acid residues may be different. It is understood that for covalently crosslinked polymers, such as hydrogels, no meaningful molecular weight ranges can be provided.

As used herein, the term "polymeric" refers to a reagent or a moiety comprising one or more polymers or polymer moieties. A polymeric reagent or moiety may optionally also comprise one or more other moieties, which in certain embodiments are selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

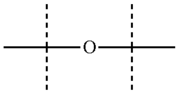,
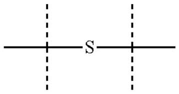,
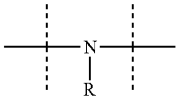,
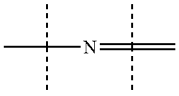,
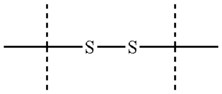,
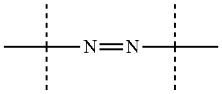,
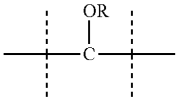,
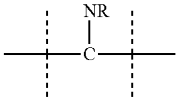,
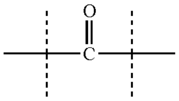,
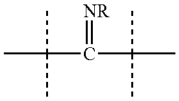,
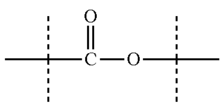,
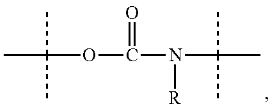,
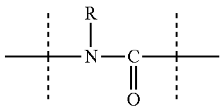,
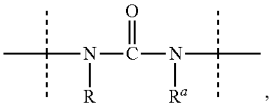,
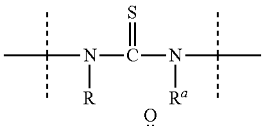, and
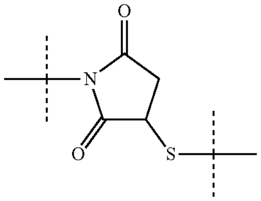, wherein dashed lines indicate attachment to the remainder of the moiety or reagent, and —R and —$R^a$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3- dimethylpropyl; and which moieties and linkages are optionally further substituted.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x +/−25%, preferably x +/−20% and more preferably x +/−10%.

As used herein, the term "number average molecular weight" means the ordinary arithmetic mean of the molecular weights of the individual polymers.

As used herein, the term "hyaluronic acid-based" in relation to a moiety or reagent means that said moiety or reagent comprises hyaluronic acid. Such hyaluronic acid-based moiety or reagent comprises at least 10% (w/w) hyaluronic acid, such as at least 20% (w/w) hyaluronic acid, such as at least 30% (w/w) hyaluronic acid, such as at least 40% (w/w) hyaluronic acid, such as at least 50% (w/w) hyaluronic acid, such as at least 60 (w/w) hyaluronic acid, such as at least 70% (w/w) hyaluronic acid, such as at least 80% (w/w) hyaluronic acid, such as at least 90% (w/w) hyaluronic acid, or such as at least 95% (w/w) hyaluronic acid. The remaining weight percentage of the hyaluronic acid-based moiety or reagent may be other moieties, such as those selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group consisting of

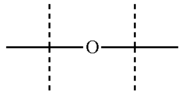,
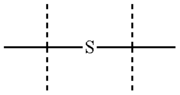,
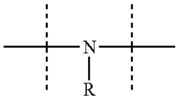,
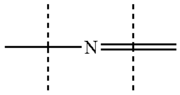,
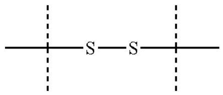,
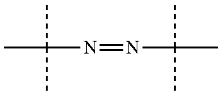,
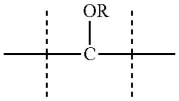,
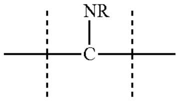,
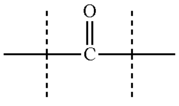,
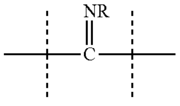, -continued

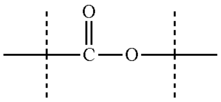,
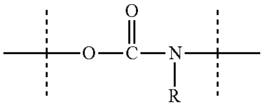,
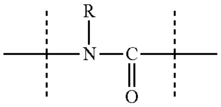,
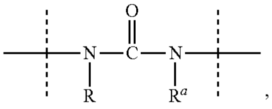,
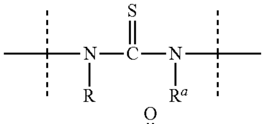, and
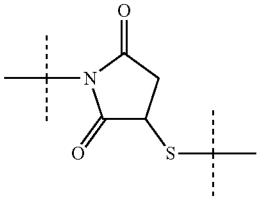, wherein dashed lines indicate attachment to the remainder of the moiety or reagent, and —R and —$R^a$ are independently of each other selected from the group consisting of —H, and $C_{1-6}$ alkyl; and which moieties and linkages are optionally further substituted.

The term "interrupted" means that a moiety is inserted between two carbon atoms or—if the insertion is at an end of said moiety—between a carbon and a hydrogen atom.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are $—CH_2—$, $—CH_2—CH_2—$, $—CH(CH_3)—$, $—CH_2—CH_2—CH_2—$, $—CH(C_2H_5)—$, $—C(CH_3)_2—$. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are $—CH_2—$, $—CH_2—CH_2—$, $—CH(CH_3)—$, $—CH_2—CH_2—CH_2—$, $—CH(C_2H_5)—$ and $—C(CH_3)_2—$. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are $-CH{=}CH_2$, $-CH{=}CH-CH_3$, $-CH_2-CH{=}CH_2$, $-CH{=}CHCH_2-CH_3$ and $-CH{=}CH-CH{=}CH_2$. When two moieties of a molecule are linked by the $C_{2-6}$ alkenyl group, then an example for such $C_{2-6}$ alkenyl is $-CH{=}CH-$. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the terms "$C_{2-10}$ alkenyl", "$C_{2-20}$ alkenyl" or "$C_{2-50}$ alkenyl" alone or in combination mean a straight-chain or branched hydrocarbon moiety comprising at least one carbon-carbon double bond having 2 to 10, 2 to 20 or 2 to 50 carbon atoms, respectively. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means a straight-chain or branched hydrocarbon moiety comprising at least one carbon-carbon triple bond having 2 to 6 carbon atoms. If present at the end of a molecule, examples are $-C{\equiv}CH$, $-CH_2-C{\equiv}CH$, $CH_2-CH_2-C{\equiv}CH$ and $CH_2-C{\equiv}C{\equiv}CH_3$. When two moieties of a molecule are linked by the alkynyl group, then an example is $-C{\equiv}C-$. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkenyl or $C_{2-50}$ alkynyl may optionally be interrupted by one or more moieties which are preferably selected from the group consisting of

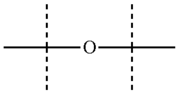 , 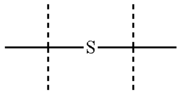 ,

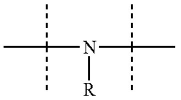 , 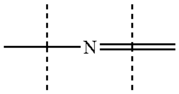 ,

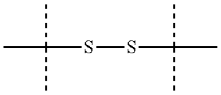 , 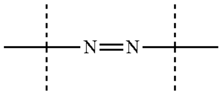 ,

-continued

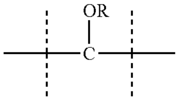 , 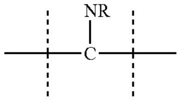 ,

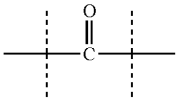 , 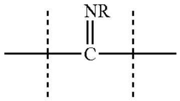 ,

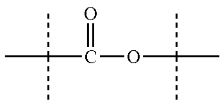 , 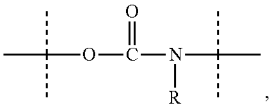 ,

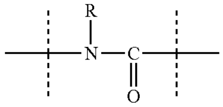 , 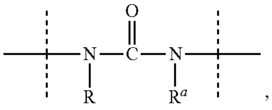 ,

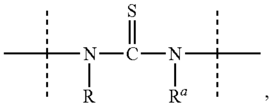 , and

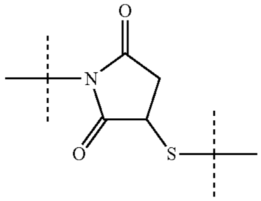 , wherein dashed lines indicate attachment to the remainder of the moiety or reagent; and —R and —$R^a$ are independently of each other selected from the group consisting of —H and $C_{1-6}$ alkyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbomane or norbomene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —$S(O)_2$—), oxygen and nitrogen (including =N(O)—) and wherein the ring is linked to the rest of a molecule via a carbon or nitrogen atom.

It is understood that the phrase "the pair $R^x/R^y$ is joined together with the atom to which they are attached to form a $C_{3-10}$ cycloalkyl or a 3- to 10-membered heterocyclyl" in relation with a moiety of the structure

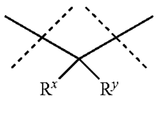

means that $R^x$ and $R^y$ form the following structure:

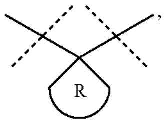

, wherein R is $C_{3-10}$ cycloalkyl or 3- to 10-membered heterocyclyl.

It is also understood that the phrase "the pair $R^x/R^y$ is joint together with the atoms to which they are attached to form a ring A" in relation with a moiety of the structure

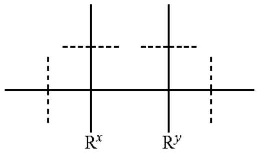

means that $R^x$ and $R^y$ form the following structure:

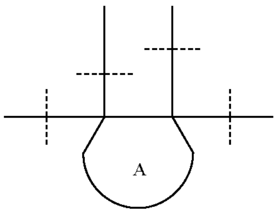

.

It is also understood that the phrase "—$R^1$ and an adjacent —$R^2$ form a carbon-carbon double bond provided that n is selected from the group consisting of 1, 2, 3 and 4" in relation with a moiety of the structure:

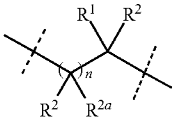

means that for example when n is 1, —$R^1$ and the adjacent —$R^2$ form the following structure:

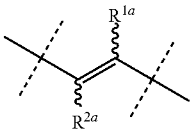

, and if for example, n is 2, $R^1$ and the adjacent —$R^2$ form the following structure:

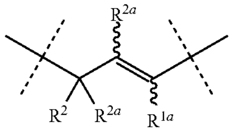

, wherein the wavy bond means that —$R^{1a}$ and —$R^{2a}$ may be either on the same side of the double bond, i.e. in cis configuration, or on opposite sides of the double bond, i.e. in trans configuration and wherein the term "adjacent" means that —R and —R are attached to carbon atoms that are next to each other.

It is also understood that the phrase "two adjacent —$R^2$ form a carbon-carbon double bond provided that n is selected from the group consisting of 2, 3 and 4" in relation with a moiety of the structure:

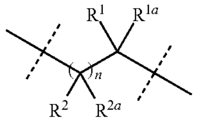

means that for example when n is 2, two adjacent —$R^2$ form the following structure:

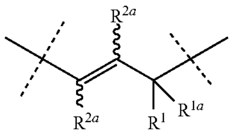

, wherein the wavy bond means that each —$R^{2a}$ may be either on the same side of the double bond, i.e. in cis configuration, or on opposite sides of the double bond, i.e. in trans configuration and wherein the term "adjacent" means that two —$R^2$ are attached to carbon atoms that are next to each other.

It is understood that the "N" in the phrase "π-electron-pair-donating heteroaromatic N" refers to nitrogen.

It is understood that "$N^+$" in the phrases "an electron-donating heteroaromatic $N^+$-comprising moiety" and "attachment to the $N^+$ of -$D^+$" refers to a positively charged nitrogen atom.

As used herein, "halogen" means fluoro, chloro, bromo or iodo. In certain embodiments halogen is fluoro or chloro.

As used herein the term "alkali metal ion" refers to $Na^+$, $K^+$, $Li^+$, $Rb^+$ and $Cs^+$. In certain embodiments "alkali metal ion" refers to $Na^+$, $K^+$ and $Li^+$.

As used herein the term "alkaline earth metal ion" refers to $Mg^{2+}$, $Ca^{2+}$, $Sr^{2+}$ and $Ba^{2+}$. In certain embodiments an alkaline earth metal ion is $Mg^{2+}$ or $Ca^{2+}$.

As used herein, the term "functional group" means a group of atoms which can react with other groups of atoms. Exemplary functional groups are carboxylic acid, primary amine, secondary amine, tertiary amine, maleimide, thiol, sulfonic acid, carbonate, carbamate, hydroxyl, aldehyde, ketone, hydrazine, isocyanate, isothiocyanate, phosphoric acid, phosphonic acid, haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the conjugates of the present invention comprise one or more acidic or basic groups, the invention also comprises their corresponding pharmaceutically or toxicologically acceptable salts, in particular their pharmaceutically utilizable salts. Thus, the conjugates of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids, or quaternary ammoniums, such as tetrabutylammonium and cetyl trimethylammonium. Conjugates of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, trifluoroacetic acid and other acids known to the person skilled in the art. For the person skilled in the art further methods are known for converting the basic group into a cation like the alkylation of an amine group resulting in a positively-charge ammonium group and an appropriate counterion of the salt. If the conjugates of the present invention simultaneously comprise acidic and basic groups, the invention also includes, in addition to the salt forms mentioned, inner salts or betaines (zwitterions). The respective salts can be obtained by customary methods, which are known to the person skilled in the art like, for example by contacting these prodrugs with an organic or inorganic acid or base in a solvent or dispersant, or by anion exchange or cation exchange with other salts. The present invention also includes all salts of the conjugates of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does not cause harm when administered to a patient and preferably means approved by a regulatory agency, such as the EMA (Europe) and/or the FDA (US) and/or any other national regulatory agency for use in animals, preferably for use in humans.

As used herein, the term "excipient" refers to a diluent, adjuvant, or vehicle with which the therapeutic, such as a drug or prodrug, is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, hyaluronic acid, propylene glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or drug moiety, together with a suitable amount of excipient so as to provide the form for proper administration to the patient. The formulation should suit the mode of administration.

The term “peptide” as used herein refers to a chain of at least 2 and up to and including 50 amino acid monomer moieties, which may also be referred to as “amino acid residues”, linked by peptide (amide) linkages. The amino acid monomers may be selected from the group consisting of proteinogenic amino acids and non-proteinogenic amino acids and may be D- or L-amino acids. The term “peptide” also includes peptidomimetics, such as peptoids, beta-peptides, cyclic peptides and depsipeptides and covers such peptidomimetic chains with up to and including 50 monomer moieties.

As used herein, the term “protein” refers to a chain of more than 50 amino acid monomer moieties, which may also be referred to as “amino acid residues”, linked by peptide linkages, in which preferably no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein, the term “oligonucleotide” refers to a nucleic acid polymer of up to 100 bases and may be both DNA and RNA. The term also includes aptamers and morpholinos.

As used herein the term “small molecule drug” refers to drugs that are organic compounds with a molecular weight of no more than 1 kDa, such as up to 900 kDa.

As used herein the term “antibiotic” refers to an antimicrobial drug for the treatment or prevention of bacterial infections, which either kills or inhibits growth of bacteria. The term also refers to drugs having antiprotozoal and antifungal activity.

As used herein, the term “biofilm” refers to a plurality of microorganisms, such as microorganisms selected from the group consisting of bacteria, archaea, protozoa, fungi and algae, such as to a plurality of bacteria, embedded within an extracellular matrix that is composed of extracellular polymeric substances, such as polysaccharides, proteins and DNA, and said extracellular matrix may comprise material from the surrounding environment, such as blood components. Biofilms may form on living and non-living surfaces and may comprise one or more species of microorganism. It is known that during the ageing process of a biofilm it becomes increasingly difficult to eradicate it, because not only do individual cells form tighter bonds with the surface, but the extracellular matrix also provides a protective environment that restricts access of the antibiotics to the microorganisms.

As used herein the term “pattern recognition receptor agonist” (“PRRA”) refers to a molecule that binds to and activates one or more immune cell-associated receptor that recognizes pathogen-associated molecular patterns (PAMPs) or damage-associated molecular patterns (DAMPs), leading to immune cell activation and/or pathogen- or damage-induced inflammatory responses. PRRs are typically expressed by cells of the innate immune system such as monocytes, macrophages, dendritic cells (DCs), neutrophils, and epithelial cells, as well as cells of the adaptive immune system.

As used herein the term “tyrosine kinase inhibitor” or “TKI” refers to a molecule that binds to and inhibits one or more cell-associated receptor or non-receptor tyrosine kinases that are activated via polypeptide growth factors, cytokines, hormones, or phosphorylation, and are involved in cellular signaling, cellular development, cellular proliferation, cellular maturation, cellular metabolism, angiogenesis, and in certain instances, tumorigenesis. Tyrosine kinases are ubiquitously expressed by virtually all cells. TKIs inhibit activation of tyrosine kinases by multiple mechanisms such as competing with, or allosterically antagonizing, binding of adenosine triphosphate (ATP) to the tyrosine kinase ATP-binding site, or by inhibiting enzymatic phosphorylation of said binding site, or inhibiting enzymatic kinase activity. In the case of receptor tyrosine kinases (RTKs), receptor TKIs may bind one or more RTKs and inhibit RTK activation as described above or by antagonizing activating ligand interactions, thus preventing receptor tyrosine kinase activation.

As used herein the terms “anti-CTLA4 drug” and “anti-CTLA4 moiety” refer to a drug or moiety, respectively, which binds to CTLA4 and which may block the interaction with its ligands B7.1 and B7.2 (CD80 and CD86). In certain embodiments such anti-CTLA4 drug or anti-CTLA4 moiety may be selected from the group consisting of antibodies, antibody fragments, affibodies, affilins, affimers, affitins, alphamabs, alphabodies, anticalins, avimers, DARPins, Fynomers®, Kunitz domain peptides, monobodies, nanoC-LAMPs, cyclic peptides, small molecules and nanobodies.

The term “VEGF antagonist,” as used herein, refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF-mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and VEGF121-gelonin (Peregrine). VEGF antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF antagonists also include nonpeptide small molecules that bind to VEGF or VEGFR and are capable of blocking, inhibiting, abrogating, reducing, or interfering with VEGF biological activities. Thus, the term “VEGF activities” specifically includes VEGF-mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or VEGF165. As used used herein "VEGF antagonists" can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib). Additional VEGF antagonists are described below.

In general, the terms "comprise" or "comprising" also encompasses "consist of" or "consisting of".

The presence of at least one degradable bond between the carbon atom marked with the * of a first moiety $Z^3$ and the direct connection to the carbon atom marked with the * of a second moiety $Z^3$ ensures that after cleavage of all such degradable bonds present in the conjugates of the present invention the hyaluronic acid strands present in said conjugate are no longer crosslinked, which allows clearance of the hyaluronic acid network It is understood that in case a degradable bond is located in a ring structure present in the direct connection of the carbon atom marked with the * of a first moiety $Z^3$ and the carbon atom marked with the * of a second moiety $Z^3$ such degradable bond is not sufficient to allow complete cleavage and accordingly one or more additional degradable bonds are present in the direct connection of the carbon atom marked with the * of a first moiety $Z^3$ and the carbon atom marked with the * of a second moiety $Z^3$.

It is understood that the phrase "a dashed line marked with § indicates a point of connection between at least two units $Z^3$ via a moiety —CL-" refers to the following structure

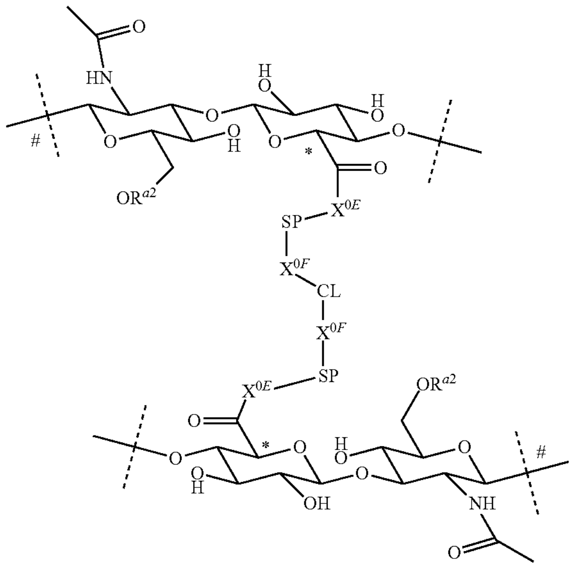

if —CL- is for example connected to two units $Z^3$, which two moieties $Z^3$ are connected at the position indicated with § via a moiety —CL-.

It is understood that the phrase "—$X^{0E}$— and/or —$X^{0F}$— form together with —SP— or parts of —SP— one or more ring structure selected from the group consisting of 4- to 7-membered heterocyclyl, 8- to 11-membered heterobicyclyl and adamantyl" refers to for example structures as shown below:

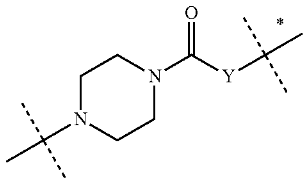
,
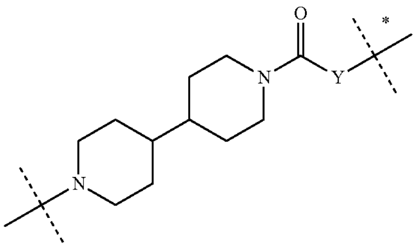
,
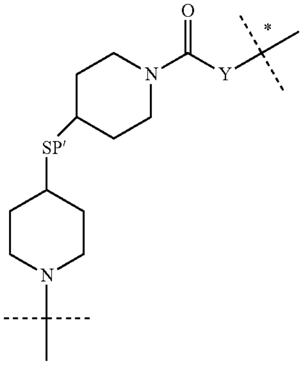
,
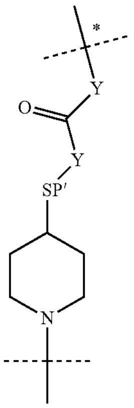
,
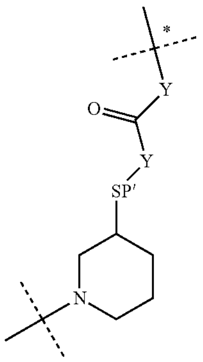
,
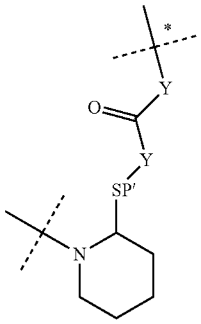
,

-continued

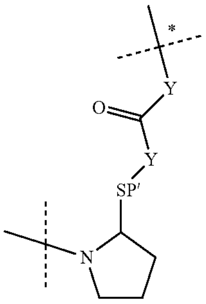

and

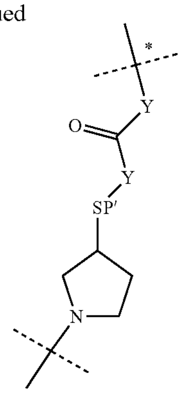

;

wherein the dashed line marked with the asterisk indicates attachment to —CL-;

the unmarked dashed line indicates attachment to the remainder of $Z^3$, i.e. to the carbonyl of the hyaluronic acid moiety;

—SP'— refers to the remainder of —SP—;

each —Y— is independently absent or is selected from the group consisting of —O—, —NR— and —S—; and each —R is independently selected from the group consisting of is independently selected from the group consisting of —H and $C_{1-6}$ alkyl; wherein $C_{1-6}$ alkyl is optionally substituted with one or more halogen, which are the same or different.

This applies analogously to other variables.

It is understood that no three-dimensionally crosslinked hydrogel can be formed if all hyaluronic acid strands of the present conjugate comprise only one unit $Z^3$, which is connected to only one unit $Z^3$ on a different hyaluronic acid strand. However, if a first unit $Z^3$ is connected to more than one unit $Z^3$ on a different strand, i.e. if —CL- is branched, such first unit $Z^3$ may be crosslinked to two or more other units $Z^3$ on two or more different hyaluronic acid strands. Accordingly, the number of units $Z^3$ per hyaluronic acid strand required for a crosslinked hyaluronic acid hydrogel depends on the degree of branching of —CL-. In certain embodiments at least 30% of all hyaluronic acid strands present in the conjugate are connected to at least two other hyaluronic acid strands. It is understood that it is sufficient if the remaining hyaluronic acid strands are connected to only one other hyaluronic acid strand.

It is understood that a moiety $Z^1$ is an unmodified disaccharide of hyaluronic acid, a moiety $Z^2$ is a disaccharide unit reversibly conjugated to a drug moiety and a moiety $Z^3$ is a disaccharide unit that is crosslinked via a moiety CL.

The conjugate of the present invention may also comprise units selected from the group consisting of $Z^4$

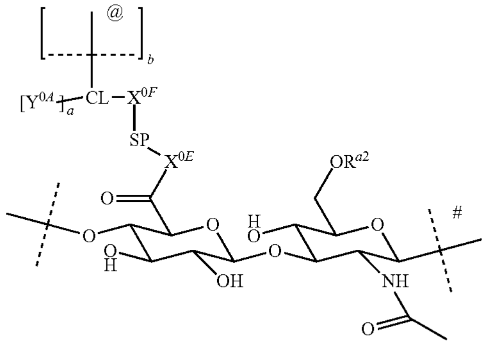

, $Z^5$

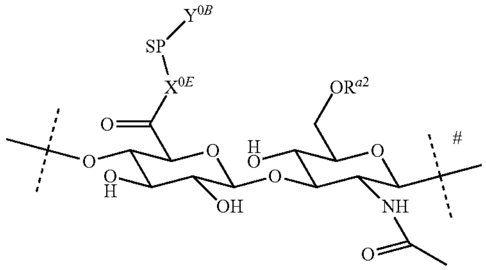

, $Z^6$

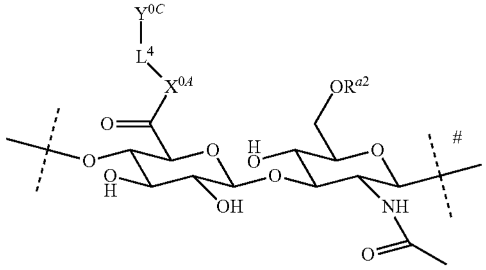

, $Z^7$

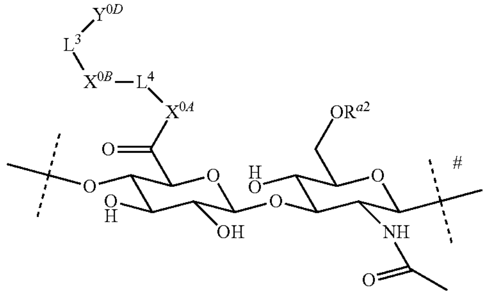

$Z^8$

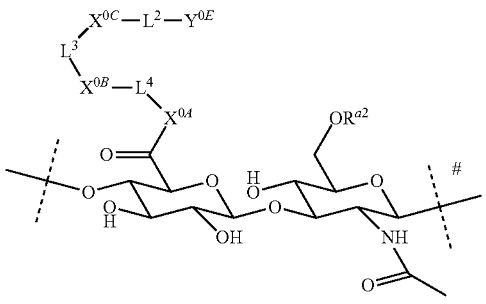

,

-continued

Z[9]

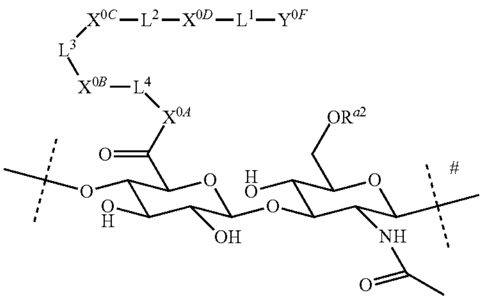

and

Z[10]

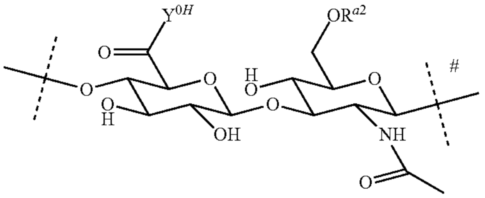

wherein an unmarked dashed line indicates a point of attachment to an adjacent unit $Z^1$, $Z^2$, $Z^3$, $Z^4$, $Z^5$, $Z^6$, $Z^7$, $Z^8$, $Z^9$ and $Z^{10}$ at a dashed line marked with #or to a hydrogen;

a dashed line marked with #indicates a point of attachment to an adjacent unit $Z^1$, $Z^2$, $Z^3$, $Z^4$, $Z^5$, $Z^6$, $Z^7$, $Z^8$, $Z^9$ and $Z^{10}$ at an unmarked dashed line or to a hydroxyl;

a dashed line marked with #indicates attachment to a moiety $—X^{0F}—$ of a moiety $Z^3$;

a indicates the number of unreacted ends of —CL- and is a positive integer;

b indicates the number of ends of —CL- connected to a moiety $—X^{0F}—$ of a moiety $Z^3$ and is 0 or a positive integer;

$-L^1-$, $-L^2-$, $-L^3-$, $-L^4-$, —SP—, —CL-, $—X^{0A}—$, $—X^{0B}—$, $—X^{0C}—$, $—X^{0D}—$, $—X^{0E}—$, $—X^{0F}—$ and $—R^{a2}$ are used as defined above;

each $—Y^{0a}$, $—Y^{0b}$, $—Y^{0c}$, $—Y^{0d}$, $—Y^{0e}$, $—Y^{0F}$ and $—Y^{0H}$ is independently a functional group;

optionally, $—Y^{0A}$ and/or $—X^{0F}—$ forms together with —CL- or parts of —CL- one or more ring structure selected from the group consisting of 4- to 7-membered heterocyclyl, 8- to 11-membered heterobicyclyl and adamantyl;

optionally, $—Y^{0B}$ and/or $—X^{0E}—$ forms together with —SP— or parts of —SP— one or more ring structure selected from the group consisting of 4- to 7-membered heterocyclyl, 8- to 11-membered heterobicyclyl and adamantyl optionally, $—Y^{0c}$ and/or $—X^{0A}—$ forms together with $-L^4-$ or parts of $-L^4-$ one or more ring structure selected from the group consisting of 4- to 7-membered heterocyclyl, 8- to 11-membered heterobicyclyl and adamantyl;

optionally, $—Y^{0D}$ and/or $—X^{0B}—$ forms together with $-L^3-$ or parts of $-L^3-$ one or more ring structure selected from the group consisting of 4- to 7-membered heterocyclyl, 8- to 11-membered heterobicyclyl and adamantyl; and optionally, $—Y^{0E}$ and/or $—X^{0C}—$ forms together with $-L^2-$ or parts of $-L^2-$ one or more ring structure selected from the group consisting of 4- to 7-membered heterocyclyl, 8- to 11-membered heterobicyclyl and adamantyl.

Units $Z^4$, $Z^5$, $Z^6$, $Z^7$, $Z^8$, $Z^9$ and $Z^{10}$ represent partly reacted or unreacted units. For example, a unit $Z^4$ represents a unit in which at least end of —CL- was not conjugated to a unit $Z^3$.

Depending on the order in which the elements of the conjugate of the present invention are assembled, different such partly reacted or unreacted units may be present. It is understood that the presence of such moieties cannot be avoided. In certain embodiments the sum of units $Z^4$, $Z^5$, $Z^6$, $Z^7$, $Z^8$, $Z^9$ and $Z^{10}$ is no more than 25% of the total number of units $Z^2$, $Z^3$, $Z^4$, $Z^5$, $Z^6$, $Z^7$, $Z^8$, $Z^9$ and $Z^{10}$ present in the conjugate, such as no more than 10%, such as no more than 15% or such as no more than 10%.

In certain embodiments variable a of $Z^4$ is selected from the group consisting of 1, 2, 3, 4, 5, 6, 7, 8, 9, 10, 11, 12, 13, 14, 15, 16, 17, 18 and 19. In certain embodiments variable a of $Z^4$ is a positive integer ranging from 20 to 200.

In certain embodiments b of $Z^4$ is selected from the group consisting of 0, 1, 2, 3, 4, 5, 6, 7, 8, 9, 10, 11, 12, 13, 14, 15, 16, 17, 18 and 19. In certain embodiments b of $Z^4$ is a positive integer ranging from 20 to 200.

It is further understood that in addition to units $Z^1$, $Z^2$, $Z^3$, $Z^4$, $Z^5$, $Z^6$, $Z^7$, $Z^8$, $Z^9$ and $Z^{10}$ a conjugate may also comprise units that are the result of cleavage of the reversible bond between -D and $-L^1-$ or of one or more of the degradable bonds present in the direct connection between any two carbon atoms marked with the * connected by a moiety —CL-, i.e. units resulting from degradation of the conjugate.

In certain embodiments each strand present in the conjugates of the present invention comprises at least 20 units, such as from 20 to 2500 units, from 25 to 2200 units, from 50 to 2000 units, from 75 to 100 units, from 75 to 100 units, from 80 to 560 units, from 100 to 250 units, from 200 to 800 units, from 20 to 1000, from 60 to 1000, from 60 to 400 or from 200 to 600 units.

In certain embodiments the moieties —CL- present in the conjugates of the present invention have different structures. In certain embodiments the moieties —CL- present in the conjugates of the present invention have the same structure.

In general, any moiety that connects at least two other moieties is suitable for use as a moiety —CL-, which may also be referred to as a "crosslinker moiety".

The at least two units $Z^3$ that are connected via a moiety —CL- may either be located on the same hyaluronic acid strand or on different hyaluronic acid strands.

The moiety —CL- may be linear or branched. In certain embodiments —CL- is linear. In certain embodiments —CL- is branched.

In certain embodiments —CL- connects two units $Z^3$. In certain embodiments —CL- connects three units $Z^3$. In certain embodiments —CL- connects four unis $Z^3$. In certain embodiments —CL- connects five units $Z^3$. In certain embodiments —CL- connects six units $Z^3$. In certain embodiments —CL- connects seven units $Z^3$. In certain embodiments —CL- connects eight units $Z^3$. In certain embodiments —CL- connects nine units $Z^3$.

If —CL- connects two units $Z^3$ —CL- may be linear or branched. If —CL- connects more than two units $Z^3$ —CL- is branched.

A branched moiety —CL- comprises at least one branching point from which at least three branches extend, which branches may also be referred to as "arms". Such branching point may be selected from the group consisting of

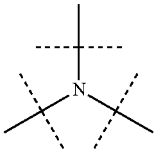, 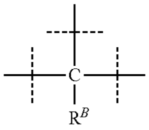 and 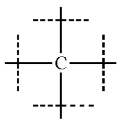, wherein dashed lines indicate attachment to an arm; and —$R^B$ is selected from the group consisting of —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more —$R^{B1}$, which are the same or different, and wherein $C_{1-6}$ alkyl, $C_{2-6}$ alkenyl and $C_{2-6}$ alkynyl are optionally interrupted with —C(O)O—, —O—, —C(O)—, —C(O)N($R^{B2}$)—, —$S(O)_2N$($R^{B2}$)—, —S(O)N($R^{B2}$)—, —$S(O)_2$—, —S(O)—, —N($R^{B2}$)$S(O)_2N$($R^{B2a}$)—, —S—, —N($R^{B2}$)—, —OC($OR^{B2}$)($R^{B2a}$)—, —N($R^{B2}$)C(O)N($R^{B2a}$)—, and —OC(O)N($R^{B2}$)—; wherein —$R^{B1}$, —$R^{B2}$ and —$R^{B2a}$ are selected from —H, $C_{1-6}$ alkyl, $C_{2-6}$ alkenyl and $C_{2-6}$ alkynyl.

In certain embodiments —$R^B$ is selected from the group consisting of —H, methyl and ethyl.

A branched moiety —CL- may comprise a plurality of branching points, such as 1, 2, 3, 4, 5, 6, 7 or more branching points, which may be the same or different.

If a moiety —CL- connects three units $Z^3$, such moiety —CL- comprises at least one branching point from which at least three arms extend.

If a moiety —CL- connects four units $Z^3$, such moiety —CL- may comprise one branching point from which four arms extend. However, alternative geometries are possible, such as at least two branching points from which at least three arms each extend. The larger the number of connected units $Z^3$, the larger the number of possible geometries is.

In a first embodiment at least 70%, such as at least 75%, such as at least 80%, such as at least 85%, such as at least 90% or such as at least 95% of the number of hyaluronic acid strands of the conjugate of the present invention comprise at least one moiety $Z^2$ and at least one moiety $Z^3$. In such embodiment units $Z^2$ and $Z^3$ can be found in essentially all hyaluronic acid strands present in the conjugates of the present invention.

Accordingly, a conjugate of this first embodiment comprises crosslinked hyaluronic acid strands to which a plurality of drug moieties are covalently and reversibly conjugated, wherein the conjugate comprises a plurality of connected units selected from the group consisting of $Z^1$

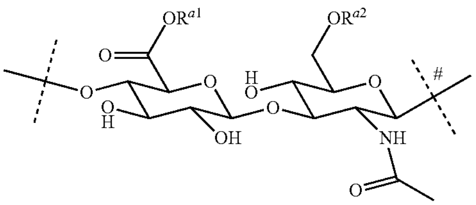,

-continued $Z^2$

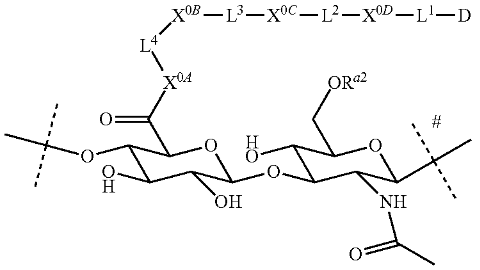

and $Z^3$

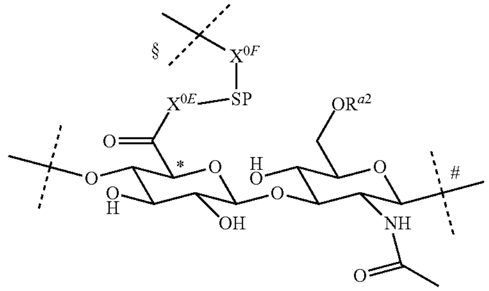, wherein an unmarked dashed line indicates a point of attachment to an adjacent unit at a dashed line marked with #or to a hydrogen;

a dashed line marked with #indicates a point of attachment to an adjacent unit at an unmarked dashed line or to a hydroxyl;

a dashed line marked with § indicates a point of connection between at least two units $Z^3$ via a moiety —CL-;

-D, -$L^1$-, -$L^2$-, -$L^3$-, -$L^4$-, —SP—, —CL-, —$X^{0A}$—, —$X^{0B}$—, —$X^{0C}$—, —$X^{0D}$—, —$X^{0E}$—, —$X^{0F}$—, —$R^{a1}$ and —$R^{a2}$ are used as defined above;

wherein all units $Z^1$ present in the conjugate may be the same or different;

all units $Z^2$ present in the conjugate may be the same or different;

all units $Z^3$ present in the conjugate may be the same or different;

the number of $Z^1$ units ranges from 1% to 98% of the total number of units present in the conjugate;

the number of $Z^2$ units ranges from 1% to 98% of the total number of units present in the conjugate, provided at least one unit $Z^2$ is present in the conjugate;

the number of $Z^3$ units ranges from 1% to 97% of the total number of units present in the conjugate, provided that at least one unit $Z^3$ is present per strand; and wherein at least 70% of all hyaluronic acid strands comprise at least one moiety $Z^2$ and at least one moiety $Z^3$.

The conjugate according to this first embodiment may also comprise units selected from the group consisting of $Z^4$, $Z^5$, $Z^6$, $Z^7$, $Z^8$, $Z^9$ and $Z^{10}$ as described above.

In a conjugate according to this first embodiment the number of units $Z^2$ ranges from 1 to 70% of all units present in the conjugate, such as from 2 to 15%, from 2 to 10%, from 16 to 39, from 40 to 65%, or from 50 to 60% of all units present in the conjugate.

In a conjugate according to this first embodiment the number of units $Z^3$ ranges from 1 to 30% of all units present in the conjugate, such as from 2 to 5%, from 5 to 20%, from 10 to 18%, or from 14 to 18% of all units present in the conjugate.

In a conjugate according to this first embodiment the number of units $Z^1$ ranges from 10 to 97% of all units present in the conjugate, such as from 20 to 40%, such as from 25 to 35%, such as from 41 to 95%, such as from 45 to 90%, such as from 50 to 70% of all units present in the conjugate.

Each degradable bond present in the direct connection between any two carbon atoms marked with the * connected by a moiety —CL- may be different or all such degradable bonds present in the conjugate may be the same.

Each direct connection between two carbon atoms marked with the * connected by a moiety —CL- may have the same or a different number of degradable bonds.

In certain embodiments the number of degradable bonds present in the conjugate of the present invention between all combinations of two carbon atoms marked with the * connected by a moiety —CL- is the same and all such degradable bonds have the same structure.

In the first embodiment the at least one degradable bond present in the direct connection between any two carbon atoms marked with the * connected by a moiety —CL- may be selected from the group consisting of ester, carbonate, sulfate, phosphate bonds, carbamate and amide bonds. It is understood that carbamates and amides are not reversible per se, and that in this context neighboring groups render these bonds reversible. In certain embodiments there is one degradable bond selected from the group consisting of ester, carbonate, sulfate, phosphate bonds, carbamate and amide bonds in the direct connection between any two carbon atoms marked with the * connected by a moiety —CL-. In certain embodiments there are two degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. In certain embodiments there are three degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. In certain embodiments there are four degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. In certain embodiments there are five degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. In certain embodiments there are six degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. It is understood that if more than two units $Z^3$ are connected by —CL- there are more than two carbons marked with * that are connected and thus there is more than one shortest connection with at least one degradable bond present. Each shortest connection may have the same or different number of degradable bonds.

In certain embodiments the at least one degradable bond, such as one, two, three, four, five, six degradable bonds, are located within —CL-.

In certain embodiments the at least one degradable bond present in the direct connection between any two carbon atoms marked with * connected by a moiety —CL- is one ester bond. In other embodiments the at least one degradable bond are two ester bonds. In other embodiments the at least one degradable bond are three ester bonds. In other embodiments the at least one degradable bond are four ester bonds. In other embodiments the at least one degradable bond are five ester bonds. In other embodiments the at least one degradable bond are six ester bonds.

In certain embodiments the at least one degradable bond present in the direct connection between any two carbon atoms marked with * connected by a moiety —CL- is one carbonate bond. In other embodiments the at least one degradable bond are two carbonate bonds. In other embodiments the at least one degradable bond are three carbonate bonds. In other embodiments the at least one degradable bond are four carbonate bonds. In other embodiments the at least one degradable bond are five carbonate bonds. In other embodiments the at least one degradable bond are six carbonate bonds.

In certain embodiments the at least one degradable bond present in the direct connection between any two carbon atoms marked with * connected by a moiety —CL- is one phosphate bond. In other embodiments the at least one degradable bond are two phosphate bonds. In other embodiments the at least one degradable bond are three phosphate bonds. In other embodiments the at least one degradable bond are four phosphate bonds. In other embodiments the at least one degradable bond are five phosphate bonds. In other embodiments the at least one degradable bond are six phosphate bonds.

In certain embodiments the at least one degradable bond present in the direct connection between any two carbon atoms marked with * connected by a moiety —CL- is one sulfate bond. In other embodiments the at least one degradable bond are two sulfate bonds. In other embodiments the at least one degradable bond are three sulfate bonds. In other embodiments the at least one degradable bond are four sulfate bonds. In other embodiments the at least one degradable bond are five sulfate bonds. In other embodiments the at least one degradable bond are six sulfate bonds.

In certain embodiments the at least one degradable bond present in the direct connection between any two carbon atoms marked with * connected by a moiety —CL- is one carbamate bond. In other embodiments the at least one degradable bond are two carbamate bonds. In other embodiments the at least one degradable bond are three carbamate bonds. In other embodiments the at least one degradable bond are four carbamate bonds. In other embodiments the at least one degradable bond are five carbamate bonds. In other embodiments the at least one degradable bond are six carbamate bonds.

In certain embodiments the at least one degradable bond present in the direct connection between any two carbon atoms marked with * connected by a moiety —CL- is one amide bond. In other embodiments the at least one degradable bond are two amide bonds. In other embodiments the at least one degradable bond are three amide bonds. In other embodiments the at least one degradable bond are four amide bonds. In other embodiments the at least one degradable bond are five amide bonds. In other embodiments the at least one degradable bond are six amide bonds.

It was found that a high degree of derivatization of the disaccharide units of hyaluronic acid, meaning that the number of units $Z^1$ is less than 80% of all units present in the conjugate, interferes with degradation of the hydrogel by certain hyaluronidases. This has the effect that less degradation by hyaluronidases occurs and that chemical cleavage of the degradable bonds becomes more relevant. This renders degradation of the conjugate more predictable. The reason for this is that the level of enzymes, such as hyaluronidases, exhibits inter-patient variability and may vary between different administration sites, whereas chemical cleavage predominantly depends on temperature and pH which are more stable parameters and thus chemical cleavage tends to be more predictable.

In some embodiments —CL- is $C_{1-50}$ alkyl, which is optionally interrupted by one or more atoms or groups selected from the group consisting of -T-, —C(O)O—, —O—, —C(O)—, —C(O)N($R^{c1}$)—, —$S(O)_2$—, —S(O)—, —S—, —N($R^{c1}$)—, —OC($OR^{c1}$)($R^{c1a}$)— and —OC(O)N($R^{c1}$)—;

wherein -T- is selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; and $R^{c1}$ and —$R^{c1a}$ are selected from the group consisting of —H and $C_{1-6}$ alkyl.

In certain embodiments such moiety —CL- comprises at least one (such as one, two, three, four, five or six) degradable bond, such as a degradable bond selected from the group consisting of ester, carbonate, sulfate, phosphate bonds, carbamate and amide bonds.

In certain embodiments —CL- is a moiety of formula (A)

(A)

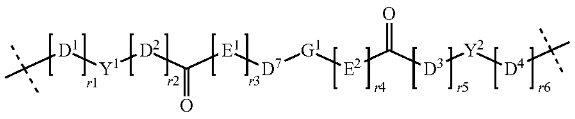

, wherein

—$Y^1$— is of formula

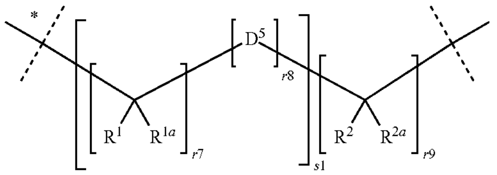

, wherein the dashed line marked with the asterisk indicates attachment to -$D^1$- and the unmarked dashed line indicates attachment to -$D^2$-;

—$Y^2$— is of formula

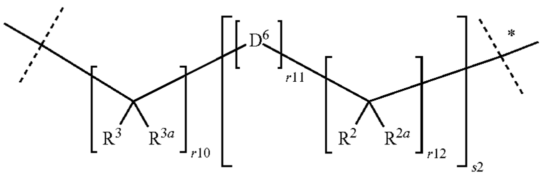

, wherein the dashed line marked with the asterisk indicates attachment to -$D^4$- and the unmarked dashed line indicates attachment to -$D^3$-;

-$E^1$- is of formula

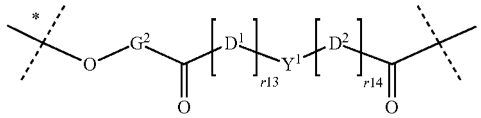

, wherein the dashed line marked with the asterisk indicates attachment to —(C═O)— and the unmarked dashed line indicates attachment to —O—;

-$E^2$- is of formula

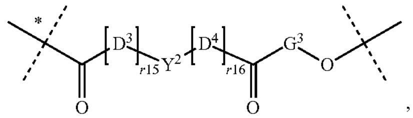

, wherein the dashed line marked with the asterisk indicates attachment to -$G^1$- and the unmarked dashed line indicates attachment to —(C═O)—;

-$G^1$- is of formula

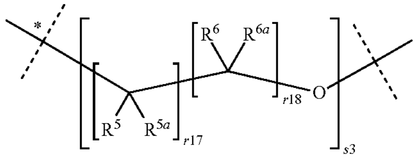

, wherein the dashed line marked with the asterisk indicates attachment to —O— and the unmarked dashed line indicates attachment to -$E^2$-;

-$G^2$- is of formula

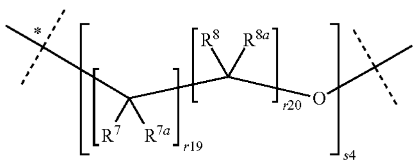

, wherein the dashed line marked with the asterisk indicates attachment to —O— and the unmarked dashed line indicates attachment to —(C═O)—;

-$G^3$- is of formula (C-vii),

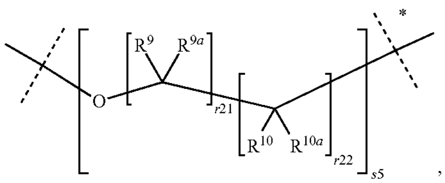

, wherein the dashed line marked with the asterisk indicates attachment to —O— and the unmarked dashed line indicates attachment to —(C═O)—;

$-D^1$-, $-D^2$-, $-D^3$-, $-D^4$-, $-D^5$-, $-D^6$- and $-D^7$- are identical or different and each is independently of the others selected from the group comprising —O—, $—NR^{11}—$, $—N^+R^{12}R^{12a}—$, —S—, —(S═O)—, $—(S(O)_2)$, —C(O)—, $—P(O)R^{13}$ and $—CR^{14}R^{14a}—$;

$—R^1$, $—R^{1a}$, $—R^2$, $—R^{2a}$, $—R^3$, $—R^{3a}$, $—R^4$, $—R^{4a}$, $—R^5$, $—R^{5a}$, $—R^6—R^{6a}$, $—R^7$, $—R^{7a}$, $—R^8$, $—R^{8a}$, $—R^9$, $—R^{9a}$, $—R^{10}$, $—R^{10a}$, $—R^{11}$, $—R^{12}$, $—R^{12a}$, $—R^{13}$, $—R^{14}$ and $—R^{14a}$ are identical or different and each is independently of the others selected from the group comprising —H and $C_{1-6}$ alkyl;

optionally, one or more of the pairs $—R^1/—R^{1a}$, $—R^2/—R^{2a}$, $—R^3/—R^{3a}$, $—R^4/—R^{4a}$, $—R^1/—R^2$, $—R^3/—R^4$, $—R^{1a}/—R^{2a}$, $—R^{3a}/—R^{4a}$, $—R^{12}/—R^{12a}$, and $—R^{14}/—R^{14a}$ form a chemical bond or are joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;

A is selected from the group consisting of phenyl, naphthyl, indenyl, indanyl and tetralinyl;

r1, r2, r5, r6, r13, r14, r15 and r16 are independently 0 or 1;

r3, r4, r7, r8, r9, r10, r11, r12 are independently 0, 1, 2, 3, or 4;

r17, r18, r19, r20, r21 and r22 are independently 1, 2, 3, 4, 5, 6, 7, 8, 9 or 10; and s1, s2, s4, s5 are independently 1, 2, 3, 4, 5 or 6.

s3 ranges from 1 to 200, preferably from 1 to 100 and more preferably from 1 to 50

In certain embodiments r1 of formula (A) is 0. In certain embodiments r1 of formula (A) is 1. In certain embodiments r2 of formula (A) is 0. In certain embodiments r2 of formula (A) is 1. In certain embodiments r5 of formula (A) is 0. In certain embodiments r5 of formula (A) is 1. In certain embodiments r6 of formula (A) is 0. In certain embodiments r6 of formula (A) is 1. In certain embodiments r13 of formula (A) is 0. In certain embodiments r13 of formula (A) is 1. In certain embodiments r14 of formula (A) is 0. In certain embodiments r14 of formula (A) is 1. In certain embodiments r15 of formula (A) is 0. In certain embodiments r15 of formula (A) is 1. In certain embodiments r16 of formula (A) is 0. In certain embodiments r16 of formula (A) is 1.

In certain embodiments r3 of formula (A) is 0. In certain embodiments r3 of formula (A) is 1. In certain embodiments r3 of formula (A) is 2. In certain embodiments r3 of formula (A) is 3. In certain embodiments r3 of formula (A) is 4. In certain embodiments r4 of formula (A) is 0. In certain embodiments r4 of formula (A) is 1. In certain embodiments r4 of formula (A) is 2. In certain embodiments r4 of formula (A) is 3. In certain embodiments r4 of formula (A) is 4. In certain embodiments r3 of formula (A) and r4 of formula (A) are both 0.

In certain embodiments r7 of formula (A) is 0. In certain embodiments r7 of formula (A) is 1. In certain embodiments r7 of formula (A) is 2. In certain embodiments r7 of formula (A) is 3. In certain embodiments r7 of formula (A) is 4. In certain embodiments r8 of formula (A) is 0. In certain embodiments r8 of formula (A) is 1. In certain embodiments r8 of formula (A) of formula (A) is 2. In certain embodiments r8 of formula (A) of formula (A) is 3. In certain embodiments r8 of formula (A) of formula (A) is 4. In certain embodiments r9 of formula (A) is 0. In certain embodiments r9 of formula (A) is 1. In certain embodiments r9 of formula (A) is 2. In certain embodiments r9 of formula (A) is 3. In certain embodiments r9 of formula (A) is 4. In certain embodiments r10 of formula (A) is 0. In certain embodiments r10 of formula (A) is 1. In certain embodiments r10 of formula (A) is 2. In certain embodiments r10 of formula (A) is 3. In certain embodiments r10 of formula (A) is 4. In certain embodiments r11 of formula (A) is 0. In certain embodiments r11 of formula (A) is 1. In certain embodiments r11 of formula (A) is 2. In certain embodiments r11 of formula (A) is 3. In certain embodiments r11 of formula (A) is 4. In certain embodiments r12 of formula (A) is 0. In certain embodiments r12 of formula (A) is 1. In certain embodiments r12 of formula (A) is 2. In certain embodiments r12 of formula (A) is 3. In certain embodiments r12 of formula (A) is 4.

In certain embodiments r17 of formula (A) is 1. In certain embodiments r17 of formula (A) is 2. In certain embodiments r17 of formula (A) is 3. In certain embodiments r18 of formula (A) is 1. In certain embodiments r18 of formula (A) is 2. In certain embodiments r18 of formula (A) is 3. In certain embodiments r19 of formula (A) is 1. In certain embodiments r19 of formula (A) is 2. In certain embodiments r19 of formula (A) is 3. In certain embodiments r20 of formula (A) is 1. In certain embodiments r20 of formula (A) is 2. In certain embodiments r20 of formula (A) is 3. In certain embodiments r21 of formula (A) is 1. In certain embodiments r21 of formula (A) is 2. In certain embodiments r21 of formula (A) is 3. In certain embodiments r22 of formula (A) is 1. In certain embodiments r22 of formula (A) is 2. In certain embodiments r22 of formula (A) is 3.

In certain embodiments s1 of formula (A) is 1. In certain embodiments s1 of formula (A) is 2. In certain embodiments s1 of formula (A) is 3. In certain embodiments s2 of formula (A) is 1. In certain embodiments s2 of formula (A) is 2. In certain embodiments s2 of formula (A) is 3. In certain embodiments s4 of formula (A) is 1. In certain embodiments s4 of formula (A) is 2. In certain embodiments s4 of formula (A) is 3.

In certain embodiments s3 of formula (A) ranges from 1 to 100. In certain embodiments s3 of formula (A) ranges from 1 to 75. In certain embodiments s3 of formula (A) ranges from 2 to 50. In certain embodiments s3 of formula (A) ranges from 2 to 40. In certain embodiments s3 of formula (A) ranges from 3 to 30. In certain embodiments s3 of formula (A) ranges from 3 to 20. In certain embodiments s3 of formula (A) ranges from 3 to 10. In certain embodiments s3 of formula (A) is about 2. In certain embodiments s3 of formula (A) is about 3. In certain embodiments s3 of formula (A) is about 4. In certain embodiments s3 of formula (A) is about 5. In certain embodiments s3 of formula (A) is about 6. In certain embodiments s3 of formula (A) is about 7. In certain embodiments s3 of formula (A) is about 8. In certain embodiments s3 of formula (A) is about 9. In certain embodiments s3 of formula (A) is about 10. In certain embodiments s3 of formula (A) is 2. In certain embodiments s3 of formula (A) is 3. In certain embodiments s3 of formula (A) is 4. In certain embodiments s3 of formula (A) is 5. In certain embodiments s3 of formula (A) is 6. In certain embodiments s3 of formula (A) is 7. In certain embodiments s3 of formula (A) is 8. In certain embodiments s3 of formula (A) is 9. In certain embodiments s3 of formula (A) is 10. In certain embodiments s3 of formula (A) is 20. In certain embodiments s3 of formula (A) is 25.

In certain embodiments —$R^1$ of formula (A) is —H. In certain embodiments —$R^1$ of formula (A) is methyl. In certain embodiments —$R^1$ of formula (A) is ethyl. In certain embodiments —$R^{1a}$ of formula (A) is —H. In certain embodiments —$R^{1a}$ of formula (A) is methyl. In certain embodiments —$R^{1a}$ of formula (A) is ethyl. In certain embodiments —$R^2$ of formula (A) is —H. In certain embodiments —$R^2$ of formula (A) is methyl. In certain embodiments —$R^2$ of formula (A) is ethyl. In certain embodiments —$R^{2a}$ of formula (A) is —H. In certain embodiments —$R^{2a}$ of formula (A) is methyl. In certain embodiments —$R^{2a}$ of formula (A) is ethyl. In certain embodiments —$R^3$ of formula (A) is —H. In certain embodiments —$R^3$ of formula (A) is methyl. In certain embodiments —$R^3$ of formula (A) is ethyl. In certain embodiments —$R^{3a}$ of formula (A) is —H. In certain embodiments —$R^{3a}$ of formula (A) is methyl. In certain embodiments —$R^{3a}$ of formula (A) is ethyl. In certain embodiments —$R^4$ of formula (A) is —H. In certain embodiments —$R^4$ of formula (A) is methyl. In certain embodiments —$R^4$ of formula (A) is methyl. In certain embodiments —$R^{4a}$ of formula (A) is —H. In certain embodiments —$R^{4a}$ of formula (A) is methyl. In certain embodiments —$R^{4a}$ of formula (A) is ethyl. In certain embodiments —$R^5$ of formula (A) is —H. In certain embodiments —$R^5$ of formula (A) is methyl. In certain embodiments —$R^5$ of formula (A) is ethyl. In certain embodiments —$R^{5a}$ of formula (A) is —H. In certain embodiments —$R^{5a}$ of formula (A) is methyl. In certain embodiments —$R^{5a}$ of formula (A) is ethyl. In certain embodiments —$R^6$ of formula (A) is —H. In certain embodiments —$R^6$ of formula (A) is methyl. In certain embodiments —$R^6$ of formula (A) is ethyl. In certain embodiments —$R^{6a}$ of formula (A) is —H. In certain embodiments —$R^{6a}$ of formula (A) is methyl. In certain embodiments —$R^{6a}$ of formula (A) is ethyl. In certain embodiments —$R^7$ of formula (A) is —H. In certain embodiments —$R^7$ of formula (A) is methyl. In certain embodiments —$R^7$ of formula (A) is ethyl. In certain embodiments —$R^8$ of formula (A) is —H. In certain embodiments —$R^8$ of formula (A) is methyl. In certain embodiments —$R^8$ of formula (A) is ethyl. In certain embodiments —$R^{8a}$ of formula (A) is —H. In certain embodiments —$R^{8a}$ of formula (A) is methyl. In certain embodiments —$R^{8a}$ of formula (A) is ethyl. In certain embodiments —$R^9$ of formula (A) is —H. In certain embodiments —$R^9$ of formula (A) is methyl. In certain embodiments —$R^9$ of formula (A) is ethyl. In certain embodiments —$R^{9a}$ of formula (A) is —H. In certain embodiments —$R^{9a}$ of formula (A) is methyl. In certain embodiments —$R^{9a}$ of formula (A) is ethyl. In certain embodiments —$R^{9a}$ of formula (A) is —H. In certain embodiments —$R^{9a}$ of formula (A) is methyl. In certain embodiments —$R^{9a}$ of formula (A) is ethyl. In certain embodiments —$R^{10}$ of formula (A) is —H. In certain embodiments —$R^{10}$ of formula (A) is methyl. In certain embodiments —$R^{10}$ of formula (A) is ethyl. In certain embodiments —$R^{10a}$ of formula (A) is —H. In certain embodiments —$R^{10a}$ of formula (A) is methyl. In certain embodiments —$R^{10a}$ of formula (A) is ethyl. In certain embodiments —$R^{11}$ of formula (A) is —H. In certain embodiments —$R^{11}$ of formula (A) is methyl. In certain embodiments —$R^1$ of formula (A) is ethyl. In certain embodiments —$R^{12}$ of formula (A) is —H. In certain embodiments —$R^2$ of formula (A) is methyl. In certain embodiments —$R^{12}$ of formula (A) is ethyl. In certain embodiments —$R^{12a}$ of formula (A) is —H. In certain embodiments —$R^{12a}$ of formula (A) is methyl. In certain embodiments —$R^{12a}$ of formula (A) is ethyl. In certain embodiments —$R^{13}$ of formula (A) is —H. In certain embodiments —$R^{13}$ of formula (A) is methyl. In certain embodiments —$R^{13}$ of formula (A) is ethyl. In certain embodiments —$R^{14}$ of formula (A) is —H. In certain embodiments —$R^{14}$ of formula (A) is methyl. In certain embodiments —$R^{14}$ of formula (A) is ethyl. In certain embodiments —$R^{14a}$ of formula (A) is —H. In certain embodiments —$R^{14a}$ of formula (A) is methyl. In certain embodiments —$R^{14a}$ of formula (A) is ethyl.

In certain embodiments -$D^1$- of formula (A) is —O—. In certain embodiments -$D^1$- of formula (A) is —$NR^{11}$—. In certain embodiments -$D_1$- of formula (A) is —$N^+R^{12}R^{12a}$—. In certain embodiments -$D^1$- of formula (A) is —S—. In certain embodiments -$D^1$- of formula (A) is —(S=O). In certain embodiments -$D^1$- of formula (A) is —$(S(O)_2)$—. In certain embodiments -$D^1$- of formula (A) is —C(O)—. In certain embodiments -$D^1$- of formula (A) is —$P(O)R^{13}$—. In certain embodiments -$D^1$- of formula (A) is —$P(O)(OR^{13})$—. In certain embodiments -$D^1$- of formula (A) is —$CR^{14}R^{14a}$—.

In certain embodiments -$D^2$- of formula (A) is —O—. In certain embodiments -$D^2$- of formula (A) is —$NR^{11}$—. In certain embodiments -$D^2$- of formula (A) is —$N^+R^{12}R^{12a}$—. In certain embodiments -$D^2$- of formula (A) is —S—. In certain embodiments -$D^2$- of formula (A) is —(S=O). In certain embodiments -$D^2$- of formula (A) is —$(S(O)_2)$—. In certain embodiments -$D^2$- of formula (A) is —C(O)—. In certain embodiments -$D^2$- of formula (A) is —$P(O)R^1$—. In certain embodiments -$D^1$- of formula (A) is —$P(O)(OR^3)$—. In certain embodiments -$D^2$- of formula (A) is —$CR^{14}R^{14a}$—.

In certain embodiments -$D^3$- of formula (A) is —O—. In certain embodiments -$D^3$- of formula (A) is —$NR^{11}$—. In certain embodiments -$D^3$- of formula (A) is —$N^+R^{12}R^{12a}$—. In certain embodiments -$D^3$- of formula (A) is —S—. In certain embodiments -$D^3$- of formula (A) is —(S=O). In certain embodiments -$D^3$- of formula (A) is —$(S(O)_2)$—. In certain embodiments -$D^3$- of formula (A) is —C(O)—. In certain embodiments -$D^3$- of formula (A) is —$P(O)R^{13}$—. In certain embodiments -$D^3$- of formula (A) is —$P(O)(OR^{13})$—. In certain embodiments -$D^3$- of formula (A) is —$CR^{14}R^{14a}$—.

In certain embodiments -$D^4$- of formula (A) is —O—. In certain embodiments -$D^4$- of formula (A) is —$NR^{11}$—. In certain embodiments -$D^4$- of formula (A) is —$N^+R^{12}R^{12a}$—. In certain embodiments -$D^4$- of formula (A) is —S—. In certain embodiments -$D^4$- of formula (A) is —(S=O). In certain embodiments -$D^4$- of formula (A) is —$(S(O)_2)$—. In certain embodiments -$D^4$- of formula (A) is —C(O)—. In certain embodiments -$D^4$- of formula (A) is —$P(O)R^{13}$—. In certain embodiments -$D^4$- of formula (A) is —$P(O)(OR^{13})$—. In certain embodiments -$D^4$- of formula (A) is —$CR^{14}R^{14a}$—.

In certain embodiments -$D^5$- of formula (A) is —O—. In certain embodiments -$D^5$- of formula (A) is —$NR^{11}$—. In certain embodiments -$D^5$- of formula (A) is —$N^+R^{12}R^{12a}$—. In certain embodiments -$D^5$- of formula (A) is —S—. In certain embodiments -$D^5$- of formula (A) is —(S=O)—. In certain embodiments -$D^5$- of formula (A) is —$(S(O)_2)$—. In certain embodiments -$D^1$- of formula (A) is —C(O)—. In certain embodiments -$D^5$- of formula (A) is —$P(O)R^{13}$—. In certain embodiments -$D^5$- of formula (A) is —$P(O)(OR^{13})$—. In certain embodiments -$D^5$- of formula (A) is —$CR^{14}R^{14a}$—.

In certain embodiments $-D^6-$ of formula (A) is —O—. In certain embodiments $-D^6-$ of formula (A) is $—NR^{11}—$. In certain embodiments $-D^6-$ of formula (A) is $—N^+R^{12}R^{12a}—$. In certain embodiments $-D^6-$ of formula (A) is —S—. In certain embodiments $-D^6-$ of formula (A) is —(S=O). In certain embodiments $-D^6-$ of formula (A) is $—(S(O)_2)—$. In certain embodiments $-D^6-$ of formula (A) is —C(O)—. In certain embodiments $-D^6-$ of formula (A) is $—P(O)R^{13}—$. In certain embodiments $-D^6-$ of formula (A) is $—P(O)(OR^{13})—$. In certain embodiments $-D^6-$ of formula (A) is $—CR^{14}R^{14a}—$.

In certain embodiments $-D^7-$ of formula (A) is —O—. In certain embodiments $-D^7-$ of formula (A) is $—NR^{11}—$. In certain embodiments $-D^7-$ of formula (A) is $—N^+R^{12}R^{12a}—$. In certain embodiments $-D^7-$ of formula (A) is —S—. In certain embodiments $-D^7-$ of formula (A) is —(S=O). In certain embodiments $-D^7-$ of formula (A) is $—(S(O)_2)—$. In certain embodiments $-D^7-$ of formula (A) is —C(O)—. In certain embodiments $-D^7-$ of formula (A) is $—P(O)R^{13}—$. In certain embodiments $-D^7-$ of formula (A) is $—P(O)(OR^{13})—$. In certain embodiments $-D^7-$ of formula (A) is $—CR^{14}R^{14a}—$.

In certain embodiments —CL- is of formula (B)

(B)

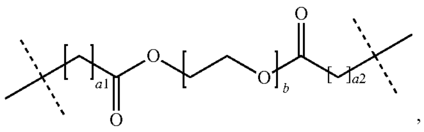

, wherein the dashed lines indicate attachment to a moiety $—X^{0F}—$;

a1 and a2 are independently selected from the group consisting of a1 and a2 are independently selected from the group consisting of 1, 2, 3, 4, 5, 6, 7, 8, 9, 10, 11, 12, 13 and 14; and b is an integer ranging from 1 to 50.

In certain embodiments a1 and a2 of formula (B) are different. In certain embodiments a1 and a2 of formula (B) are the same.

In certain embodiments a1 of formula (B) is 1. In certain embodiments a1 of formula (B) is 2. In certain embodiments a1 of formula (B) is 3. In certain embodiments a1 of formula (B) is 4. In certain embodiments a1 of formula (B) is 5. In certain embodiments a1 of formula (B) is 6. In certain embodiments a1 of formula (B) is 7. In certain embodiments a1 of formula (B) is 8. In certain embodiments a1 of formula (B) is 9. In certain embodiments a1 of formula (B) is 10.

In certain embodiments a2 of formula (B) is 1. In certain embodiments a2 of formula (B) is 2. In certain embodiments a2 of formula (B) is 3. In certain embodiments a2 of formula (B) is 4. In certain embodiments a2 of formula (B) is 5. In certain embodiments a2 of formula (B) is 6. In certain embodiments a2 of formula (B) is 7. In certain embodiments a2 of formula (B) is 8. In certain embodiments a2 of formula (B) is 9. In certain embodiments a2 of formula (B) is 10.

In certain embodiments a1 and a2 of formula (B) are both 1. In certain embodiments a1 and a2 of formula (B) are both 2. In certain embodiments a1 and a2 of formula (B) are both 3. In certain embodiments a1 and a2 of formula (B) are both 4. In certain embodiments a1 and a2 of formula (B) are both 5. In certain embodiments a1 and a2 of formula (B) are both 6. In certain embodiments a1 and a2 of formula (B) are both 7. In certain embodiments a1 and a2 of formula (B) are both 8. In certain embodiments a1 and a2 of formula (B) are both 9. In certain embodiments a1 and a2 of formula (B) are both 10.

In certain embodiments a1 and a2 of formula (B) are both 1 and b of formula (B) is 3. In certain embodiments a1 and a2 of formula (B) are both 1 and b of formula (B) is 4. In certain embodiments a1 and a2 of formula (B) are both 1 and b of formula (B) is 5. In certain embodiments a1 and a2 of formula (B) are both 1 and b of formula (B) is 6. In certain embodiments a1 and a2 of formula (B) are both 1 and b of formula (B) is 7. In certain embodiments a1 and a2 of formula (B) are both 1 and b of formula (B) is 8. In certain embodiments a1 and a2 of formula (B) are both 1 and b of formula (B) is 9. In certain embodiments a1 and a2 of formula (B) are both 1 and b of formula (B) is 10. In certain embodiments a1 and a2 of formula (B) are both 1 and b of formula (B) is 20. In certain embodiments a1 and a2 of formula (B) are both 1 and b of formula (B) is 25.

In certain embodiments a1 and a2 of formula (B) are both 2 and b of formula (B) is 3. In certain embodiments a1 and a2 of formula (B) are both 2 and b of formula (B) is 4. In certain embodiments a1 and a2 of formula (B) are both 2 and b of formula (B) is 5. In certain embodiments a1 and a2 of formula (B) are both 2 and b of formula (B) is 6. In certain embodiments a1 and a2 of formula (B) are both 2 and b of formula (B) is 7. In certain embodiments a1 and a2 of formula (B) are both 2 and b of formula (B) is 8. In certain embodiments a1 and a2 of formula (B) are both 2 and b of formula (B) is 9. In certain embodiments a1 and a2 of formula (B) are both 2 and b of formula (B) is 10. In certain embodiments a1 and a2 of formula (B) are both 2 and b of formula (B) is 20. In certain embodiments a1 and a2 of formula (B) are both 2 and b of formula (B) is 25.

In certain embodiments a1 and a2 of formula (B) are both 3 and b of formula (B) is 3. In certain embodiments a1 and a2 of formula (B) are both 3 and b of formula (B) is 4. In certain embodiments a1 and a2 of formula (B) are both 3 and b of formula (B) is 5. In certain embodiments a1 and a2 of formula (B) are both 3 and b of formula (B) is 6. In certain embodiments a1 and a2 of formula (B) are both 3 and b of formula (B) is 7. In certain embodiments a1 and a2 of formula (B) are both 3 and b of formula (B) is 8. In certain embodiments a1 and a2 of formula (B) are both 3 and b of formula (B) is 9. In certain embodiments a1 and a2 of formula (B) are both 3 and b of formula (B) is 10. In certain embodiments a1 and a2 of formula (B) are both 3 and b of formula (B) is 20. In certain embodiments a1 and a2 of formula (B) are both 3 and b of formula (B) is 25.

In certain embodiments a1 and a2 of formula (B) are both 4 and b of formula (B) is 3. In certain embodiments a1 and a2 of formula (B) are both 4 and b of formula (B) is 4. In certain embodiments a1 and a2 of formula (B) are both 4 and b of formula (B) is 5. In certain embodiments a1 and a2 of formula (B) are both 4 and b of formula (B) is 6. In certain embodiments a1 and a2 of formula (B) are both 4 and b of formula (B) is 7. In certain embodiments a1 and a2 of formula (B) are both 4 and b of formula (B) is 8. In certain embodiments a1 and a2 of formula (B) are both 4 and b of formula (B) is 9. In certain embodiments a1 and a2 of formula (B) are both 4 and b of formula (B) is 10. In certain embodiments a1 and a2 of formula (B) are both 4 and b of formula (B) is 20. In certain embodiments a1 and a2 of formula (B) are both 4 and b of formula (B) is 25.

In certain embodiments a1 and a2 of formula (B) are both 5 and b of formula (B) is 3. In certain embodiments a1 and a2 of formula (B) are both 5 and b of formula (B) is 4. In certain embodiments a1 and a2 of formula (B) are both 5 and b of formula (B) is 5. In certain embodiments a1 and a2 of formula (B) are both 5 and b of formula (B) is 6. In certain embodiments a1 and a2 of formula (B) are both 5 and b of formula (B) is 7. In certain embodiments a1 and a2 of formula (B) are both 5 and b of formula (B) is 8. In certain embodiments a1 and a2 of formula (B) are both 5 and b of formula (B) is 9. In certain embodiments a1 and a2 of formula (B) are both 5 and b of formula (B) is 10. In certain embodiments a1 and a2 of formula (B) are both 5 and b of formula (B) is 20. In certain embodiments a1 and a2 of formula (B) are both 5 and b of formula (B) is 25.

In certain embodiments a1 and a2 of formula (B) are both 6 and b of formula (B) is 3. In certain embodiments a1 and a2 of formula (B) are both 6 and b of formula (B) is 4. In certain embodiments a1 and a2 of formula (B) are both 6 and b of formula (B) is 5. In certain embodiments a1 and a2 of formula (B) are both 6 and b of formula (B) is 6. In certain embodiments a1 and a2 of formula (B) are both 6 and b of formula (B) is 7. In certain embodiments a1 and a2 of formula (B) are both 6 and b of formula (B) is 8. In certain embodiments a1 and a2 of formula (B) are both 6 and b of formula (B) is 9. In certain embodiments a1 and a2 of formula (B) are both 6 and b of formula (B) is 10. In certain embodiments a1 and a2 of formula (B) are both 6 and b of formula (B) is 20. In certain embodiments a1 and a2 of formula (B) are both 6 and b of formula (B) is 25.

In certain embodiments a1 and a2 of formula (B) are both 7 and b of formula (B) is 3. In certain embodiments a1 and a2 of formula (B) are both 7 and b of formula (B) is 4. In certain embodiments a1 and a2 of formula (B) are both 7 and b of formula (B) is 5. In certain embodiments a1 and a2 of formula (B) are both 7 and b of formula (B) is 6. In certain embodiments a1 and a2 of formula (B) are both 7 and b of formula (B) is 7. In certain embodiments a1 and a2 of formula (B) are both 7 and b of formula (B) is 8. In certain embodiments a1 and a2 of formula (B) are both 7 and b of formula (B) is 9. In certain embodiments a1 and a2 of formula (B) are both 7 and b of formula (B) is 10. In certain embodiments a1 and a2 of formula (B) are both 7 and b of formula (B) is 20. In certain embodiments a1 and a2 of formula (B) are both 7 and b of formula (B) is 25.

In certain embodiments a1 and a2 of formula (B) are both 8 and b of formula (B) is 3. In certain embodiments a1 and a2 of formula (B) are both 8 and b of formula (B) is 4. In certain embodiments a1 and a2 of formula (B) are both 8 and b of formula (B) is 5. In certain embodiments a1 and a2 of formula (B) are both 8 and b of formula (B) is 6. In certain embodiments a1 and a2 of formula (B) are both 8 and b of formula (B) is 7. In certain embodiments a1 and a2 of formula (B) are both 8 and b of formula (B) is 8. In certain embodiments a1 and a2 of formula (B) are both 8 and b of formula (B) is 9. In certain embodiments a1 and a2 of formula (B) are both 8 and b of formula (B) is 10. In certain embodiments a1 and a2 of formula (B) are both 8 and b of formula (B) is 20. In certain embodiments a1 and a2 of formula (B) are both 8 and b of formula (B) is 25.

In certain embodiments a1 and a2 of formula (B) are both 9 and b of formula (B) is 3. In certain embodiments a1 and a2 of formula (B) are both 9 and b of formula (B) is 4. In certain embodiments a1 and a2 of formula (B) are both 9 and b of formula (B) is 5. In certain embodiments a1 and a2 of formula (B) are both 9 and b of formula (B) is 6. In certain embodiments a1 and a2 of formula (B) are both 9 and b of formula (B) is 7. In certain embodiments a1 and a2 of formula (B) are both 9 and b of formula (B) is 8. In certain embodiments a1 and a2 of formula (B) are both 9 and b of formula (B) is 9. In certain embodiments a1 and a2 of formula (B) are both 9 and b of formula (B) is 10. In certain embodiments a1 and a2 of formula (B) are both 9 and b of formula (B) is 20. In certain embodiments a1 and a2 of formula (B) are both 9 and b of formula (B) is 25.

In certain embodiments a1 and a2 of formula (B) are both 10 and b of formula (B) is 3. In certain embodiments a1 and a2 of formula (B) are both 10 and b of formula (B) is 4. In certain embodiments a1 and a2 of formula (B) are both 10 and b of formula (B) is 5. In certain embodiments a1 and a2 of formula (B) are both 10 and b of formula (B) is 6. In certain embodiments a1 and a2 of formula (B) are both 10 and b of formula (B) is 7. In certain embodiments a1 and a2 of formula (B) are both 10 and b of formula (B) is 8. In certain embodiments a1 and a2 of formula (B) are both 10 and b of formula (B) is 9. In certain embodiments a1 and a2 of formula (B) are both 10 and b of formula (B) is 10. In certain embodiments a1 and a2 of formula (B) are both 10 and b of formula (B) is 20. In certain embodiments a1 and a2 of formula (B) are both 10 and b of formula (B) is 25.

In certain embodiments b of formula (B) ranges from 1 to 500. In certain embodiments b of formula (B) ranges from 2 to 250. In certain embodiments b of formula (B) ranges from 3 to 100. In certain embodiments b of formula (B) ranges from 3 to 50. In certain embodiments b of formula (B) ranges from 3 to 25. In certain embodiments b of formula (B) is 2. In certain embodiments b of formula (B) is 3. In certain embodiments b of formula (B) is 4. In certain embodiments b of formula (B) is 5. In certain embodiments b of formula (B) is 6. In certain embodiments b of formula (B) is 7. In certain embodiments b of formula (B) is 8. In certain embodiments b of formula (B) is 9. In certain embodiments b of formula (B) is 10. In certain embodiments b of formula (B) is 20. In certain embodiments b of formula (B) is 25.

In certain embodiments —CL- is of formula (B-i)

(B-i)

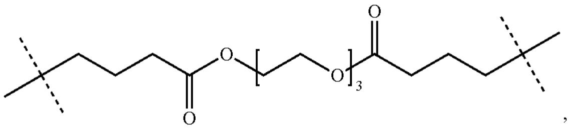

, wherein the dashed lines indicate attachment to a moiety —$X^{0F}$—.

In certain embodiments —CL- is of formula (C)

(C)

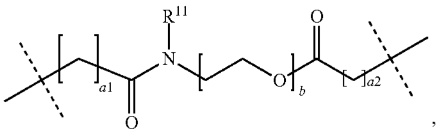

, wherein the dashed lines indicate attachment to a moiety —$X^{0F}$—;

a1 and a2 are independently selected from the group consisting of 1, 2, 3, 4, 5, 6, 7, 8, 9, 10, 11, 12, 13 and 14;

b is an integer ranging from 1 to 50; and

—$R^{11}$ is selected from the group comprising —H and $C_{1-6}$ alkyl.

In certain embodiments a1 and a2 of formula (C) are different. In certain embodiments a1 and a2 of formula (B) are the same.

In certain embodiments a1 of formula (C) is 1. In certain embodiments a1 of formula (C) is 2. In certain embodiments a1 of formula (C) is 3. In certain embodiments a1 of formula (C) is 4. In certain embodiments a1 of formula (C) is 5. In certain embodiments a1 of formula (C) is 6. In certain embodiments a1 of formula (C) is 7. In certain embodiments a1 of formula (C) is 8. In certain embodiments a1 of formula (C) is 9. In certain embodiments a1 of formula (C) is 10.

In certain embodiments a2 of formula (C) is 1. In certain embodiments a2 of formula (C) is 2. In certain embodiments a2 of formula (C) is 3. In certain embodiments a2 of formula (C) is 4. In certain embodiments a2 of formula (C) is 5. In certain embodiments a2 of formula (C) is 6. In certain embodiments a2 of formula (C) is 7. In certain embodiments a2 of formula (C) is 8. In certain embodiments a2 of formula (C) is 9. In certain embodiments a2 of formula (C) is 10.

In certain embodiments a1 and a2 of formula (C) are both 1. In certain embodiments a1 and a2 of formula (C) are both 2. In certain embodiments a1 and a2 of formula (C) are both 3. In certain embodiments a1 and a2 of formula (C) are both 4. In certain embodiments a1 and a2 of formula (C) are both 5. In certain embodiments a1 and a2 of formula (C) are both 6. In certain embodiments a1 and a2 of formula (C) are both 7. In certain embodiments a1 and a2 of formula (C) are both 8. In certain embodiments a1 and a2 of formula (C) are both 9. In certain embodiments a1 and a2 of formula (C) are both 10.

In certain embodiments a1 and a2 of formula (C) are both 1 and b of formula (C) is 3. In certain embodiments a1 and a2 of formula (C) are both 1 and b of formula (C) is 4. In certain embodiments a1 and a2 of formula (C) are both 1 and b of formula (C) is 5. In certain embodiments a1 and a2 of formula (C) are both 1 and b of formula (C) is 6. In certain embodiments a1 and a2 of formula (C) are both 1 and b of formula (C) is 7. In certain embodiments a1 and a2 of formula (C) are both 1 and b of formula (C) is 8. In certain embodiments a1 and a2 of formula (C) are both 1 and b of formula (C) is 9. In certain embodiments a1 and a2 of formula (C) are both 1 and b of formula (C) is 10. In certain embodiments a1 and a2 of formula (C) are both 1 and b of formula (C) is 20. In certain embodiments a1 and a2 of formula (C) are both 1 and b of formula (C) is 25.

In certain embodiments a1 and a2 of formula (C) are both 2 and b of formula (C) is 3. In certain embodiments a1 and a2 of formula (C) are both 2 and b of formula (C) is 4. In certain embodiments a1 and a2 of formula (C) are both 2 and b of formula (C) is 5. In certain embodiments a1 and a2 of formula (C) are both 2 and b of formula (C) is 6. In certain embodiments a1 and a2 of formula (C) are both 2 and b of formula (C) is 7. In certain embodiments a1 and a2 of formula (C) are both 2 and b of formula (C) is 8. In certain embodiments a1 and a2 of formula (C) are both 2 and b of formula (C) is 9. In certain embodiments a1 and a2 of formula (C) are both 2 and b of formula (C) is 10. In certain embodiments a1 and a2 of formula (C) are both 2 and b of formula (C) is 20. In certain embodiments a1 and a2 of formula (C) are both 2 and b of formula (C) is 25.

In certain embodiments a1 and a2 of formula (C) are both 3 and b of formula (C) is 3. In certain embodiments a1 and a2 of formula (C) are both 3 and b of formula (C) is 4. In certain embodiments a1 and a2 of formula (C) are both 3 and b of formula (C) is 5. In certain embodiments a1 and a2 of formula (C) are both 3 and b of formula (C) is 6. In certain embodiments a1 and a2 of formula (C) are both 3 and b of formula (C) is 7. In certain embodiments a1 and a2 of formula (C) are both 3 and b of formula (C) is 8. In certain embodiments a1 and a2 of formula (C) are both 3 and b of formula (C) is 9. In certain embodiments a1 and a2 of formula (C) are both 3 and b of formula (C) is 10. In certain embodiments a1 and a2 of formula (C) are both 3 and b of formula (C) is 20. In certain embodiments a1 and a2 of formula (C) are both 3 and b of formula (C) is 25.

In certain embodiments a1 and a2 of formula (C) are both 4 and b of formula (C) is 3. In certain embodiments a1 and a2 of formula (C) are both 4 and b of formula (C) is 4. In certain embodiments a1 and a2 of formula (C) are both 4 and b of formula (C) is 5. In certain embodiments a1 and a2 of formula (C) are both 4 and b of formula (C) is 6. In certain embodiments a1 and a2 of formula (C) are both 4 and b of formula (C) is 7. In certain embodiments a1 and a2 of formula (C) are both 4 and b of formula (C) is 8. In certain embodiments a1 and a2 of formula (C) are both 4 and b of formula (C) is 9. In certain embodiments a1 and a2 of formula (C) are both 4 and b of formula (C) is 10. In certain embodiments a1 and a2 of formula (C) are both 4 and b of formula (C) is 20. In certain embodiments a1 and a2 of formula (C) are both 4 and b of formula (C) is 25.

In certain embodiments a1 and a2 of formula (C) are both 5 and b of formula (C) is 3. In certain embodiments a1 and a2 of formula (C) are both 5 and b of formula (C) is 4. In certain embodiments a1 and a2 of formula (C) are both 5 and b of formula (C) is 5. In certain embodiments a1 and a2 of formula (C) are both 5 and b of formula (C) is 6. In certain embodiments a1 and a2 of formula (C) are both 5 and b of formula (C) is 7. In certain embodiments a1 and a2 of formula (C) are both 5 and b of formula (C) is 8. In certain embodiments a1 and a2 of formula (C) are both 5 and b of formula (C) is 9. In certain embodiments a1 and a2 of formula (C) are both 5 and b of formula (C) is 10. In certain embodiments a1 and a2 of formula (C) are both 5 and b of formula (C) is 20. In certain embodiments a1 and a2 of formula (C) are both 5 and b of formula (C) is 25.

In certain embodiments a1 and a2 of formula (C) are both 6 and b of formula (C) is 3. In certain embodiments a1 and a2 of formula (C) are both 6 and b of formula (C) is 4. In certain embodiments a1 and a2 of formula (C) are both 6 and b of formula (C) is 5. In certain embodiments a1 and a2 of formula (C) are both 6 and b of formula (C) is 6. In certain embodiments a1 and a2 of formula (C) are both 6 and b of formula (C) is 7. In certain embodiments a1 and a2 of formula (C) are both 6 and b of formula (C) is 8. In certain embodiments a1 and a2 of formula (C) are both 6 and b of formula (C) is 9. In certain embodiments a1 and a2 of formula (C) are both 6 and b of formula (C) is 10. In certain embodiments a1 and a2 of formula (C) are both 6 and b of formula (C) is 20. In certain embodiments a1 and a2 of formula (C) are both 6 and b of formula (C) is 25.

In certain embodiments a1 and a2 of formula (C) are both 7 and b of formula (C) is 3. In certain embodiments a1 and a2 of formula (C) are both 7 and b of formula (C) is 4. In certain embodiments a1 and a2 of formula (C) are both 7 and b of formula (C) is 5. In certain embodiments a1 and a2 of formula (C) are both 7 and b of formula (C) is 6. In certain embodiments a1 and a2 of formula (C) are both 7 and b of formula (C) is 7. In certain embodiments a1 and a2 of formula (C) are both 7 and b of formula (C) is 8. In certain embodiments a1 and a2 of formula (C) are both 7 and b of formula (C) is 9. In certain embodiments a1 and a2 of formula (C) are both 7 and b of formula (C) is 10. In certain embodiments a1 and a2 of formula (C) are both 7 and b of formula (C) is 20. In certain embodiments a1 and a2 of formula (C) are both 7 and b of formula (C) is 25.

In certain embodiments a1 and a2 of formula (C) are both 8 and b of formula (C) is 3. In certain embodiments a1 and a2 of formula (C) are both 8 and b of formula (C) is 4. In certain embodiments a1 and a2 of formula (C) are both 8 and b of formula (C) is 5. In certain embodiments a1 and a2 of formula (C) are both 8 and b of formula (C) is 6. In certain embodiments a1 and a2 of formula (C) are both 8 and b of formula (C) is 7. In certain embodiments a1 and a2 of formula (C) are both 8 and b of formula (C) is 8. In certain embodiments a1 and a2 of formula (C) are both 8 and b of formula (C) is 9. In certain embodiments a1 and a2 of formula (C) are both 8 and b of formula (C) is 10. In certain embodiments a1 and a2 of formula (C) are both 8 and b of formula (C) is 20. In certain embodiments a1 and a2 of formula (C) are both 8 and b of formula (C) is 25.

In certain embodiments a1 and a2 of formula (C) are both 9 and b of formula (C) is 3. In certain embodiments a1 and a2 of formula (C) are both 9 and b of formula (C) is 4. In certain embodiments a1 and a2 of formula (C) are both 9 and b of formula (C) is 5. In certain embodiments a1 and a2 of formula (C) are both 9 and b of formula (C) is 6. In certain embodiments a1 and a2 of formula (C) are both 9 and b of formula (C) is 7. In certain embodiments a1 and a2 of formula (C) are both 9 and b of formula (C) is 8. In certain embodiments a1 and a2 of formula (C) are both 9 and b of formula (C) is 9. In certain embodiments a1 and a2 of formula (C) are both 9 and b of formula (C) is 10. In certain embodiments a1 and a2 of formula (C) are both 9 and b of formula (C) is 20. In certain embodiments a1 and a2 of formula (C) are both 9 and b of formula (C) is 25.

In certain embodiments a1 and a2 of formula (C) are both 10 and b of formula (C) is 3. In certain embodiments a1 and a2 of formula (C) are both 10 and b of formula (C) is 4. In certain embodiments a1 and a2 of formula (C) are both 10 and b of formula (C) is 5. In certain embodiments a1 and a2 of formula (C) are both 10 and b of formula (C) is 6. In certain embodiments a1 and a2 of formula (C) are both 10 and b of formula (C) is 7. In certain embodiments a1 and a2 of formula (C) are both 10 and b of formula (C) is 8. In certain embodiments a1 and a2 of formula (C) are both 10 and b of formula (C) is 9. In certain embodiments a1 and a2 of formula (C) are both 10 and b of formula (C) is 10. In certain embodiments a1 and a2 of formula (C) are both 10 and b of formula (C) is 20. In certain embodiments a1 and a2 of formula (C) are both 10 and b of formula (C) is 25.

In certain embodiments b of formula (C) ranges from 1 to 500. In certain embodiments b of formula (C) ranges from 2 to 250. In certain embodiments b of formula (C) ranges from 3 to 100. In certain embodiments b of formula (C) ranges from 3 to 50. In certain embodiments b of formula (C) ranges from 3 to 25. In certain embodiments b of formula (C) is 2. In certain embodiments b of formula (C) is 3. In certain embodiments b of formula (C) is 4. In certain embodiments b of formula (C) is 5. In certain embodiments b of formula (C) is 6. In certain embodiments b of formula (C) is 7. In certain embodiments b of formula (C) is 8. In certain embodiments b of formula (C) is 9. In certain embodiments b of formula (C) is 10. In certain embodiments b of formula (C) is 20. In certain embodiments b of formula (C) is 25.

In certain embodiments —$R^{11}$ of formula (C) is —H. In certain embodiments —$R^{11}$ of formula (C) is methyl. In certain embodiments —$R^{11}$ of formula (C) is ethyl. In certain embodiments —$R^{11}$ of formula (C) is n-propyl. In certain embodiments —$R^{11}$ of formula (C) is isopropyl. In certain embodiments —$R^{11}$ of formula (C) is n-butyl. In certain embodiments —$R^{11}$ of formula (C) is isobutyl. In certain embodiments —$R^{11}$ of formula (C) is sec-butyl. In certain embodiments —$R^{11}$ of formula (C) is tert-butyl. In certain embodiments —$R^{11}$ of formula (C) is n-pentyl. In certain embodiments —$R^{11}$ of formula (C) is 2-methylbutyl. In certain embodiments —$R^{11}$ of formula (C) is 2,2-dimethylpropyl. In certain embodiments —$R^{11}$ of formula (C) is n-hexyl. In certain embodiments —$R^{11}$ of formula (C) is 2-methylpentyl. In certain embodiments —$R^{11}$ of formula (C) is 3-methylpentyl. In certain embodiments —$R^{11}$ of formula (C) is 2,2-dimethylbutyl. In certain embodiments —$R^{11}$ of formula (C) is 2,3-dimethylbutyl. In certain embodiments —$R^{11}$ of formula (C) is 3,3-dimethylpropyl.

In certain embodiments —CL- is of formula (C-i)

(C-i)

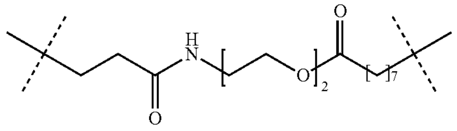

wherein the dashed lines indicate attachment to a moiety —$X^{0F}$—.

Specific embodiments for —$R^{a1}$, —$R^{a2}$, -$L^1$-, -$L^2$-, -$L^3$-, -$L^4$-, —SP—, —$X^{0A}$—, —$X^{0B}$—, —$X^{0C}$—, —$X^{0D}$—, —$X^{0E}$—, —$X^{0F}$— and -D of the first embodiment are as described below.

In certain embodiments —CL- is of formula (D)

(D)

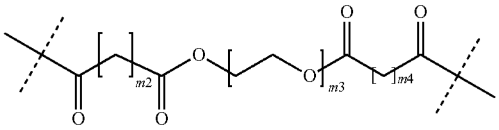

, wherein the dashed lines indicate attachment to a moiety —$X^{0F}$—; and m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 of formula (D) is an integer selected from the group consisting of 2, 3, 4, 5, 6, 7, 8, 9 and 10. In certain embodiments m2 of formula (D) is an integer selected from the group consisting of 3, 4, 5, 6 and 7. In certain embodiments m2 of formula (D) is 3. In certain embodiments m2 of formula (D) is 4. In certain embodiments m2 of formula (D) is 5. In certain embodiments m2 of formula (D) is 6. In certain embodiments m2 of formula (D) is 7. In certain embodiments m3 of formula (D) is an integer selected from the group consisting of 1, 2, 3, 4, 5, 6, 7, 8, 9 and 10. In certain embodiments m3 of formula (D) is an integer selected from the group consisting of 1, 2, 3, 4, and 5. In certain embodiments m3 of formula (D) is 1. In certain embodiments m3 of formula (D) is 2. In certain embodiments m3 of formula (D) is 3. In certain embodiments m3 of formula (D) is 4. In certain embodiments m4 of formula (D) is an integer selected from the group consisting of 2, 3, 4, 5, 6, 7, 8, 9 and 10. In certain embodiments m4 of formula (D) is an integer selected from the group consisting of 3, 4, 5, 6 and 7. In certain embodiments m4 of formula (D) is 3. In certain embodiments m4 of formula (D) is 4. In certain embodiments m4 of formula (D) is 5. In certain embodiments m4 of formula (D) is 6. In certain embodiments m4 of formula (D) is 7.

In certain embodiments a moiety —$X^{0E}$—SP—$X^{0F}$—CL-$X^{0F}$—SP—$X^{0E}$— has the structure of formula (D-i)

(D-i)

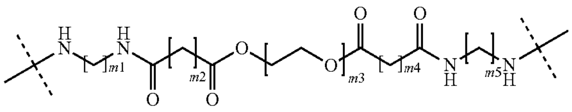

;

wherein dashed lines indicate attachment to the carbonyl of the hyaluronic acid; and m1, m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-i) is an integer selected from the group consisting of 2, 3, 4, 5, and 6. In certain embodiments m1 of formula (D-i) is 3. In certain embodiments m2 of formula (D-i) is an integer selected from the group consisting of 2, 3, 4, 5, 6, 7, 8, 9 and 10. In certain embodiments m2 of formula (D-i) is an integer selected from the group consisting of 3, 4, 5, 6 and 7. In certain embodiments m2 of formula (D-i) is 3. In certain embodiments m2 of formula (D-i) is 4. In certain embodiments m2 of formula (D-i) is 5. In certain embodiments m2 of formula (D-i) is 6. In certain embodiments m2 of formula (D-i) is 7. In certain embodiments m3 of formula (D-i) is an integer selected from the group consisting of 1, 2, 3, 4, 5, 6, 7, 8, 9 and 10. In certain embodiments m3 of formula (D-i) is an integer selected from the group consisting of 1, 2, 3, 4, and 5. In certain embodiments m3 of formula (D-i) is 1. In certain embodiments m3 of formula (D-i) is 2. In certain embodiments m3 of formula (D-i) is 3. In certain embodiments m3 of formula (D-i) is 4. In certain embodiments m4 of formula (D-i) is an integer selected from the group consisting of 2, 3, 4, 5, 6, 7, 8, 9 and 10. In certain embodiments m4 of formula (D-i) is an integer selected from the group consisting of 3, 4, 5, 6 and 7. In certain embodiments m4 of formula (D-i) is 3. In certain embodiments m4 of formula (D-i) is 4. In certain embodiments m4 of formula (D-i) is 5. In certain embodiments m4 of formula (D-i) is 6. In certain embodiments m4 of formula (D-i) is 7. In certain embodiments m5 of formula (D-i) is an integer selected from the group consisting of 2, 3, 4, 5 and 6. In certain embodiments m5 of formula (D-1) is 3.

In certain embodiments —CL- is of formula (D-ii)

(D-ii)

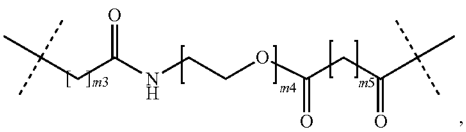

, wherein dashed lines indicate attachment to a moiety —$X^{0F}$;

m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-ii) is an integer selected from the group consisting of 1, 2, 3, 4 and 5. In certain embodiments m3 of formula (D-ii) is 2. In certain embodiments m4 of formula (D-ii) is an integer selected from the group consisting of 1, 2, 3, 4, 5, 6, 7, 8, 9 and 10. In certain embodiments m4 of formula (D-ii) is 1. In certain embodiments m4 of formula (D-ii) is 2. In certain embodiments m4 of formula (D-ii) is 3. In certain embodiments m4 of formula (D-ii) is 4. In certain embodiments m5 of formula (D-ii) is an integer selected from 2, 3, 4, 5, 6, 7, 8, 9 and 10. In certain embodiments m5 of formula (D-ii) is 3. In certain embodiments m5 of formula (D-ii) is 4. In certain embodiments m5 of formula (D-ii) is 5. In certain embodiments m5 of formula (D-ii) is 6. In certain embodiments m5 of formula (D-ii) is 7.

In certain embodiments a moiety —$X^{0E}$—SP—$X^{0F}$—CL-$X^{0F}$—SP—$X^{0E}$— has the structure of formula (D-iii)

(D-iii)

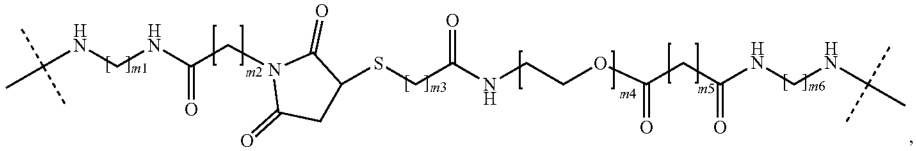

, wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-iii) is an integer selected from the group consisting of 2, 3, 4, 5 and 6. In certain embodiments m1 of formula (D-iii) is 3. In certain embodiments m2 is an integer selected from the group consisting of 1, 2, 3, 4 and 5. In certain embodiments m2 of formula (D-iii) is 2. In certain embodiments m3 of formula (D-iii) is an integer selected from the group consisting of 1, 2, 3, 4 and 5. In certain embodiments m3 of formula (D-iii) is 2. In certain embodiments m4 of formula (D-iii) is an integer selected from the group consisting of 1, 2, 3, 4, 5, 6, 7, 8, 9 and 10. In certain embodiments m4 of formula (D-iii) is 1. In certain embodiments m4 of formula (D-iii) is 2. In certain embodiments m4 of formula (D-iii) is 3. In certain embodiments m4 of formula (D-iii) is 4. In certain embodiments m5 of formula (D-iii) is an integer selected from 2, 3, 4, 5, 6, 7, 8, 9 and 10. In certain embodiments m5 of formula (D-iii) is 3. In certain embodiments m5 of formula (D-iii) is 4. In certain embodiments m5 of formula (D-iii) is 5. In certain embodiments m5 of formula (D-iii) is 6. In certain embodiments m5 of formula (D-iii) is 7. In certain embodiments m6 of formula (D-iii) is an integer selected from the group consisting of 2, 3, 4, 5 and 6. In certain embodiments m6 of formula (D-iiii) is 3.

In certain embodiments —CL- is of formula (D-iv):

(D-iv)

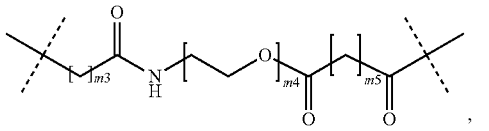

wherein dashed lines indicate attachment to a moiety —$X^{0F}$;

dashed lines indicate attachment to the carbonyl of the hyaluronic acid; and m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-iv) is an integer selected from the group consisting of 1, 2, 3, 4 and 5. In certain embodiments m3 of formula (D-iv) is 2. In certain embodiments m4 of formula (D-iv) is an integer selected from the group consisting of 1, 2, 3, 4, 5, 6, 7, 8, 9 and 10. In certain embodiments m4 of formula (D-iv) is 1. In certain embodiments m4 of formula (D-iv) is 2. In certain embodiments m4 of formula (D-iv) is 3. In certain embodiments m4 of formula (D-iv) is 4. In certain embodiments m5 of formula (D-iv) is an integer selected from 2, 3, 4, 5, 6, 7, 8, 9 and 10. In certain embodiments m5 of formula (D-iv) is 3. In certain embodiments m5 of formula (D-iv) is 4. In certain embodiments m5 of formula (D-iv) is 5. In certain embodiments m5 of formula (D-iv) is 6. In certain embodiments m5 of formula (D-iv) is 7.

In certain embodiments a moiety —$X^{0E}$—SP—$X^{0F}$—CL-$X^{0F}$—SP—$X^{0E}$— has the structure of formula (D-v)

(D-v)

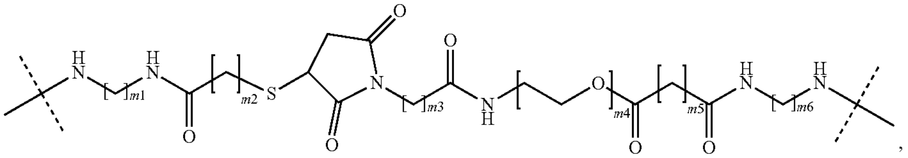

wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-v) is an integer selected from the group consisting of 2, 3, 4, 5 and 6. In certain embodiments m1 of formula (D-v) is 3. In certain embodiments m2 is an integer selected from the group consisting of 1, 2, 3, 4 and 5. In certain embodiments m2 of formula (D-v) is 2. In certain embodiments m3 of formula (D-v) is an integer selected from the group consisting of 1, 2, 3, 4 and 5. In certain embodiments m3 of formula (D-v) is 2. In certain embodiments m4 of formula (D-v) is an integer selected from the group consisting of 1, 2, 3, 4, 5, 6, 7, 8, 9 and 10. In certain embodiments m4 of formula (D-v) is 1. In certain embodiments m4 of formula (D-v) is 2. In certain embodiments m4 of formula (D-v) is 3. In certain embodiments m4 of formula (D-v) is 4. In certain embodiments m5 of formula (D-v) is an integer selected from 2, 3, 4, 5, 6, 7, 8, 9 and 10. In certain embodiments m5 of formula (D-v) is 3. In certain embodiments m5 of formula (D-v) is 4. In certain embodiments m5 of formula (D-v) is 5. In certain embodiments m5 of formula (D-v) is 6. In certain embodiments m5 of formula (D-v) is 7. In certain embodiments m6 of formula (D-v) is an integer selected from the group consisting of 2, 3, 4, 5 and 6. In certain embodiments m6 of formula (D-v) is 3.

In certain embodiments —CL- is of formula (D-vi)

(D-vi)

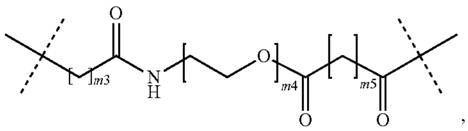

wherein dashed lines indicate attachment to a moiety —$X^{0F}$—;

m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-vi) is an integer selected from the group consisting of 1, 2, 3, 4 and 5. In certain embodiments m3 of formula (D-vi) is 1. In certain embodiments m3 of formula (D-vi) is 2. In certain embodiments m4 of formula (D-vi) is an integer selected from the group consisting of 1, 2, 3, 4, 5, 6, 7, 8, 9 and 10. In certain embodiments m4 of formula (D-vi) is 1. In certain embodiments m4 of formula (D-vi) is 2. In certain embodiments m4 of formula (D-vi) is 3. In certain embodiments m4 of formula (D-vi) is 4. In certain embodiments m5 of formula (D-vi) is an integer selected from 2, 3, 4, 5, 6, 7, 8, 9 and 10. In certain embodiments m5 of formula (D-vi) is 3. In certain embodiments m5 of formula (D-vi) is 4. In certain embodiments m5 of formula (D-vi) is 5. In certain embodiments m5 of formula (D-vi) is 6. In certain embodiments m5 of formula (D-vi) is 7.

In certain embodiments a moiety —$X^{0E}$—SP—$X^{0F}$—CL-$X^{0F}$—SP—$X^{0E}$— has the structure of formula (D-vii)

(D-vii)

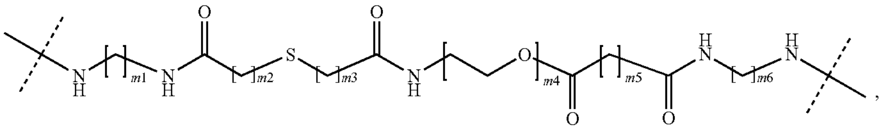

wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-vii) is an integer selected from the group consisting of 2, 3, 4, 5 and 6. In certain embodiments m1 of formula (D-vii) is 3. In certain embodiments m2 of formula (D-vii) is an integer selected from the group consisting of 1, 2, 3, 4 and 5. In certain embodiments m2 of formula (D-vii) is 1. In certain embodiments m2 of formula (D-vii) is 2. In certain embodiments m3 of formula (D-vii) is an integer selected from the group consisting of 1, 2, 3, 4 and 5. In certain embodiments m3 of formula (D-vii) is 1. In certain embodiments m3 of formula (D-vii) is 2. In certain embodiments m4 of formula (D-vii) is an integer selected from the group consisting of 1, 2, 3, 4, 5, 6, 7, 8, 9 and 10. In certain embodiments m4 of formula (D-vii) is 1. In certain embodiments m4 of formula (D-vii) is 2. In certain embodiments m4 of formula (D-vii) is 3. In certain embodiments m4 of formula (D-vii) is 4. In certain embodiments m5 of formula (D-vii) is an integer selected from 2, 3, 4, 5, 6, 7, 8, 9 and 10. In certain embodiments m5 of formula (D-vii) is 3. In certain embodiments m5 of formula (D-vii) is 4. In certain embodiments m5 of formula (D-vii) is 5. In certain embodiments m5 of formula (D-vii) is 6. In certain embodiments m5 of formula (D-vii) is 7. In certain embodiments m6 of formula (D-vii) is an integer selected from the group consisting of 2, 3, 4, 5 and 6. In certain embodiments m6 of formula (D-vii) is 3.

In certain embodiments —CL- is of formula (D-viii)

(D-viii)

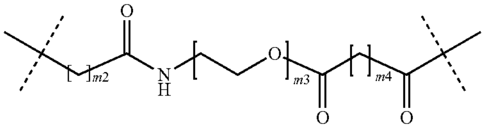

wherein dashed lines indicate attachment to a moiety $—X^{0F}$;

m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-viii) is an integer selected from the group consisting of 2, 3, 4, 5 and 6. In certain embodiments m1 of formula (D-viii) is 3. In certain embodiments m2 is an integer selected from the group consisting of 1, 2, 3, 4 and 5. In certain embodiments m2 of formula (D-viii) is 2. In certain embodiments m2 of formula (D-viii) is 5. In certain embodiments m3 of formula (D-viii) is an integer selected from the group consisting of 1, 2, 3, 4, 5, 6, 7, 8, 9 and 10. In certain embodiments m3 of formula (D-viii) is an integer selected from the group consisting of 1, 2, 3 and 4. In certain embodiments m3 of formula (D-viii) is 1. In certain embodiments m3 of formula (D-viii) is 2. In certain embodiments m3 of formula (D-viii) is 3. In certain embodiments m3 of formula (D-viii) is 4. In certain embodiments m4 of formula (D-viii) is an integer selected from the group consisting of 2, 3, 4, 5, 6, 7, 8, 9 and 10. In certain embodiments m4 of formula (D-viii) is an integer selected from the group consisting of 3, 4, 5, 6 and 7. In certain embodiments m4 of formula (D-viii) is 3. In certain embodiments m4 of formula (D-viii) is 4. In certain embodiments m4 of formula (D-viii) is 5. In certain embodiments m4 of formula (D-viii) is 6. In certain embodiments m4 of formula (D-viii) is 7. In certain embodiments m5 of formula (D-viii) is an integer selected from 2, 3, 4, 5 and 6. In certain embodiments m5 of formula (D-viii) is 3.

In certain embodiments a moiety $—X^{0E}—SP—X^{0F}—CL-X^{0F}—SP—X^{0E}—$ has the structure of formula (D-ix)

(D-ix)

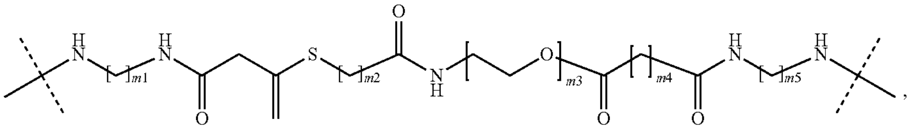

wherein dashed lines indicate attachment to the carbonyl of the hyaluronic acid; and m1, m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-ix) is an integer selected from the group consisting of 2, 3, 4, 5 and 6. In certain embodiments m1 of formula (D-ix) is 3. In certain embodiments m2 is an integer selected from the group consisting of 1, 2, 3, 4 and 5. In certain embodiments m2 of formula (D-ix) is 2. In certain embodiments m2 of formula (D-ix) is 5. In certain embodiments m3 of formula (D-ix) is an integer selected from the group consisting of 1, 2, 3, 4, 5, 6, 7, 8, 9 and 10. In certain embodiments m3 of formula (D-ix) is an integer selected from the group consisting of 1, 2, 3 and 4. In certain embodiments m3 of formula (D-ix) is 1. In certain embodiments m3 of formula (D-ix) is 2. In certain embodiments m3 of formula (D-ix) is 3. In certain embodiments m3 of formula (D-ix) is 4. In certain embodiments m4 of formula (D-ix) is an integer selected from the group consisting of 2, 3, 4, 5, 6, 7, 8, 9 and 10. In certain embodiments m4 of formula (D-ix) is an integer selected from the group consisting of 3, 4, 5, 6 and 7. In certain embodiments m4 of formula (D-ix) is 3. In certain embodiments m4 of formula (D-ix) is 4. In certain embodiments m4 of formula (D-ix) is 5. In certain embodiments m4 of formula (D-ix) is 6. In certain embodiments m4 of formula (D-ix) is 7. In certain embodiments m5 of formula (D-ix) is an integer selected from 2, 3, 4, 5 and 6. In certain embodiments m5 of formula (D-ix) is 3.

In certain embodiments —CL- is of formula (D-x)

(D-x)

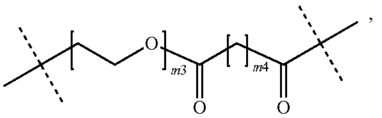

dashed lines indicate attachment to a moiety —$X^{0F}$—;

m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-x) is an integer selected from the group consisting of 1, 2, 3, 4, 5, 6, 7, 8, 9 and 10. In certain embodiments m3 of formula (D-x) is an integer selected from the group consisting of 1, 2, 3 and 4. In certain embodiments m3 of formula (D-x) is 1. In certain embodiments m3 of formula (D-x) is 2. In certain embodiments m3 of formula (D-x) is 3. In certain embodiments m3 of formula (D-x) is 4. In certain embodiments m4 of formula (D-x) is an integer selected from the group consisting of 2, 3, 4, 5, 6, 7, 8, 9 and 10. In certain embodiments m4 of formula (D-x) is an integer selected from the group consisting of 3, 4, 5, 6 and 7. In certain embodiments m4 of formula (D-x) is 3. In certain embodiments m4 of formula (D-x) is 4. In certain embodiments m4 of formula (D-x) is 5. In certain embodiments m4 of formula (D-x) is 6. In certain embodiments m4 of formula (D-x) is 7.

In certain embodiments a moiety —$X^{0E}$—SP—$X^{0F}$—CL-$X^{0F}$—SP—$X^{0E}$— has the structure of formula (D-xi)

(D-xi) is 5. In certain embodiments m3 of formula (D-xi) is an integer selected from the group consisting of 1, 2, 3, 4, 5, 6, 7, 8, 9 and 10. In certain embodiments m3 of formula (D-xi) is an integer selected from the group consisting of 1, 2, 3 and 4. In certain embodiments m3 of formula (D-xi) is 1. In certain embodiments m3 of formula (D-xi) is 2. In certain embodiments m3 of formula (D-xi) is 3. In certain embodiments m3 of formula (D-xi) is 4. In certain embodiments m4 of formula (D-xi) is an integer selected from the group consisting of 2, 3, 4, 5, 6, 7, 8, 9 and 10. In certain embodiments m4 of formula (D-xi) is an integer selected from the group consisting of 3, 4, 5, 6 and 7. In certain embodiments m4 of formula (D-xi) is 3. In certain embodiments m4 of formula (D-xi) is 4. In certain embodiments m4 of formula (D-xi) is 5. In certain embodiments m4 of formula (D-xi) is 6. In certain embodiments m4 of formula (D-xi) is 7. In certain embodiments m5 of formula (D-xi) is an integer selected from 2, 3, 4, 5 and 6. In certain embodiments m5 of formula (D-xi) is 3.

In certain embodiments —CL- is of formula (D-xii)

(D-xii)

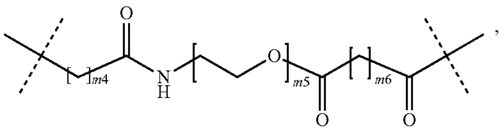

wherein dashed lines indicate attachment to a moiety —$X^{0F}$—;

m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m4 of formula (D-xii) is an integer selected from the group consisting of 1, 2, 3, 4 and 5. In certain embodiments m4 of formula (D-xii) is 1. In certain embodiments m4 of formula (D-xii) is 5. In certain embodiments m5 of formula (D-xii) is an integer selected from 1, 2, 3, 4, 5, 6, 7, 8, 9 and 10. In certain embodiments m5 of formula (D-xii) is an integer selected from the group consisting of 1, 2, 3 and 4. In certain embodiments m5 of formula (D-xii) is 1. In certain embodiments m5 of formula (D-xi)

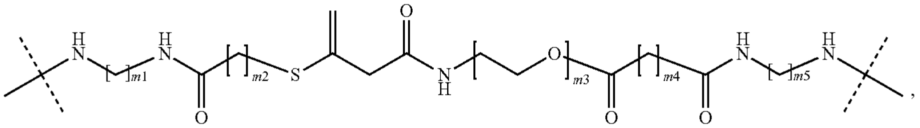

wherein dashed lines indicate attachment to the carbonyl of the hyaluronic acid; and each m1, m2, m3, m4 and m5 is independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xi) is an integer selected from the group consisting of 2, 3, 4, 5 and 6. In certain embodiments m1 of formula (D-xi) is 3. In certain embodiments m2 is an integer selected from the group consisting of 1, 2, 3, 4 and 5. In certain embodiments m2 of formula (D-xi) is 2. In certain embodiments m2 of formula (D-xii) is 2. In certain embodiments m5 of formula (D-xii) is 3. In certain embodiments m5 of formula (D-xii) is 4. In certain embodiments m6 of formula (D-xii) is an integer selected from the group consisting of 2, 3, 4, 5, 6, 7, 8, 9 and 10. In certain embodiments m6 of formula (D-xii) is an integer selected from the group consisting of 3, 4, 5, 6 and 7. In certain embodiments m6 of formula (D-xii) is 3. In certain embodiments m6 of formula (D-xii) is 4. In certain embodiments m6 of formula (D-xii) is 5. In certain embodiments m6 of formula (D-xii) is 6. In certain embodiments m6 of formula (D-xii) is 7.

In certain embodiments a moiety —$X^{0E}$—SP—$X^{0F}$—CL-$X^{0F}$—SP—$X^{0E}$— has the structure of formula (D-xiii)

(D-xiii)

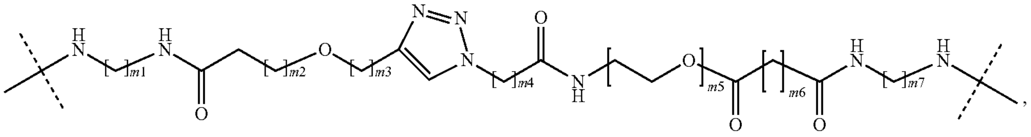

wherein dashed lines indicate attachment to the carbonyl of the hyaluronic acid; and m1, m2, m3, m4, m5, m6 and m7 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xiii) is an integer selected from the group consisting of 2, 3, 4, 5 and 6. In certain embodiments m1 of formula (D-xiii) is 3. In certain embodiments m2 of formula (D-xiii) is an integer selected from the group consisting of 1, 2, 3, 4 and 5. In certain embodiments m2 of formula (D-xiii) is 1. In certain embodiments m3 of formula (D-xiii) is an integer selected from the group consisting of 1, 2, 3, 4 and 5. In certain embodiments m3 of formula (D-xiii) is 1. In certain embodiments m4 of formula (D-xiii) is an integer selected from the group consisting of 1, 2, 3, 4 and 5. In certain embodiments m4 of formula (D-xiii) is 1. In certain embodiments m4 of formula (D-xiii) is 5. In certain embodiments m5 of formula (D-xiii) is an integer selected from 1, 2, 3, 4, 5, 6, 7, 8, 9 and 10. In certain embodiments m5 of formula (D-xiii) is an integer selected from the group consisting of 1, 2, 3 and 4. In certain embodiments m5 of formula (D-xiii) is 1. In certain embodiments m5 of formula (D-xiii) is 2. In certain embodiments m5 of formula (D-xiii) is 3. In certain embodiments m5 of formula (D-xiii) is 4. In certain embodiments m6 of formula (D-xiii) is an integer selected from the group consisting of 2, 3, 4, 5, 6, 7, 8, 9 and 10. In certain embodiments m6 of formula (D-xiii) is an integer selected from the group consisting of 3, 4, 5, 6 and 7. In certain embodiments m6 of formula (D-xiii) is 3. In certain embodiments m6 of formula (D-xiii) is 4. In certain embodiments m6 of formula (D-xiii) is 5. In certain embodiments m6 of formula (D-xiii) is 6. In certain embodiments m6 of formula (D-xiii) is 7. In certain embodiments m7 of formula (D-xiii) is an integer selected from the group consisting of 2, 3, 4, 5 and 6. In certain embodiments m7 of formula (D-xiii) is 3. In certain embodiments m7 of formula (D-xiii) is 4.

In certain embodiments —CL- is of formula (D-xiv)

(D-xiv)

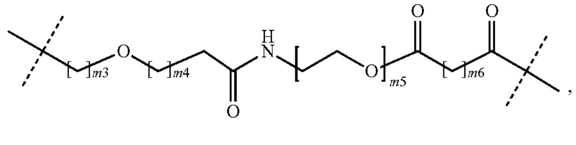

wherein dashed lines indicate attachment to a moiety $—X^{0F}—$;

m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-xiv) is an integer selected from the group consisting of 1, 2, 3, 4 and 5. In certain embodiments m3 is 1. In certain embodiments m3 of formula (D-xiv) is 5. In certain embodiments m4 of formula (D-xiv) is an integer selected from the group consisting of 1, 2, 3, 4 and 5. In certain embodiments m4 of formula (D-xiv) is 1. In certain embodiments m5 is an integer selected from the group consisting of 1, 2, 3, 4, 5, 6, 7, 8, 9 and 10. In certain embodiments m5 of formula (D-xiv) is an integer selected from the group consisting of 1, 2, 3 and 4. In certain embodiments m5 of formula (D-xiv) is 1. In certain embodiments m5 of formula (D-xiv) is 2. In certain embodiments m5 of formula (D-xiv) is 3. In certain embodiments m5 of formula (D-xiv) is 4. In certain embodiments m6 of formula (D-xiv) is an integer selected from the group consisting of 2, 3, 4, 5, 6, 7, 8, 9 and 10. In certain embodiments m6 of formula (D-xiv) is 3. In certain embodiments m6 of formula (D-xiv) is 4. In certain embodiments m6 of formula (D-xiv) is 5. In certain embodiments m6 of formula (D-xiv) is 6. In certain embodiments m6 of formula (D-xiv) is 7.

In certain embodiments a moiety $—X^{0E}—SP—X^{0F}—CL-X^{0F}—SP—X^{0E}—$ has the structure of formula (D-xv)

(D-xv)

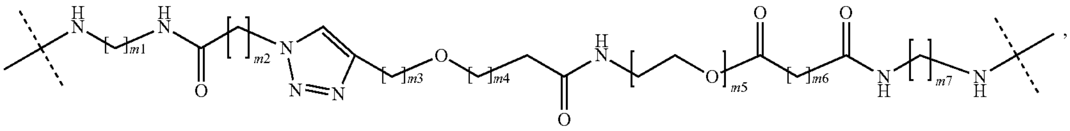

wherein dashed lines indicate attachment to the carbonyl of the hyaluronic acid; and m1, m2, m3, m4, m5, m6 and m7 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xv) is an integer selected from the group consisting of 2, 3, 4, 5 and 6. In certain embodiments m1 of formula (D-xv) is 3. In certain embodiments of m2 of formula (D-xv) is an integer selected from the group consisting of 1, 2, 3, 4 and 5. In certain embodiments m2 of formula (D-xv) is 1. In certain embodiments m3 of formula (D-xv) is an integer selected from the group consisting of 1, 2, 3, 4 and 5. In certain embodiments m3 is 1. In certain embodiments m3 of formula (D-xv) is 5. In certain embodiments m4 of formula (D-xv) is an integer selected from the group consisting of 1, 2, 3, 4 and 5. In certain embodiments m4 of formula (D-xv) is 1. In certain embodiments m5 is an integer selected from the group consisting of 1, 2, 3, 4, 5, 6, 7, 8, 9 and 10. In certain embodiments m5 of formula (D-xv) is an integer selected from the group consisting of 1, 2, 3 and 4. In certain embodiments m5 of formula (D-xv) is 1. In certain embodiments m5 of formula (D-xv) is 2. In certain embodiments m5 of formula (D-xv) is 3. In certain embodiments m5 of formula (D-xv) is 4. In certain embodiments m6 of formula (D-xv) is an integer selected from the group consisting of 2, 3, 4, 5, 6, 7, 8, 9 and 10. In certain embodiments m6 of formula (D-xv) is 3. In certain embodiments m6 of formula (D-xv) is 4. In certain embodiments m6 of formula (D-xv) is 5. In certain embodiments m6 of formula (D-xv) is 6. In certain embodiments m6 of formula (D-xv) is 7. In certain embodiments m7 of formula (D-xv) is an integer selected from the group consisting of 2, 3, 4, 5 and 6. In certain embodiments m7 of formula (D-xv) is 4.

In certain embodiments —CL- is of formula (D-xvi)

(D-xvi)

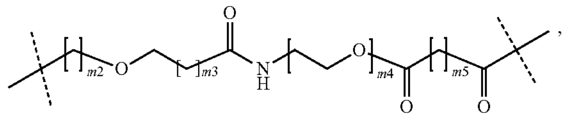

wherein dashed lines indicate attachment to a moiety —$X^{0F}$—;

m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments of m2 of formula (D-xvi) is an integer selected from the group consisting of 1, 2, 3, 4 and 5. In certain embodiments m2 of formula (D-xvi) is 1. In certain embodiments m3 of formula (D-xvi) is an integer selected from the group consisting of 1, 2, 3, 4 and 5. In certain embodiments m3 is 1. In certain embodiments m4 of formula (D-xvi) is an integer selected from the group consisting of 1, 2, 3, 4, 5, 6, 7, 8, 9 and 10. In certain embodiments m4 of formula (D-xvi) is an integer selected from the group consisting of 1, 2, 3 and 4. In certain embodiments m4 of formula (D-xvi) is 1. In certain embodiments m4 of formula (D-xvi) is 2. In certain embodiments m4 of formula (D-xvi) is 3. In certain embodiments m4 of formula (D-xvi) is 4. In certain embodiments m5 is an integer selected from the group consisting of 2, 3, 4, 5, 6, 7, 8, 9 and 10. In certain embodiments m5 of formula (D-xvi) is an integer selected from the group consisting of 3, 4, 5, 6, and 7. In certain embodiments m5 of formula (D-xvi) is 3. In certain embodiments m5 of formula (D-xvi) is 4. In certain embodiments m5 of formula (D-xvi) is 5. In certain embodiments m5 of formula (D-xvi) is 6. In certain embodiments m5 of formula (D-xvi) is 7.

In certain embodiments a moiety —$X^{0E}$—SP—$X^{0F}$—CL-$X^{0F}$—SP—$X^{0E}$— has the structure of formula (D-xvii)

wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xvii) is an integer selected from the group consisting of 2, 3, 4, 5 and 6. In certain embodiments m1 of formula (D-xvii) is 3. In certain embodiments m1 of formula (D-xvii) is 4. In certain embodiments of m2 of formula (D-xvii) is an integer selected from the group consisting of 1, 2, 3, 4 and 5. In certain embodiments m2 of formula (D-xvii) is 1. In certain embodiments m3 of formula (D-xvii) is an integer selected from the group consisting of 1, 2, 3, 4 and 5. In certain embodiments m3 is 1. In certain embodiments m4 of formula (D-xvii) is an integer selected from the group consisting of 1, 2, 3, 4, 5, 6, 7, 8, 9 and 10. In certain embodiments m4 of formula (D-xvii) is an integer selected from the group consisting of 1, 2, 3 and 4. In certain embodiments m4 of formula (D-xvii) is 1. In certain embodiments m4 of formula (D-xvii) is 2. In certain embodiments m4 of formula (D-xvii) is 3. In certain embodiments m4 of formula (D-xvii) is 4. In certain embodiments m5 of formula (D-xvii) is an integer selected from the group consisting of 2, 3, 4, 5, 6, 7, 8, 9 and 10. In certain embodiments m5 of formula (D-xvii) is an integer selected from the group consisting of 3, 4, 5, 6, and 7. In certain embodiments m5 of formula (D-xvii) is 3. In certain embodiments m5 of formula (D-xvii) is 4. In certain embodiments m5 of formula (D-xvii) is 5. In certain embodiments m5 of formula (D-xvii) is 6. In certain embodiments m5 of formula (D-xvii) is 7. In certain embodiments m6 of formula (D-xvii) is an integer selected from the group consisting of 2, 3, 4, 5 and 6. In certain embodiments m6 of formula (D-xvii) is 3.

In certain embodiments —CL- is of formula (D-xviii)

(D-xviii)

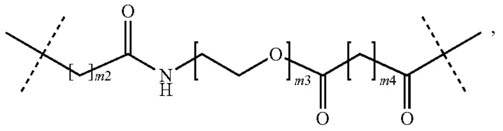

wherein dashed lines indicate attachment to a moiety —$X^{0F}$—;

m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 of formula (D-xviii) is an integer selected from the group consisting of 1, 2, 3, 4 and 5. In certain embodiments m2 of formula (D-xviii) is 1. In (D-xvii)

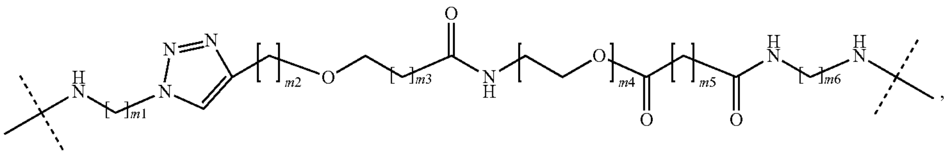

certain embodiments m3 of formula (D-xviii) is an integer selected from the group consisting of 1, 2, 3, 4, 5, 6, 7, 8, 9 and 10. In certain embodiments m3 of formula (D-xviii) is an integer selected from the group consisting of 1, 2, 3 and 4. In certain embodiments m3 of formula (D-xviii) is 1. In certain embodiments m3 of formula (D-xviii) is 2. In certain embodiments m3 of formula (D-xix) is 3. In certain embodiments m3 of formula (D-xviii) is 4. In certain embodiments m4 of formula (D-xviii) is an integer selected from the group consisting of 2, 3, 4, 5, 6, 7, 8, 9 and 10. In certain embodiments m4 of formula (D-xviii) is an integer selected from the group consisting of 3, 4, 5, 6 and 7. In certain embodiments m4 of formula (D-xviii) is 3. In certain embodiments m4 of formula (D-xviii) is 4. In certain embodiments m4 of formula (D-xviii) is 5. In certain embodiments m4 of formula (D-xviii) is 6.

In certain embodiments a moiety —$X^{0E}$—SP—$X^{0F}$—CL-$X^{0F}$—SP—$X^{0E}$— has the structure of formula (D-xix)

(D-xix)

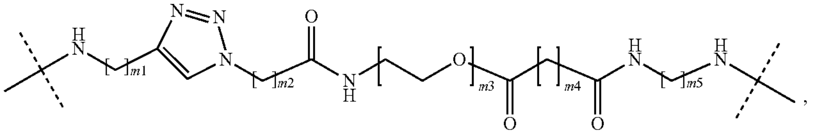

wherein dashed lines indicate attachment to the carbonyl of the hyaluronic acid; and m1, m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xix) is an integer selected from the group consisting of 1, 2, 3, 4, 5, 6, 7 and 8. In certain embodiments m1 of formula (D-xix) is 1. In certain embodiments m2 of formula (D-xix) is an integer selected from the group consisting of 1, 2, 3, 4 and 5. In certain embodiments m2 of formula (D-xix) is 1. In certain embodiments m3 of formula (D-xix) is an integer selected from the group consisting of 1, 2, 3, 4, 5, 6, 7, 8, 9 and 10. In certain embodiments m3 of formula (D-xix) is an integer selected from the group consisting of 1, 2, 3 and 4. In certain embodiments m3 of formula (D-xix) is 1. In certain embodiments m3 of formula (D-xix) is 2. In certain embodiments m3 of formula (D-xix) is 3. In certain embodiments m3 of formula (D-xix) is 4. In certain embodiments m4 of formula (D-xix) is an integer selected from the group consisting of 2, 3, 4, 5, 6, 7, 8, 9 and 10. In certain embodiments m4 of formula (D-xix) is an integer selected from the group consisting of 3, 4, 5, 6 and 7. In certain embodiments m4 of formula (D-xix) is 3. In certain embodiments m4 of formula (D-xix) is 4. In certain embodiments m4 of formula (D-xix) is 5. In certain embodiments m4 of formula (D-xix) is 6. In certain embodiments m4 of formula (D-xix) is 7. In certain embodiments m5 of formula (D-xix) is an integer selected from the group consisting of 2, 3, 4, 5 and 6. In certain embodiments m5 of formula (D-xix) is 3.

In certain embodiments —CL- is of formula (D-xx)

(D-xx)

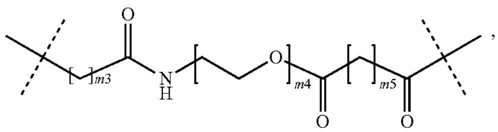

wherein dashed lines indicate attachment to a moiety —$X^{0F}$—;

m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-xx) is an integer selected from the group consisting of the group 2, 3, 4, 5, 6, 7, 8, 9 and 10. In certain embodiments m3 of formula (D-xx) is an integer selected from the group consisting of 3, 4, 5, 6 and 7. In certain embodiments m3 of formula (D-xx) is 3. In certain embodiments m3 is 4. In certain embodiments m3 of formula (D-xx) is 5. In certain embodiments m3 of formula (D-xx) is 6. In certain embodiments m3 of formula (D-xxi is 7. In certain embodiments m4 of formula (D-xx) is an integer selected from the group consisting of 1, 2, 3, 4, 5, 6, 7, 8, 9 and 10. In certain embodiments m4 of formula (D-xx) is an integer selected from the group consisting of 1, 2, 3 and 4. In certain embodiments m4 of formula (D-xx) is 1. In certain embodiments m4 of formula (D-xx) is 2. In certain embodiments m4 of formula (D-xx) is 3. In certain embodiments m4 of formula (D-xx) is 4. In certain embodiments m5 of formula (D-xx) is an integer selected from the group consisting of 2, 3, 4, 5, 6, 7, 8, 9 and 10. In certain embodiments m5 of formula (D-xx) is an integer selected from the group consisting of 3, 4, 5, 6 and 7. In certain embodiments m5 of formula (D-xx) is 3. In certain embodiments m5 of formula (D-xx) is 4. In certain embodiments m5 of formula (D-xx) is 5. In certain embodiments m5 of formula (D-xx) is 6. In certain embodiments m5 of formula (D-xx) is 7.

In certain embodiments a moiety —$X^{0E}$—SP—$X^{0F}$—CL-$X^{0F}$—SP—$X^{0E}$— has the structure of formula (D-xxi) or (D-xxi')

(D-xxi)

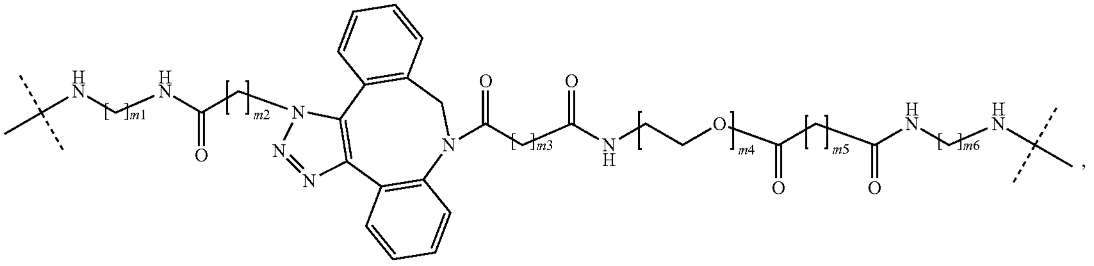

(D-xxi')

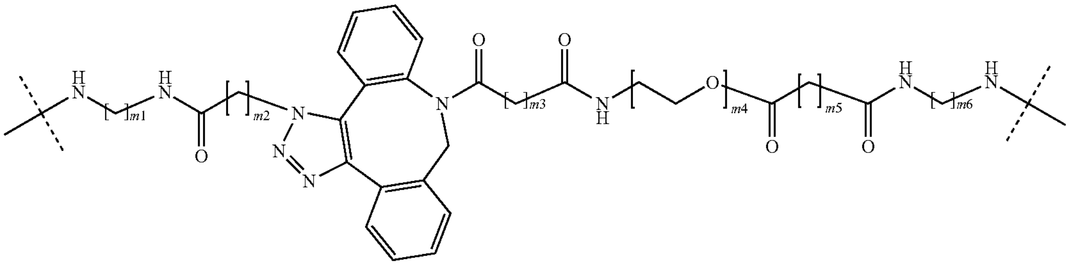

wherein dashed lines indicate attachment to the carbonyl of the hyaluronic acid; and each m1, m2, m3, m4, m5 and m6 is independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxi) or (D-xxi') is an integer selected from the group consisting of 2, 3, 4, 5 and 6. In certain embodiments m1 of formula (D-xxi) or (D-xxi') is 3. In certain embodiments m1 of formula (D-xxi) or (D-xxi') is 4. In certain embodiments m2 of formula (D-xxi) or (D-xxi') is an integer selected from the group consisting of 1, 2, 3, 4 and 5. In certain embodiments m2 of formula (D-xxi) or (D-xxi') is 1. In certain embodiments m3 of formula (D-xxi) or (D-xxi') is an integer selected from the group consisting of the group 2, 3, 4, 5, 6, 7, 8, 9 and 10. In certain embodiments m3 of formula (D-xxi) or (D-xxi') is an integer selected from the group consisting of 3, 4, 5, 6 and 7. In certain embodiments m3 of formula (D-xxi) or (D-xxi') is 3. In certain embodiments m3 is 4. In certain embodiments m3 of formula (D-xxi) or (D-xxi') is 5. In certain embodiments m3 of formula (D-xxi) or (D-xxi') is 6. In certain embodiments m3 of formula (D-xxi) or (D-xxi') is 7. In certain embodiments m4 of formula (D-xxi) or (D-xxi') is an integer selected from the group consisting of 1, 2, 3, 4, 5 6, 7, 8, 9 and 10. In certain embodiments m4 of formula (D-xxi) or (D-xxi') is an integer selected from the group consisting of 1, 2, 3 and 4. In certain embodiments m4 of formula (D-xxi) or (D-xxi') is 1. In certain embodiments m4 of formula (D-xxi) or (D-xxi') is 2. In certain embodiments m4 of formula (D-xxi) or (D-xxi') is 3. In certain embodiments m4 of formula (D-xxi) or (D-xxi') is 4. In certain embodiments m5 of formula (D-xxi) or (D-xxi') is an integer selected from the group consisting of 2, 3, 4, 5, 6, 7, 8, 9 and 10. In certain embodiments m5 of formula (D-xxi) or (D-xxi') is an integer selected from the group consisting of 3, 4, 5, 6 and 7. In certain embodiments m5 of formula (D-xxi) or (D-xxi') is 3. In certain embodiments m5 of formula (D-xxi) or (D-xxi') is 4. In certain embodiments m5 of formula (D-xxi) or (D-xxi') is 5. In certain embodiments m5 of formula (D-xxi) or (D-xxi') is 6. In certain embodiments m5 of formula (D-xxi) or (D-xxi') is 7. In certain embodiments m6 of formula (D-xxi) or (D-xxi') is an integer selected from the group consisting of 2, 3, 4, 5 and 6. In certain embodiments m6 of formula (D-xxi) or (D-xxi') is 3. In certain embodiments m6 of formula (D-xxi) or (D-xxi') is 4.

In certain embodiments —CL- is of formula (D-xxii)

(D-xxii)

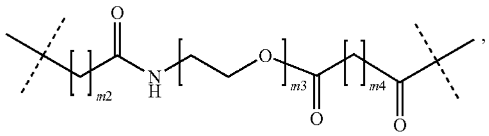

wherein dashed lines indicate attachment to a moiety $—X^{0F}$;

m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 (D-xxiii) or (D-xxiii') is an integer selected from the group consisting of 2, 3, 4, 5, 6, 7, 8, 9, and 10. In certain embodiments m2 (D-xxiii) or (D-xxiii') is an integer selected from the group consisting of 3, 4, 5, 6 and 7. In certain embodiments m2 (D-xxiii) or (D-xxiii') is 3. In certain embodiments m2 (D-xxiii) or (D-xxiii') is 4. In certain embodiments m2 (D-xxiii) or (D-xxiii') is 5. In certain embodiments m2 (D-xxiii) or (D-xxiii') is 6. In certain embodiments m2 (D-xxiii) or (D-xxiii') is 7. In certain embodiments m3 (D-xxiii) or (D-xxiii') is an integer selected from the group consisting of 1, 2, 3, 4, 5, 6, 7, 8, 9 and 10. In certain embodiments m3 (D-xxiii) or (D-xxiii') is is an integer selected from the group consisting of 1, 2, 3 and 4. In certain embodiments m3 (D-xxiii) or (D-xxiii') is 1. In certain embodiments m3 (D-xxiii) or (D-xxiii') is 2. In certain embodiments m3 (D-xxiii) or (D-xxiii') is 3. In certain embodiments m3 (D-xxiii) or (D-xxiii') is 4. In certain embodiments m4 (D-xxiii) or (D-xxiii') is an integer selected from the group consisting of 2, 3, 4, 5, 6, 7, 8, 9 and 10. In certain embodiments m4 (D-xxiii) or (D-xxiii') is an integer selected from the group consisting of 3, 4, 5, 6 and 7. In certain embodiments m4 (D-xxiii) or (D-xxiii') is 3. In certain embodiments m4 is 4. In certain embodiments m4 (D-xxiii) or (D-xxiii') is 5. In certain embodiments m4 (D-xxiii) or (D-xxiii') is 6. In certain embodiments m4 (D-xxiii) or (D-xxiii') is 7.

In certain embodiments a moiety —$X^{0E}$—SP—$X^{0F}$—CL-$X^{0F}$—SP—$X^{0E}$— has the structure of formula (D-xxiii) or (D-xxiii')

certain embodiments m4 (D-xxiii) or (D-xxiii') is an integer selected from the group consisting of 3, 4, 5, 6 and 7. In certain embodiments m4 (D-xxiii) or (D-xxiii') is 3. In certain embodiments m4 is 4. In certain embodiments m4 (D-xxiii) or (D-xxiii') is 5. In certain embodiments m4 (D-xxiii) or (D-xxiii') is 6. In certain embodiments m4 (D-xxiii) or (D-xxiii') is 7. In certain embodiments m5 (D-xxiii) or (D-xxiii') is an integer selected from the group consisting of 2, 3, 4, 5 and 6. In certain embodiments m5 (D-xxiii) or (D-xxiii') is 3. In certain embodiments m5 (D-xxiii) or (D-xxiii') is 4.

(D-xxiii)

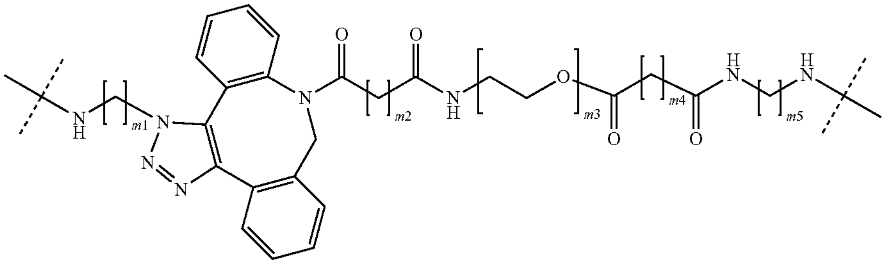

, (D-xxiii')

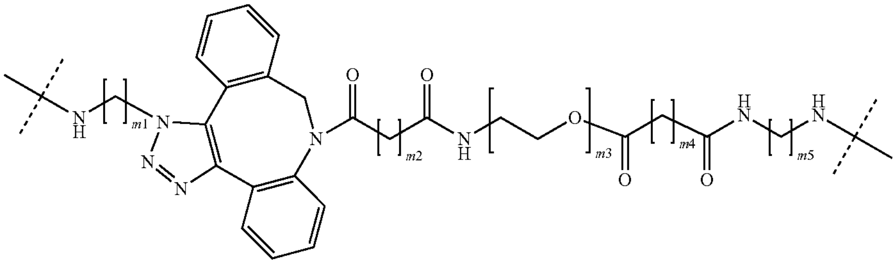

, wherein dashed lines indicate attachment to the carbonyl of the hyaluronic acid; and m1, m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxiii) or (D-xxiii') is an integer selected from the group consisting of 1, 2, 3, 4 and 5. In certain embodiments m1 (D-xxiii) or (D-xxiii') is 1. In certain embodiments m2 (D-xxiii) or (D-xxiii') is an integer selected from the group consisting of 2, 3, 4, 5, 6, 7, 8, 9, and 10. In certain embodiments m2 (D-xxiii) or (D-xxiii') is an integer selected from the group consisting of 3, 4, 5, 6 and 7. In certain embodiments m2 (D-xxiii) or (D-xxiii') is 3. In certain embodiments m2 (D-xxiii) or (D-xxiii') is 4. In certain embodiments m2 (D-xxiii) or (D-xxiii') is 5. In certain embodiments m2 (D-xxiii) or (D-xxiii') is 6. In certain embodiments m2 (D-xxiii) or (D-xxiii') is 7. In certain embodiments m3 (D-xxiii) or (D-xxiii') is an integer selected from the group consisting of 1, 2, 3, 4, 5, 6, 7, 8, 9 and 10. In certain embodiments m3 (D-xxiii) or (D-xxiii') is is an integer selected from the group consisting of 1, 2, 3 and 4. In certain embodiments m3 (D-xxiii) or (D-xxiii') is 1. In certain embodiments m3 (D-xxiii) or (D-xxiii') is 2. In certain embodiments m3 (D-xxiii) or (D-xxiii') is 3. In certain embodiments m3 (D-xxiii) or (D-xxiii') is 4. In certain embodiments m4 (D-xxiii) or (D-xxiii') is an integer selected from the group consisting of 2, 3, 4, 5, 6, 7, 8, 9 and 10. In In certain embodiments —CL- is of formula (D-xxiv)

(D-xxiv)

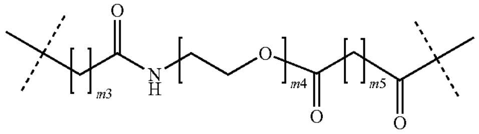

, wherein dashed lines indicate attachment to a moiety —$X^{0F}$—;

m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-xxiv) is an integer selected from the group consisting of 1, 2, 3, 4 and 5. In certain embodiments m3 of formula (D-xxiv) is 1. In certain embodiments m4 of formula (D-xxiv) is an integer selected from the group consisting of 1, 2, 3, 4, 5, 6, 7, 8, 9 and 10. In certain embodiments m4 of formula (D-xxiv) is an integer selected from the group consisting of 1, 2, 3 and 4. In certain embodiments m4 of formula (D-xxiv) is 1. In certain embodiments m4 of formula (D-xxiv) is 2. In certain embodiments m4 of formula (D-xxiv) is 3. In certain embodiments m4 of formula (D-xxiv) is 4. In certain embodiments m5 of formula (D-xxiv) is an integer selected from the group consisting of 2, 3, 4, 5, 6, 7, 8, 9 and 10. In certain embodiments m5 of formula (D-xxiv) is an integer selected from the group consisting of 3, 4, 5, 6 and 7. In certain embodiments m5 of formula (D-xxiv) is 3. In certain embodiments m5 of formula (D-xxiv) is 4. In certain embodiments m5 of formula (D-xxiv) is 5. In certain embodiments m5 of formula (D-xxiv) is 6. In certain embodiments m5 of formula (D-xxiv) is 7.

In certain embodiments a moiety $—X^{0E}—SP—X^{0F}—CL-X^{0F}—SP—X^{0E}—$ has the structure of formula (D-xxv) or (D-xxv')

(D-xxv)

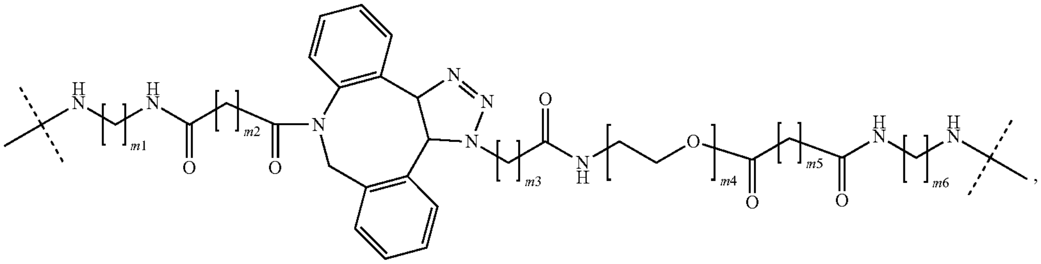

(D-xxvi)

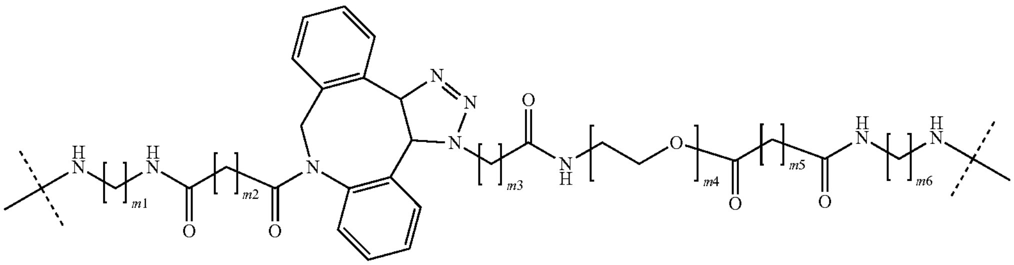

wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxv) or (D-xxv') is an integer selected from the group consisting of 2, 3, 4, 5 and 6. In certain embodiments m1 of formula (D-xxv) or (D-xxv') is 3. In certain embodiments m1 of formula (D-xxv) or (D-xxv') is 4. In certain embodiments m2 of formula (D-xxv) or (D-xxv') is an integer selected from the group consisting of 2, 3, 4, 5, 6, 7, 8, 9, and 10. In certain embodiments m2 of formula (D-xxv) or (D-xxv') is an integer selected from the group consisting of 3, 4, 5, 6 and 7. In certain embodiments m2 of formula (D-xxv) or (D-xxv') is 3. In certain embodiments m2 of formula (D-xxv) or (D-xxv') is 4. In certain embodiments m2 of formula (D-xxv) or (D-xxv') is 5. In certain embodiments m2 of formula (D-xxv) or (D-xxv') is 6. In certain embodiments m2 of formula (D-xxv) or (D-xxv') is 7. In certain embodiments m3 of formula (D-xxv) or (D-xxv') is an integer selected from the group consisting of 1, 2, 3, 4 and 5. In certain embodiments m3 of formula (D-xxv) or (D-xxv') is 1. In certain embodiments m4 of formula (D-xxv) or (D-xxv') is an integer selected from the group consisting of 1, 2, 3, 4, 5, 6, 7, 8, 9 and 10. In certain embodiments m4 of formula (D-xxv) or (D-xxv') is an integer selected from the group consisting of 1, 2, 3 and 4. In certain embodiments m4 of formula (D-xxv) or (D-xxv') is 1. In certain embodiments m4 of formula (D-xxv) or (D-xxv') is 2. In certain embodiments m4 of formula (D-xxv) or (D-xxv') is 3. In certain embodiments m4 of formula (D-xxv) or (D-xxv') is 4. In certain embodiments m5 of formula (D-xxv) or (D-xxv') is an integer selected from the group consisting of 2, 3, 4, 5, 6, 7, 8, 9 and 10. In certain embodiments m5 of formula (D-xxv) or (D-xxv') is an integer selected from the group consisting of 3, 4, 5, 6 and 7. In certain embodiments m5 of formula (D-xxv) or (D-xxv') is 3. In certain embodiments m5 of formula (D-xxv) or (D-xxv') is 4. In certain embodiments m5 of formula (D-xxv) or (D-xxv') is 5. In certain embodiments m5 of formula (D-xxv) or (D-xxv') is 6. In certain embodiments m5 of formula (D-xxv) or (D-xxv') is 7. In certain embodiments m6 of formula (D-xxv) or (D-xxv') is an integer selected from 2, 3, 4 5 and 6. In certain embodiments m6 of formula (D-xxv) or (D-xxv') is 3. In certain embodiments m6 of formula (D-xxv) or (D-xxv') is 4.

In certain embodiments —CL- is of formula (D-xxvi)

(D-xxvi)

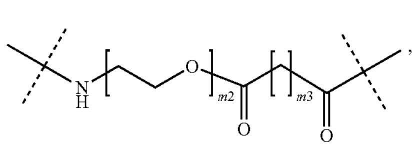

wherein dashed lines indicate attachment to a moiety $—X^{0F}—$;

m2 and m3 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 of formula (D-xxvi) is an integer selected from the group consisting of 1, 2, 3, 4, 5, 6, 7, 8, 9 and 10. In certain embodiments m2 of formula (D-xxvi) is an integer selected from the group consisting of 1, 2, 3 and 4. In certain embodiments m2 of formula (D-xxvi) is 1. In certain embodiments m2 of formula (D-xxvi) is 2. In certain embodiments m2 of formula (D-xxvi) is 3. In certain embodiments m2 of formula (D-xxvi) is 4. In certain embodiments m3 of formula (D-xxvi) is an integer selected from the group consisting of 2, 3, 4, 5, 6, 7, 8, 9 and 10. In certain embodiments m3 of formula (D-xxvi) is an integer selected from the group consisting of 3, 4, 5, 6 and 7. In certain embodiments m3 of formula (D-xxvi) is 3. In certain embodiments m3 of formula (D-xxvi) is 4. In certain embodiments m3 of formula (D-xxvi) is 5. In certain embodiments m3 of formula (D-xxvi) is 6. In certain embodiments m3 of formula (D-xxvi) is 7.

In certain embodiments a moiety —$X^{0E}$—SP—$X^{0F}$—CL-$X^{0F}$—SP—$X^{0E}$— has the structure of formula (D-xxvii) or (D-xxvii')

(D-xxvii)

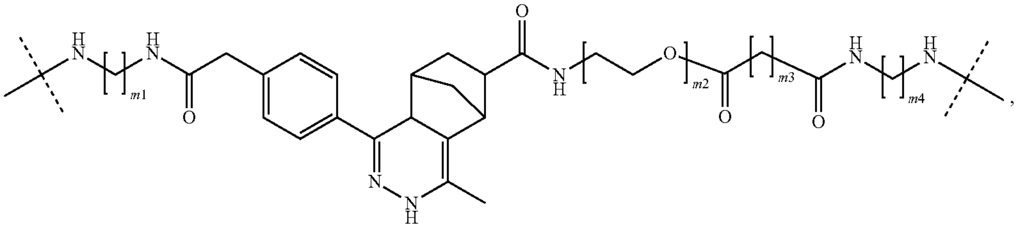

(D-xxvii')

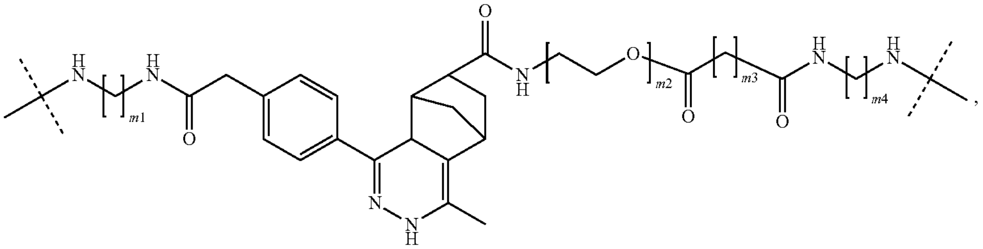

wherein dashed lines indicate attachment to the carbonyl of the hyaluronic acid; and m1, m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxvii) or (D-xxvii') is an integer selected from the group consisting of 2, 3, 4, 5 and 6. In certain embodiments m1 of formula (D-xxvii) or (D-xxvii') is 3. In certain embodiments m1 of formula (D-xxvii) or (D-xxvii') is 4. In certain embodiments m2 of formula (D-xxvii) or (D-xxvii') is an integer selected from the group consisting of 1, 2, 3, 4, 5, 6, 7, 8, 9 and 10. In certain embodiments m2 of formula (D-xxvii) or (D-xxvii') is an integer selected from the group consisting of 1, 2, 3 and 4. In certain embodiments m2 of formula (D-xxvii) or (D-xxvii') is 1. In certain embodiments m2 of formula (D-xxvii) or (D-xxvii') is 2. In certain embodiments m2 of formula (D-xxvii) or (D-xxvii') is 3. In certain embodiments m2 of formula (D-xxvii) or (D-xxvii') is 4. In certain embodiments m3 of formula (D-xxvii) or (D-xxvii') is an integer selected from the group consisting of 2, 3, 4, 5, 6, 7, 8, 9 and 10. In certain embodiments m3 of formula (D-xxvii) or (D-xxvii') is an integer selected from the group consisting of 3, 4, 5, 6 and 7. In certain embodiments m3 of formula (D-xxvii) or (D-xxvii') is 3. In certain embodiments m3 of formula (D-xxvii) or (D-xxvii') is 4. In certain embodiments m3 of formula (D-xxvii) or (D-xxvii') is 5. In certain embodiments m3 of formula (D-xxvii) or (D-xxvii') is 6. In certain embodiments m3 of formula (D-xxvii) or (D-xxvii') is 7. In certain embodiments m4 of formula (D-xxvii) or (D-xxvii') is an integer selected from the group consisting of 2, 3, 4, 5 and 6. In certain embodiments m4 of formula (D-xxvii) or (D-xxvii') is 3. In certain embodiments m4 of formula (D-xxvii) or (D-xxvii') is 4.

In certain embodiments —CL- is of formula (D-xxviii)

(D-xxviii)

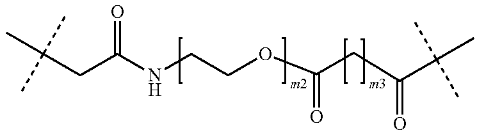

wherein dashed lines indicate attachment to a moiety —$X^{0F}$—;

m2 and m3 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 of formula (D-xxviii) is an integer selected from the group consisting of 1, 2, 3, 4, 5, 6, 7, 8, 9 and 10. In certain embodiments m2 of formula (D-xxviii) is an integer selected from the group consisting of 1, 2, 3 and 4. In certain embodiments m2 of formula (D-xxviii) is 1. In certain embodiments m2 of formula (D-xxviii) is 2. In certain embodiments m2 of formula (D-xxviii) is 3. In certain embodiments m2 of formula (D-xxviii) is 4. In certain embodiments m3 of formula (D-xxviii) is an integer selected from the group consisting of 2, 3, 4, 5, 6, 7, 8, 9 and 10. In certain embodiments m3 of formula (D-xxviii) is an integer selected from the group consisting of 3, 4, 5, 6 and 7. In certain embodiments m3 of formula (D-xxviii) is 3. In certain embodiments m3 of formula (D-xxviii) is 4. In certain embodiments m3 of formula (D-xxviii) is 5. In certain embodiments m3 of formula (D-xxviii) is 6. In certain embodiments m3 of formula (D-xxviii) is 7.

In certain embodiments a moiety —$X^{0E}$—SP—$X^{0F}$—CL-$X^{0F}$—SP—$X^{0E}$— has the structure of formula (D-xxix) or (D-xxix')

(D-xxix)

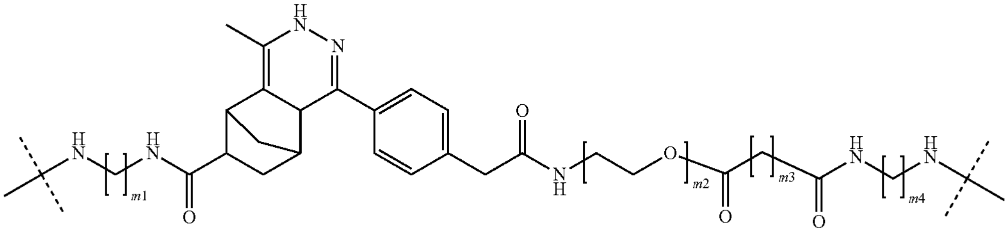

(D-xxix')

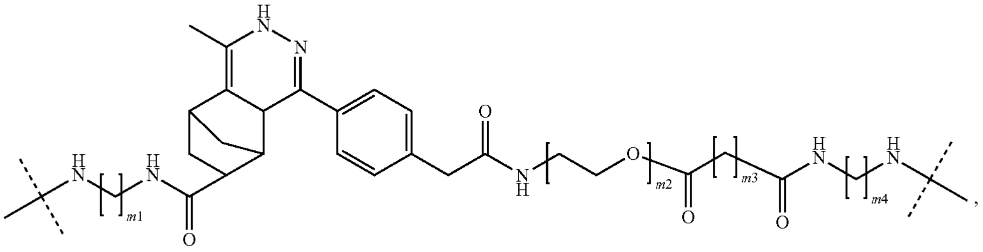

wherein dashed lines indicate attachment to the carbonyl of the hyaluronic acid; and m1, m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxix) or (D-xxix') is an integer selected from the group consisting of 2, 3, 4, 5 and 6. In certain embodiments m1 of formula (D-xxix) or (D-xxix') is 3. In certain embodiments m1 of formula (D-xxix) or (D-xxix') is 4. In certain embodiments m2 of formula (D-xxix) or (D-xxix') is an integer selected from the group consisting of 1, 2, 3, 4, 5, 6, 7, 8, 9 and 10. In certain embodiments m2 of formula (D-xxix) or (D-xxix') is an integer selected from the group consisting of 1, 2, 3 and 4. In certain embodiments m2 of formula (D-xxix) or (D-xxix') is 1. In certain embodiments m2 of formula (D-xxix) or (D-xxix') is 2. In certain embodiments m2 of formula (D-xxix) or (D-xxix') is 3. In certain embodiments m2 of formula (D-xxix) or (D-xxix') is 4. In certain embodiments m3 of formula (D-xxix) or (D-xxix') is an integer selected from the group consisting of 2, 3, 4, 5, 6, 7, 8, 9 and 10. In certain embodiments m3 of formula (D-xxix) or (D-xxix') is an integer selected from the group consisting of 3, 4, 5, 6 and 7. In certain embodiments m3 of formula (D-xxix) or (D-xxix') is 3. In certain embodiments m3 of formula (D-xxix) or (D-xxix') is 4. In certain embodiments m3 of formula (D-xxix) or (D-xxix') is 5. In certain embodiments m3 of formula (D-xxix) or (D-xxix') is 6. In certain embodiments m3 of formula (D-xxix) or (D-xxix') is 7. In certain embodiments m4 of formula (D-xxix) or (D-xxix') is an integer selected from the group consisting of 2, 3, 4, 5 and 6. In certain embodiments m4 of (D-xxix) or (D-xxix') is 3. In certain embodiments m4 of formula (D-xxix) or (D-xxix') is 4.

In a second embodiment the moiety —CL- is selected from the group consisting of (C-i)

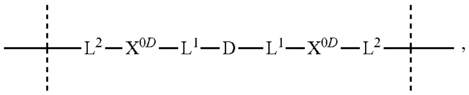

and

-continued (C-ii)

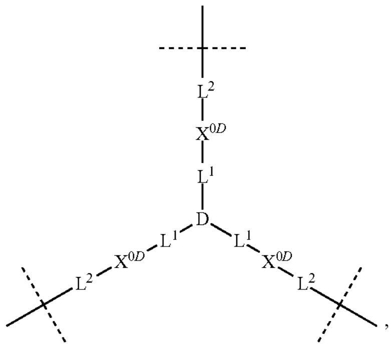

wherein each dashed line indicates attachment to a moiety $—X^{0F}—$; and $-L^1-$, $-L^2-$, $—X^{0D}—$ and -D are used as defined for $Z^2$.

It is understood that in formula (C-i) two functional groups of the drug are conjugated to one moiety $-L^1-$ each and that in formula (C-ii) three functional groups of the drug are conjugated to one moiety $-L^1-$ each. The moiety —CL- of formula (C-i) connects two moieties $Z^3$ and the moiety —CL- of formula (C-ii) connects three moieties $Z^3$, which may be on the same or different hyaluronic acid strand. In this embodiment —CL- comprises at least two degradable bonds, if —CL- is of formula (C-i) or at least three degradable bonds, if —CL- is of formula (C-ii), namely the degradable bonds that connect D with a moiety $-L^1-$. A conjugate may only comprise moieties —CL- of formula (C-i), may only comprise moieties —CL- of formula (C-ii) or may comprise moieties —CL- of formula (C-i) and formula (C-ii).

Accordingly, a conjugate of this second embodiment comprises crosslinked hyaluronic acid strands to which a plurality of drug moieties are covalently and reversibly conjugated, wherein the conjugate comprises a plurality of connected units selected from the group consisting of

Z1

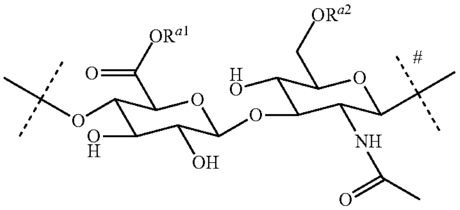

Z2

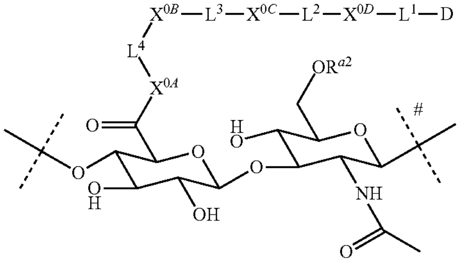

Z3

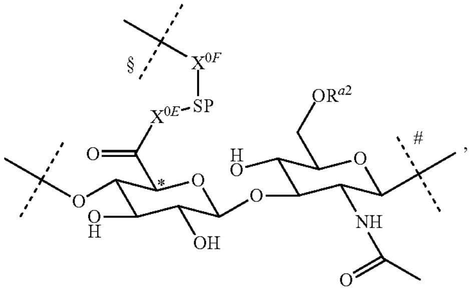

wherein an unmarked dashed line indicates a point of attachment to an adjacent unit at a dashed line marked with #or to a hydrogen;

a dashed line marked with #indicates a point of attachment to an adjacent unit at an unmarked dashed line or to a hydroxyl;

a dashed line marked with § indicates a point of connection between at least two units $Z^3$ via a moiety —CL-;

each —CL- comprises at least one degradable bond between the two carbon atoms marked with the * connected by a moiety —CL- and each —CL- is independently selected from the group consisting of formula (C-i) and (C-ii)

(C-i)

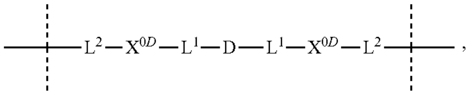

and

-continued (C-ii)

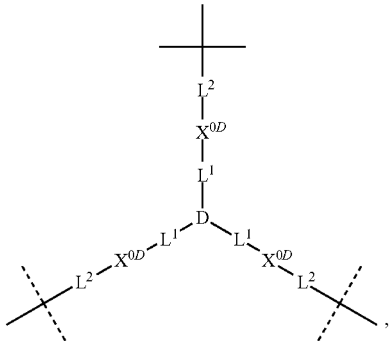

wherein dashed lines indicate attachment to a moiety $—X^{0F}—$ of a unit $Z^3$;

-D, $-L^1-$, $-L^2-$, $-L^3-$, —SP—, $—X^{0A}—$, $—X^{0B}—$, $—X^{0C}—$, $—X^{0D}—$, $—X^{0E}—$, $X^{0F}—$, $—R^{a1}$ and $—R^{a2}$ are used as defined above;

wherein all units $Z^1$ present in the conjugate may be the same or different;

all units $Z^2$ present in the conjugate may be the same or different;

all units $Z^3$ present in the conjugate may be the same or different;

the number of $Z^1$ units ranges from 1% to 98% of the total number of units present in the conjugate;

the number of $Z^2$ units ranges from 0% to 98% of the total number of units present in the conjugate;

the number of $Z^3$ units ranges from 1% to 97% of the total number of units present in the conjugate, provided that at least one unit $Z^3$ is present per strand which is connected to at least one unit $Z^3$ on a different hyaluronic acid strand.

The conjugate according to this second embodiment may also comprise units selected from the group consisting of $Z^4$, $Z^5$, $Z^6$, $Z^7$, $Z^8$, $Z^9$ and $Z^{10}$ as described above. For $Z^4$ variable a is 1 and b is 0 for a moiety —CL- of formula (C-i), and if —CL- is of formula (C-ii) variable a may be 1 with b being also 1 or variable a may be 2 with b being 0.

This embodiment has the effect that for synthesizing a conjugate of the present invention there is no need to separate monoconjugates $Y^{0G}$-$L^2$-$X^{0D}$-$L^1$-D from bisconjugates $Y^{0G}$-$L^2$-$X^{0D}$-$L^1$-D-$L^1$-$X^{0D}$-$L^2$- $Y^{0G}$ or even trisconjugates, in which three moieties $Y^{0G}$-$L^2$-$X^{0D}$-$L^1$- are conjugated to one moiety D. A mixture of both or all three can directly be used for conjugation: Conjugation of a monoconjugate $Y^{0G}$-$L^2$-$X^{0D}$-$L^1$-D to a unit $Z^7$ results in the formation of a unit $Z^2$, whereas the bis- and/or trisconjugate are conjugated to units $Z^5$ to thus enable crosslinking and result in the formation of units $Z^3$. $Y^{0G}$ is a functional group, which is used as defined as for $—Y^{0A}—Y^{0B}—Y^{0C}$ and $—Y^{0D}$ below. Such synthesis may also be done with mixtures comprising higher conjugates, such as tetra-, penta-, hexa- or heptaconjugates, and such embodiments for —CL-, i.e. moieties —CL- in which one moiety D is conjugated to four, five, six or seven or more moieties $-L^1-$, are also included in the present invention. Accordingly, also covered are conjugates comprising a moiety —CL- in the form of tetra-, penta-, hexa- and/or hepta- or higher conjugates.

In a conjugate according to this second embodiment the number of units $Z^2$ ranges from 0 to 70% of all units present in the conjugate, such as from 2 to 15%, from 2 to 10%, from 16 to 39, from 40 to 65%, or from 50 to 60% of all units present in the conjugate.

In a conjugate according to this second embodiment the number of units $Z^3$ ranges from 1 to 30% of all units present in the conjugate, such as from 2 to 5%, from 5 to 20%, from 10 to 18%, or from 14 to 18% of all units present in the conjugate.

In a conjugate according to this second embodiment the number of units $Z^1$ ranges from 10 to 97% of all units present in the conjugate, such as from 20 to 40%, such as from 25 to 35%, such as from 41 to 95%, such as from 45 to 90%, such as from 50 to 70% of all units present in the conjugate.

More specific embodiments for -D, $-L^1-$, $-L^2-$ $-L^3-$, $-L^4-$, —SP—, $—X^{0A}—$, $—X^{0B}—$, $—X^{0C}—$, $—X^{0D}—$, $—X_{0E}—$, $—X^{0F}—$, $—R^{a1}$ and $—R^{a2}$ of the second embodiment are as described below.

In a third embodiment the moiety —CL- is a moiety (D-i)

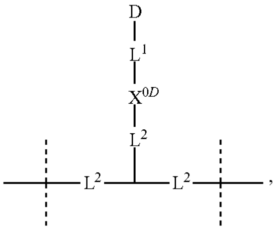

wherein each dashed line indicates attachment to a moiety $—X^{0F}—$ of a unit $Z^3$.

It is understood that a moiety —CL- of formula (D-i) comprises at least one branching point, which branching point may be selected from the group consisting of

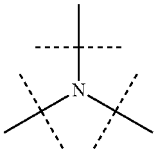
,
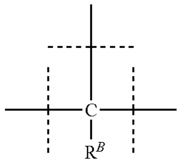
and
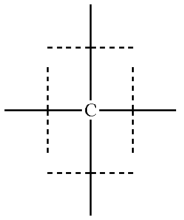
, wherein dashed lines indicate attachment to an arm; and $—R^B$ is selected from the group consisting of —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $—R^{B1}$, which are the same or different, and wherein $C_{1-6}$ alkyl, $C_{2-6}$ alkenyl and $C_{2-6}$ alkynyl are optionally interrupted with —C(O)O—, —O—, —C(O)—, $—C(O)N(R^{B2})—$, $—S(O)_2N(R^{B2})—$, $—S(O)N(R^{B2})—$, $—S(O)_2—$, —S(O)—, $—N(R^{B2})S(O)_2N(R^{B2a})$, —S—, $—N(R^{B2})—$, $—OC(OR^{B2})(R^{B2a})—$, $—N(R^{B2})C(O)N(R^{B2a})—$, and $—OC(O)N(R^{B2})—$; wherein $—R^{B1}$, $—R^{B2}$ and $—R^{B2a}$ are selected from —H, $C_{1-6}$ alkyl, $C_{2-6}$ alkenyl and $C_{2-6}$ alkynyl.

In certain embodiments $—R^B$ is selected from the group consisting of —H, methyl and ethyl.

Accordingly, a conjugate of the third embodiment comprises crosslinked hyaluronic acid strands to which a plurality of drug moieties are covalently and reversibly conjugated, wherein the conjugate comprises a plurality of connected units selected from the group consisting of $Z^1$

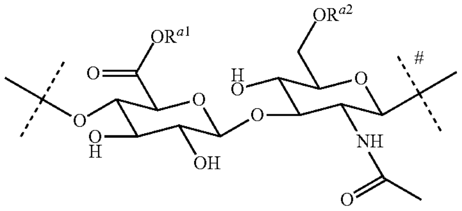

$Z^2$

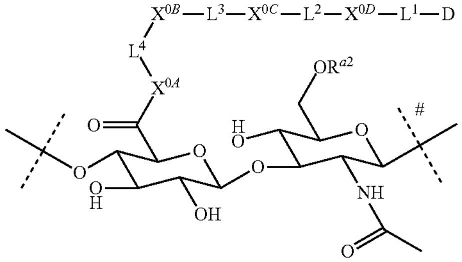

and $Z^3$

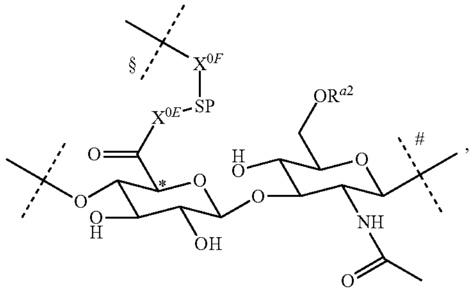

, wherein an unmarked dashed line indicates a point of attachment to an adjacent unit at a dashed line marked with #or to a hydrogen;

a dashed line marked with #indicates a point of attachment to an adjacent unit at an unmarked dashed line or to a hydroxyl;

a dashed line marked with § indicates a point of connection between two units $Z^3$ via a moiety —CL-;

each —CL- comprises at least one degradable bond between the two carbon atoms marked with the * connected by a moiety —CL- and each —CL- is independently of formula (D-i)

(D-i)

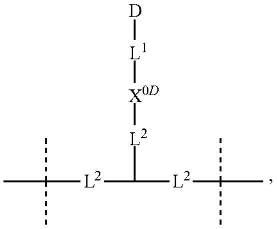

wherein dashed lines indicate attachment to a moiety —$X^{0F}$— of a unit $Z^3$;

-D, -$L^1$-, -$L^2$-, -$L^3$, -$L^4$-, —SP—, —$X^{0A}$—, —$X^{0B}$—, —$X^{0C}$—, —$X^{0D}$—, —$X_{0E}$—, —$X^{0F}$—, —$R^{a1}$ and —$R^{a2}$ are used as defined above;

wherein all units $Z^1$ present in the conjugate may be the same or different;

all units $Z^2$ present in the conjugate may be the same or different;

all units $Z^3$ present in the conjugate may be the same or different;

the number of units $Z^1$ ranges from 1% to 99% of the total number of units present in the conjugate;

the number of units $Z^2$ ranges from 0% to 98% of the total number of units present in the conjugate; and the number of units $Z^3$ ranges from 1% to 97% of the total number of units present in the conjugate, provided that at least one unit $Z^3$ is present per strand.

The conjugate according to this third embodiment may also comprise units selected from the group consisting of $Z^4$, $Z^5$, $Z^6$, $Z^7$, $Z^8$, $Z^9$ and $Z^{10}$ as described above. For $Z^4$ variable a is 1 and variable b is 0 in this third embodiment.

In a conjugate according to this third embodiment the number of units $Z^2$ ranges from 0 to 70% of all units present in the conjugate, such as from 2 to 15%, from 2 to 10%, from 16 to 39, from 40 to 65%, or from 50 to 60% of all units present in the conjugate.

In a conjugate according to this third embodiment the number of units $Z^3$ ranges from 1 to 30% of all units present in the conjugate, such as from 2 to 5%, from 5 to 20%, from 10 to 18%, or from 14 to 18% of all units present in the conjugate.

In a conjugate according to this third embodiment the number of units $Z^1$ ranges from 10 to 97% of all units present in the conjugate, such as from 20 to 40%, such as from 25 to 35%, such as from 41 to 95%, such as from 45 to 90%, such as from 50 to 70% of all units present in the conjugate.

In this third embodiment —CL- comprises a moiety -$L^2$-$X^{0C}$-$L^1$-D, so the presence of units $Z^2$ is optional in this embodiment. In certain embodiment no units $Z^2$ are present in the third embodiment. In certain embodiments the conjugate according to the third embodiment also comprises units $Z^2$. The presence of units $Z^2$ may have the effect that in case of a high drug loading is desired, which in this embodiment also means a high degree of crosslinking, an undesired high degree of crosslinking can be avoided by the presence of units $Z^2$.

More specific embodiments for -D, -$L^1$-, -$L^2$-, -$L^3$-, -$L^4$-, —SP—, $X^{0A}$—, —$X^{0B}$—, —$X^{0C}$—, —$X^{0D}$—, —$X^{0E}$—, —$X^{0F}$—, —$R^{a1}$ and —$R^{a2}$ of the second embodiment are as described below.

In certain embodiments each —$X^{0A}$— and —$X^{0E}$— is independently either absent or selected from the group consisting of (x-1)

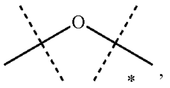

(x-2)

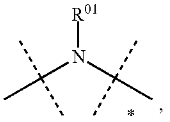

(x-3)

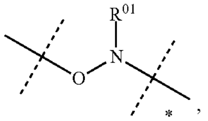

(x-4)

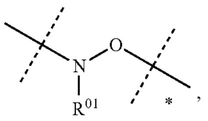

(x-5)

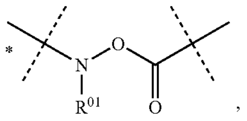

(x-6)

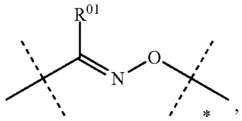

(x-7)

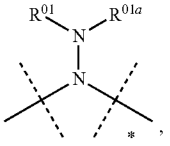

(x-8)

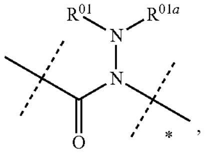

(x-9)

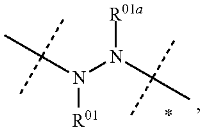

(x-10)

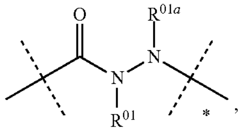

-continued (x-11)

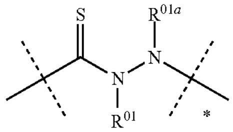
, (x-12)

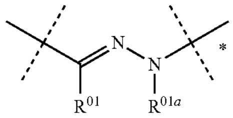
, (x-13)

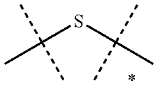
, (x-14)

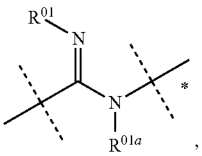
, (x-15)

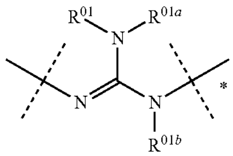
and (x-16)

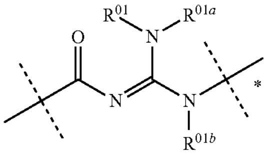
;

wherein unmarked dashed lines indicate attachment to $-L^4-$ for $—X^{0A}—$ and to —SP— for $—X^{0E}—$; dashed lines marked with an asterisk indicate attachment to the carbonyl of the hyaluronic acid;

each $—R^{01}$, $—R^{01a}$ and $—R^{01b}$ is independently selected from the group consisting of halogen, —H, —CN, $-T^0$, $C_{1-50}$ alkyl, $C_{2-50}$ alkenyl, and $C_{2-50}$ alkynyl; wherein $-T^0$, $C_{1-50}$ alkyl, $C_{2-50}$ alkenyl, and $C_{2-50}$ alkynyl are optionally substituted with one or more $—R^{02}$ which are the same or different, and wherein $C_{1-50}$ alkyl, $C_{2-50}$ alkenyl, and $C_{2-50}$ alkynyl are optionally interrupted by one or more groups selected from the group consisting of $-T^0-$, —C(O)O—, —O—, —C(O)—, $—C(O)N(R^{03})—$, $—S(O)_2N(R^{03})—$, $—S(O)N(R^{03})—$, $—S(O)_2—$, —S(O)—, $—N(R^{03})S(O)_2N(R^{03a})—$, —S—, $—N(R^{03})—$, $—OC(OR^{03})(R^{03a})—$, $—N(R^{03})C(O)N(R^{03a})$ and $—OC(O)N(R^{03})—$;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more $—R^{02}$, which are the same or different; and each $—R^{02}$, $—R^{03}$ and $—R^{03a}$ is independently selected from the group consisting of —H and $C_{1-6}$ alkyl; wherein $C_{1-6}$ alkyl is optionally substituted with one or more halogen, which are the same or different.

In certain embodiments each $—X^{0A}—$ and $—X^{0E}—$ is independently a linkage selected from the group consisting of formula x-1, x-2, x-3, x-4, x-6, x-9, x-10, x-11, x-12, x-13, x-14, x-15 and x-16, In certain embodiments each $—X^{0A}—$ and $—X^{0E}—$ is independently a linkage selected from the group consisting of formula x-1, x-2, x-3, x-4, x-6, x-9, x-10, x-12, x-13 and x-15.

In certain embodiments each $—X^{0A}—$ and $—X^{0E}—$ is independently a linkage selected from the group consisting of formula x-1, x-2, x-9 and x-10.

In certain embodiments each $X^{0A}—$ and $X^{0E}—$ is independently a linkage selected from the group consisting of formula x-1, x-2 and x-10.

In certain embodiments $X^{0A}—$ is of formula x-1. In certain embodiments $—X^{0A}—$ is of formula x-2. In certain embodiments $X^{0A}—$ is of formula x-3. In certain embodiments $—X^{0A}—$ is of formula x-4. In certain embodiments $—X^{0A}—$ is of formula x-5. In certain embodiments $—X^{0A}—$ is of formula x-6. In certain embodiments $—X^{0A}—$ is of formula x-7. In certain embodiments $—X^{0A}—$ is of formula x-8. In certain embodiments $X^{0A}—$ is of formula x-9. In certain embodiments $X^{0A}—$ is of formula x-10. In certain embodiments $—X^{0A}—$ is of formula x-11. In certain embodiments $—X^{0A}—$ is of formula x-12. In certain embodiments $—X^{0A}—$ is of formula x-13. In certain embodiments $—X^{0A}—$ is of formula x-14. In certain embodiments $—X^{0A}—$ is of formula x-15. In certain embodiments $X^{0A}—$ is of formula x-16.

In certain embodiments $X^{0E}—$ is of formula x-1. In certain embodiments $—X^{0E}—$ is of formula x-2. In certain embodiments $—X^{0E}—$ is of formula x-3. In certain embodiments $—X^{0E}—$ is of formula x-4. In certain embodiments $—X^{0E}—$ is of formula x-5. In certain embodiments $—X^{0E}—$ is of formula x-6. In certain embodiments $X^{0E}—$ is of formula x-7. In certain embodiments $—X^{0E}$ is of formula x-8. In certain embodiments $—X^{0E}—$ is of formula x-9. In certain embodiments $—X^{0E}—$ is of formula x-10. In certain embodiments $—X^{0E}—$ is of formula x-11. In certain embodiments $—X^{0E}—$ is of formula x-12. In certain embodiments $—X^{0E}—$ is of formula x-13. In certain embodiments $—X^{0E}—$ is of formula x-14. In certain embodiments $—X^{0E}—$ is of formula x-15. In certain embodiments $X^{0E}—$ is of formula x-16.

In certain embodiments each $—X^{0B}—$, $—X^{0C}—$, $—X^{0D}—$ and $—X^{0F}—$ is independently either absent or selected from the group consisting of (x-17)

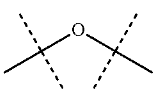

(x-18)

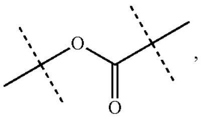
, (x-19)

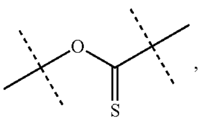
,

-continued
(x-20)
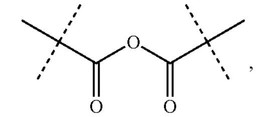
(x-21)
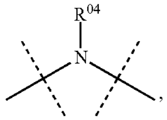
(x-22)
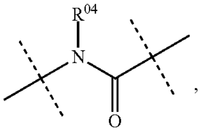
(x-23)
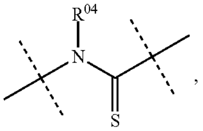
(x-24)
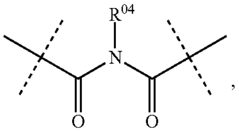
(x-25)
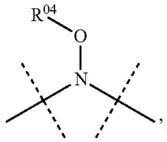
(x-26)
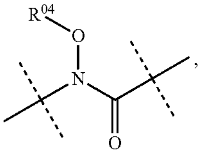
(x-27)
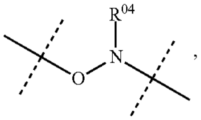
(x-28)
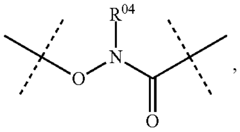
(x-29)
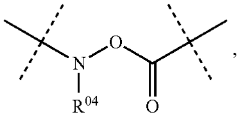
(x-30)
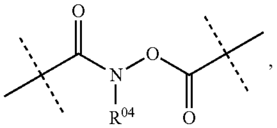
-continued
(x-31)
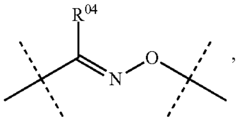
(x-32)
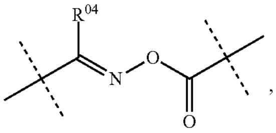
(x-33)
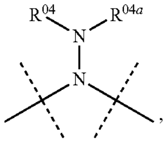
(x-34)
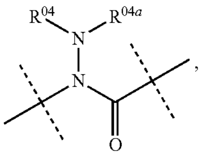
(x-35)
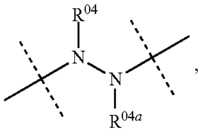
(x-36)
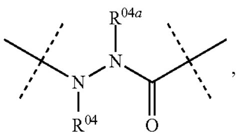
(x-37)
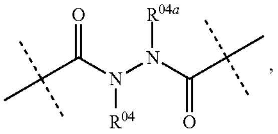
(x-38)
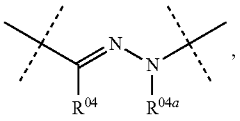
(x-39)
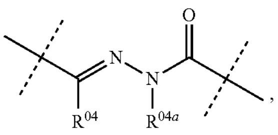
(x-40)
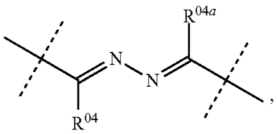
(x-41)
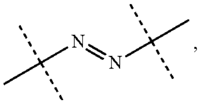

-continued
(x-42)
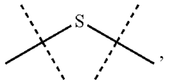
(x-43)
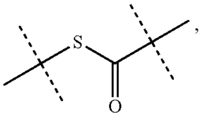
(x-44)
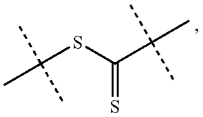
(x-45)
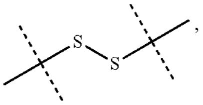
(x-46)
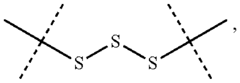
(x-47)
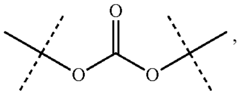
(x-48)
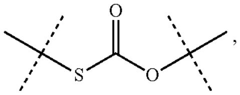
(x-49)
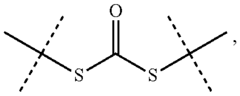
(x-50)
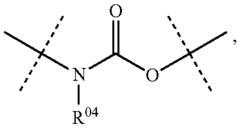
(x-51)
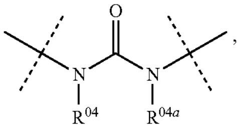
(x-52)
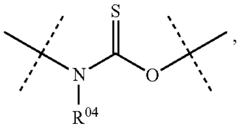
(x-53)
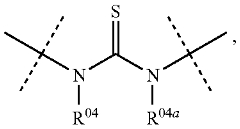
(x-54)
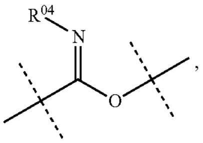
-continued
(x-55)
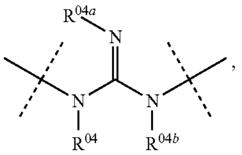
(x-56)
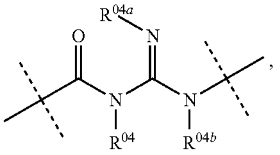
(x-57)
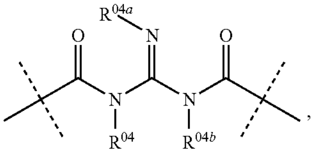
(x-58)
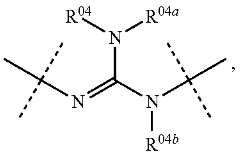
(x-59)
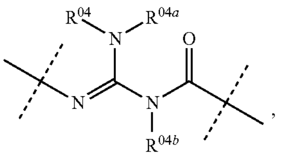
(x-60)
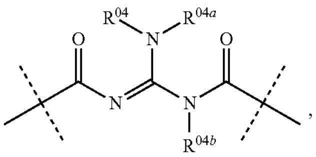
(x-61)
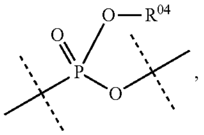
(x-62)
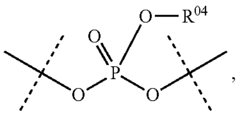
(x-63)
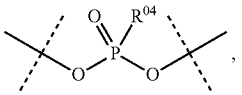
(x-64)
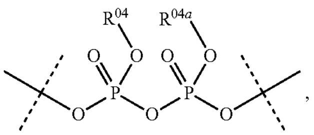

-continued
(x-65)
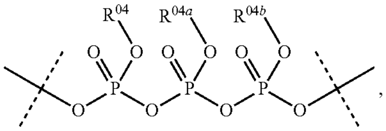
(x-66)
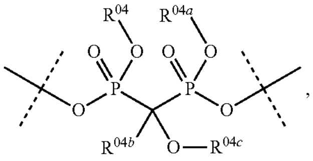
(x-67)
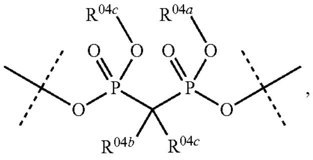
(x-68)
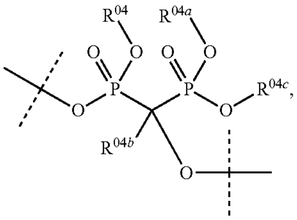
(x-69)
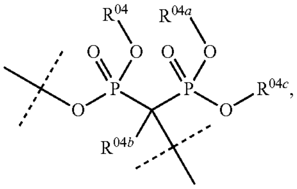
(x-70)
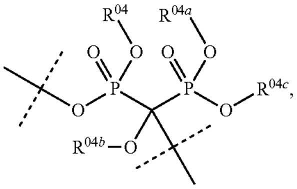
(x-71)
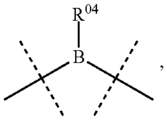
(x-72)
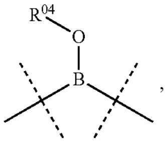
(x-73)
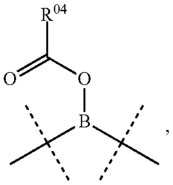
-continued
(x-74)
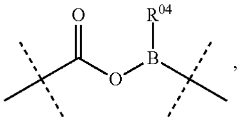
(x-75)
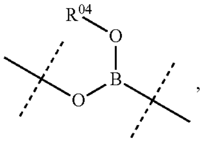
(x-76)
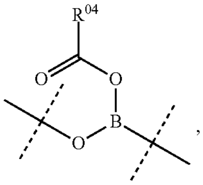
(x-77)
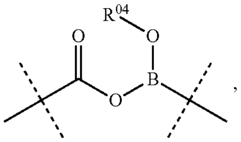
(x-78)
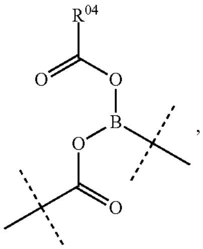
(x-79)
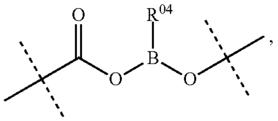
(x-80)
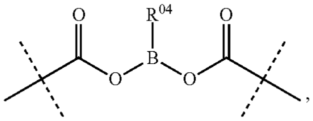
(x-81)
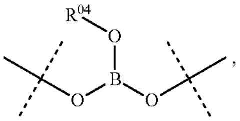
(x-82)
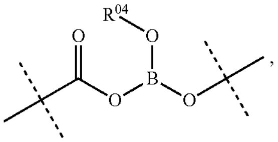
(x-83)
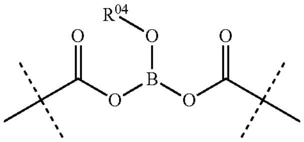

-continued
(x-84)
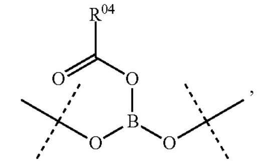
(x-85)
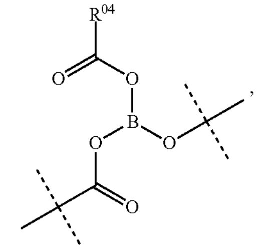
(x-86)
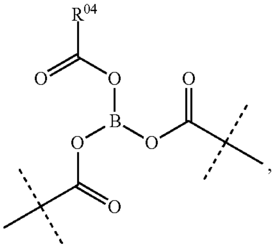
(x-87)
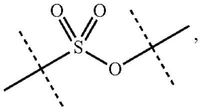
(x-88)
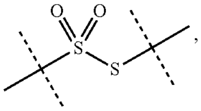
(x-89)
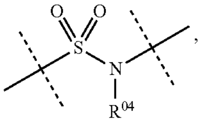
(x-90)
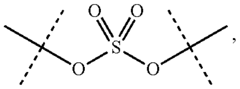
(x-91)
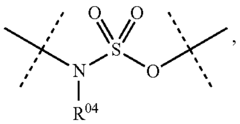
(x-92)
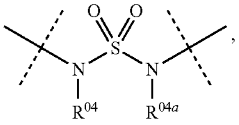
(x-93)
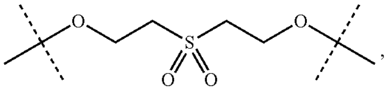
-continued
(x-94)
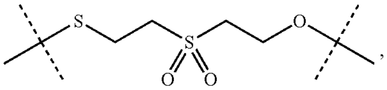
(x-95)
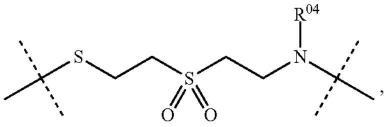
(x-96)
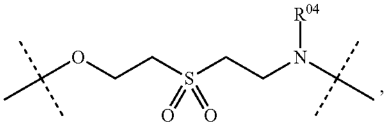
(x-97)
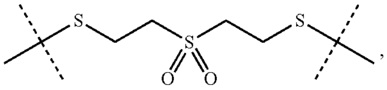
(x-98)
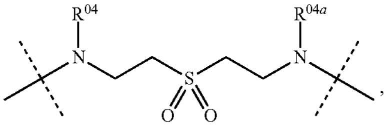
(x-99)
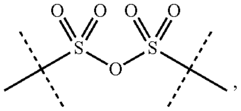
(x-100)
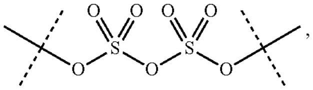
(x-101)
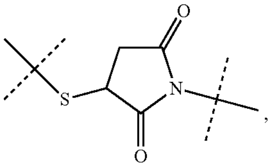
(x-102)
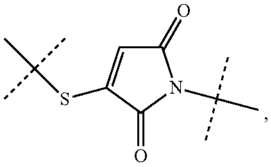
(x-103)
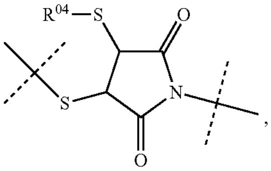
(x-104)
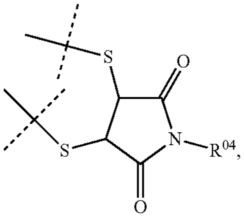

-continued
(x-105)
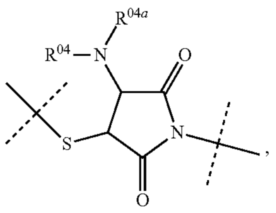
(x-106)
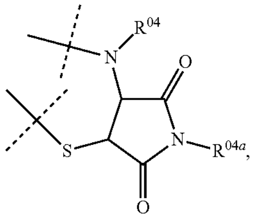
(x-107)
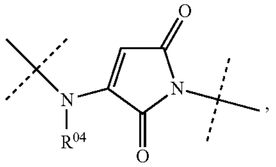
(x-108)
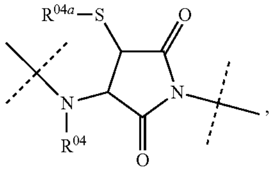
(x-109)
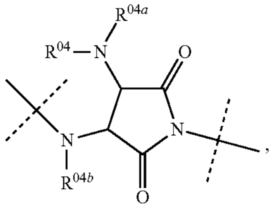
(x-110)
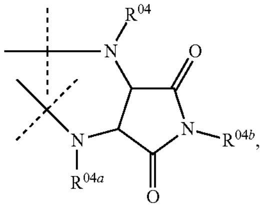
(x-111)
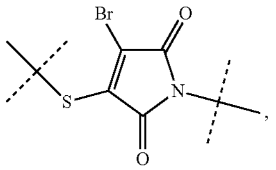
(x-112)
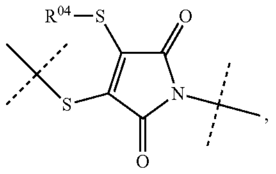
-continued
(x-113)
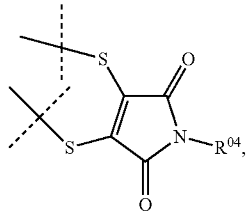
(x-114)
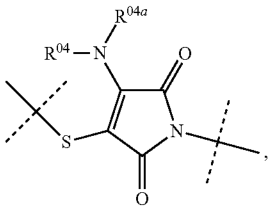
(x-115)
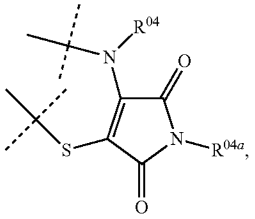
(x-116)
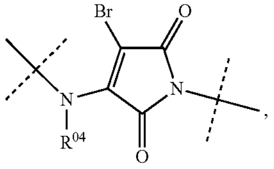
(x-117)
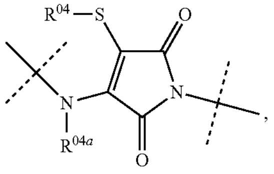
(x-118)
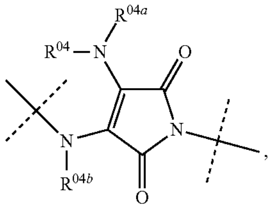
(x-119)
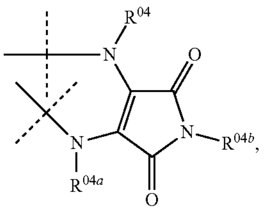

-continued
(x-120)
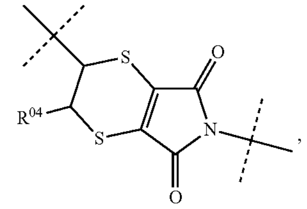
(x-121)
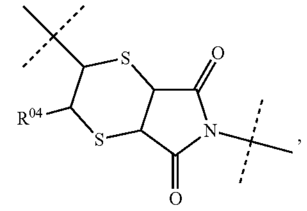
(x-122)
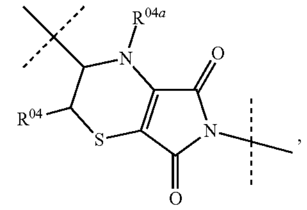
(x-123)
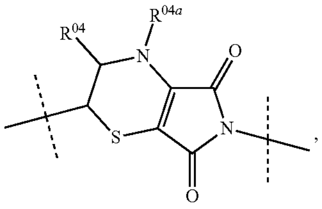
(x-124)
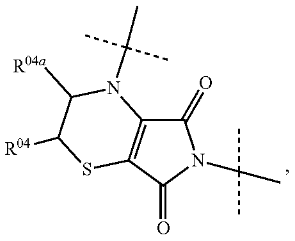
(x-125)
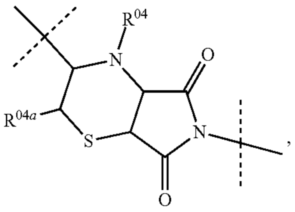
(x-126)
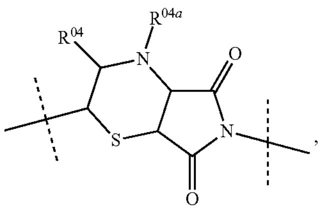
-continued
(x-127)
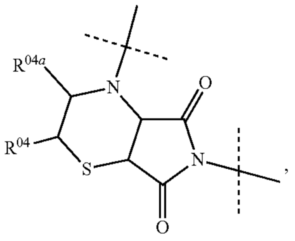
(x-128)
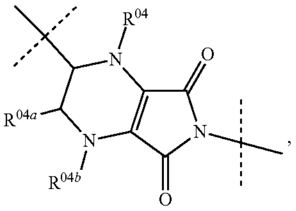
(x-129)
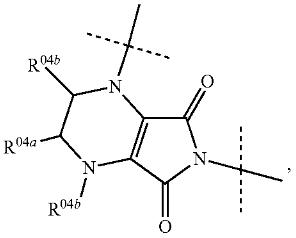
(x-130)
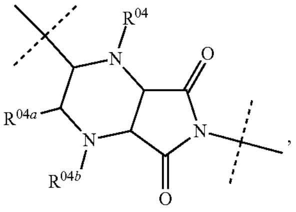
(x-131)
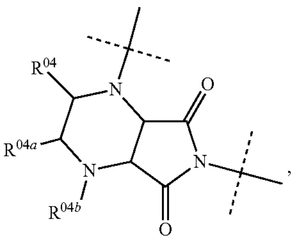
(x-132)
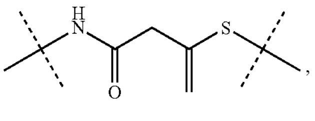
(x-133)
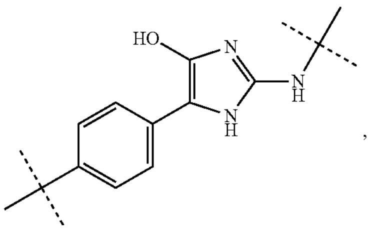

-continued
(x-134)
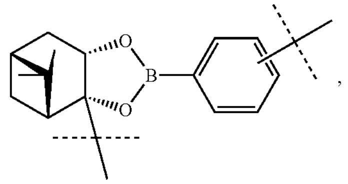
(x-135)
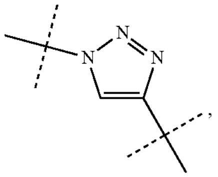
(x-136)
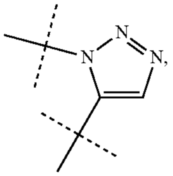
(x-137)
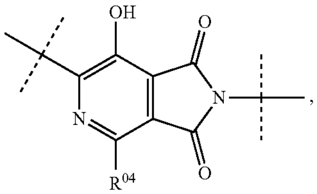
(x-138)
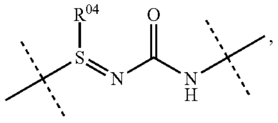
(x-139)
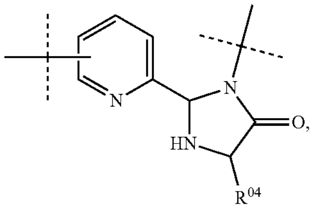
(x-140)
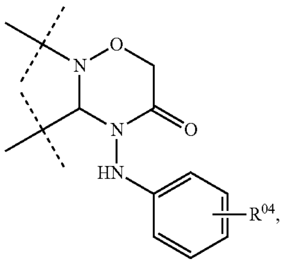
(x-141)
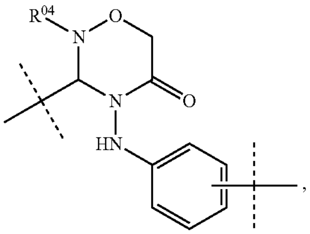
-continued
(x-142)
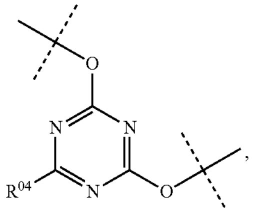
(x-143)
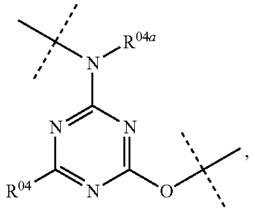
(x-144)
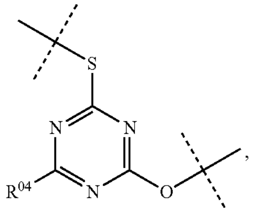
(x-145)
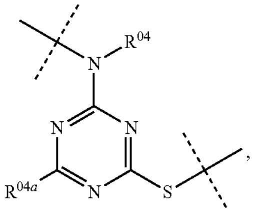
(x-146)
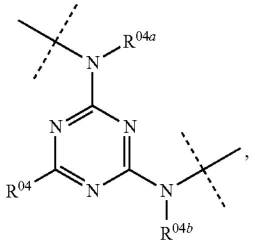
(x-147)
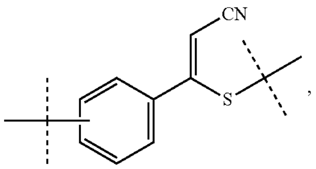
(x-148)
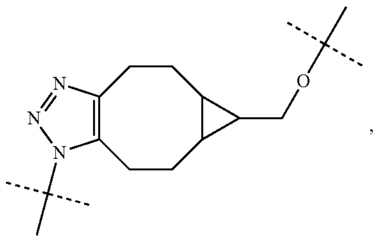

-continued
(x-149)
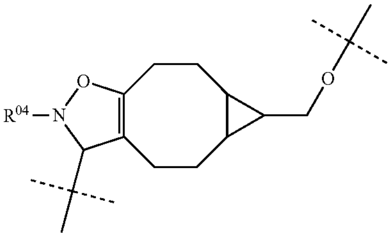
,
(x-150)
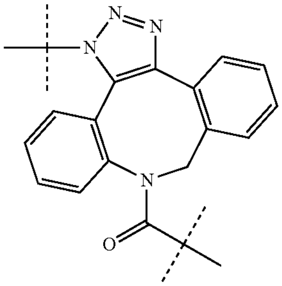
,
(x-151)
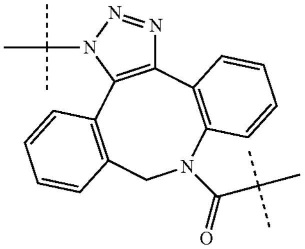
,
(x-152)
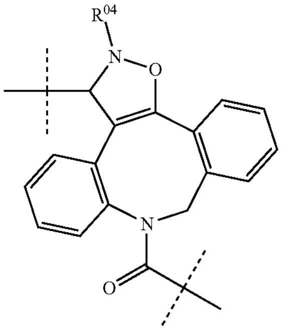
,
(x-153)
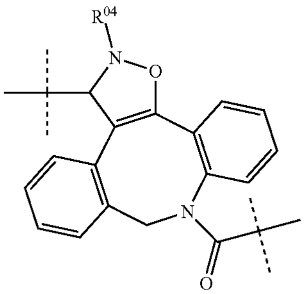
,
-continued
(x-154)
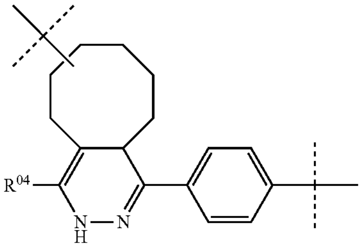
,
(x-155)
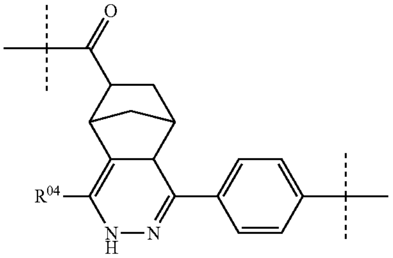
,
(x-156)
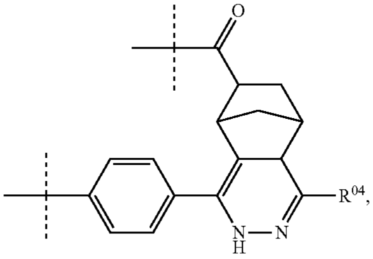
,
(x-157)
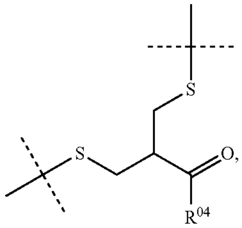
,
(x-158)
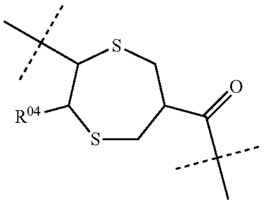
,
(x-159)
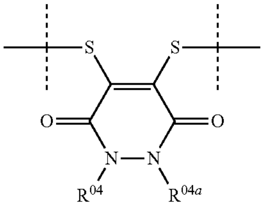
, -continued
(x-160)
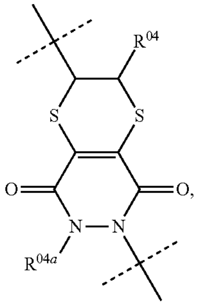
(x-161)
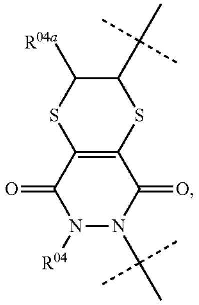
(x-162)
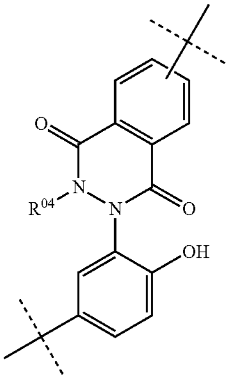
,
(x-163)
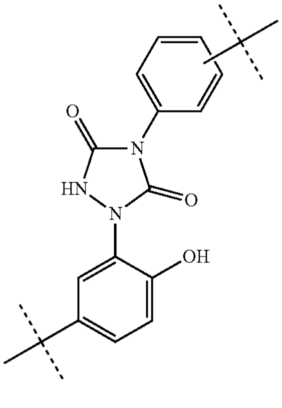
,
-continued
(x-164)
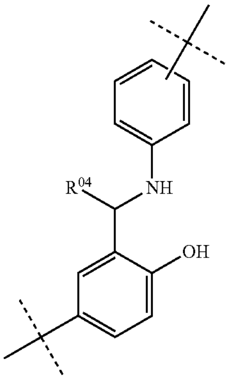
,
(x-165)
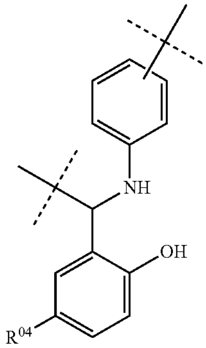
,
(x-166)
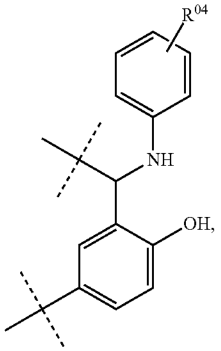
(x-167)
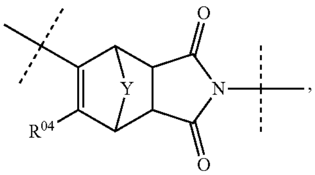
,
(x-168)
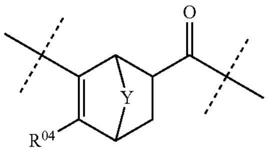
,
(x-169)
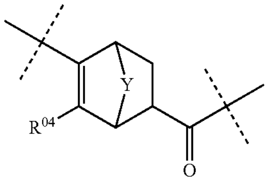
, -continued (x-170)

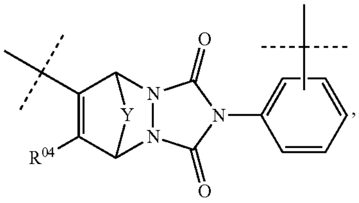

(x-171)

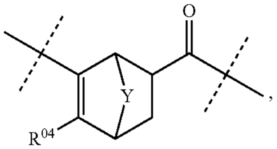

(x-172)

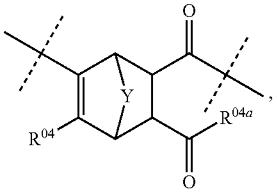

(x-173)

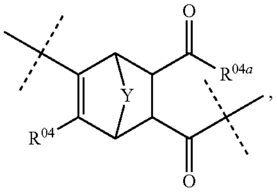

(x-174)

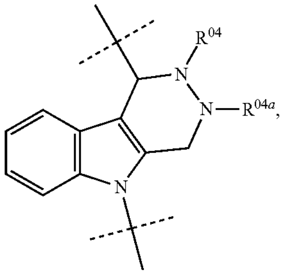

(x-175)

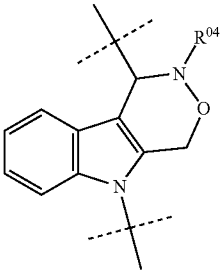

and (x-176)

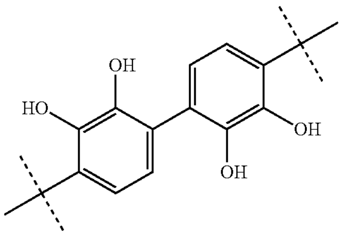

;

wherein

Y is selected from the group consisting of —O—, —S—, —$NR^{05}$—, —$CR^{05}R^{05a}$.

each —$R^{04}$, —$R^{04a}$, —$R^{04b}$, —$R^{04c}$, —$R^{05}$ and —$R^{05a}$ is independently selected from the group consisting of halogen, —H, —CN, -$T^0$, $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more —$R^{06}$, which are the same or different, and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N($R^{07}$)—, —$S(O)_2N$($R^{07}$)—, —S(O)N($R^{07}$)—, —$S(O)_2$—, —S(O)—, —N($R^{07}$)$S(O)_2N$($R^{07a}$)—, —S—, —N($R^{07}$)—, —OC($OR^{07}$)($R^{07a}$)—, —N($R^{07}$)C(O)N($R^{07a}$)—, and —OC(O)N($R^{07}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{06}$, which are the same or different; and each —$R^{06}$, —$R^{07}$ and —$R^{07a}$ is independently selected from the group consisting of —H and $C_{1-6}$ alkyl; wherein $C_{1-6}$ alkyl is optionally substituted with one or more halogen, which are the same or different.

In certain embodiments each —$X^{0B}$-, —$X^{0C}$—, —$X^{0D}$— and —$X^{0F}$— is independently a linkage selected from the group consisting of formula x-17, x-18, x-19, x-20, x-21, x-22, x-23, x-25, x-26, x-27, x-28, x-29, x-30, x-31, x-32, x-35, x-36, x-37, x-38, x-39, x-41, x-42, x-43, x-45, x-46, x-47, x-48, x-49, x-50, x-51, x-52, x-53, x-54, x-55, x-56, x-57, x-58, x-59, x-60, x-61, x-62, x-64, x-65, x-66, x-75, x-76, x-77, x-78, x-79, x-80, x-81, x-82, x-83, x-84, x-85, x-87, x-88, x-89, x-90, x-91, x-92, x-93, x-97, x-98, x-101, x-102, x-103, x-104, x-105, x-106, x-107, x-108, x-109, x-110, x-111, x-112, x-113, x-114, x-115, x-116, x-117, x-118, x-119, x-132, x-133, x-134, x-135, x-137, x-138, x-139, x-140, x-141, x-142, x-146, x-147, x-148, x-150, x-151, x-154, x-155, x-156, x-157, x-159, x-160, x-161, x-162, x-163, x-167, x-170, x-174, x-175 and x-176.

In certain embodiments each —$X^{0B}$—, —$X^{0C}$—, —$X^{0D}$— and —$X^{0F}$— is independently a linkage selected from the group consisting of formula x-17, x-18, x-21, x-22, x-23, x-26, x-28, x-29, x-31, x-32, x-36, x-37, x-38, x-41, x-42, x-43, x-45, x-47, x-48, x-49, x-50, x-51, x-52, x-53, x-54, x-56, x-57, x-59, x-60, x-61, x-62, x-64, x-65, x-66, x-75, x-77, x-79, x-80, x-81, x-82, x-83, x-87, x-88, x-89, x-90, x-91, x-92, x-93, x-97, x-98, x-101, x-102, x-103, x-104, x-111, x-112, x-113, x-132, x-133, x-134, x-135, x-137, x-138, x-139, x-140, x-141, x-142, x-146, x-147, x-148, x-150, x-151, x-154, x-155, x-156, x-157, x-159, x-160, x-161, x-162, x-163, x-167, x-170, x-174, x-175 and x-176.

In certain embodiments each $X^{0B}$—, —$X^{0C}$—, —$X^{0D}$— and —$X^{0F}$— is independently a linkage selected from the group consisting of formula x-17, x-18, x-21, x-22, x-31, x-36, x-37, x-38, x-42, x-45, x-47, x-50, x-51, x-54, x-56, x-59, x-88, x-89, x-90, x-91, x-92, x-93, x-97, x-101, x-102, x-104, x-113, x-132, x-135, x-147, x-148, x-150, x-151, x-154, x-155, x-156, x-157, x-159, x-163, x-167, x-170, x-174, x-175 and x-176.

In certain embodiments each —$X^{0B}$—, —$X^{0C}$—, —$X^{0D}$— and —$X^{0F}$— is independently a linkage selected from the group consisting of formula x-18, x-22, x-37, x-45, x-47, x-50, x-51, x-101, x-135, x-148, x-150 and x-151.

In certain embodiments —$X^{0B}$— is of formula x-18. In certain embodiments —$X^{0B}$— is of formula x-22. In certain embodiments —$X^{0B}$— is of formula x-37. In certain embodiments —$X^{0B}$— is of formula x-45. In certain embodiments —$X^{0B}$— is of formula x-47. In certain embodiments —$X^{0B}$— is of formula x-50. In certain embodiments —$X^{0B}$— is of formula x-51. In certain embodiments $X^{0B}$— is of formula x-101. In certain embodiments —$X^{0B}$— is of formula x-135. In certain embodiments —$X^{0B}$— is of formula x-148. In certain embodiments —$X^{0B}$— is of formula x-150. In certain embodiments —$X^{0B}$— is of formula x-151.

In certain embodiments —$X^{0C}$— is of formula x-18. In certain embodiments —$X^{0C}$— is of formula x-22. In certain embodiments —$X^{0C}$— is of formula x-37. In certain embodiments —$X^{0C}$— is of formula x-45. In certain embodiments —$X^{0C}$— is of formula x-47. In certain embodiments —$X^{0C}$— is of formula x-50. In certain embodiments —$X^{0C}$— is of formula x-51. In certain embodiments —$X^{0C}$— is of formula x-101. In certain embodiments —$X^{0C}$— is of formula x-135. In certain embodiments —$X^{0C}$— is of formula x-148. In certain embodiments —$X^{0C}$— is of formula x-150. In certain embodiments —$X^{0C}$— is of formula x-151.

In certain embodiments —$X^{0D}$— is of formula x-18. In certain embodiments —$X^{0D}$— is of formula x-22. In certain embodiments —$X^{0D}$— is of formula x-37. In certain embodiments —$X^{0D}$— is of formula x-45. In certain embodiments $X^{0D}$— is of formula x-47. In certain embodiments $X^{0D}$— is of formula x-50. In certain embodiments —$X^{0D}$— is of formula x-51. In certain embodiments —$X^{0D}$— is of formula x-101. In certain embodiments —$X^{0D}$— is of formula x-135. In certain embodiments —$X^{0D}$— is of formula x-148. In certain embodiments —$X^{0D}$— is of formula x-150. In certain embodiments —$X^{0D}$— is of formula x-151.

In certain embodiments —$X^{0F}$ is of formula x-18. In certain embodiments —$X^{0F}$— is of formula x-22. In certain embodiments —$X^{0F}$— is of formula x-37. In certain embodiments —$X^{0F}$— is of formula x-45. In certain embodiment —$X^{0F}$— Of formula x-47. In certain embodiments —$X^{0F}$— is of formula x-50. In certain embodiments —$X^{0F}$— is of formula x-51. In certain embodiments —$X^{0F}$— is of formula x-101. In certain embodiments —$X^{0F}$— is of formula x-135. In certain embodiments —$X^{0F}$— is of formula x-148. In certain embodiments —$X^{0F}$— is of formula x-150. In certain embodiments —$X^{0F}$— is of formula x-151.

In certain embodiments each —$Y^{0A}$, —$Y^{0B}$, —$Y^{0C}$, —$Y^{0D}$ is individually selected from the group consisting of (y-1)

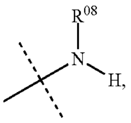

(y-2)

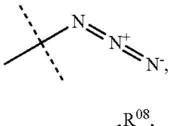

(y-3)

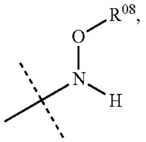

-continued (y-4)

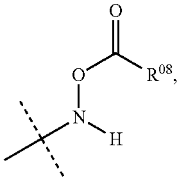

(y-5)

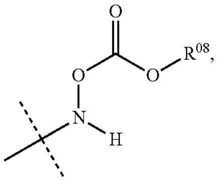

(y-6)

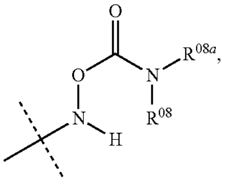

(y-7)

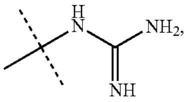

(y-8)

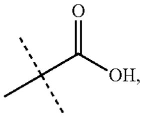

(y-9)

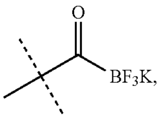

(y-10)

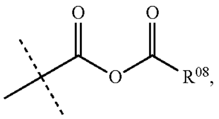

(y-11)

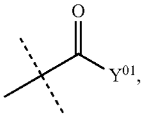

(y-12)

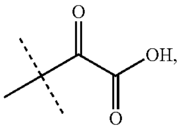

(y-13)

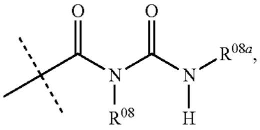

(y-14)

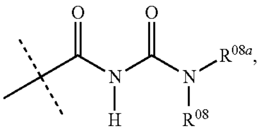

-continued
(y-15)
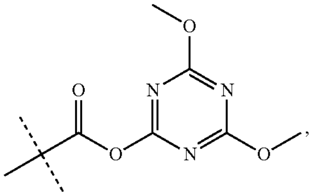
(y-16)
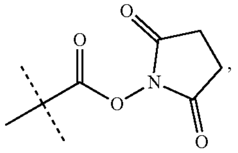
(y-17)
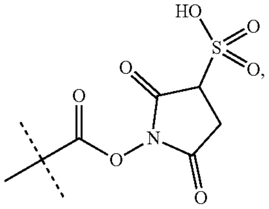
(y-18)
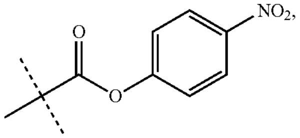
(y-19)
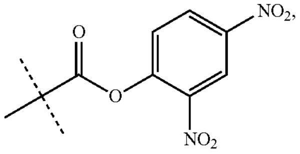
(y-20)
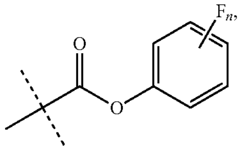
(y-21)
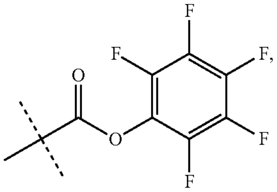
(y-22)
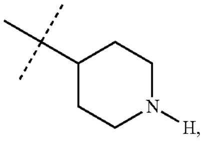
(y-22a)
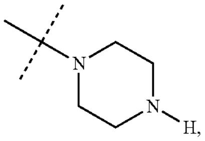
-continued
(y-23)
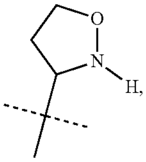
(y-24)
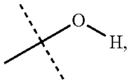
(y-25)
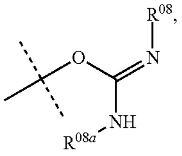
(y-26)
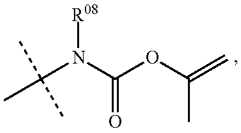
(y-27)
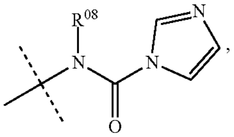
(y-28)
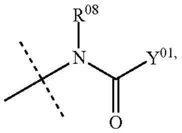
(y-29)
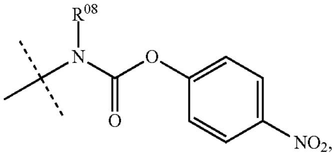
(y-30)
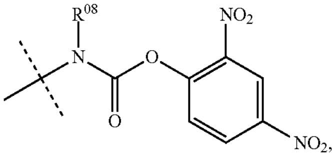
(y-31)
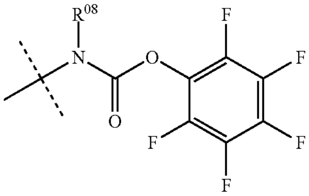
(y-32)
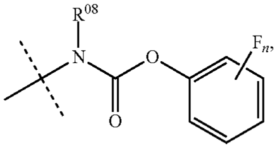

-continued
(y-33)
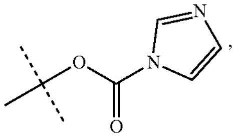
(y-34)
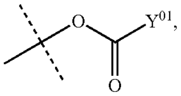
(y-35)
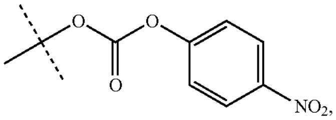
(y-36)
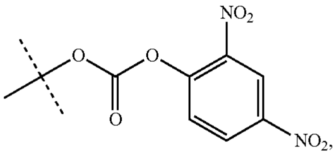
(y-37)
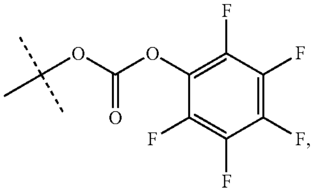
(y-38)
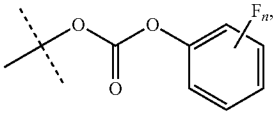
(y-39)
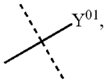
(y-40)
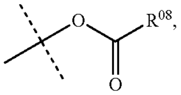
(y-41)
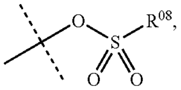
(y-42)
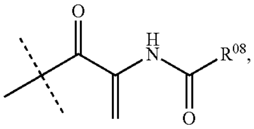
(y-43)
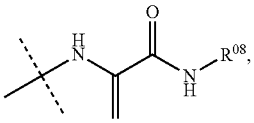
(y-44)
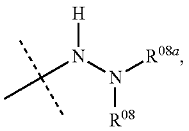
-continued
(y-45)
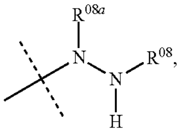
(y-46)
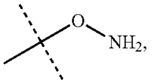
(y-47)
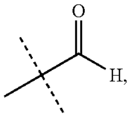
(y-48)
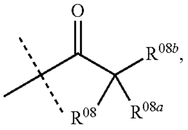
(y-49)
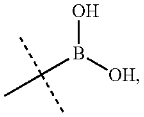
(y-50)
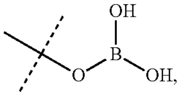
(y-51)
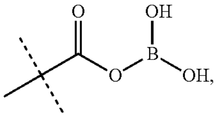
(y-52)
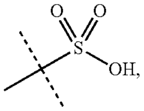
(y-53)
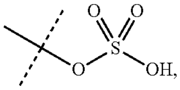
(y-54)
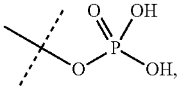
(y-55)
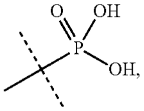
(y-56)
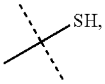
(y-57)
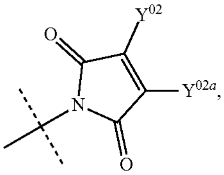

-continued
(y-58)
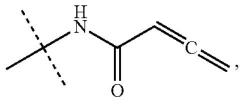
(y-59)
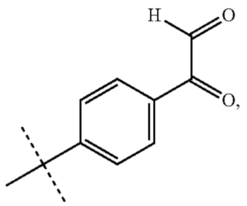
(y-60)
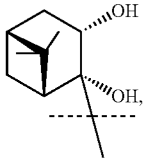
(y-61)
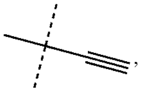
(y-62)
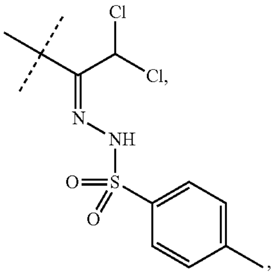
(y-63)
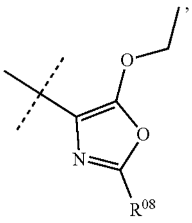
(y-64)
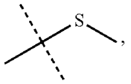
(y-65)
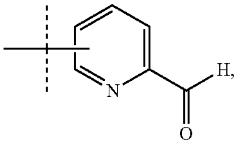
(y-66)
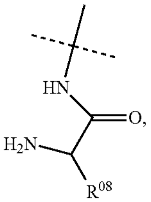
-continued
(y-67)
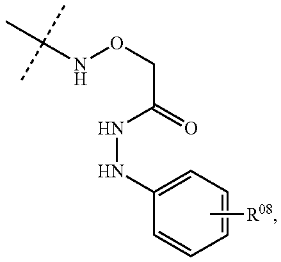
(y-68)
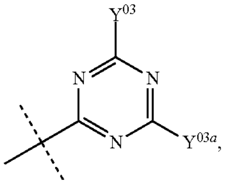
(y-69)
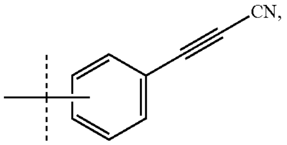
(y-70)
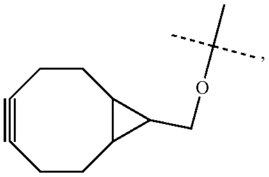
(y-71)
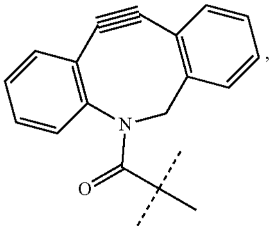
(y-72)
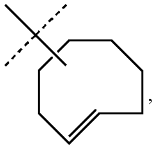
(y-73)
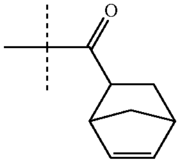
(y-74)
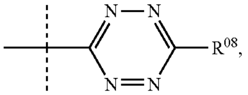

-continued (y-75)

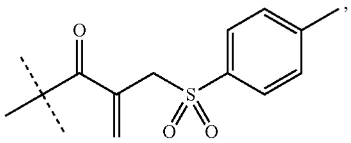

(y-76)

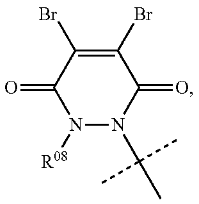

(y-77)

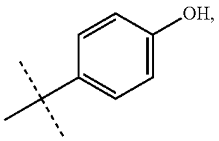

(y-78)

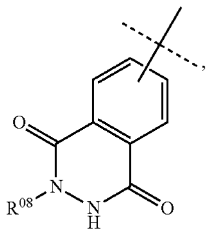

(y-79)

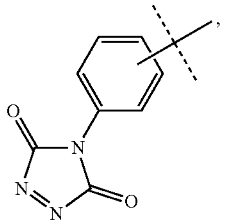

(y-80)

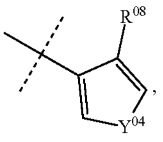

(y-81)

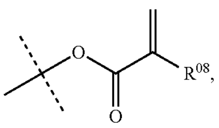

(y-82)

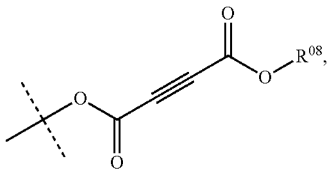

-continued (y-83)

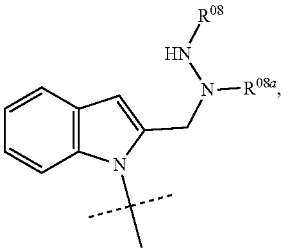

(y-84)

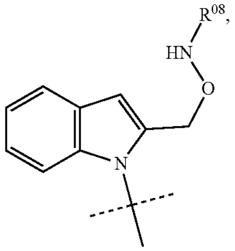

(y-85)

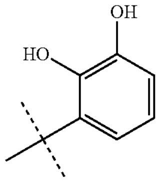

and (y-86)

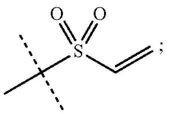

wherein each —$R^{08}$, —$R^{08a}$ and —$R^{08b}$ is independently selected from the group consisting of halogen, —H, —CN, -$T^0$, $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more —$R^{09}$, which are the same or different, and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N($R^{010}$)—, —$S(O)_2N(R^{010})$—, —S(O)N($R^{010}$)—, —$S(O)_2$—, —S(O)—, —$N(R^{101})S(O)_2N(R^{010a})$—, —S—, —N($R^{010}$)—, —OC($OR^{010}$)($R^{101a}$)—, —N($R^{010}$)C(O)N($R^{010a}$)—, and —OC(O)N($R^{010}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{09}$, which are the same or different;

each —$R^{09}$, —$R^{010}$ and —$R^{010a}$ is independently selected from the group consisting of —H and $C_{1-6}$ alkyl; wherein $C_{1-6}$ alkyl is optionally substituted with one or more halogen, which are the same or different;

each $T^y$ is independently a ring comprising 5, 6 or 7 atoms of which at least one is a heteroatom;

each —$Y^{01}$ is independently selected from the group consisting of —F, —Cl, —Br and —I;

each n is independently 1, 2, 3 or 4;

each —$Y^{02}$ and —$Y^{02a}$ is independently selected from the group consisting of —H and —Br;

each —$Y^{03}$ and —$Y^{03a}$ is independently selected from the group consisting of —F, —Cl, —Br, —I, —OR, —$NR^{011}R^{011a}$ and —$SR^{011}$;

each —$Y^{04}$— is independently selected from —O—, —S—, —$NR^{011}$—, —$C^{011}R^{011a}$—; and each —$R^{011}$ and —$R^{011a}$ is independently selected from the group consisting of halogen, —H, —CN, -$T^0$, $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more —$R^{012}$, which are the same or different, and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N($R^{013}$)—, —$S(O)_2N(R^{013})$—, —S(O)N($R^{013}$)—, —$S(O)_2$—, —S(O)—, —N($R^{013}$)$S(O)_2N(R^{013a})$—, —S—, —N($R^{013}$), —OC($OR^{013}$)($R^{013a}$)—, —N($R^{013}$)C(O)N($R^{013a}$)— and —OC(O)N($R^{013}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{012}$, which are the same or different; and each —$R^{12}$, —$R^{013}$ and —$R^{013a}$ is independently selected from the group consisting of —H and $C_{1-6}$ alkyl; wherein $C_{1-6}$ alkyl is optionally substituted with one or more halogen, which are the same or different.

In certain embodiments each —$Y^{0a}$, —$Y^{0B}$, —$Y^{0C}$, —$Y^{0D}$ and $Y^{0E}$ is independently a functional group selected from the group consisting of formula y-1, y-2, y-3, y-7, y-8, y-9, y-10, y-11, y-12, y-13, y-14, y-15, y-16, y-17, y-18, y-21, y-22, y-22a, y-23, y-24, y-27, y-28, y-29, y-31, y-33, y-35, y-37, y-39, y-40, y-41, y-42, y-43, y-45, y-46, y-47, y-49, y-52, y-53, y-54, y-55, y-56, y-57, y-59, y-61, y-62, y-64, y-70, y-71, y-72, y-73, y-74, y-77, y-79, y-80, y-85 and y-86.

In certain embodiments each —$Y^{0A}$—, —$Y^{0B}$, —$Y^{0C}$, —$Y^{0D}$ and —$Y^{0E}$ is independently a functional group selected from the group consisting of formula y-1, y-2, y-3, y-7, y-8, y-9, y-12, y-13, y-14, y-15, y-16, y-17, y-18, y-21, y-22, y-22a, y-23, y-24, y-27, y-28, y-29, y-31, y-39, y-45, y-46, y-47, y-52, y-53, y-54, y-55, y-56, y-57, y-59, y-61, y-68, y-70, y-71, y-72, y-73, y-74, y-77, y-79, y-80, y-85 and y-86.

In certain embodiments each —$Y^{0A}$—, —$Y^{0B}$, —$Y^{0C}$, —$Y^{0D}$ and —$Y^{0E}$ is independently a functional group selected from the group consisting of formula y-1, y-2, y-7, y-8, y-9, y-13, y-14, y-15, y-16, y-21, y-22, y-22a, y-24, y-39, y-56, y-57, y-60, y-70, y-71 and y-86.

In certain embodiments each —$Y^{0A}$—, —$Y^{0B}$, —$Y^{0C}$, —$Y^{0D}$ and —$Y^{0E}$ is independently a functional group selected from the group consisting of formula y-1, y-2, y-8, y-9, y-13, y-14, y-16, y-22, y-22a, y-39, y-56, y-57, y-61, y-70, y-71 and y-86.

In certain embodiments each —$Y^{0A}$—, —$Y^{0B}$, —$Y^{0C}$, —$Y^{0D}$ and —$Y^{0E}$ is independently a functional group selected from the group consisting of formula y-1, y-2, y-8, y-9, y-16, y-22, y-22a, y-39, y-56, y-57, y-61, y-70, y-71 and y-86.

In certain embodiments —$Y^{0A}$ is of formula y-1. In certain embodiments —$Y^{0A}$ is of formula y-2. In certain embodiments —$Y^{0A}$ is of formula y-8. In certain embodiments —$Y^{0A}$ is of formula y-9. In certain embodiments —$Y^{0A}$ is of formula y-16. In certain embodiments —$Y^{0A}$ is of formula y-22. In certain embodiments —$Y^{0A}$ is of formula y-22a. In certain embodiments —$Y^{0A}$ is of formula y-39. In certain embodiments —$Y^{0A}$ is of formula y-56. In certain embodiments —$Y^{0A}$ is of formula y-57. In certain embodiments —$Y^{0A}$ is of formula y-61. In certain embodiments —$Y^{0A}$ is of formula y-70. In certain embodiments —$Y^{0A}$ is of formula y-71. In certain embodiments —$Y^{0A}$ is of formula y-86.

In certain embodiments —$Y^{0B}$ is of formula y-1. In certain embodiments —$Y^{0B}$ is of formula y-2. In certain embodiments —$Y^{0B}$ is of formula y-8. In certain embodiments —$Y^{0B}$ is of formula y-9. In certain embodiments —$Y^{0B}$ is of formula y-16. In certain embodiments —$Y^{0B}$ is of formula y-22. In certain embodiments —$Y^{0B}$ is of formula y-22a. In certain embodiments —$Y^{0B}$ is of formula y-39. In certain embodiments —$Y^{0B}$ is of formula y-56. In certain embodiments —$Y^{0B}$ is of formula y-57. In certain embodiments —$Y^{0B}$ is of formula y-61. In certain embodiments —$Y^{0B}$ is of formula y-70. In certain embodiments —$Y^{0B}$ is of formula y-71. In certain embodiments —$Y^{0B}$ is of formula y-86.

In certain embodiments —$Y^{0C}$ is of formula y-1. In certain embodiments —$Y^{0C}$ is of formula y-2. In certain embodiments —$Y^{0C}$ is of formula y-8. In certain embodiments —$Y^{0C}$ is of formula y-9. In certain embodiments —$Y^{0C}$ is of formula y-16. In certain embodiments —$Y^{0C}$ is of formula y-22. In certain embodiments —$Y^{0C}$ is of formula y-22a. In certain embodiments —$Y^{0C}$ is of formula y-39. In certain embodiments —$Y^{0C}$ is of formula y-56. In certain embodiments —$Y^{0C}$ is of formula y-57. In certain embodiments —$Y^{0C}$ is of formula y-61. In certain embodiments —$Y^{0C}$ is of formula y-70. In certain embodiments —$Y^{0C}$ is of formula y-71. In certain embodiments —$Y^{0C}$ is of formula y-86.

In certain embodiments —$Y^{0D}$ is of formula y-1. In certain embodiments —$Y^{0D}$ is of formula y-2. In certain embodiments —$Y^{0D}$ is of formula y-8. In certain embodiments —$Y^{0D}$ is of formula y-9. In certain embodiments —$Y^{0D}$ is of formula y-16. In certain embodiments —$Y^{0D}$ is of formula y-22. In certain embodiments —$Y^{0D}$ is of formula y-22a. In certain embodiments —$Y^{0D}$ is of formula y-39. In certain embodiments —$Y^{0D}$ is of formula y-56. In certain embodiments —$Y^{0D}$ is of formula y-57. In certain embodiments —$Y^{0D}$ is of formula y-61. In certain embodiments —$Y^{0D}$ is of formula y-70. In certain embodiments —$Y^{0D}$ is of formula y-71. In certain embodiments —$Y^{0D}$ is of formula y-86.

In certain embodiments —$Y^{0E}$ is of formula y-1. In certain embodiment is of formula y-2. In certain embodiments —$Y^{0E}$ is of formula y-8. In certain embodiments —$Y^{0E}$ is of formula y-9. In certain embodiments —$Y^{0E}$ is of formula y-16. In certain embodiments —$Y^{0E}$ is of formula y-22. In certain embodiments —$Y^{0E}$ is of formula y-22a. In certain embodiments —$Y^{0E}$ is of formula y-39. In certain embodiments —$Y^{0F}$ is of formula y-56. In certain embodiments —$Y^{0E}$ is of formula y-57. In certain embodiments —$Y^{0E}$ is of formula y-61. In certain embodiments —$Y^{0E}$ is of formula y-70. In certain embodiments —$Y^{0E}$ is of formula y-71. In certain embodiments —$Y^{0E}$ is of formula y-86.

In certain embodiments —$Y^{0F}$ is selected from the group consisting of (y-87)

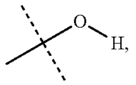

-continued (y-88)

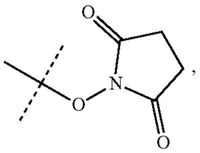

(y-89)

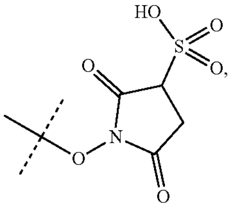

(y-90)

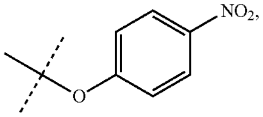

(y-91)

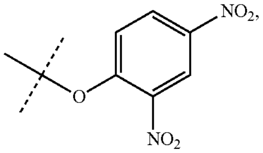

(y-92)

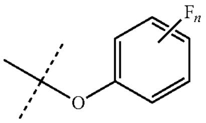

and (y-93)

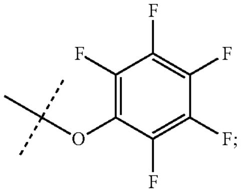

wherein each n is independently 1, 2, 3, or 4.

In certain embodiments each —$Y^{0F}$ is independently a functional group selected from the group consisting of formula y-87, y-88, y-89, y-90 and y-91.

In certain embodiments each —$Y^{0F}$ is independently a functional group selected from the group consisting of formula y-87, y-88 and y-93.

In certain embodiments all —$Y^{0F}$ present in the conjugates of the present invention are of formula y-87. In certain embodiments all —$Y^{0F}$ present in the conjugates of the present invention are of formula y-88. In certain embodiments all —$Y^{0F}$ present in the conjugates of the present invention are of formula y-93.

In certain embodiments each —$Y^{0F}$ is independently a functional group selected from the group consisting of formula y-87 and y-88.

Each —$Y^{0H}$ is independently selected from the group consisting of (y'-1)

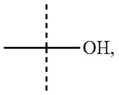

(y'-2)

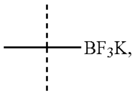

(y'-3)

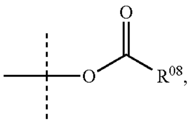

(y'-4)

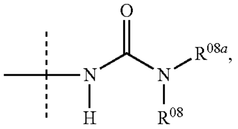

(y'-5)

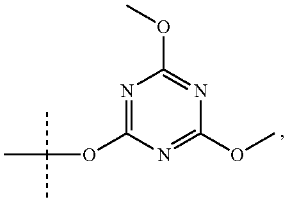

(y'-6)

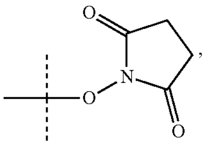

(y'-7)

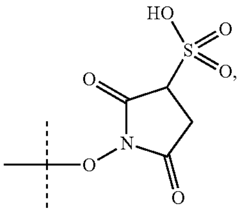

(y'-8)

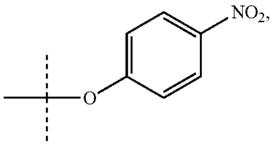

(y'-9)

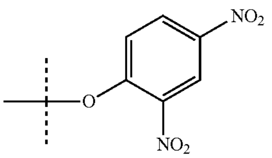

and (y'-10)

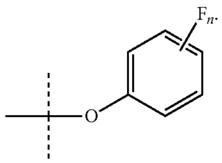

In certain embodiments —$Y^{0H}$ is of formula y'-1. In certain embodiments —$Y^{0H}$ is of formula y'-2. In certain embodiments —$Y^{0H}$ is of formula y'-3. In certain embodiments —$Y^{0H}$ is of formula y'-4. In certain embodiments —$Y^{0H}$ is of formula y'-5. In certain embodiments —$Y^{0H}$ is of formula y'-6. In certain embodiments —Y is of formula y'-7. In certain embodiments —$Y^{0H}$ of of formula y'-8. In certain embodiments —$Y^{0H}$ is of formula y'-9. In certain embodiments —$Y^{0H}$ is of formula y'-10.

The moieties -D present in the conjugates of the present invention may be identical or different.

-D is a drug moiety that is covalently and reversibly conjugated to -$L^1$-. -D may be selected from the group consisting of peptides, proteins, oligonucleotides and small molecule drug moieties. In certain embodiments -D is a peptide drug moiety. In certain embodiments -D is a protein drug moiety. In certain embodiments -D is an oligonucleotide drug moiety. In certain embodiments -D is a small molecule drug moiety. In certain embodiments -D is a peptide or protein.

In one embodiment all moieties -D of a conjugate are identical. In another embodiment the conjugate comprises more than one type of -D, i.e. two or more different types of -D, such as two different types of -D, three different types of -D, four different types of -D or five different types of -D.

If the conjugates of the present comprise more than one type of -D, all moieties -D may be connected to the same type of -$L^1$- or may be connected to different types of -$L^1$-, i.e. a first type of -D may be connected to a first type of -$L^1$-, a second type of -D may be connected to a second type of -$L^1$- and so on. Using different types of -$L^1$- may in certain embodiments allow different release kinetics for different types of -D, such as for example a faster release for a first type of -D, a medium release for a second type of -D and a slow release for a third type of -D. Accordingly, in certain embodiments the conjugates of the present invention comprise one type of -$L^1$-. In certain embodiments the conjugates of the present invention comprise two types of -$L^1$-. In certain embodiments the conjugates of the present invention comprise three types of -$L^1$-. In certain embodiments the conjugates of the present invention comprise four types of -$L^1$-.

In certain embodiments the conjugates of the present invention comprise one type of -D and one type of -$L^1$-. In certain embodiments the conjugates of the present invention comprise two types of -D and two types of -$L^1$-. In certain embodiments the conjugates of the present invention comprise three types of -D and three types of -$L^1$-. In certain embodiments the conjugates of the present invention comprise four types of -D and four types of -$L^1$-. In certain embodiments the conjugates of the present invention comprise two types of -D and one type of -$L^1$-, i.e. both types of drug are released with the same release kinetics. In certain embodiments the conjugates of the present invention comprise three types of -D and one type of -$L^1$-. Alternatively, the conjugates of the present invention may comprise one type of -D, but more than one type of -$L^1$-, such as two, three or four types of -$L^1$-. This allows the combination of different release kinetics for the same drug, such as a quick initial boost obtained from a moiety -$L^1$- with a short release half-life, followed by a sustained release from a moiety -$L^1$- with a long release half-life.

The moiety -$L^1$- is conjugated to -D via a functional group of -D, which functional group is in certain embodiments selected from the group consisting of carboxylic acid, primary amine, secondary amine, thiol, sulfonic acid, carbonate, carbamate, hydroxyl, aldehyde, ketone, hydrazine, isothiocyanate, phosphoric acid, phosphonic acid, acryloyl, hydroxylamine, sulfate, vinyl sulfone, vinyl ketone, diazoalkane, guanidine, aziridine, amide, imide, imine, urea, amidine, guanidine, sulfonamide, phosphonamide, phorphoramide, hydrazide and selenol. In certain embodiments -$L^1$- is conjugated to -D via a functional group of -D selected from the group consisting of carboxylic acid, primary amine, secondary amine, thiol, sulfonic acid, carbonate, carbamate, hydroxyl, aldehyde, ketone, hydrazine, isothiocyanate, phosphoric acid, phosphonic acid, acryloyl, hydroxylamine, sulfate, vinyl sulfone, vinyl ketone, diazoalkane, guanidine, amidine and aziridine. In certain embodiments -$L^1$- is conjugated to -D via a functional group of -D selected from the group consisting of hydroxyl, primary amine, secondary amine, amidine, thiol and carboxylic acid.

In certain embodiments -$L^1$- is conjugated to -D via a hydroxyl group of -D.

In certain embodiments -$L^1$- is conjugated to -D via a primary amine group of -D.

In certain embodiments -$L^1$- is conjugated to -D via a secondary amine group of -D.

In certain embodiments -$L^1$- is conjugated to -D via a carboxylic acid group of -D.

In certain embodiments -$L^1$- is conjugated to -D via an amidine group of -D.

The moiety -$L^1$- may be connected to -D through any type of linkage, provided that it is reversible. In certain embodiments -$L^1$- is connected to -D through a linkage selected from the group consisting of amide, ester, carbamate, acetal, aminal, imine, oxime, hydrazine, disulfide, acylguanidine, acylamidine, carbonate, phosphate, sulfate, urea, hydrazide, thioester, thiophosphate, thiosulfate, sulfonamide, sulfoamidine, sulfaguanidine, phosphoramide, phosphoamidine, phosphoguanidine, phosphonamide, phosphonamidine, phosphonguanidine, phosphonate, borate and imide. In certain embodiments -$L^1$- is connected to -D through a linkage selected from the group consisting of amide, ester, carbonate, carbamate, acetal, aminal, imine, oxime, hydrazine, disulfide, acylamidine and acylguanidine. In certain embodiments -$L^1$- is connected to -D through a linkage selected from the group consisting of amide, ester, carbonate, acylamide and carbamate. It is understood that some of these linkages may not be reversible per se, but that in the present invention neighboring groups comprised in -$L^1$- render these linkages reversible.

In certain embodiments -$L^1$- is connected to -D through an ester linkage. In certain embodiments -$L^1$- is connected to -D through a carbonate linkage. In certain embodiments -$L^1$- is connected to -D through an acylamidine linkage. In certain embodiments -$L^1$- is connected to -D through a carbamate linkage. In certain embodiments -$L^1$- is connected to -D through an amide linkage.

In certain embodiments -D is an antibiotic moiety, for example an antibiotic selected from the group consisting of aminoglycosides, tetracycline antibiotics, amphenicols, pleuromutilins, macrolid antibiotics, lincosamides, steroid antibiotics, antifolate antibiotics, sulfonamides, topoisomerase inhibitors, quinolones, fluoroquinolones, nitroimidazole antibiotics, nitrofuran antibiotics, rifamycins, glycopeptides, penicillins, cephalosporins, monobactams, beta-lactamase inhibitors, polymyxin antibiotics, lipopeptide antibiotics, oxazolidinon, antimicrobial peptides, antimicrobial proteins, porphyrins, azole antifungals, polyenes, antiprotozoal drugs, fosfomycin, cycloserine, and bacitracin.

In certain embodiments -D is an aminoglycoside, such as an aminoglycoside selected from the group consisting of streptomycin, dihydrostreptomycin, neomycin, paromomycin, amikacin, kanamycin, tobramycin, spectinomycin, hygromycin b, gentamicin, plazomicin, verdamicin, netilmicin, astromicin and sisomicin. In certain embodiments -D is amikacin. In certain embodiments -D is kanamycin. In certain embodiments -D is tobramycin. In certain embodiments -D is gentamicin. In another embodiment -D is plazomicin.

In certain embodiments -D is a tetracycline antibiotic, such as a tetracycline antibiotic selected from the group consisting of doxycycline, chloretetracycline, tetracycline, metacycline, minocycline, oxytetracycline and glycocyclines, such as a glycocyclines selected from the group consisting of tigecycline, omadacycline and sarecycline. In certain embodiments -D tetracycline. In certain embodiments -D is minocycline. In certain embodiments -D is oxytetracycline. In certain embodiments -D is tigecycline. In certain embodiments -D is omadacycline. In another embodiment -D is sarecycline.

In certain embodiments -D is an amphenicol, such as an amphenicol selected from the group consisting of chloramphenicol, thiamphenicol, azidamfenicol and florfenicol.

In certain embodiments -D is a pleuromutilin, such as a pleuromutilin selected from the group consisting of azamulin, lefamulin, tiamulin and valnemulin.

In certain embodiments -D is a macrolid antibiotic, such as a macrolid antibiotic selected from the group consisting of azithromycin, boromycin, clarithromycin, oleandomycin, erythromycin, roxithromycin, spiramycin, telithromycin and tylosine.

In certain embodiments -D is a lincosamide, such as a lincosamide selected from the group consisting of clindamycin and lincomycin. In certain embodiments -D is clindamycin.

In certain embodiments -D is a steroid antibiotic, such as fusidic acid.

In certain embodiments -D is an antifolate antibiotic, such as an antifolate antibiotic selected from the group consisting of trimethoprim and iclaprim.

In certain embodiments -D is a sulfonamide, such as a sulfonamide selected from the group consisting of sufathiazole, sulfamethoxazole, sulfadiazine and sulfamerazine.

In certain embodiments -D is a topoisomerase inhibitor, such as a topoisomerase inhibitor selected from the group consisting of flumequine, nalidixic acid, oxolinic acid and pipemidic acid. In certain embodiments -D is nalidixic acid.

In certain embodiments -D is a quinolone or fluroquinolone, such as a quinolone or fluroquinolone selected from the group consisting of nemonoxacin, ciprofloxacin, ofloxacin, norfloxacin, pefloxacin, levofloxacin, sparfloxacin, moxifloxacin, gatifloxacin, difloxacin, enrofloxacin, marbofloxacin, delafloxacin and nemonovobiocin. In certain embodiments -D is ciprofloxacin. In certain embodiments -D is levofloxacin. In certain embodiments -D is delafloxacin.

In certain embodiments -D is a nitroimidazole antibiotic, such as metronidazole.

In certain embodiments -D is a nitrofuran antibiotic, such as a nitrofuran antibiotic selected from the group consisting of nitrofurantoin and furazolidone.

In certain embodiments -D is a rifamycin, such as rifampicin.

In certain embodiments -D is a glycopeptide, such as a glycoprotein selected from the group consisting of vancomycin, oritavancin, telavancin, dalbavancin and teicoplanin. In certain embodiments -D is vancomycin. In certain embodiments -D is oritavancin. In certain embodiments -D is telavancin. In another embodiment -D is dalbavancin.

In certain embodiments -D is a penicillin, such as a penicillin selected from the group consisting of penams, penems and carbapenems. In certain embodiments such penams are selected from the group consisting of amoxicillin, ampicillin, carbenicillin, ticarcillin, temocillin, aziocillin, piperacillin, mezlocillin, mecillinam, benzylpenicillin, cloxacillin, dicloxacillin, flucloxacillin, oxacillin, methicillin and nafcillin. In certain embodiments such penems and carbapenes are selected from the group consisting of faropenem, ertapenem, doripenem, thiopenem, sulopenem, imipenem and meropenem. In certain embodiments -D is imipenem. In another embodiment -D is meropenem.

In certain embodiments -D is a cephalosporin, such as a cephalosporin selected from the group consisting of cefazolin, cefadroxil, cefradine, cefaclor, cefamandole, cefminox, cefotiam, cefprozil, cefuroxime, cefoxitin, cefotetan, cefmetazole, cefixime, ceftriaxone, ceftazidime, cefoperazone, cefpodoxime, cefdinir, cefditoren, cefotaxime, cefsulodin, cefteram, ceftibuten, ceftizoxime, cefepime, cefozopran, cefpirome, ceftaroline and ceftobiprole. In certain embodiments -D is cefazolin. In certain embodiments -D is cephalexin. In certain embodiments -D is ceftaroline. In certain embodiments -D is ceftobiprole. Cepholosporins are also known as cephamycins.

In certain embodiments -D is a monobactam, such as aztreonam.

In certain embodiments -D is a beta-lactamase inhibitor, such as a beta-lactamase inhibitor selected from the group consisting of sulbactam, tazobactam, clavulanic acid and cefdinir.

In certain embodiments -D is a polymycin antibiotic, such as a polymcin antibiotic selected from the group consisting of colistin and polymyxin B. In certain embodiments -D is colistin. In certain embodiments -D is polymyxin B.

In certain embodiments -D is a lipopeptide antibiotic, such as a lipopeptide antibiotic selected from the group consisting of daptomycin, arylomycins and gramicidin. In certain embodiments -D is daptomycin. Daptomycin has the following chemical structure

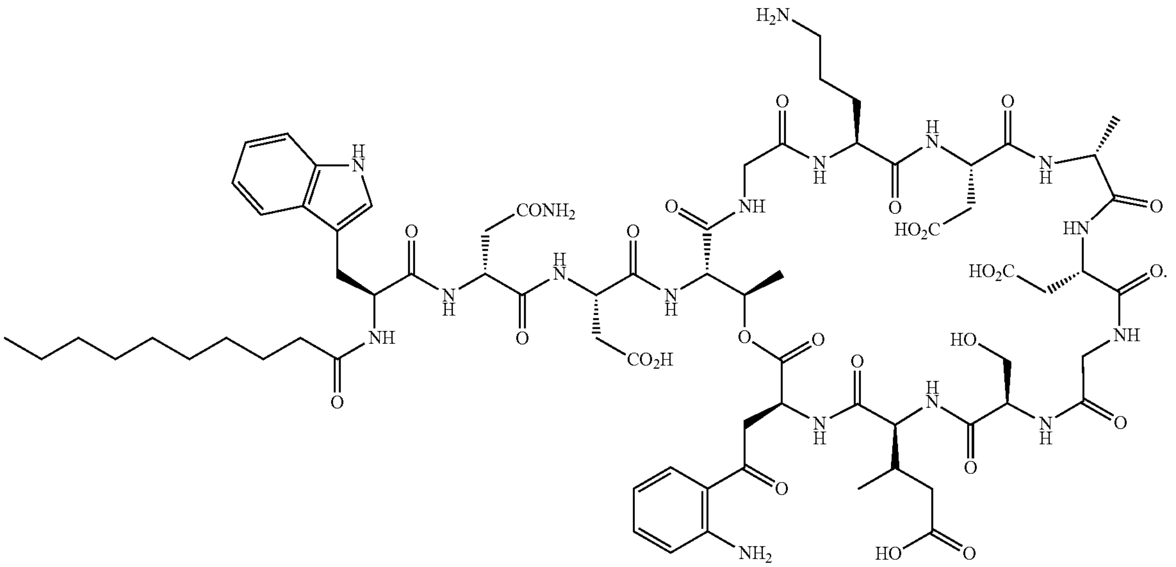 [SMILES: CCCCCCCCCC(=O)N[C@@H](Cc1c[nH]c2ccccc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H](C(C)CC(=O)O)C(=O)N[C@@H](CC(=O)c2ccccc2N)C(=O)O[C@@H]1C]

In certain embodiments -D is an oxazolidinon, such as an oxazolidinon selected from the group consisting of linezolid, tedizolid, esperezolid, posizolid, radezolid, sutezolid and cadazolid. In certain embodiments -D is tedizolid.

In certain embodiments -D is an antimicrobial peptide, such as an antimicrobial peptide selected from the group consisting of cationic amphipathic peptides (CAP) and host defense proteins (HDP). In certain embodiments such CAP is selected from the group consisting of omiganan pentahydrochloride and novispirin g-10. In certain embodiments such HDP is brilacidin.

In certain embodiments -D is an antimicrobial protein, such as lysins.

In certain embodiments -D is a porphyrin, such as exeporfinium chloride.

In certain embodiments -D is an azole antifungal, such as an azole antifungal selected from the group consisting of fluconazole, isavuconazonium sulfate, posaconazole, itraconazole, voriconazole, albaconazole and miconazole. In certain embodiments -D is fluconazole. In certain embodiments -D is voriconazole. In certain embodiments -D is albaconazole.

In certain embodiments -D is a polyene, such as a polyene selected from the group consisting of amphotericin, echinocandins, flucytosine, tavaborole and triterpinoids. In certain embodiments an echinocandin is selected from the group consisting of caspofungin, micafungin, anidulafungin, cilofungin and rezafungin. In certain embodiments -D is amphotericin. In certain embodiments -D is caspofungin. In certain embodiments -D is micafungin. In certain embodiments -D is anidulafungin. In certain embodiments -D is cilofungin. In certain embodiments -D is rezafungin.

In certain embodiments -D is an antiprotozoal drug moiety, such as an antiprotozoal drug moiety selected from the list comprising eflornithine, furazolidone, melarsoprol, nifursemizone, ornidazole, pentamidine, pyrimethamine, quinapyramine, tinidazole, chlorproguanil, proguanil, atovaquone, dehydroemetine, diloxanide, eflomithine, halofantrine, lumefantrine, mepacrine, miltefosine, nitazoxanide, tizoxanide, pyronaridine, suramin, amodiaquine, chloroquine, hydroxychloroquine, primaquine, pamaquine, tafenoquine, mefloquine, artemether, artemisinin, artemotil, artesunate and dihydroartemisinin.

If the conjugate comprises more than one type of -D, one such combination may be a beta-lactamase inhibitor and an antibiotic selected from the group consisting of penicillins, cephalosporins and monobactam antibiotics. Accordingly, in certain embodiments the conjugates of the present invention may comprise a beta-lactamase inhibitor and a penicillin. In certain embodiments the conjugates of the present invention may comprise a beta-lactamase inhibitor and a cephalosporin. In certain embodiments the conjugates of the present invention may comprise a beta-lactamase inhibitor and a monobactam antibiotic.

If -D is daptomycin, $-L^1-$ is in certain embodiments connected via the primary amine of the ornithine side chain. In certain embodiments such daptomycin is connected to $-L^1-$ via the primary amine of the ornithine side chain via an amide linkage.

In certain embodiments -D is a pattern recognition receptor agonist ("PRRA"). Such PRRA may for example be selected from the group consisting of Toll-like receptor (TLR) agonists, NOD-like receptors (NLRs), RIG-I-like receptors, cytosolic DNA sensors, STING, and aryl hydrocarbon receptors (AhR).

In certain embodiments -D is a Toll-like receptor agonist. In certain embodiments -D is a NOD-like receptor. In certain embodiments -D is a RIG-I-like receptor. In certain embodiments -D is a cytosolic DNA sensor. In certain embodiments -D is a STING. In certain embodiments -D is an aryl hydrocarbon receptor.

If -D is a Toll-like receptor agonist, such Toll-like receptor agonists may be selected from the group consisting of agonists of TLR1/2, such as peptidoglycans, lipoproteins, Pam3CSK4, Amplivant, SLP-AMPLIVANT, HESPECTA, ISA101 and ISA201; agonists of TLR2, such as LAM-MS, LPS-PG, LTA-BS, LTA-SA, PGN-BS, PGN-EB, PGN-EK, PGN-SA, CL429, FSL-1, Pam2CSK4, Pam3CSK4, zymosan, CBLB612, SV-283, ISA204, SMP105, heat killed *Listeria monocytogenes*; agonists of TLR3, such as poly(A:U), poly(I:C) (poly-ICLC), rintatolimod, apoxxim, IPH3102, poly-ICR, PRV300, RGCL2, RGIC.1, Riboxxim (RGC100, RGIC100), Riboxxol (RGIC50) and Riboxxon; agonists of TLR4, such as lipopolysaccharides (LPS), neoceptin-3, glucopyranosyl lipid adjuvant (GLA), GLA-SE, G100, GLA-AF, clinical center reference endotoxin (CCRE), monophosphoryl lipid A, grass MATA MPL, PEPA10, ONT-10 (PET-Lipid A, oncothyreon), G-305, ALD046, CRX527, CRX675 (RC527, RC590), GSK1795091, OM197MPAC, OM294DP and SAR439794; agonists of TLR2/4, such as lipid A, OM174 and PGN007; agonists of TLR5, such as flagellin, entolimod, mobilan, protectan CBLB501; agonists of TLR6/2, such as diacylated lipoproteins, diacylated lipopeptides, FSL-1, MALP-2 and CBLB613; agonists of TLR7, such as CL264, CL307, imiquimod (R837), TMX-101, TMX-201, TMX-202, TMX302, gardiquimod, S-27609, 851, UC-IV150, 852A (3M-001, PF-04878691), loxoribine, polyuridylic acid, GSK2245035, GS-9620, RO6864018 (ANA773, RG7795), R07020531, isatoribine, AN0331, ANA245, ANA971, ANA975, DSP0509, DSP3025 (AZD8848), GS986, MBS2, MBS5, RG7863 (RO6870868), sotirimod, SZU101 and TQA3334; agonists of TLR8, such as ssPolyUridine, ssRNA40, TL8-506, XG-1-236, VTX-2337 (motolimod), VTX-1463, VTX378, VTX763, DN1508052 and GS9688; agonists of TLR7/8, such as CL075, CL097, poly(dT), resiquimod (R-848, VML600, S28463), MED19197 (3M-052), NKTR262, DV1001, IM04200, IPH3201 and VTX1463; agonists of TLR9, such as CpG DNA, CpG ODN, lefitolimod (MGN1703), SD-101, QbG10, CYT003, CYT003-QbG10, DUK-CpG-001, CpG-7909 (PF-3512676), GNKG168, EMD 1201081, IMO-2125, IMO-2055, CpG10104, AZD1419, AST008, IM02134, MGN1706, IRS 954, 1018 ISS, actilon (CPG10101), ATP00001, AVE0675, AVE7279, CMP001, DIMS0001, DIMS9022, DIMS9054, DIMS9059, DV230, DV281, EnanDIM, heplisav (V270), kappaproct (DIMS0150), NJP834, NPI503, SAR21609 and tolamba; and agonists of TLR7/9, such as DV1179.

In certain embodiments -D is an agonist of TLR1/2. In certain embodiments -D is an agonist of TLR2. In certain embodiments -D is an agonist of TLR3. In certain embodiments -D is an agonist of TLR4. In certain embodiments -D is an agonist of TLR2/4. In certain embodiments -D is an agonist of TLR5. In certain embodiment -D is an agonist of TLR6/2. In certain embodiments -D is an agonist of TLR7. In certain embodiments -D is an agonist of TLR8. In certain embodiments -D is an agonist of TLR7/8. In certain embodiments -D is an agonist of TLR9.

Examples for CpG ODN are ODN 1585, ODN 2216, ODN 2336, ODN 1668, ODN 1826, ODN 2006, ODN 2007, ODN BW006, ODN D-SLO1, ODN 2395, ODN M362 and ODN D-SL03.

In certain embodiments at least some moieties -D of the conjugate are imiquimod, such as about 10%, about 20%, about 30%, about 40%, about 50%, about 60%, about 70%, about 80%, about 90% or 100% of all moieties -D present in the conjugate. In certain embodiments at least some moieties -D of the conjugate are resiquimod, such as about 10%, about 20%, about 30%, about 40%, about 50%, about 60%, about 70%, about 80%, about 90% or 100% of all moieties -D present in the conjugate. In certain embodiments at least some moieties -D of the conjugate are SD-101, such as about 10%, about 20%, about 30%, about 40%, about 50%, about 60%, about 70%, about 80%, about 90% or 100% of all moieties -D present in the conjugate. In certain embodiments at least some moieties -D of the conjugate are CMP001, such as about 10%, about 20%, about 30%, about 40%, about 50%, about 60%, about 70%, about 80%, about 90% or 100% of all moieties -D present in the conjugate.

If -D is a NOD-like receptor, such NOD-like receptor may be selected from the group consisting of agonists of NOD1, such as C12-iE-DAP, C14-Tri-LAN-Gly, iE-DAP, iE-Lys, and Tri-DAP; and agonists of NOD2, such as L18-MDP, MDP, M-TriLYS, murabutide and N-glycolyl-MDP.

In certain embodiments -D is an agonist of NOD1. In certain embodiments -D is an agonist of NOD2.

If -D is a RIG-I-like receptor, such RIG-I-like receptor may be selected from the group consisting of 3p-hpRNA, 5'ppp-dsRNA, 5'ppp RNA (M8), 5'OH RNA with kink (CBS-13-BPS), 5'PPP SLR, KIN100, KIN 101, KIN1000, KIN1400, KIN1408, KIN1409, KIN1148, KIN131A, poly (dA:dT), SB9200, RGT100 and hiltonol.

If -D is a cytosolic DNA sensor, such cytosolic DNA sensor may be selected from the group consisting of cGAS agonists, dsDNA-EC, G3-YSD, HSV-60, ISD, ODN TTAGGG (A151), poly(dG:dC) and VACV-70.

If -D is a STING, such STING may be selected from the group consisting of MK-1454, ADU-S100 (MIW815), 2'3'-cGAMP, 3'3'-cGAMP, c-di-AMP, c-di-GMP, cAIMP (CL592), cAIMP difluor (CL614), cAIM(PS)2 difluor (Rp/Sp) (CL656), 2'2'-cGAMP, 2'3'-cGAM(PS)2 (Rp/Sp), 3'3'-cGAM fluorinated, c-di-AMP fluorinated, 2'3'-c-di-AMP, 2'3'-c-di-AM(PS)2 (Rp,Rp), c-di-GMP fluorinated, 2'3'-c-di-GMP, c-di-IMP, c-di-UMP and DMXAA (vadimezan, ASA404).

In certain embodiments -D is MK-1454. In certain embodiments -D is ADU-S100 (MIW815). In certain embodiments -D is 2'3'-cGAMP.

If -D is an aryl hydrocarbon receptor (AhR), such AhR may be selected from the group consisting of FICZ, ITE and L-kynurenine.

In certain embodiments -D is selected from the group consisting of a biocidal molecule, a cytotoxic agent, a chemotherapeutic agent, an anti-hormonal agent, a radioisotope, a photosensitizer, an enzyme, a hormone, an antibody, an interleukin, an immune stimulatory molecule, an immune suppressing molecule, and a DNA-damaging agent. It is understood that a conjugate of the present invention may comprise a combination of two or more such drugs.

In one embodiment -D is a cytotoxic agent that inhibits or prevents the function of cells and/or causes destruction of cells. Examples of cytotoxic agents include chemotherapeutic agents and toxins, such as small molecule toxins or enzymatically active toxins of bacterial, fungal, plant or animal origin, including synthetic analogues and derivatives thereof. The cytotoxic agent may be selected from the group consisting of an auristatin, a DNA minor groove binding agent, a DNA minor groove alkylating agent, a tubulin disruptor, an enediyne, a lexitropsin, a duocarmycin, a taxane, anthracyclines, a puromycin, a dolastatin, a maytansinoid and a vinca alkaloid or a combination of two or more thereof. It is understood that a conjugate of the present invention may comprise a combination of two or more such drugs.

In one embodiment -D is a chemotherapeutic agent selected from the group consisting of a topoisomerase inhibitor; an alkylating agent, such as a nitrogen mustard; an ethylenime; an alkylsulfonate; a triazene; a piperazine; a nitrosurea; an antimetabolite, such as mercaptopurine, thioguanine or 5-fluorouracil; an antibiotic, such as an anthracycline, dactinomycin, bleomycin, adriamycin, mithramycin or dactinomycin; a mitotic disrupter, such as a plant alkaloid, such as vincristine and/or a microtubule antagonist such as paclitaxel; a DNA intercalating agent, such as carboplatin and/or cisplatin; a DNA synthesis inhibitor; a DNA-RNA transcription regulator; an enzyme inhibitor; a gene regulator; a hormone response modifier; a hypoxia-selective cytotoxin, such as tirapazamine; an epidermal growth factor inhibitor; an anti-vascular agent such as xanthenone 5,6-dimethylxanthenone-4-acetic acid; a radiation-activated prodrug, such as nitroarylmethyl quaternary (NMQ) salts; and a bioreductive drug. It is understood that a conjugate of the present invention may comprise a combination of two or more such drugs.

The chemotherapeutic agent may be selected from the group consisting of Erlotinib (TARCEVA®), Bortezomib (VELCADE®), Fulvestrant (FASLODEX®), Sunitinib (Sutent®), Letrozole (FEMARA®), Anastrozole (Arimidex®), Imatinib mesylate (GLEEVEC®), Vatalanib (PTK787/ZK 222584), Oxaliplatin (Eloxatin®), 5-FU (5-fluorouracil), Leucovorin, Rapamycin (Sirolimus, RAPAMUNE®), Everolimus (Afinitor®), Lapatinib (Tykerb/Tyverb®), Lonafamib (SCH 66336), Sorafenib (Nexavar®), and Gefitinib (IRESSA®), AG1478, AG1571 (SU 5271; Sugen). It is understood that a conjugate of the present invention may comprise a combination of two or more such chemotherapeutic agents.

The chemotherapeutic agent may be an alkylating agent such as thiotepa, CYTOXAN® and/or cyclosphosphamide; an alkyl sulfonate, such as busulfan, improsulfan and/or piposulfan; an aziridine, such as benzodopa, carboquone, meturedopa and/or uredopa; ethylenimines and/or methylamelamines, such as altretamine, triethylenemelamine, triethylenepbosphoramide, triethylenethiophosphoramide and/or trimethylomelamine; acetogenin, such as bullatacin and/or bullatacinone; camptothecin; bryostatin; callystatin; cryptophycins; dolastatin; duocarmycin; eleutherobin; pancratistatin; sarcodictyin; spongistatin; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide and/or uracil mustard; nitrosureas, such as carmustine, chlorozotocin, fotemustine, lomustine, nimustine, and/or ranimnustine; dynemicin; bisphosphonates, such as clodronate; an esperamicin; a neocarzinostatin chromophore; aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN®, doxorubicin, such as morpholino-doxorubicin, cyanomorpholino-doxorubicin, 2-pyrrolino-doxorubicin, deoxydoxorubicin, epirubicin, esorubicin, idarubicin, marcellomycin, mitomycins, such as mitomycin C; mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogues, such as fludarabine, 6-mercaptopurine, thiamiprine, thioguanine; pyrimidine analogues, such as ancitabine, azacitidine, 6-azauridine, carmofur, cytarabine, dideoxyuridine, doxifluridine, enocitabine, floxuridine; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; macrocyclic depsipeptides, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofiran; spirogermanium; tenuazonic acid; triaziquone; 2,2',2"-trichlorotriethylamine; trichothecenes, such as verracurin A, roridin A and/or anguidine; urethan; vindesine; dacarbazine; mannomustine; mitobronitol; mitolactol; pipobroman; gacytosine; arabinoside; cyclophosphamide; thiotepa; taxoids such as TAXOL®, paclitaxel, abraxane, and/or TAXOTERE®, doxetaxel; chloranbucil; GEMZAR®, gemcitabine; 6-thioguanine; mercaptopurine; methotrexate; platinum analogues, such as cisplatin and carboplatin; vinblastine; platinum; etoposide; ifosfamide; mitoxantrone; vincristine; NAVELBINE®, vinorelbine; novantrone; teniposide; edatrexate; daunomycin; aminopterin; xeloda; ibandronate; topoisomerase inhibitor RFS 2000; difluoromethylomithine (DMFO); retinoids, such as retinoic acid; capecitabine; and pharmaceutically acceptable salts, acids; and derivatives thereof. It is understood that a conjugate of the present invention may comprise a combination of two or more such chemotherapeutic agents.

-D may be a tubulin disruptor, such as a taxane, such as paclitaxel and docetaxel, vinca alkaloids, discodermolide, epothilones A and B, desoxyepothilone, cryptophycins, curacin A, combretastatin A-4-phosphate, BMS 247550, BMS 184476, BMS 188791; RPR 109881A, EPO 906, TXD 258, ZD 6126, vinflunine, LU 103793, dolastatin 10, monomethyl auristatin E (MMAE), monomethyl auristatin F (MMAF), E7010, T138067 and T900607, colchicine, phenstatin, chalcones, indanocine, oncocidin, vincristine, vinblastine, vinorelbine, vinflunine, halichondrin B, isohomohalichondrin B, ER-86526, pironetin, spongistatin 1, spiket P, cryptophycin 1, LU103793 (cematodin or cemadotin), rhizoxin, sarcodictyin, eleutherobin, laulilamide, VP-16 and D-24851 and pharmaceutically acceptable salts, acids, derivatives and combinations of two or more of any of the above. The drug may also be a drug that drug that inhibits cyclin-dependent kinases (CDKs), such as Dinaciclib (SCH-727965).

-D may be a DNA intercalator, such as an acridine, actinomycin, anthracycline, benzothiopyranoindazole, pixantrone, crisnatol, brostallicin, CI-958, doxorubicin (adriamycin), actinomycin D, daunorubicin (daunomycin), bleomycin, idarubicin, mitoxantrone, cyclophosphamide, melphalan, mitomycin C, bizelesin, etoposide, mitoxantrone, SN-38, carboplatin, cis-platin, actinomycin D, amsacrine, DACA, pyrazoloacridine, irinotecan and topotecan and pharmaceutically acceptable salts, acids, derivatives or combinations of two or more of any of the above.

-D may be an anti-hormonal agent that acts to regulate or inhibit hormone action on tumors, such as an anti-estrogen or selective estrogen receptor modulator, including tamoxifen, raloxifene, droloxifene, 4-hydroxytamoxifen, trioxifene, keoxifene, LYl 17018, onapristone, and/or fareston toremifene and pharmaceutically acceptable salts, acids, derivatives or combinations of two or more of any of the above.

-D may be an aromatase inhibitor that inhibits the enzyme aromatase, which regulates estrogen production in the adrenal glands such as, for example, 4(5)-imidazoles, aminoglutethimide, megestrol acetate, AROMASIN®, exemestane, formestanie, fadrozole, RIVISOR®, vorozole, FEMARA®, letrozole, ARIMIDEX® and/or anastrozole and pharmaceutically acceptable salts, acids, derivatives or combinations of two or more of any of the above.

-D may be an anti-androgen such as flutamide, nilutamide, bicalutamide, leuprolide, goserelin, triptorelin and/or troxacitabine, abiraterone, enzalutamide and pharmaceutically acceptable salts, acids, derivatives or combinations of two or more of any of the above.

-D may be a protein kinase inhibitor, a lipid kinase inhibitor or an anti-angiogenic agent. Exemplary kinase inhibitors are Lapatinib, AZD-2171, ET180CH Indirubin-3'-oxime, NSC-154020, PD 169316, Quercetin, Roscovitine, Triciribine, ZD 1839, 5-Iodotubercidin, Adaphostin, Aloisine, Alsterpaullone, Aminogenistein, API-2, Apigenin, Arctigenin, ARRY-334543, Axitinib (AG-013736), AY-22989, AZD-2171 Bisindolylmaleimide IX, CC1-779, Chelerythrine, DMPQ, DRB, Edelfosine, ENMD-981693, Erbstatin analog, Erlotinib, Fasudil, Gefitinib (ZD1839), H-7, H-8, H-89, HA-100, HA-1004, HA-1077, HA-1100, Hydroxyfasudil, Kenpaullone, KN-62, KY 12420, LFM-A13, Luteolin, LY294002, Mallotoxin, ML-9, MLN608, NSC 226080, NSC-231634, NSC-664704, NSC-680410, NU6102, Olomoucine, Oxindole I, PD153035, PD98059, Phloridzin, Piceatannol, Picropodophyllin, PKI, PP1, PP2, PTK787/ZK222584, Purvalanol A, Rapamune, Rapamycin, Ro 31-8220, Rottlerin, SB202190, SB203580, Sirolimus, SL327, SP600 125, Staurosporine, STI-571, SU1498, SU4312, SU5416, SU5416 (Semaxanib), SU6656, SU6668, syk inhibitor, TBB, TCN, Tyrphostin AG 1024, Tyrphostin AG 490, Tyrphostin AG 825, Tyrphostin AG 957, U0126, W-7, Wortmannin, Y-27632, Zactima (ZD6474), and ZM 252868. Approved TKIs for cancer therapy include, for example, Sorafenib and Sunitinib. KIs currently under clinical investigation for use in anti-cancer therapies and/or novel indications are, for example, MK0457, VX-680, ZD6474, MLN8054, AZD2171, SNS-032, PTK787/ZK222584, Sorafinib (BAY43-9006), SU5416, SU6668 AMG706, Zactima (ZD6474), MP-412, Dasatinib, CEP-701 (Lestaurtinib), XL647, XL999, Tykerb (Lapatinib), MLN518 (formerly known as CT53518), PKC412, ST1571, AMN107, AEE788, OSI-930, OSI-817, Sunitinib maleate (Sutent SU11248), Vatalanib (PTK787/ZK 222584), SNS-032, SNS-314 and Axitinib (AG-013736). Gefitinib and Erlotinib are two orally available EGFR-TKIS. Thus, in certain embodiments the kinase inhibitor is a tyrosine kinase inhibitor, such as a multi-kinase inhibitor. A "multi-kinase inhibitor" is an inhibitor that acts on more than one specific kinase. Multi-kinase inhibitors are for example the so-called DGF out-binders, such as imatinib, sorafenib, lapatinib, BIRB-796 and AZD-1152. Other multi-kinase inhibitors are AMG706, Zactima (ZD6474), MP-412, Sorafenib (BAY 43-9006), dasatinib, CEP-701 (lestaurtinib), XL647, XL999, Tykerb (lapatinib), MLN518 (formerly known as CT53518), PKC412, ST1571, AEE788, OSI-930, OSI-817, Sutent (sunitinib maleate), axitinib (AG-013736), erlotinib, gefitinib, lenvatinib, temsirolismus and nilotinib AMN107. In certain embodiments such multi-kinase inhibitor is selected from the group consisting of Sunitinib, axitinib, lenvatinib and/or Sorafenib or a pharmaceutically acceptable salt or derivative, such as for example a malate or a tosylate thereof. The term "derivative" refers to a chemical modification still retaining kinase inhibitory function of the parent molecule. Examples for derivatives are disclosed e.g. in the patent applications mentioned below. Sunitinib targets multiple receptor tyrosine kinase inhibitors, including PDGFR, KIT and VEGFR, and is a potent and selective anti-angiogenesis agent. Sunitinib or its L-malate salt is also referred to as SU 11248, SUO11248, Sunitinib malate (USAN/WHO designation) or SUTENT (L-malate salt).

In certain embodiments -D is a VEGF neutralizing prodrug selected from the groupconsisting of antisense RNA, antisense DNA, ribozymes or RNAi molecules targeting a VEGF nucleic acid; anti-VEGF aptamers, anti-VEGF antibodies, anti-VEGF antibody fragments, DARPins and soluble VEGF receptor decoys that prevent binding of a VEGF to its cognate receptor; antisense, ribozymes, and RNAi molecules targeting a cognate VEGF receptor (VEGFR) nucleic acid; anti-VEGFR aptamers or anti-VEGFR antibodies that bind to a cognate VEGFR receptor; anti-VEGFR antibody fragments that bind to a cognate VEGFR receptor and VEGFR tyrosine kinase inhibitors.

Such VEGF neutralizing prodrug may be selected from the group consisting of ranibizumab, bevacizumab, pegaptanib, aflibercept, MP0112, KH902, ESBA1008, AL 39324, ALG-1001, and bevasiranib and/or fragments thereof.

In certain embodiments -D is a CTLA-4 pathway-inhibiting amount of an anti-CTLA-4 antibody or a PD-1 pathway-inhibiting amount of an anti-PD-1/anti-PD-L1 antibody. With regard to anti-PD-1 and anti-PD-L1 antibodies, these are known and include nivolumab and pembrolizumab, AMP-224, atezolizumab, durvalumab, avelumab, cemiplimab, tremelimumab and ipilimumab.

Such antibodies (or fragments thereof) are antagonistic for immune-checkpoint function. Many such antibodies are known in the art, such as pembrolizumab (MK-3475, Merck), nivolumab (BM1S936558, Bristol-Myers Squibb), pidilizumab (CT-011, Cure Tech Ltd.), AMP-224 (Merck), MDX-1105 (Medarex), MEDI4736 (MedImmune), atezolizumab (MPDL3280A) (Genentech), avelumab (Merck KGaA/Pfizer), BMS-936559 (Bristol-Myers Squibb), ipilimumab (Bristol-Myers Squibb), durvalumab (Astrazeneca) and tremelimumab (Pfizer). Anti-KIR antibodies such as lirlumab (Innate Pharma) and IPH2101 (Innate Pharma) may perform similar functions in NK cells.

Assays for determining whether a given compound can act as an anti-CTLA-4 antibody, anti-PD-L1 antibody or anti-PD-1 antibody can be determined through routing experimentation by one of ordinary skill in the art.

In alternative embodiments, combination with an antibody-drug conjugate (ADC) may be desired. ADCs are particularly effective for reducing tumor burden without significant systemic toxicity and may act to improve the effectiveness of the immune response induced by checkpoint inhibitor antibodies. Exemplary ADCs approved for therapeutic use include gemtuzumab ozogamicin for AML, brentuximab vedotin, inotuzumab ozogamicin, trastuzumab emtansine. Numerous other candidate ADCs are currently in clinical testing, such as glembatumomab vedotin, SAR3419, SAR56658, AMG-172, AMG-595, BAY-94-9343, BIIB015, BT062, SGN-75, SGN-CD19A, vorsetuzumab mafodotin, ABT-414, ASG-5ME, ASG-22ME, ASG-16M8F, IMGN-529, IMGN-853, MDX-1203, MLN-0264, RG-7450, RG-7458, RG-7593, RG-7596, RG-7598, RG-7599, RG-7600, RG-7636, anti-PSMA ADC, lorvotuzumab mertansine, milatuzumab-doxorubicin, IMMU-130 and IMMU-132.

In certain embodiments -D a radionuclide such as radioisotopes of technetium, indium, yttrium, copper, lutetium or rhenium.

-D may be an antibody that may be used for cancer therapy, such as hA19 (anti -CD19, U.S. Pat. No. 7,109,304), hRl (anti-IGF-1R, U.S. Pat. No. 9,441,043), hPAM4 (anti-MUC5ac, U.S. Pat. No. 7,282,567), hA20 (anti-CD20, U.S. Pat. No. 7,151,164), hIMMU31 (anti-AFP, U.S. Pat. No. 7,300,655), hLLI (anti-CD74, U.S. Pat. No. 7,312,318), hLL2 (anti-CD22, U.S. Pat. No. 5,789,554), hMu-9 (anti-CSAP, U.S. Pat. No. 7,387,772), hL243 (anti-HLA-DR, U.S. Pat. No. 7,612,180), hMN-14 (anti-CEACAMS, U.S. Pat. No. 6,676,924), HMN 15 (anti-CEACAM6, U.S. Pat. No.

8,287,865), hRS7 (anti EGP-1, U.S. Pat. No. 7,238,785), hMN-3 (anti-CEACAM, U.S. Pat. No. 7,541,440), Ab124 and Ab125 (anti-CXCR4, U.S. Pat. No. 7,138,496). The Examples section of each cited patent or application are incorporated herein by reference. The antibodies may be of various isotypes, such as human IgG1, IgG2, IgG3 or IgG4, or may comprise human IgG1 hinge and constant region sequences. The antibodies or fragments thereof may be chimeric human-mouse, humanized (human framework and murine hypervariable (CDR) regions), or fully human, as well as variations thereof, such as half-IgG4 antibodies (referred to as "unibodies"), as described by van der Neut Kolfschoten et al. (Science 2007; 317: 1554-1557). In certain embodiments the antibodies or fragments thereof may be designed or selected to comprise human constant region sequences that belong to specific allotypes, which may result in reduced immunogenicity when administered to a human subject. Preferred allotypes for administration include a non-Glm1 allotype (nGlm1), such as Glm3, Glm3, 1, Glm3,2 or Glm3,1,2. More preferably, the allotype is selected from the group consisting of the nGlm1, Glm3, nGlm1,2 and Km3 allotypes. Combination therapy with immunostimulatory antibodies has been reported to enhance efficacy, for example against tumor cells. Morales—Kastresana et al. (2013, Clin Cancer Res 19: 6151-62) showed that the combination of anti-PD-1 (10B5) antibody with anti-CD137 (108) and anti-OX40 (OX86) antibodies provided enhanced efficacy in a transgenic mouse model of hepatocellular carcinoma. Alternative antibodies that may be used for -D may be abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), pembrolizumab (anti-PD-1 receptor), nivolumab (anti-PD-1 receptor), ipilimumab (anti-CTLA-4), abagovomab (anti CA-125), adecatumumab (anti-EpCAM), atlizumab (anti IL-6 receptor), benralizumab (anti-CD125), obinutuzumab (GA101, anti-CD20), CC49 (anti-TAG-72), AB-PG1-XG1026 (anti-PSMA), $D^2$/B (anti-PSMA), tocilizumab (anti-IL-6 receptor), basiliximab (anti-CD25), daclizumab (anti-CD25), efalizumab (anti-CD11a), GA101 (anti-CD20), atalizumab (anti-alpha 4 integrin), omalizumab (anti-IgE); anti-TNF-alpha antibodies such as anti-transforming growth factor-beta, anti-colony stimulating factor -1 receptor (CSF1-R) Ab, CDP571, MTNFAI, M2TNFAI, M3TNFAI, M3TNFABI, M302B, M303, infliximab, certolizumab pegol, anti-CD40L, adalimumab, BENLYSTA; anti-CD38 antibodies such as MORO3087, MOR202, HuMax-CD38 or daratumumab. These checkpoint inhibitors may be administered in combination with one or more other immunomodulators to enhance the immune response. An immunomodulator may be selected from the group consisting of a cytokine, a chemokine, a stem cell growth factor, a lymphotoxin, an hematopoietic factor, a colony stimulating factor (CSF), erythropoietin, thrombopoietin, tumor necrosis factor-alpha (TNF), TNF-beta, granulocyte-colony stimulating factor (G-CSF), granulocyte macrophage-colony stimulating factor (GM-CSF), interferon-alpha, interferon-beta, interferon-gamma, interferon-lambda, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrins, NGF-beta, platelet-growth factor, TGF-alpha, TGF-beta, insulin-like growth factor-I, insulin like growth factor-II, macrophage-CSF (M-CSF), IL-1, IL-lalpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, LIF, FLT-3, angiostatin, thrombospondin, endostatin, and lymphotoxin.

Examples of antibodies also include fragments thereof and also include bispecific antibodies, Bi-specific T-cell Engager (BiTE), Dual-Affinity Re-Targeting (DART) and nanobodies, such as those described for example in U.S. Pat. No. 8,907,065, WO2017087589A2, and WO2017087588A1, which are herewith incorporated by reference.

-D may be a RIG-I agonist, such as the RIG-I agonists KIN700, KIN1148, KIN600, KIN500, KIN100, KIN101, KIN400, KIN2000, RGT100 or SB-9200.

-D may also be an MDA-5 agonist, such as MDA-5 agonists nucleic acid band 2 (NAB2) or poly(I:C).

-D may also be a NOD1 or NOD2 agonist, such as iE-DAP or MDP, respectively.

-D may also be a TLR1 agonist, a TLR2 agonist, a TLR3 agonist, a TLR4 agonist, a TLR5 agonist, a TLR6 agonist, a TLR7 agonist, a TLR8 agonist, a TLR9 agonist, or a TLR10 agonist. The drug can be selected from a group consisting of S-27609, CL307, UC IV150, imiquimod, gardiquimod, resiquimod, motolimod, Rintatolimod, VTS-1463GS-9620, GSK224.5035, TMX-101, TMX-201, TMX-202, isatoribine, AZD8848, MEDI9197, 3M-051, 3M-852, 3M-052, 3M-854A, S-34240, KU34B, CL663, CBLB612, CBLB613, MALP2S, OPN305, OM174, SMP105, MCT475, Apoxxim®, RGIC®100, RGIC®50, G100 Glucopyranosyl lipid, GSK1795091, IM08400, Loxoribine, Agatolimod, IM02125, Lefitolimod, SD101, Litenimod, CMP001, IM02055, AST008, DV281 or GNKG168.

-D may be a STING activator comprising one or more cyclic dinucleotides include, but are not limited to, one or more of c-di-AMP, c-di-GMP, c-di-IMP, c-AMP-GMP, c-AMP-IMP, c-GMP-IMP and analogs thereof. The drug can be selected from a group consisting of ADU-S100, MK-1454, SRCB-0001, SB11285 or GSK53.

-D may also be selected from the group consisting of antibodies, nanobodies, and ligands targeting immunomodulatory receptors, such as Lag-3, Tim-3, TIGIT, GITR, CD28, CD40, ICOS, ILT2 (PMID: 29123965), ILT3 (PMID: 30126665), ILT4 (PMID: 29649510), MARCO (PMID: 27210762), LAIR1 (PMID: 25915125), BAG3). -D may be selected from a group consisting of relatlimab (BMS-986016), AVA017, B1754111, ENUM006, GSK2831781, IKT2013, IMP761, INCAGN2385, LAG525, MK4280, REGN3767, Sym016, Sym022, TSR033, TSR075, XmAB22841, BGB-A425, ENUM005, IMM1802, INCAGN2390, LY3321367, MBG453, Sym016, Sym023. MK7684, AB154, AGEN1307, BMS986207, CASC674, COM902, ENUM009, EOS884448, NB6253, OMP313M32, Tiragolumab (RG6058). MS-986156, AMG228, AVA018, CK302, FPA154, GITRL-Fc, GWN323, INCAGN1876, JNJ64164711, LKZ145, MEDI1873, MK1248, MK4166, TRX518, ADC1013, APX005M, CD40 Agonist, CD40 Ligand CELLDEX, CDX1140, CGEN40, ChiLob 7/4, DNP005, HCD122 (lucatumumab), MEDI5083, Mega CD40L, SEACD40, SGN40

(dacetuzumab), JTX2011, HP-F1 anti-ILT2/CD85j blocking antibody (IgG1) and TRX385.

Additionally, -D may be a modulator of tumor metabolism, such as a drug inhibiting the adenosine pathway (anti-CD73 antibodies or nanobodies, adenosine receptor agonists or antagonists), tryptophan metabolism (IDO, TDO, and IDO/TDO dual inhibitors), or arginine pathway (arginase or arginase inhibitors). -D may be selected from a group consisting of but not limited to IPH53, SRF373, IB-MECA, Cl-IB-MECA, TP455, and PBF-509.

-D may also be a small molecule drug, antibody or nanobody targeting chemokines and chemokine receptors. Examples of chemokines or chemokine receptors that can be targeted are CXCL1, CXCL2, CXCL3, CXCL5, CXCL6, CXCL7, CXCL8, CCR2, CCR4, CCR5, CCR10, CXCR2, and CXCR4. -D may be selected from the group consisting of AT008, HGS004, PRO140, CXCR2 monoclonal antibodies, 515H7 monoclonal antibody PIERRE FABRE, AT007, AT009, and CXCR4 monoclonal antibody NORTHWEST.

In certain embodiments D-H or D-OH is a drug that modulates the activity of one or more protein(s) selected from the group comprising basic fibroblast growth factors (bFGF), acidic fibroblast growth factors (aFGF), transforming growth factors alpha (TGFa), transforming growth factors beta (TGF$), platelet-derived growth factor (PDGF), angiogenin, platelet-derived endothelial cell growth factor (PD-ECGF), interleukin-1 (IL-1), interleukin-8 (IL-8), interleukin-12, vascular endothelial growth factor (VEGF), angiopoietin-I, Del-I, follistatin, granulocyte colony-stimulating factor (G-CSF), hepatocyte growth factor (HGF), leptin, midkine, placental growth factor, pleiotrophin (PTN), progranulin, proliferin, tumor necrosis factor-alpha (TNF-alpha), angioarrestin, angiostatin plasminogen fragment, antiangiogenic anti-thrombin III, cartilage-derived inhibitor (CDI), CDS9 complement fragment, endostatin collagen XVIII fragment, fibronectin fragment, gro-beta, heparinases, heparin hexasaccharide fragment, human chorionic gonadotropin (hCG), interferon alpha/beta/gamma, interferon inducible protein (IP-IO), kringle S plasminogen fragment, metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), retinoids, tetrahydrocortisol-S, thrombospondin-I (TSP-I), vasculostatin, vasostatin calreticulin fragment, prostaglandin receptor, insulin-like growth factor-I (IGF-I), sphingosine-1-phosphate, factor D, RTP801, inhibitors of complement, α2 adrenergic agonist, mTOR, ciliary neurotrophic factor (CNTF), brain-derived neurotrophic factor (BDNF), glial cell-derived neurotrophic factor (GDNF), lens epithelium derived growth factor (LEDGF), rod-derived cone viability factor (RdCVF), pigment epithelium-derived factor (PEDF), neutrophil-activating protein, monocyte chemoattractant protein, macrophage-inflammatory protein, small inducible secreted (SIS) proteins, platelet factor, platelet basic protein, melanoma growth stimulating activity, epidermal growth factor, nerve growth factor, bone morphogenic proteins, bone growth cartilage-inducing factor, interleukins, interleukin inhibitors, interleukin receptors, hematopoietic factors, granulocyte colony stimulating factor, macrophage colony stimulating factor, granulocyte-macrophage colony stimulating factor, inhibin, and activing. In some aspects -D is a VEGF antagonist.

In certain embodiments -D may be an antibody moiety. Any suitable antibody (e.g., anti-VEGF antibody) may be used. For example, the antibody may specifically bind to an antigen selected from the group consisting of VEGF; interleukin-1 beta (IL-1β); interleukin-6 (IL-6); interleukin-6 receptor (IL-6R); interleukin-13 (IL-13); IL-13 receptor (IL-13R); PDGF (e.g., PDGF-BB); angiopoietin; angiopoietin 2 (Ang2); Tie2; SIP; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, membrane-bound VEGF-receptor (mbVEGFR), or soluble VEGF receptor (sVEGFR)); ST-2 receptor; and a protein genetically linked to age-related macular degeneration (AMD) risk (e.g., complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A). Such antibodies can be useful, for example, for reducing angiogenesis and/or for treating or delaying the progression of a disorder associated with pathological angiogenesis (e.g., ocular disorders or cell proliferative disorders).

In certain embodiments -D may be an anti VEGF antibody or fragment thereof. The anti VEGF antibody fragment may be, for example, be selected from Fab, Fab-C, Fab'-SH, Fv, scFv, and $(Fab')_2$ fragments.

In certain embodiments, the antibody may be G6.31 AARR or a variant thereof as described in U.S. Pat. No. 10,072,075 and International Application No. PCT/US2018/023857, the disclosures of which are incorporated herein by reference. In such embodiments, the antibody may be, for example, G6.31 AARR expressed in Fab format, or a variant version of G6.31 AARR that lacks reactivity to anti-human IgG.

In certain embodiments -D is a TKI moiety.

In certain embodiments -D is selected from the group consisting of receptor tyrosine kinase inhibitors, intracellular kinase inhibitors, cyclin dependent kinase inhibitors, phosphoinositide-3-kinase (PI3K) inhibitors, mitogen-activated protein kinase inhibitors, inhibitors of nuclear factor kappa-β kinase (IKK), and Wee-1 inhibitors.

In certain embodiments -D is a receptor tyrosine kinase inhibitor. Examples for such receptor tyrosine kinase inhibitors are EGF receptor inhibitors, VEGF receptor inhibitors, C-KIT Receptor inhibitors, ERBB2 (HER2) inhibitors, ERBB3 receptor inhibitors, FGF receptor inhibitors, AXL receptor inhibitors and MET receptor inhibitors.

In certain embodiments -D is an EGF receptor inhibitor, such as afatinib, cetuximab, erlotinib, gefitinib, pertuzumab and margetuximab.

In certain embodiments -D is a VEGF receptor inhibitor, such as axitinib, lenvatinib, pegaptanib and linifanib (ABT-869). In certain embodiments -D is axitinib. In certain embodiments -D is lenvatinib.

In certain embodiments -D is a C-KIT Receptor inhibitor such as CDX0158 (KTN0158).

In certain embodiments -D is an ERBB2 (HER2) inhibitor, such as herceptin (trastuzumab).

In certain embodiments -D is an ERBB3 receptor inhibitor, such as CDX3379 (MEDI3379, KTN3379) and AZD8931 (sapitinib).

In certain embodiments -D is an FGF receptor inhibitor such as erdafitinib.

In certain embodiments -D is an AXL receptor inhibitor such as BGB324 (BGB 324, R 428, R428, bemcentinib) and SLC391.

In certain embodiments -D is a MET receptor inhibitor, such as CGEN241 or tivantinib. In certain embodiments -D is tivantinib.

In certain embodiments -D is an intracellular kinase inhibitor. Examples for such intracellular kinase inhibitors are Bruton's tyrosine kinase (BTK) inhibitors, spleen tyrosine kinase inhibitors, Bcr-Abl tyrosine kinase inhibitors, Janus kinase inhibitors and multi-specific tyrosine kinase inhibitors.

In certain embodiments -D is a BTK inhibitor, such as ibrutinib, acalabrutinib, GS-4059, spebrutinib, BGB-3111, HM71224, zanubrutinib, ARQ531, BI-BTK1 and vecabrutinib.

In certain embodiments -D is a spleen tyrosine kinase inhibitor, such as fostamatinib.

In certain embodiments -D is a Ber-Abl tyrosine kinase inhibitor, such as imatinib and nilotinib.

In certain embodiments -D is a Janus kinase inhibitor, such as ruxolitinib, tofacitinib and fedratinib.

In certain embodiments -D is a multi-specific tyrosine kinase inhibitor, such as bosutinib, crizotinib, cabozantinib, dasatinib, entrectinib, lapatinib, mubritinib, pazopanib, sorafenib, sunitinib, SU6656 and vandetanib. In certain embodiments -D is crizotinib. In certain embodiments -D is cabozantinib which is an inhibitor of c-Met, VEGFR2, AXL and RET.

In certain embodiments -D is a cyclin dependent kinase inhibitor. Examples for cyclin dependent kinase inhibitors are copanlisib, ribociclib, palbociclib, abemaciclib, trilaciclib, purvalanol A, olomucine II and MK-7965. In certain embodiments -D is copanlisib.

In certain embodiments -D is a phophoinositide-3-kinase inhibitor. Examples for phophoinositide-3-kinase inhibitors are IPI549, GDc-0326, pictilisib, serabelisib, IC-87114, AMG319, seletalisib, idealisib and CUDC907.

In certain embodiments -D is a mitogen-activated protein kinase inhibitor. Examples for mitogen-activated protein kinase inhibitors are Ras/farnesyl transferase inhibitors, Raf inhibitors, MEK inhibitors and ERK inhibitors.

In certain embodiments -D is a Ras/farnesyl transferase inhibitor, such as tipirafinib and LB42708.

In certain embodiments -D is a Raf inhibitor, such as regorafenib, encorafenib, vemurafenib, dabrafenib, sorafenib, PLX-4720, GDC-0879, AZ628, lifirafenib, PLX7904 and RO5126766.

In certain embodiments -D is a MEK inhibitor, such as cobimetinib, trametinib, binimetinib, selumetinib, pimasertib, refametinib and PD0325901. In certain embodiments -D or drug is cobimetinib.

In certain embodiments -D is an ERK inhibitor, such as MK-8353, GDC-0994, ulixertinib and SCH772984.

In certain embodiments -D is an inhibitors of nuclear factor IKK. Examples for inhibitors of nuclear factor kappa-β kinase (IKK) are BPI-003 and AS602868.

In certain embodiments -D is a Wee-1 inhibitor. An example of a Wee-1 inhibitor is adavosertib.

In certain embodiments -D is selected from the group consisting of lenvatinib, axitinib, cobimetinib, crizotinib, tivantinib, copanlisib and cabozantinib.

In certain embodiments -D is an anti-CTLA4 moiety. In certain embodiments -D is selected from the group consisting of wild-type $F_e$ anti-CTLA4 antibodies, Fc enhanced for effector function/FcγR binding anti-CTLA4 antibodies, anti-CTLA4 antibodies conditionally active in tumor microenvironment, anti-CTLA4 small molecules, CTLA4 antagonist fusion proteins, anti-CTLA4 anticalins, anti-CTLA4 nanobodies and anti-CTLA4 multispecific biologics based on antibodies, scFVs or other formats. In certain embodiments -D is a wild-type $F_e$ anti-CTLA4 antibody. In certain embodiments -D is a Fc enhanced for effector function/FcγR binding anti-CTLA4 antibody. In certain embodiments -D is an anti-CTLA4 antibodies conditionally active in tumor microenvironment. In certain embodiments -D is an anti-CTLA4 small molecule. In certain embodiments -D is a CTLA4 antagonist fusion protein. In certain embodiments -D is an anti-CTLA4 anticalin. In certain embodiments -D is an anti-CTLA4 nanobody. In certain embodiments -D is an anti-CTLA4 multispecific biologic based on an antibody, scFV or other format. In certain embodiments -D is an anti-CTLA4 multispecific biologic based on an antibody. In certain embodiments -D is an anti-CTLA4 multispecific based on a scFV.

Exemplary wild-type Fc anti-CTLA4 antibody are selected from the group consisting of ipilimumab, tremelimumab, MK-1308, CBT509 (also known as APL-509), ONC392, IB1310, CG0161, BCD145, ADU1604, AGEN1884 and CS1002. In certain embodiments -D is ipilimumab. In certain embodiments -D is tremelimumab.

Exemplary Fc enhanced for effector function/FeyR binding anti-CTLA4 antibodies are selected from the group consisting of AGEN1181 and anti-CTLA-4 SlFbody.

Exemplary anti-CTLA4 antibodies conditionally active in tumor microenvironment are selected from the group consisting of BMS-986249 and BA3071.

An exemplary anti-CTLA4 small molecules is BPI-002.

An exemplary CTLA4 antagonist fusion protein is FPT155.

An exemplary anti CTLA4 anticalin is PRS010.

Exemplary anti-CTLA4 multispecific biologics are selected from the group consisting of TE1254, XmAb22841, XmAb20717, MEDI5752, MGD019, ALPN-202, ATOR-1015 and ATOR-1144.

It is understood that the conjugates of the present invention are prodrugs.

The moiety $-L^1-$ is a linker moiety from which -D is preferably released in its free form, i.e. in the form of D-H or D-OH. Such moieties are also known as "prodrug linkers" or "reversible prodrug linkers" and are known in the art, such as for example the reversible linker moieties disclosed in WO 2005/099768 A2, WO 2006/136586 A2, WO 2011/089216 A1, WO 2013/024053 A1, WO 2011/012722 A1, WO 2011/089214 A1, WO 2011/089215 A1, WO 2013/024052 A1 and WO 2013/160340 A1, which are incorporated by reference herewith.

In certain embodiments the moiety $-L^1-$ is as disclosed in WO 2009/095479 A2. Accordingly, in certain embodiments the moiety $-L^1-$ is of formula (I):

(I)

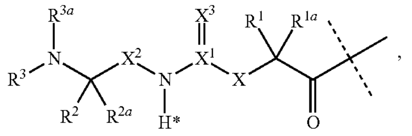

wherein the dashed line indicates the attachment to a nitrogen, hydroxyl or thiol of -D;

—X— is selected from the group consisting of $—C(R^4R^{4a})—$, $—N(R^4)—$, —O—, $—C(R^4R^{4a})—C(R^5R^{5a})—$, $—C(R^5R^{5a})—C(R^4R^{4a})—$, $—C(R^4R^{4a})—N(R^6)—$, $—N(R^6)—C(R^4R^{4a})—$, $—C(R^4R^{4a})—O—$, $—O—C(R^4R^{4a})—$, and $—C(R^7R^{7a})—$, $X^1$ is selected from the group consisting of C and S(O);

$X^2$— is selected from the group consisting of $—C(R^8R^{8a})—$ and $—C(R^8R^{8a})—C(R^9R^{9a})—$;

$=X^3$ is selected from the group consisting of =O, =S, and =N—CN;

—$R^1$, —$R^{1a}$, —$R^2$, —$R^{2a}$, —$R^4$, —$R^{4a}$, —$R^5$, —$R^{5a}$, —$R^6$, —$R^8$, —$R^{8a}$, —$R^9$ and —$R^{9a}$ are independently selected from the group consisting of —H and $C_{1-6}$ alkyl;

—$R^3$ and —$R^{3a}$ are independently selected from the group consisting of —H and $C_{1-6}$ alkyl, provided that in case one of —$R^3$ and —$R^{3a}$ or both are other than —H they are connected to N to which they are attached through an $sp^3$-hybridized carbon atom;

$R^7$ is selected from the group consisting of —N($R^{10}R^{10a}$) and —$NR^{10}$—(C═O)—$R^{11}$;

$R^{7a}$, —$R^{10}$, —$R^{10a}$ and —$R^{11}$ are independently selected from the group consisting of —H and $C_{1-6}$ alkyl;

optionally, one or more of the pairs —$R^{1a}$/—$R^{4a}$, —$R^{1a}$/—$R^{5a}$, —$R^{1a}$/—$R^{7a}$, —$R^{4a}$/—$R^{5a}$ and —$R^{8a}$/—$R^{9a}$ form a chemical bond;

optionally, one or more of the pairs —$R^{1a}$/—$R^{4a}$, —$R^2$/—$R^{2a}$, —$R^4$/—$R^{4a}$, —$R^5$/—$R^{5a}$, —$R^8$/—$R^{8a}$ and —$R^9$/—$R^{9a}$ are joined together with the atom to which they are attached to form a $C_{3-10}$ cycloalkyl or 3- to 10-membered heterocyclyl;

optionally, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^8$/—$R^9$ and —$R^2$/—$R^3$ are joined together with the atoms to which they are attached to form a ring A;

optionally, —$R^3$/—$R^{3a}$ are joined together with the nitrogen atom to which they are attached to form a 3- to 10-membered heterocycle;

A is selected from the group consisting of phenyl; naphthyl; indenyl; indanyl;

tetralinyl; $C_{3-10}$ cycloalkyl; 3- to 10-membered heterocyclyl; and 8- to 11-membered heterobicyclyl; and wherein -$L^1$- is substituted with —$X^{0D}$— $L^2$- and wherein -$L^1$- is optionally further substituted, provided that the hydrogen marked with the asterisk in formula (I) is not replaced by —$X^{0D}$-$L^2$- or a substituent.

The optional further substituents of -$L^1$- of formula (I) are as described above.

In certain embodiments -$L^1$- of formula (I) is substituted with one moiety —$X^{0D}$-$L^2$-.

In certain embodiments -$L^1$- of formula (I) is not further substituted.

It is understood that if —$R^3$/—$R^{3a}$ of formula (I) are joined together with the nitrogen atom to which they are attached to form a 3- to 10-membered heterocycle, only such 3- to 10-membered heterocycles may be formed in which the atoms directly attached to the nitrogen are $sp^3$-hybridized carbon atoms. In other words, such 3- to 10-membered heterocycle formed by —$R^3$/—$R^{3a}$ together with the nitrogen atom to which they are attached has the following structure:

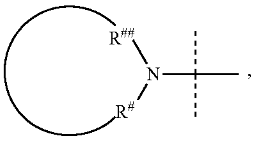

wherein the dashed line indicates attachment to the rest of -$L^1$-;

the ring comprises 3 to 10 atoms comprising at least one nitrogen; and $R^{\#}$and $R^{\#\#}$represent an $sp^3$-hydridized carbon atom.

It is also understood that the 3- to 10-membered heterocycle may be further substituted.

Exemplary embodiments of suitable 3- to 10-membered heterocycles formed by —$R^3$/—$R^{3a}$ of formula (I) together with the nitrogen atom to which they are attached are the following:

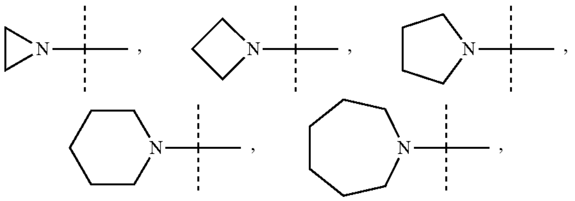

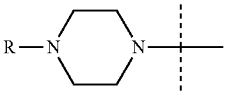

and

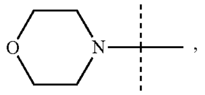

wherein dashed lines indicate attachment to the rest of the molecule; and

—R is selected from the group consisting of —H and $C_{1-6}$ alkyl.

-$L^1$- of formula (I) may optionally be further substituted. In general, any substituent may be used as far as the cleavage principle is not affected, i.e. the hydrogen marked with the asterisk in formula (I) is not replaced and the nitrogen of the moiety

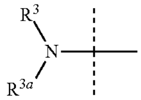

of formula (I) remains part of a primary, secondary or tertiary amine, i.e. —$R^3$ and —$R^{3a}$ are independently of each other —H or are connected to —N< through an $sp^3$-hybridized carbon atom.

In certain embodiments —$R^1$ of formula (I) is —H, which —H is substituted with —$X^{0D}$-$L^2$-. In certain embodiments —$R^{1a}$ of formula (I) is —H, which —H is substituted with —$X^{0D}$-$L^2$-. In certain embodiments —$R^2$ of formula (I) is —H, which —H is substituted with —$X^{0D}$-$L^2$-. In certain embodiments —$R^{2a}$ of formula (I) is —H, which —H is substituted with —$X^{0D}$-$L^2$-. In certain embodiments —$R^3$ of formula (I) is —H, which —H is substituted with —$X^{0D}$-$L^2$-. In certain embodiments —$R^{3a}$ of formula (I) is —H, which —H is substituted with —$X^{0D}$-$L^2$-. In certain embodiments —$R^4$ of formula (I) is —H, which —H is substituted with —$X^{0D}$-$L^2$-. In certain embodiments —$R^5$ of formula (I) is —H, which —H is substituted with —$X^{0D}$-$L^2$-. In certain embodiments —$R^{5a}$ of formula (I) is —H, which —H is substituted with —$X^{0D}$-$L^2$-. In certain embodiments —$R^6$ of formula (I) is —H, which —H is substituted with —$X^{0D}$-$L^2$-. In certain embodiments —$R^7$ of formula (I) is —H, which —H is substituted with —$X^{0D}$-$L^2$-. In certain embodiments —$R^{7a}$ of formula (I) is —H, which —H is substituted with —$X^{0D}$-$L^2$-. In certain embodiments —$R^8$ of formula (I) is —H, which —H is substituted with —$X^{0D}$-$L^2$-. In certain embodiments —$R^{8a}$ of formula (I) is —H, which —H is substituted with —$X^{0D}$-$L^2$-. In certain embodiments —$R^9$ of formula (I) is —H, which —H is substituted with —$X^{0D}$-$L^2$-. In certain embodiments —$R^{9a}$ of formula (I) is —H, which —H is substituted with —$X^{0D}$-$L^2$-. In certain embodiments —$R^{10}$ of formula (I) is —H, which —H is substituted with $—X^{0D}$-$L^2$-. In certain embodiments $—R^1$ of formula (I) is —H, which —H is substituted with $—X^{0D}$-$L^2$-.

In certain embodiments —X— of formula (I) is selected from the group consisting of $—C(R^4R^{4a})—$, $—N(R^4)—$ and $—C(R^7R^{7a})—$.

In certain embodiments —X— of formula (I) is $—C(R^4R^{4a})—$.

In certain embodiments —X— of formula (I) is $—N(R^4)—$.

In certain embodiments —X— of formula (I) is $—C(R^7R^{7a})—$.

In certain embodiments $—R^7$ of formula (I) is $—NR^{10}—(C{=}O)—R^{11}$.

In certain embodiments $—R^{7a}$ of formula (I) is selected from —H, methyl and ethyl.

In certain embodiments $—R^{7a}$ of formula (I) is —H.

In certain embodiments $—R^{10}$ of formula (I) is selected from —H, methyl and ethyl.

In certain embodiments $—R^{10}$ of formula (I) is methyl. In certain embodiments $—R^{10}$ is —H.

In certain embodiments $—R^{10a}$ of formula (I) is selected from —H, methyl and ethyl.

In certain embodiments $—R^{10a}$ of formula (I) is methyl. In certain embodiments $—R^{10a}$ is —H.

In certain embodiments $—R^{11}$ of formula (I) is selected from —H, methyl and ethyl. In certain embodiments $—R^{11}$ is —H.

In certain embodiments $—R^{11}$ of formula (I) is substituted with $—X^{0D}$-$L^2$.

In certain embodiments $X^{11}$ of formula (I) is C.

In certain embodiments $=X^3$ of formula (I) is =O.

In certain embodiments $—X^2—$ of formula (I) is $—C(R^8R^{8a})—$.

In certain embodiments $—X^2—$ of formula (I) is $—C(R^8R^{8a})—C(R^9R^{9a})—$.

In certain embodiments $—R^8$ and $—R^{8a}$ of formula (I) are independently selected from the group consisting of —H, methyl and ethyl. In certain embodiments at least one of $—R^8$ and $—R^{8a}$ of formula (I) is —H. In certain embodiments both $—R^8$ and $—R^{8a}$ of formula (I) are —H.

In certain embodiments $—R^1$ and $—R^{1a}$ of formula (I) are independently selected from the group consisting of —H, methyl and ethyl. In certain embodiments at least one of $—R^1$ and $—R^{1a}$ of formula (I) is —H. In certain embodiments both $—R^1$ and $—R^{1a}$ of formula (I) are —H.

In certain embodiments $—R^2$ and $—R^{2a}$ of formula (I) are independently selected from the group consisting of —H, methyl and ethyl. In certain embodiments at least one of $—R^2$ and $—R^{2a}$ of formula (I) is —H. In certain embodiments both $—R^2$ and $—R^{2a}$ of formula (I) are —H.

In certain embodiments $—R^3$ and $—R^{3a}$ of formula (I) are independently selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of $—R^3$ and $—R^{3a}$ of formula (I) is —H. In certain embodiments both $—R^3$ and $—R^{3a}$ of formula (I) are —H. In certain embodiments at least one of $—R^3$ and $—R^{3a}$ of formula (I) is methyl. In certain embodiments both $—R^3$ and $—R^{3a}$ of formula (I) are methyl.

In certain embodiments $—R^4$ and $—R^{4a}$ of formula (I) are independently selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of $—R^4$ and $—R^{4a}$ of formula (I) is —H. In certain embodiments both $—R^4$ and $—R^{4a}$ of formula (I) are —H. In certain embodiments at least one of $—R^4$ and $—R^{4a}$ of formula (I) is methyl. In certain embodiments both $—R^4$ and $—R^{4a}$ of formula (I) are methyl.

In certain embodiments $—R^5$ and $—R^{5a}$ of formula (I) are independently selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of $—R^5$ and $—R^{5a}$ of formula (I) is —H. In certain embodiments both $—R^5$ and $—R^{5a}$ of formula (I) are —H. In certain embodiments at least one of $—R^5$ and $—R^{5a}$ of formula (I) is methyl. In certain embodiments both $—R^5$ and $—R^{5a}$ of formula (I) are methyl.

In certain embodiments $—R^6$ of formula (I) is selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments $—R^6$ of formula (I) is —H. In certain embodiments $—R^6$ of formula (I) is methyl.

In certain embodiments $—R^9$ and $—R^{9a}$ of formula (I) are independently selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of $—R^9$ and $—R^{9a}$ of formula (I) is —H. In certain embodiments both $—R^9$ and $—R^{9a}$ of formula (I) are —H. In certain embodiments at least one of $—R^9$ and $—R^{9a}$ of formula (I) is methyl. In certain embodiments both $—R^9$ and $—R^{9a}$ of formula (I) are methyl.

In certain embodiments -D is connected to -$L^1$- of formula (I) through a nitrogen of -D by forming an amide bond. It is understood that the carbonyl to the left of the dashed line and the nitrogen of -D form the amide bond.

In certain embodiments the nitrogen that connects -D to -$L^1$- by forming an amide bond is provided by a primary or secondary amine of -D.

In certain embodiments the moiety -$L^1$- is of formula (Ia):

(Ia)

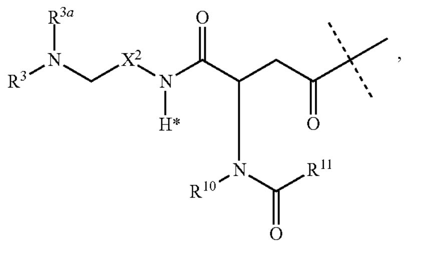

wherein the dashed line indicates the attachment to a nitrogen of -D by forming an amide bond;

$—R^3$, $—R^{3a}$, $—R^{10}$, $—R^{11}$ and $—X^2—$ are used as defined in formula (I); and wherein -$L^1$- is substituted with $—X^{0D}$-$L^2$- and wherein -$L^1$- is optionally further substituted, provided that the hydrogen marked with the asterisk in formula (Ia) is not replaced by $—X^{0D}$-$L^2$- or a substituent.

The optional further substituents of $-L^1-$ of formula (Ia) are as described above.

In certain embodiments $-L^1-$ of formula (Ia) is substituted with one moiety $—X^{0D}-L^2-$.

In certain embodiments the moiety $-L^1-$ of formula (Ia) is not further substituted.

In certain embodiments $—X^2—$ of formula (Ia) is $—C(R^8R^{8a})$.

In certain embodiments $—X^2—$ of formula (Ia) is $—C(R^4R^{4a})—C(R^5R^{5a})—$.

In certain embodiments $—R^8$ and $—R^{8a}$ of formula (Ia) are independently selected from the group consisting of —H, methyl and ethyl. In certain embodiments at least one of $—R^8$ and $—R^{8a}$ of formula (Ia) is —H. In certain embodiments both $—R^8$ and $—R^{8a}$ of formula (Ia) are —H.

In certain embodiments $—R^3$ and $—R^{3a}$ of formula (Ia) are independently selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of $—R^3$ and $—R^{3a}$ of formula (Ia) is methyl. In certain embodiments $—R^3$ of formula (Ia) is methyl and $—R^{3a}$ of formula (Ia) is —H. In certain embodiments both $—R^3$ and $—R^{3a}$ of formula (Ia) are methyl.

In certain embodiments $—R^{10}$ of formula (Ia) is selected from —H, methyl and ethyl. In certain embodiments $—R^{10}$ of formula (Ia) is methyl.

In certain embodiments $—R^{11}$ of formula (Ia) is selected from —H, methyl and ethyl. In certain embodiments $—R^{11}$ of formula (Ia) is —H.

In certain embodiments $—R^{11}$ of formula (Ia) is substituted with $—X^{0D}-L^2-$.

-D is connected to $-L^1-$ of formula (Ia) through a nitrogen of -D by forming an amide bond. In certain embodiments said nitrogen is provided by a primary or secondary amine of -D.

In certain embodiments the moiety $-L^1-$ is of formula (Ib):

(Ib)

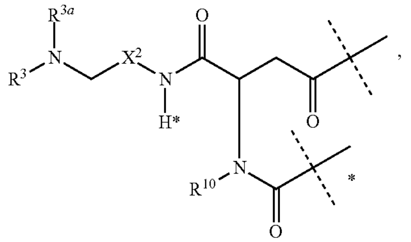

wherein wherein the dashed line indicates the attachment to a nitrogen of -D by forming an amide bond;

the dashed line marked with the asterisk indicates attachment to $—X^{0D}-L^2-$; $—R^3$, $—R^{3a}$, $—R^{10}$ and $—X^2—$ are used as defined in formula (I); and wherein $-L^1-$ is optionally further substituted, provided that the hydrogen marked with the asterisk in formula (Ib) is not replaced by a substituent.

The optional further substituents of $-L^1-$ of formula (Ib) are as described above.

In certain embodiments the moiety $-L^1-$ of formula (Ib) is not further substituted.

In certain embodiments $—X^2—$ of formula (Ib) is-C $(R^8R^{8a})—$.

In certain embodiments $—X^2—$ of formula (Ib) is $—C(R^4R^{4a})—C(R^5R^{5a})—$.

In certain embodiments $—R^8$ and $—R^{8a}$ of formula (Ib) are independently selected from the group consisting of —H, methyl and ethyl. In certain embodiments at least one of $—R^8$ and $—R^{8a}$ of formula (Ib) is —H. In certain embodiments both $—R^8$ and $—R^{8a}$ of formula (Ib) are —H.

In certain embodiments $—R^3$ and $—R^{3a}$ of formula (Ib) are independently selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of $—R^3$ and $—R^{3a}$ of formula (Ib) is methyl. In certain embodiments $—R^3$ of formula (Ia) is methyl and $—R^{3a}$ of formula (Ib) is —H. In certain embodiments both $—R^3$ and $—R^{3a}$ of formula (Tb) are methyl.

In certain embodiments $—R^{10}$ of formula (Ib) is selected from —H, methyl and ethyl. In certain embodiments $—R^{10}$ of formula (Ib) is methyl.

-D is connected to $-L^1-$ of formula (Ib) through a nitrogen of -D by forming an amide bond. In certain embodiments said nitrogen is provided by a primary or secondary amine of -D.

In certain embodiments the moiety $-L^1-$ is of formula (Ic):

(Ic)

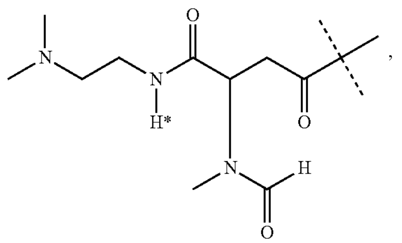

wherein the dashed line indicates the attachment to a nitrogen of -D by forming an amide bond; and wherein $-L^1-$ is substituted with $—X^{0D}-L^2-$ and wherein $-L^1-$ is optionally further substituted, provided that the hydrogen marked with the asterisk in formula (Ic) is not replaced by $—X^{0D}-L^2-$ or a substituent.

The optional further substituents of $-L^1-$ of formula (Ic) are as described above.

In certain embodiments $-L^1-$ of formula (Ic) is substituted with one moiety $—X^{0D}-L^2-$.

In certain embodiments the moiety $-L^1-$ of formula (Ic) is not further substituted.

-D is connected to $-L^1-$ of formula (Ic) through a nitrogen of -D by forming an amide bond. In certain embodiments said nitrogen is provided by a primary or secondary amine of -D.

In certain embodiments the moiety $-L^1-$ is of formula (Id):

(Id)

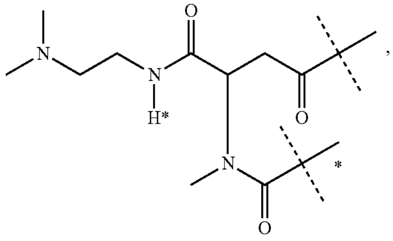

wherein the dashed line indicates the attachment to a nitrogen of -D by forming an amide bond;

the dashed line marked with the asterisk indicates attachment to $-X^{0D}-L^2-$; and wherein $-L^1-$ is optionally further substituted, provided that the hydrogen marked with the asterisk in formula (Id) is not replaced by a substituent.

In certain embodiments the moiety $-L^1-$ of formula (Id) is not further substituted.

-D is connected to $-L^1-$ of formula (Id) through a nitrogen of -D by forming an amide bond. In certain embodiments said nitrogen is provided by a primary or secondary amine of -D.

In certain embodiments the moiety $-L^1-$ is of formula (Ie)

(Ie)

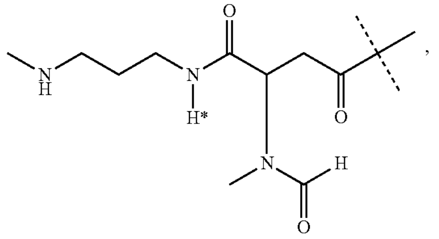

wherein the dashed line indicates the attachment to a nitrogen of -D by forming an amide bond; and wherein $-L^1-$ is substituted with $-X^{0D}-L^2-$ and wherein $-L^1-$ is optionally further substituted, provided that the hydrogen marked with the asterisk in formula (Ie) is not replaced by $-X^{0D}-L^2-$ or a substituent.

The optional further substituents of $-L^1-$ of formula (Ie) are as described above.

In certain embodiments $-L^1-$ of formula (Ie) is substituted with one moiety $-X^{0D}-L^2-$.

In certain embodiments the moiety $-L^1-$ of formula (Ie) is not further substituted.

-D is connected to $-L^1-$ of formula (Ie) through a nitrogen of -D by forming an amide bond. In certain embodiments said nitrogen is provided by a primary or secondary amine of -D.

In certain embodiments the moiety $-L^1-$ is of formula (If):

(If)

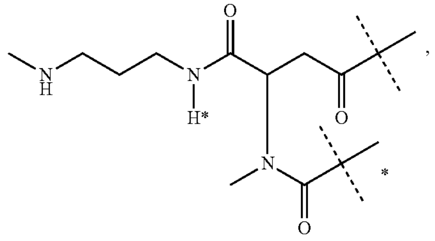

wherein the dashed line indicates the attachment to a nitrogen of -D by forming an amide bond;

the dashed line marked with the asterisk indicates attachment to $-X^{0D}-L^2-$; and wherein $-L^1-$ is optionally further substituted, provided that the hydrogen marked with the asterisk in formula (If) is not replaced by a substituent.

In certain embodiments the moiety $-L^1-$ of formula (If) is not further substituted.

-D is connected to $-L^1-$ of formula (If) through a nitrogen of -D by forming an amide bond. In certain embodiments said nitrogen is provided by a primary or secondary amine of -D.

In certain embodiments $-L^1-$ is disclosed in WO 2016/020373 A1. Accordingly, in certain embodiments the moiety $-L^1-$ is of formula (II):

(II)

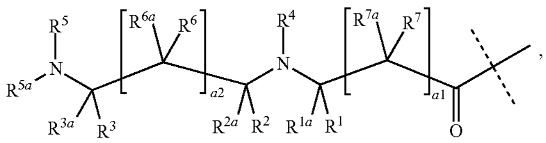

wherein the dashed line indicates attachment to a primary or secondary amine or hydroxyl of -D by forming an amide or ester linkage, respectively;

$-R^1$, $-R^{1a}$, $-R^2$, $-R^{2a}$, $-R^3$ and $-R^{3a}$ are independently of each other selected from the group consisting of $-H$, $-C(R^8R^{8a}R^{8b})$, $-C(=O)R^8$, $-C\equiv N$, $-C(=NR^8)R^{8a}$, $-CR^8(=CR^{8a}R^{8b})$, $-C\equiv CR^8$ and -T;

$-R^4$, $-R^5$ and $-R^{5a}$ are independently of each other selected from the group consisting of $-H$, $-C(R^9R^{9a}R^{9b})$ and -T;

a1 and a2 are independently of each other 0 or 1;

each $-R^6$, $-R^{6a}$, $-R^7$, $-R^{7a}$, $-R^8$, $-R^{8a}$, $-R^{8b}$, $-R^9$, $-R^{9a}$, $-R^{9b}$ are independently of each other selected from the group consisting of $-H$, halogen, $-CN$, $-COOR^{10}$, $-OR^{10}$, $-C(O)R^{10}$, $-C(O)N(R^{10}R^{10a})$, $-S(O)_2N(R^{10}R^{10a})$, $-S(O)N(R^{10}R^{10a})$, $-S(O)_2R^{10}$, $-S(O)R^{10}$, $-N(R^{10})S(O)_2N(R^{10a}R^{10b})$, $-SR^{10}$, $-N(R^{10}R^{10a})$, $-NO_2$, $-OC(O)R^{10}$, $-N(R^{10})C(O)R^{10a}$, $-N(R^{10})S(O)_2R^{10a}$, $-N(R^{10})S(O)R^{10a}$, $-N(R^{10})C(O)OR^{10a}$, $-N(R^{10})C(O)N(R^{10a}R^{10b})$, $-OC(O)N(R^{10}R^{10a})$, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more $-R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —$S(O)_2N(R^{12})$—, —S(O)N($R^{12}$)—, —$S(O)_2$—, —S(O)—, —N($R^{12}$)$S(O)_2N(R^{12a})$—, —S—, —N($R^{12}$)—, —OC($OR^{12}$)($R^{12a}$)—-N($R^{12}$)C(O)N($R^{12a}$)—, and —OC(O)N($R^{12}$)—;

each —$R^{10}$, —$R^{10a}$, —$R^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —$S(O)_2N(R^{12})$—, —S(O)N($R^{12}$)—, —$S(O)_2$—, —S(O)—, —N($R^{12}$)$S(O)_2N(R^{12a})$—, —S—, —N($R^{12}$)—, —OC($OR^{12}$)($R^{12a}$)—, —N($R^{12}$)C(O)N($R^{12a}$ and —OC(O)N($R^{12}$)—;

each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T is independently optionally substituted with one or more —$R^1$, which are the same or different; each —$R^{11}$ is independently of each other selected from halogen, —CN, oxo (═O), —$COOR^{13}$, —OR, —C(O)$R^{13}$, —C(O)N($R^{13}R^{13a}$), —$S(O)_2N(R^{13}R^{13a})$, —S(O)N($R^{13}R^{13a}$), —$S(O)_2R^{13}$, —$S(O)R^{13}$, —N($R^{13}$)$S(O)_2N(R^{13a}R^{13b})$, —$SR^{13}$, —N($R^{13}R^{13a}$), —$NO_2$, —OC(O)$R^{13}$, —N($R^{13}$)C(O)$R^{13a}$, —N($R^{13}$)$S(O)_2R^{13a}$, —N($R^{13}$)S(O)$R^{13a}$, —N($R^{13}$)C(O)$OR^{13a}$, —N($R^{13}$)C(O)N($R^{13a}R^{13b}$), —OC(O)N($R^{13}R^{13a}$), and $C_{1-6}$ alkyl; wherein $C_{1-6}$ alkyl is optionally substituted with one or more halogen, which are the same or different;

each —$R^2$, —$R^{12a}$, —$R^{13}$, —$R^{13a}$, —$R^{13b}$ is independently selected from the group consisting of —H, and $C_{1-6}$ alkyl; wherein $C_{1-6}$ alkyl is optionally substituted with one or more halogen, which are the same or different;

optionally, one or more of the pairs —$R^1$/—$R^{1a}$, —$R^2$/—$R^{2a}$, —$R^3$/—$R^{3a}$, —$R^6$/—$R^{6a}$, —$R^1$/—$R^{7a}$ are joined together with the atom to which they are attached to form a $C_{3-10}$ cycloalkyl or a 3- to 10-membered heterocyclyl;

optionally, one or more of the pairs —$R^1$/—$R^2$, —$R^1$/—$R^3$, —$R^1$/—$R^4$, —$R^1$/—$R^5$, —$R^1$/—$R^6$, —$R^1$/—$R^7$, —$R^2$/—$R^3$, —$R^2$/—$R^4$, —$R^2$/—$R^5$, —$R^2$/—$R^6$, —$R^2$/—$R^7$, —$R^3$/—$R^4$, —$R^3$/—$R^5$, —$R^3$/—$R^6$, —$R^3$/—$R^7$, —$R^4$/—$R^5$, —$R^4$/—$R^6$, —$R^4$/—$R^7$, —$R^5$/—$R^6$, —$R^5$/—$R^7$, —$R^6$/—$R^7$ are joint together with the atoms to which they are attached to form a ring A;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein -$L^1$- is substituted with —$X^{0D}$-$L^2$- and wherein -$L^1$- is optionally further substituted.

The optional further substituents of -$L^1$- of formula (II) are as described above.

In certain embodiments -$L^1$- of formula (II) is substituted with one moiety —$X^{0D}$-$L^2$-.

In certain embodiments -$L^1$- of formula (II) is not further substituted.

Additional embodiments for -$L^1$- are disclosed in EP1536334B1, WO2009/009712A1, WO2008/034122A1, WO2009/143412A2, WO2011/082368A2, and U.S. Pat. No. 8,618,124B2, which are herewith incorporated by reference in their entirety.

Further embodiments for -$L^1$- are disclosed in U.S. Pat. No. 8,946,405B2 and U.S. Pat. No. 8,754,190B2, which are herewith incorporated by reference in their entirety. Accordingly, in certain embodiments -$L^1$- is of formula (III):

(III)

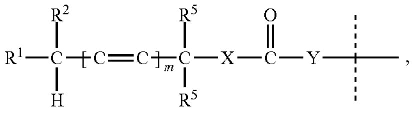

wherein the dashed line indicates attachment to -D through a functional group of -D selected from the group consisting of —OH, —SH and —$NH_2$;

m is 0 or 1;

at least one or both of —$R^1$ and —$R^2$ is/are independently of each other selected from the group consisting of —CN, —$NO_2$, optionally substituted aryl, optionally substituted heteroaryl, optionally substituted alkenyl, optionally substituted alkynyl, —C(O)$R^3$, —S(O)$R^3$, —$S(O)_2R^3$, and —$SR^4$, one and only one of —$R^1$ and —$R^2$ is selected from the group consisting of —H, optionally substituted alkyl, optionally substituted arylalkyl, and optionally substituted heteroarylalkyl;

—$R^3$ is selected from the group consisting of —H, optionally substituted alkyl, optionally substituted aryl, optionally substituted arylalkyl, optionally substituted heteroaryl, optionally substituted heteroarylalkyl, —$OR^9$ and —N($R^9$)$_2$;

—$R^4$ is selected from the group consisting of optionally substituted alkyl, optionally substituted aryl, optionally substituted arylalkyl, optionally substituted heteroaryl, and optionally substituted heteroarylalkyl;

each —$R^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;

—$R^9$ is selected from the group consisting of —H and optionally substituted alkyl;

—Y— is absent and —X— is —O— or —S—; or

—Y— is —N(Q)$CH_2$— and —X— is —O—;

Q is selected from the group consisting of optionally substituted alkyl, optionally substituted aryl, optionally substituted arylalkyl, optionally substituted heteroaryl and optionally substituted heteroarylalkyl;

optionally, —$R^1$ and —$R^2$ may be joined to form a 3 to 8-membered ring; and optionally, both —$R^9$ together with the nitrogen to which they are attached form a heterocyclic ring; and wherein -$L^1$- is substituted with —$X^{0D}$-$L^2$- and wherein -$L^1$- is optionally further substituted.

Only in the context of formula (III) the terms used have the following meaning:

The term "alkyl" as used herein includes linear, branched or cyclic saturated hydrocarbon groups of 1 to 8 carbon atoms, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted. Optional substituents on any group, including the above, include halo, nitro, cyano, —OR, —SR, $—NR_2$, —OCOR, —NRCOR, —COOR, $—CONR_2$, —SOR, $—SO_2R$, $—SONR_2$, $—SO_2N\ R_2$, wherein each R is independently alkyl, alkenyl, alkynyl, aryl or heteroaryl, or two R groups taken together with the atoms to which they are attached form a ring.

In certain embodiments $-L^1-$ of formula (III) is substituted with one moiety $—X^{0D}-L^2-$.

Another embodiment for $-L^1-$ is disclosed in WO2013/036857A1, which is herewith incorporated by reference in its entirety. Accordingly, in certain embodiments $-L^1-$ is of formula (IV):

(IV)

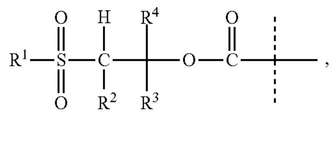

wherein the dashed line indicates attachment to -D through an amine functional group of -D;

$—R^1$ is selected from the group consisting of optionally substituted $C_1$-$C_6$ linear, branched, or cyclic alkyl; optionally substituted aryl; optionally substituted heteroaryl; alkoxy; and $—NR^{52}$;

$—R^2$ is selected from the group consisting of —H; optionally substituted $C_1$-$C_6$ alkyl; optionally substituted aryl; and optionally substituted heteroaryl;

$—R^3$ is selected from the group consisting of —H; optionally substituted $C_1$-$C_6$ alkyl; optionally substituted aryl; and optionally substituted heteroaryl;

$—R^4$ is selected from the group consisting of —H; optionally substituted $C_1$-$C_6$ alkyl; optionally substituted aryl; and optionally substituted heteroaryl;

each $—R^5$ is independently of each other selected from the group consisting of —H; optionally substituted $C_1$-$C_6$ alkyl; optionally substituted aryl; and optionally substituted heteroaryl; or when taken together two $—R^5$ can be cycloalkyl or cycloheteroalkyl; and wherein $-L^1-$ is substituted with $—X^{0D}-L^2-$ and wherein $-L^1-$ is optionally further substituted.

Only in the context of formula (IV) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiszolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketne; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

In certain embodiments $-L^1-$ of formula (IV) is substituted with one moiety $—X^{0D}— L^2-$.

A further embodiment for $-L^1-$ is disclosed in U.S. Pat. No. 7,585,837B2, which is herewith incorporated by reference in its entirety. Accordingly, in certain embodiments $-L^1-$ is of formula (V):

(V)

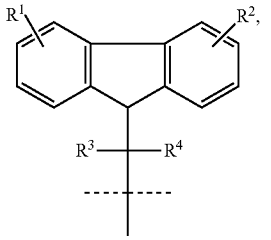

wherein the dashed line indicates attachment to -D through an amine functional group of -D;

$R^1$ and $R^2$ are independently selected from the group consisting of hydrogen, alkyl, alkoxy, alkoxyalkyl, aryl, alkaryl, aralkyl, halogen, nitro, $—SO_3H$, $—SO_2NHR^5$, amino, ammonium, carboxyl, $PO_3H_2$, and $OPO_3H_2$;

$R^3$, $R^4$, and $R^5$ are independently selected from the group consisting of hydrogen, alkyl, and aryl; and wherein $-L^1-$ is substituted with $—X^{0D}-L^2-$ and wherein $-L^1-$ is optionally further substituted.

Suitable substituents for formulas (V) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Only in the context of formula (V) the terms used have the following meaning:

The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

In certain embodiments $-L^1-$ of formula (V) is substituted with one moiety $—X^{0D}-L^2-$.

In certain embodiments $-L^1-$ of formula (V) is not further substituted.

A further embodiment for $-L^1-$ is disclosed in WO2002/089789A1, which is herewith incorporated by reference in its entirety. Accordingly, in certain embodiments $-L^1-$ is of formula (VI):

(VI)

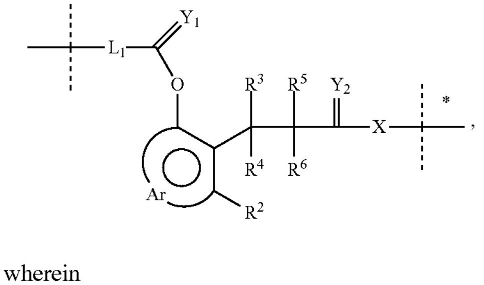

wherein the dashed line indicates attachment to -D through an amine functional group of -D;

$L_1$ is a bifunctional linking group, $Y_1$ and $Y_2$ are independently 0, S or $NR^7$;

$R^2$, $R^3$, $R^4$, $R^5$, $R^6$ and $R^7$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula (VI) forms a multisubstituted aromatic hydrocarbon or a multisubstituted heterocyclic group;

X is a chemical bond or a moiety that is actively transported into a target cell, a hydrophobic moiety, or a combination thereof, y is 0 or 1; and wherein $-L^1-$ is substituted with $—X^{0D}-L^2-$ and wherein $-L^1-$ is optionally further substituted.

Only in the context of formula (VI) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moieities such as methoxy; and phenoxy includes moieties such as 3-nitrophenoxy. Halo-shall be understood to include fluoro, chloro, iodo and bromo.

In certain embodiments $-L^1-$ of formula (VI) is substituted with one moiety $—X^{0D}-L^2-$.

In certain embodiments $-L^1-$ of formula (VI) is not further substituted.

In certain embodiments $-L^1-$ comprises a substructure of formula (VII)

(VII)

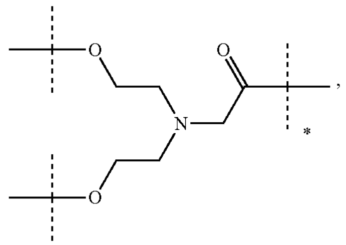

wherein the dashed line marked with the asterisk indicates attachment to a nitrogen of -D by forming an amide bond;

the unmarked dashed lines indicate attachment to the remainder of $-L^1-$; and wherein $-L^1-$ is substituted with $—X^{0D}-L^2-$ and wherein $-L^1-$ is optionally further substituted.

The optional further substituents of $-L^1-$ of formula (VII) are as described above.

In certain embodiments $-L^1-$ of formula (VII) is substituted with one moiety $—X^{0D}-L^2-$.

In certain embodiments $-L^1-$ of formula (VII) is not further substituted.

In certain embodiments $-L^1-$ comprises a substructure of formula (VIII)

(VIII)

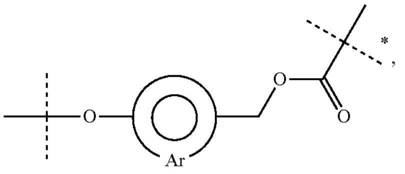

wherein the dashed line marked with the asterisk indicates attachment to a nitrogen of -D by forming a carbamate bond;

the unmarked dashed lines indicate attachment to the remainder of $-L^1-$; and wherein $-L^1-$ is substituted with $—X^{0D}-L^2-$ and wherein $-L^1-$ is optionally further substituted.

The optional further substituents of $-L^1-$ of formula (VIII) are as described above.

In certain embodiments $-L^1-$ of formula (VIII) is substituted with one moiety $X^{0D}-L^2-$.

It is understood that the phrase "$-L^1-$ is substituted with $—X^{0D}-L^2-$" means that $-L^2-$ is attached to $-L^1-$ via $—X^{0D}—$, which is either absent or a linkage, and that the moiety $—X^{0D}-L^2-$ is not attached to $-L^1-$ via $-L^2-$.

In certain embodiments $-L^1-$ of formula (VIII) is not further substituted.

In certain embodiments $-L^1-$ is of formula (IX)

(IX)

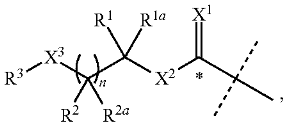

wherein the dashed line indicates the attachment to a π-electron-pair-donating heteroaromatic N of -D;

n is an integer selected from the group consisting of 0, 1, 2, 3 and 4;

$=X^1$ is selected from the group consisting of $=O$, $=S$ and $=N(R^4)$;

$—X^2—$ is selected from the group consisting of $—O—$, $—S—$, $—N(R^5)—$ and $—C(R^6)(R^{6a})—$;

$—X^{0A}—$ is selected from the group consisting of

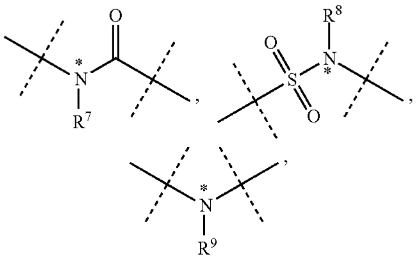

$—C(R^{10})(R^{10a})—$, $—C(R^{11})(R^{11a})—C(R^{12})(R^{12a})—$, $—O—$ and $—C(O)—$;

$—R^1$, $—R^{1a}$, $—R^6$, $—R^{6a}$, $—R^{10}$, $—R^{10a}$, $—R^{11}$, $—R^{11a}$, $—R^{12}$, $—R^{12a}$ and each of $—R^2$ and $—R^{2a}$ are independently selected from the group consisting of $—H$, $—C(O)OH$, halogen, $—CN$, $—OH$, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $—R^{13}$, which are the same or different; and wherein $C_{1-6}$ alkyl, $C_{2-6}$ alkenyl and $C_{2-6}$ alkynyl are optionally interrupted by one or more groups selected from the group consisting of -T-, $—C(O)O—$, $—O—$, $—C(O)—$, $—C(O)N(R^{14})—$, $—S(O)_2N(R^{14})—$, $—S(O)N(R^{14})—$, $—S(O)_2—$, $—S(O)—$, $—N(R^{14})S(O)_2N(R^{14a})—$, $—S—$, $—N(R^{14})—$, $—OC(OR^{14})(R^{14a})—$; $—N(R^{14})C(O)N(R^{14a})—$ and $—OC(O)N(R^{14})—$;

$—R^3$, $—R^4$, $—R^5$, $—R^7$, $—R^8$ and $—R^9$ are independently selected from the group consisting of $—H$, -T, $—CN$, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $—R^{13}$, which are the same or different; and wherein $C_{1-6}$ alkyl, $C_{2-6}$ alkenyl and $C_{2-6}$ alkynyl are optionally interrupted by one or more groups selected from the group consisting of -T-, $—C(O)O—$, $—O—$, $—C(O)—$, $—C(O)N(R^{14})—$, $—S(O)_2N(R^{14})—$, $—S(O)N(R^{14})—$, $—S(O)_2—$, $—S(O)—$, $—N(R^{14})S(O)_2N(R^{14a})—$, $—N(R^{14})—$, $—OC(OR^{14})(R^{14a})—$, $—N(R^{14})C(O)N(R^{14a})—$ and $—OC(O)N(R^{14})—$;

each T is independently selected from the group consisting of phenyl, naphthyl, indenyl, indanyl, tetralinyl, $C_{3-10}$ cycloalkyl, 3- to 10-membered heterocyclyl and 8- to 11-membered heterobicyclyl; wherein each T is independently optionally substituted with one or more $—R^{13}$, which are the same or different;

wherein $—R^{13}$ is selected from the group consisting of $—H$, $—NO_2$, $—OCH_3$, $—CN$, $—N(R^{14})(R^{14a})$, $—OH$, $—C(O)OH$ and $C_{1-6}$ alkyl; wherein $C_{1-6}$ alkyl is optionally substituted with one or more halogen, which are the same or different;

wherein $—R^{14}$ and $—R^{14a}$ are independently selected from the group consisting of $—H$ and $C_{1-6}$ alkyl; wherein $C_{1-6}$ alkyl is optionally substituted with one or more halogen, which are the same or different;

optionally, one or more of the pairs $—R^1/—R^{1a}$, $—R^2/—R^{2a}$, two adjacent $R^2$, $—R^6/—R^{6a}$, $—R^{10}/—R^{10a}$, $—R^{11}/—R^{11a}$ and $—R^{12}/—R^{12a}$ are joined together with the atom to which they are attached to form a $C_{3-10}$ cycloalkyl, 3- to 10-membered heterocyclyl or an 8- to 11-membered heterobicyclyl;

optionally, one or more of the pairs $—R^1/—R^2$, $—R^1/—R^5$, $—R^1/—R^6$, $—R^1/—R^9$, $—R^1/—R^{10}$, $—R^3/—R^{6a}$, $—R^4/—R^5$, $—R^{4a}/—R^5$, $—R^4/—R^6$, $—R^5/—R^{10}$, $—R^6/—R^{10}$ and $—R^{4a}/—R^6$ are joined together with the atoms to which they are attached to form a ring -A-;

wherein -A- is selected from the group consisting of phenyl, naphthyl, indenyl, indanyl, tetralinyl, $C_{3-10}$ cycloalkyl, 3- to 10-membered heterocyclyl and 8- to 11-membered heterobicyclyl;

optionally, $—R^1$ and an adjacent $—R^2$ form a carbon-carbon double bond provided that n is selected from the group consisting of 1, 2, 3 and 4;

optionally, two adjacent $—R^2$ form a carbon-carbon double bond provided that n is selected from the group consisting of 2, 3 and 4;

provided that if $—X^2—$ is $—N(R^5)—$, $—X^3—$ is selected from the group consisting of

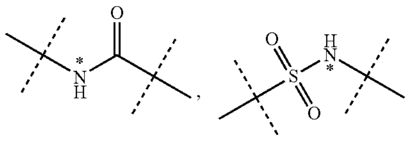

and

-continued

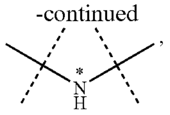

and the distance between the nitrogen atom marked with an asterisk and the carbon atom marked with an asterisk in formula (IX) is 5, 6 or 7 atoms and if present the carbon-carbon double bond formed between —$R^1$ and —$R^2$ or two adjacent —$R^2$ is in a cis configuration; and wherein -$L^1$- is substituted with —$X^{0D}$-$L^2$- and wherein -$L^1$- is optionally further substituted.

It is understood that two adjacent —$R^2$ in formula (IX) can only exist if n is at least 2.

It is understood that the expression "distance between the nitrogen atom marked with an asterisk and the carbon atom marked with an asterisk" refers to the total number of atoms in the shortest distance between the nitrogen and carbon atoms marked with the asterisk and also includes the nitrogen and carbon atoms marked with the asterisk. For example, in the structure below, n is 1 and the distance between the nitrogen marked with an asterisk and the carbon marked with an asterisk is 5:

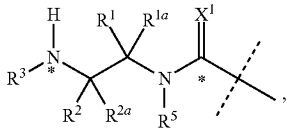

and in the structure below, n is 2, —$R^1$ and —$R^{1a}$ form a cyclohexal and the distance between the nitrogen marked with an asterisk and the carbon marked with an asterisk is 6:

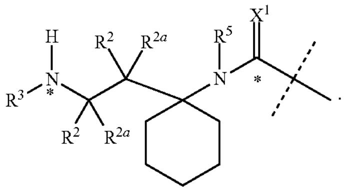

The optional further substituents of -$L^1$- of formula (IX) are as described elsewhere herein.

In certain embodiments -$L^1$- of formula (IX) is not further substituted.

In certain embodiments =$X^1$ of formula (IX) is =O. In certain embodiments =$X^1$ of formula (IX) is =S. In certain embodiments =$X^1$ of formula (IX) is =N($R^4$).

In certain embodiments —$X^2$— of formula (IX) is —O—. In certain embodiments —$X^2$— of formula (IX) is —S—. In certain embodiments —$X^2$— of formula (IX) is —N($R^5$)—. In certain embodiments —$X^2$— of formula (IX) is —C($R^6$)($R^{6a}$)—.

In certain embodiments —$X^3$— of formula (IX) is

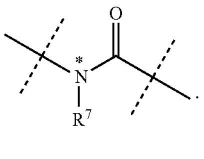

In certain embodiments —$X^3$— of formula (IX) is

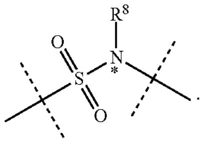

In certain embodiments —$X^3$— of formula (IX) is

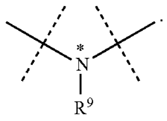

In certain embodiments —$X^3$— of formula (IX) is —C($R^{10}$)($R^{10a}$)—. In certain embodiments —$X^3$— of formula (IX) is —C($R^{11}$)($R^{11a}$)—C($R^{12}$)($R^{12a}$)—. In certain embodiments —$X^3$— of formula (IX) is —O—. In certain embodiments —$X^3$— of formula (IX) is —C(O)—.

In certain embodiments —$X^2$— of formula (IX) is —N($R^5$)—, —$X^3$— is

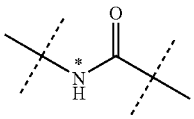

and the distance between the nitrogen atom marked with an asterisk and the carbon atom marked with an asterisk in formula (IX) is 5 atoms.

In certain embodiments —$X^2$— of formula (IX) is —N($R^5$)—, —$X^3$— is

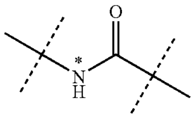

and the distance between the nitrogen atom marked with an asterisk and the carbon atom marked with an asterisk in formula (IX) is 6 atoms.

In certain embodiments —$X^2$— of formula (IX) is —N($R^5$)—, —$X^3$— is

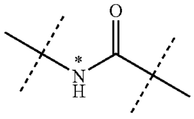

and the distance between the nitrogen atom marked with an asterisk and the carbon atom marked with an asterisk in formula (IX) is 7 atoms.

In certain embodiments —$X^2$— of formula (IX) is —N($R^5$)—, —$X^3$— is

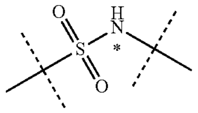

and the distance between the nitrogen atom marked with an asterisk and the carbon atom marked with an asterisk in formula (IX) is 5 atoms.

In certain embodiments —$X^2$— of formula (IX) is —$N(R^5)$—, —$X^3$— is

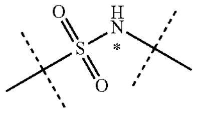

and the distance between the nitrogen atom marked with an asterisk and the carbon atom marked with an asterisk in formula (IX) is 6 atoms.

In certain embodiments —$X^2$— of formula (IX) is —$N(R^5)$—, —$X^3$— is

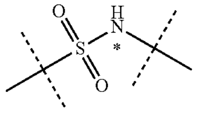

and the distance between the nitrogen atom marked with an asterisk and the carbon atom marked with an asterisk in formula (IX) is 7 atoms.

In certain embodiments —$X^2$— of formula (IX) is —$N(R^5)$—, —$X^3$— is

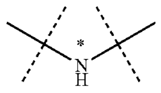

and the distance between the nitrogen atom marked with an asterisk and the carbon atom marked with an asterisk in formula (IX) is 5 atoms.

In certain embodiments —$X^2$— of formula (IX) is —$N(R^5)$—, —$X^3$— is

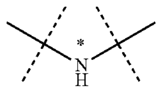

and the distance between the nitrogen atom marked with an asterisk and the carbon atom marked with an asterisk in formula (IX) is 6 atoms.

In certain embodiments —$X^2$— of formula (IX) is —$N(R^5)$—, —$X^3$— is

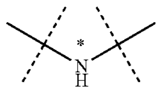

and the distance between the nitrogen atom marked with an asterisk and the carbon atom marked with an asterisk in formula (IX) is 7 atoms.

In certain embodiments =$X^1$ of formula (IX) is =O, —$X^2$— of formula (IX) is —$C(R^6)(R^{6a})$— —$X^3$— of formula (IX) is

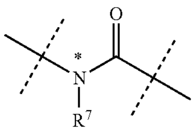

and —$R^3$ of formula (IX) does not comprise an amine.

In certain embodiments —$R^1$, —$R^{1a}$, —$R^6$, —$R^{6a}$, —$R^{10}$, —$R^{10a}$, —$R^{11}$, —$R^{11a}$, —$R^{12}$, —$R^{12a}$ and each of —$R^2$ and —$R^{2a}$ of formula (IX) are independently selected from the group consisting of —H, —C(O)OH, halogen, —CN, —OH, $C_{1-6}$ alkyl, $C_{2-6}$ alkenyl and $C_{2-6}$ alkynyl.

In certain embodiments —$R^1$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^1$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^1$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^1$ of formula (IX) is selected from the group consisting of —H, —C(O) OH, —OH and $C_{1-6}$ alkyl. In certain embodiments —$R^1$ of formula (IX) is —H. In certain embodiments —$R^1$ of formula (IX) is —C(O)OH. In certain embodiments —$R^1$ of formula (IX) is halogen. In certain embodiments —$R^1$ of formula (IX) is —F. In certain embodiments —$R^1$ of formula (IX) is —CN. In certain embodiments —$R^1$ of formula (IX) is —OH. In certain embodiments —$R^1$ of formula (IX) is $C_{1-6}$ alkyl. In certain embodiments —$R^1$ of formula (IX) is $C_{2-6}$ alkenyl. In certain embodiments —$R^1$ of formula (IX) is $C_{2-6}$ alkynyl. In certain embodiments —$R^1$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{1a}$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^{1a}$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^{1a}$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^{1a}$ of formula (IX) is selected from the group consisting of —H, —C(O) OH, —OH and $C_{1-6}$ alkyl. In certain embodiments -Ria of formula (IX) is —H. In certain embodiments —$R^{1a}$ of formula (IX) is —C(O)OH. In certain embodiments -Ria of formula (IX) is halogen. In certain embodiments —$R^{1a}$ of formula (IX) is —F. In certain embodiments —$R^{1a}$ of formula (IX) is —CN. In certain embodiments —$R^{1a}$ of formula (IX) is —OH. In certain embodiments —$R^{1a}$ of formula (IX) is $C_{1-6}$ alkyl. In certain embodiments —$R^{1a}$ of formula (IX) is $C_{2-6}$ alkenyl. In certain embodiments —$R^{1a}$ of formula (IX) is $C_{2-6}$ alkynyl. In certain embodiments —$R^{1a}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^6$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^6$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^6$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^6$ of formula (IX) is selected from the group consisting of —H, —C(O) OH, —OH and $C_{1-6}$ alkyl. In certain embodiments —$R^6$ of formula (IX) is —H. In certain embodiments —$R^6$ of formula (IX) is —C(O)OH. In certain embodiments —$R^6$ of formula (IX) is halogen. In certain embodiments —$R^6$ of formula (IX) is —F. In certain embodiments —R of formula (IX) is —CN. In certain embodiments —$R^6$ of formula (IX) is —OH. In certain embodiments —$R^6$ of formula (IX) is $C_{1-6}$ alkyl. In certain embodiments —$R^6$ of formula (IX) is $C_{2-6}$ alkenyl. In certain embodiments —$R^6$ of formula (IX) is $C_{2-6}$ alkynyl. In certain embodiments —$R^6$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{6a}$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^{6a}$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^{6a}$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^{6a}$ of formula (IX) is selected from the group consisting of —H, —C(O) OH, —OH and $C_{1-6}$ alkyl. In certain embodiments —$R^{6a}$ of formula (IX) is —H. In certain embodiments —$R^{6a}$ of formula (IX) is —C(O)OH. In certain embodiments —$R^{6a}$ of formula (IX) is halogen. In certain embodiments —$R^{6a}$ of formula (IX) is —F. In certain embodiments —$R^{6a}$ of formula (IX) is —CN. In certain embodiments —$R^{6a}$ of formula (IX) is —OH. In certain embodiments —$R^{6a}$ of formula (IX) is $C_{1-6}$ alkyl. In certain embodiments —$R^{6a}$ of formula (IX) is $C_{2-6}$ alkenyl. In certain embodiments —$R^{6a}$ of formula (IX) is $C_{2-6}$ alkynyl. In certain embodiments —$R^{6a}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{10}$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^{10}$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^{10}$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^{10}$ of formula (IX) is selected from the group consisting of —H, —C(O) OH, —OH and $C_{1-6}$ alkyl. In certain embodiments —$R^{10}$ of formula (IX) is —H. In certain embodiments —$R^{10}$ of formula (IX) is —C(O)OH. In certain embodiments —$R^{10}$ of formula (IX) is halogen. In certain embodiments —$R^{10}$ of formula (IX) is —F. In certain embodiments —$R^{10}$ of formula (IX) is —CN. In certain embodiments —$R^{10}$ of formula (IX) is —OH. In certain embodiments —$R^{10}$ of formula (IX) is $C_{1-6}$ alkyl. In certain embodiments —$R^{10}$ of formula (IX) is $C_{2-6}$ alkenyl. In certain embodiments —$R^{10}$ of formula (IX) is $C_{2-6}$ alkynyl. In certain embodiments —$R^{10}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{10a}$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^{10a}$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^{10a}$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^{10a}$ of formula (IX) is selected from the group consisting of —H, —C(O)OH, —OH and $C_{1-6}$ alkyl. In certain embodiments —$R^{10a}$ of formula (IX) is —H. In certain embodiments —$R^{10a}$ of formula (IX) is —C(O)OH. In certain embodiments —$R^{10a}$ of formula (IX) is halogen. In certain embodiments —$R^{10a}$ of formula (IX) is —F. In certain embodiments —$R^{10a}$ of formula (IX) is —CN. In certain embodiments —$R^{10a}$ of formula (IX) is —OH. In certain embodiments —$R^{11a}$ of formula (IX) is $C_{1-6}$ alkyl. In certain embodiments —$R^{10a}$ of formula (IX) is $C_{2-6}$ alkenyl. In certain embodiments —$R^{11a}$ of formula (IX) is $C_{2-6}$ alkynyl. In certain embodiments —$R^{10a}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{11}$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^{11}$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^{11}$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^{11}$ of formula (IX) is selected from the group consisting of —H, —C(O) OH, —OH and $C_{1-6}$ alkyl. In certain embodiments —$R^{11}$ of formula (IX) is —H. In certain embodiments —$R^{11}$ of formula (IX) is —C(O)OH. In certain embodiments —$R^{11}$ of formula (IX) is halogen. In certain embodiments —$R^{11}$ of formula (IX) is —F. In certain embodiments —$R^1$ of formula (IX) is —CN. In certain embodiments —$R^{11}$ of formula (IX) is —OH. In certain embodiments —$R^{11}$ of formula (IX) is $C_{1-6}$ alkyl. In certain embodiments —$R^1$ of formula (IX) is $C_{2-6}$ alkenyl. In certain embodiments —$R^1$ of formula (IX) is $C_{2-6}$ alkynyl. In certain embodiments —$R^{11}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{11a}$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^{11a}$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^{11a}$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^{11a}$ of formula (IX) is selected from the group consisting of —H, —C(O)OH, —OH and $C_{1-6}$ alkyl. In certain embodiments —$R^{11a}$ of formula (IX) is —H. In certain embodiments —$R^{11a}$ of formula (IX) is —C(O)OH. In certain embodiments —$R^{11a}$ of formula (IX) is halogen. In certain embodiments —$R^{11a}$ of formula (IX) is —F. In certain embodiments —$R^{Ia}$ of formula (IX) is —CN. In certain embodiments —$R^{11a}$ of formula (IX) is —OH. In certain embodiments —$R^{11a}$ of formula (IX) is $C_{1-6}$ alkyl. In certain embodiments —$R^{11a}$ of formula (IX) is $C_{2-6}$ alkenyl. In certain embodiments —$R^{11a}$ of formula (IX) is $C_{2-6}$ alkynyl. In certain embodiments —$R^{11a}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{12}$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^{12}$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^{2}$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^{12}$ of formula (IX) is selected from the group consisting of —H, —C(O)OH, —OH and $C_{1-6}$ alkyl. In certain embodiments —$R^{2}$ of formula (IX) is —H. In certain embodiments —$R^{12}$ of formula (IX) is —C(O)OH. In certain embodiments —$R^{12}$ of formula (IX) is halogen. In certain embodiments —$R^{12}$ of formula (IX) is —F. In certain embodiments —$R^{12}$ of formula (IX) is —CN. In certain embodiments —$R^{12}$ of formula (IX) is —OH. In certain embodiments —$R^{12}$ of formula (IX) is $C_{1-6}$ alkyl. In certain embodiments —$R^{2}$ of formula (IX) is $C_{2-6}$ alkenyl. In certain embodiments —$R^{12}$ of formula (IX) is $C_{2-6}$ alkynyl. In certain embodiments —$R^{12}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{12a}$ of formula (IX) is selected from the group consisting of —H, —C(O)OH, halogen, —CN, —OH, $C_{1-6}$ alkyl, $C_{2-6}$ alkenyl and $C_{2-6}$ alkynyl. In certain embodiments —$R^{12a}$ of formula (IX) is selected from the group consisting of —H, —C(O)OH, —CN, —OH, $C_{1-6}$ alkyl, $C_{2-6}$ alkenyl and $C_{2-6}$ alkynyl. In certain embodiments —$R^{2a}$ of formula (IX) is selected from the group consisting of —H, —C(O)OH, halogen, —OH, $C_{1-6}$ alkyl, $C_{2-6}$ alkenyl and $C_{2-6}$ alkynyl. In certain embodiments —$R^{12a}$ of formula (IX) is selected from the group consisting of —H, —C(O)OH, —OH and $C_{1-6}$ alkyl. In certain embodiments —$R^{12a}$ of formula (IX) is —H. In certain embodiments —$R^{12a}$ of formula (IX) is —C(O)OH. In certain embodiments —$R^{12a}$ of formula (IX) is halogen. In certain embodiments —$R^{12a}$ of formula (IX) is —F. In certain embodiments —$R^{12a}$ of formula (IX) is —CN. In certain embodiments —$R^{12a}$ of formula (IX) is —OH. In certain embodiments —$R^{12a}$ of formula (IX) is $C_{1-6}$ alkyl. In certain embodiments —$R^{12a}$ of formula (IX) is $C_{2-6}$ alkenyl. In certain embodiments —$R^{12a}$ of formula (IX) is $C_{2-6}$ alkynyl. In certain embodiments —$R^{12a}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments each of —$R^{2}$ of formula (IX) is independently selected from the group consisting of —H, —C(O)OH, halogen, —CN, —OH, $C_{1-6}$ alkyl, $C_{2-6}$ alkenyl and $C_{2-6}$ alkynyl. In certain embodiments each of —$R^{2}$ of formula (IX) is independently selected from the group consisting of —H, —C(O)OH, —CN, —OH, $C_{1-6}$ alkyl, $C_{2-6}$ alkenyl and $C_{2-6}$ alkynyl. In certain embodiments each of —$R^{2}$ of formula (IX) is independently selected from the group consisting of —H, —C(O)OH, halogen, —OH, $C_{1-6}$ alkyl, $C_{2-6}$ alkenyl and $C_{2-6}$ alkynyl. In certain embodiments each of —$R^{2}$ of formula (IX) is independently selected from the group consisting of —H, —C(O)OH, —OH and $C_{1-6}$ alkyl. In certain embodiments each of —$R^{2}$ of formula (IX) is —H. In certain embodiments each of —$R^{2}$ of formula (IX) is —C(O)OH. In certain embodiments each of —$R^{2}$ of formula (IX) is halogen. In certain embodiments each of —$R^{2}$ of formula (IX) is —F. In certain embodiments each of —$R^{2}$ of formula (IX) is —CN. In certain embodiments each of —$R^{2}$ of formula (IX) is —OH. In certain embodiments each of —$R^{2}$ of formula (IX) is $C_{1-6}$ alkyl. In certain embodiments each of —$R^{2}$ of formula (IX) is $C_{2-6}$ alkenyl. In certain embodiments each of —$R^{2}$ of formula (IX) is $C_{2-6}$ alkynyl. In certain embodiments each of —$R^{2}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments each of —$R^{2a}$ of formula (IX) is independently selected from the group consisting of —H, —C(O)OH, halogen, —CN, —OH, $C_{1-6}$ alkyl, $C_{2-6}$ alkenyl and $C_{2-6}$ alkynyl. In certain embodiments each of —$R^{2a}$ of formula (IX) is independently selected from the group consisting of —H, —C(O)OH, —CN, —OH, $C_{1-6}$ alkyl, $C_{2-6}$ alkenyl and $C_{2-6}$ alkynyl. In certain embodiments each of —$R^{2a}$ of formula (IX) is independently selected from the group consisting of —H, —C(O)OH, halogen, —OH, $C_{1-6}$ alkyl, $C_{2-6}$ alkenyl and $C_{2-6}$ alkynyl. In certain embodiments each of —$R^{2a}$ of formula (IX) is independently selected from the group consisting of —H, —C(O)OH, —OH and $C_{1-6}$ alkyl. In certain embodiments each of —$R^{2a}$ of formula (IX) is —H. In certain embodiments each of —$R^{2a}$ of formula (IX) is —C(O)OH. In certain embodiments each of —$R^{2a}$ of formula (IX) is halogen. In certain embodiments each of —$R^{2a}$ of formula (IX) is —F. In certain embodiments each of —$R^{2a}$ of formula (IX) is —CN. In certain embodiments each of —$R^{2a}$ of formula (IX) is —OH. In certain embodiments each of —$R^{2a}$ of formula (IX) is $C_{1-6}$ alkyl. In certain embodiments each of —$R^{2a}$ of formula (IX) is $C_{2-6}$ alkenyl. In certain embodiments each of —$R^{2a}$ of formula (IX) is $C_{2-6}$ alkynyl. In certain embodiments each of —$R^{2a}$ of formula (IX) is selected from the group consisting of —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methylbutyl, 1-methylbutyl and 1-ethylpropyl.

In certain embodiments —$R^{3}$, —$R^{4}$, —$R^{5}$, —$R^{7}$, —$R^{8}$ and —$R^{9}$ of formula (IX) are independently selected from the group consisting of —H, -T, —CN, $C_{1-6}$ alkyl, $C_{2-6}$ alkenyl and $C_{2-6}$ alkynyl. In certain embodiments —$R^{3}$, —$R^{4}$, —$R^{5}$, —$R^{7}$, —$R^{8}$ and —$R^{9}$ of formula (IX) are independently selected from the group consisting of —H, -T, —CN, $C_{1-6}$ alkyl and $C_{2-6}$ alkenyl. In certain embodiments —$R^{3}$, —$R^{4}$, —$R^{5}$, —$R^{1}$, —$R^{8}$ and —$R^{9}$ of formula (IX) are independently selected from the group consisting of —H, -T, —CN and $C_{1-6}$ alkyl. In certain embodiments —$R^{3}$, —$R^{4}$, —$R^5$, —$R^7$, —$R^8$ and —$R^9$ of formula (IX) are independently selected from the group consisting of —H, -T and $C_{1-6}$ alkyl. In certain embodiments —$R^3$, —$R^4$, —$R^5$, —$R^7$, —$R^8$ and —$R^9$ of formula (IX) are independently selected from the group consisting of —H and $C_{1-6}$ alkyl.

In certain embodiments —$R^3$ of formula (IX) is selected from the group consisting of —H, -T, —CN, $C_{1-6}$ alkyl, $C_{2-6}$ alkenyl and $C_{2-6}$ alkynyl. In certain embodiments —$R^3$ of formula (IX) is —H. In certain embodiments —$R^3$ of formula (IX) is -T. In certain embodiments —$R^3$ of formula (IX) is —CN. In certain embodiments —$R^3$ of formula (IX) is $C_{1-6}$ alkyl. In certain embodiments —$R^3$ of formula (IX) is $C_{2-6}$ alkenyl. In certain embodiments —$R^3$ of formula (IX) is $C_{2-6}$ alkynyl.

In certain embodiments —$R^4$ of formula (IX) is selected from the group consisting of —H, -T, —CN, $C_{1-6}$ alkyl, $C_{2-6}$ alkenyl and $C_{2-6}$ alkynyl. In certain embodiments —$R^4$ of formula (IX) is —H. In certain embodiments —$R^4$ of formula (IX) is -T. In certain embodiments —$R^4$ of formula (IX) is —CN. In certain embodiments —$R^4$ of formula (IX) is $C_{1-6}$ alkyl. In certain embodiments —$R^4$ of formula (IX) is $C_{2-6}$ alkenyl. In certain embodiments —$R^4$ of formula (IX) is $C_{2-6}$ alkynyl.

In certain embodiments —$R^5$ of formula (IX) is selected from the group consisting of —H, -T, —CN, $C_{1-6}$ alkyl, $C_{2-6}$ alkenyl and $C_{2-6}$ alkynyl. In certain embodiments —$R^5$ of formula (IX) is —H. In certain embodiments —$R^5$ of formula (IX) is -T. In certain embodiments —$R^5$ of formula (IX) is —CN. In certain embodiments —$R^5$ of formula (IX) is $C_{1-6}$ alkyl. In certain embodiments —$R^5$ of formula (IX) is $C_{2-6}$ alkenyl. In certain embodiments —$R^5$ of formula (IX) is $C_{2-6}$ alkynyl.

In certain embodiments —$R^7$ of formula (IX) is selected from the group consisting of —H, -T, —CN, $C_{1-6}$ alkyl, $C_{2-6}$ alkenyl and $C_{2-6}$ alkynyl. In certain embodiments —$R^7$ of formula (IX) is —H. In certain embodiments —$R^7$ of formula (IX) is -T. In certain embodiments —$R^7$ of formula (IX) is —CN. In certain embodiments —$R^7$ of formula (IX) is $C_{1-6}$ alkyl. In certain embodiments —$R^7$ of formula (IX) is $C_{2-6}$ alkenyl. In certain embodiments —$R^7$ of formula (IX) is $C_{2-6}$ alkynyl.

In certain embodiments —$R^8$ of formula (IX) is selected from the group consisting of —H, -T, —CN, $C_{1-6}$ alkyl, $C_{2-6}$ alkenyl and $C_{2-6}$ alkynyl. In certain embodiments —$R^8$ of formula (IX) is —H. In certain embodiments —$R^8$ of formula (IX) is -T. In certain embodiments —$R^8$ of formula (IX) is —CN. In certain embodiments —$R^8$ of formula (IX) is $C_{1-6}$ alkyl. In certain embodiments —$R^8$ of formula (IX) is $C_{2-6}$ alkenyl. In certain embodiments —$R^8$ of formula (IX) is $C_{2-6}$ alkynyl.

In certain embodiments —$R^9$ of formula (IX) is selected from the group consisting of —H, -T, —CN, $C_{1-6}$ alkyl, $C_{2-6}$ alkenyl and $C_{2-6}$ alkynyl. In certain embodiments —$R^9$ of formula (IX) is —H. In certain embodiments —$R^9$ of formula (IX) is -T. In certain embodiments —$R^9$ of formula (IX) is —CN. In certain embodiments —$R^9$ of formula (IX) is $C_{1-6}$ alkyl. In certain embodiments —$R^9$ of formula (IX) is $C_{2-6}$ alkenyl. In certain embodiments —$R^9$ of formula (IX) is $C_{2-6}$ alkynyl.

In certain embodiments T of formula (IX) is selected from the group consisting of phenyl, naphthyl, indenyl, indanyl, tetralinyl, $C_{3-10}$ cycloalkyl, 3- to 10-membered heterocyclyl and 8- to 11-membered heterobicyclyl. In certain embodiments T of formula (IX) is phenyl. In certain embodiments T of formula (IX) is naphthyl. In certain embodiments T of formula (IX) is indenyl. In certain embodiments T of formula (IX) is indanyl. In certain embodiments T of formula (IX) is tetralinyl. In certain embodiments T of formula (IX) is $C_{3-10}$ cycloalkyl. In certain embodiments T of formula (IX) is 3- to 10-membered heterocyclyl. In certain embodiments T of formula (IX) is 8- to 11-membered heterobicyclyl.

In certain embodiments T of formula (IX) is substituted with one or more —$R^{13}$, which are the same or different.

In certain embodiments T of formula (IX) is substituted with one —$R^{13}$.

In certain embodiments T of formula (IX) is not substituted with —$R^{13}$.

In certain embodiments —$R^3$ of formula (IX) is selected from the group consisting of —H, —$NO_2$, —$OCH_3$, —CN, —$N(R^{14})(R^{14a})$, —OH, —C(O)OH and $C_{1-6}$ alkyl.

In certain embodiments —$R^{13}$ of formula (IX) is —H. In certain embodiments —$R^{13}$ of formula (IX) is —$NO_2$. In certain embodiments —$R^3$ of formula (IX) is —$OCH_3$. In certain embodiments —$R^{13}$ of formula (IX) is —CN. In certain embodiments —$R^{13}$ of formula (IX) is —$N(R^{14})(R^{14a})$. In certain embodiments —$R^{13}$ of formula (IX) is —OH. In certain embodiments —$R^{13}$ of formula (IX) is —C(O)OH. In certain embodiments —$R^{13}$ of formula (IX) is $C_{1-6}$ alkyl.

In certain embodiments —$R^{14}$ and —$R^{14a}$ of formula (IX) are independently selected from the group consisting of —H and $C_{1-6}$ alkyl. In certain embodiments —$R^{14}$ of formula (IX) is —H. In certain embodiments —$R^{14}$ of formula (IX) is $C_{1-6}$ alkyl. In certain embodiments —$R^{14a}$ of formula (IX) is —H. In certain embodiments —$R^{14a}$ of formula (IX) is $C_{1-6}$ alkyl.

In certain embodiments n of formula (IX) is selected from the group consisting of 0, 1, 2 and 3. In certain embodiments n of formula (IX) is selected from the group consisting of 0, 1 and 2. In certain embodiments n of formula (IX) is selected from the group consisting of 0 and 1. In certain embodiments n of formula (IX) is 0. In certain embodiments n of formula (I) is 1. In certain embodiments n of formula (IX) is 2. In certain embodiments n of formula (I) is 3. In certain embodiments n of formula (IX) is 4.

In certain embodiments -$L^1$- of formula (IX) is connected to -D through a linkage selected from the group consisting of amide, carbamate, dithiocarbamate, 0-thiocarbamate, S-thiocarbamate, urea, thiourea, thioamide, amidine and guanidine. It is understood that some of these linkages may not be reversible per se, but that in the present invention neighboring groups present in -$L^1$-, such as for example amide, primary amine, secondary amine and tertiary amine, render these linkages reversible.

In certain embodiments -$L^1$- of formula (XI) is conjugated to -D through an amide linkage, i.e. =$X^1$ is =O and —$X^2$— is —$C(R^6)(R^{6a})$—.

In certain embodiments -$L^1$- of formula (IX) is conjugated to -D through a carbamate linkage, i.e. =$X^1$ is =O and —$X^2$— is —O—.

In certain embodiments -$L^1$- of formula (IX) is conjugated to -D through a dithiocarbamate linkage, i.e. =$X^1$ is =S and —$X^2$— is —S—.

In certain embodiments -$L^1$- of formula (IX) is conjugated to -D through an O-thiocarbamate linkage, i.e. =$X^1$ is =S and —$X^2$— is —O—.

In certain embodiments -$L^1$- of formula (IX) is conjugated to -D through a S-thiocarbamate linkage, i.e. =$X^1$ is =O and —$X^2$— is —S—.

In certain embodiments -$L^1$- of formula (IX) is conjugated to -D through a urea linkage, i.e. =$X^1$ is =O and —$X^2$— is —$N(R^5)$—.

In certain embodiments $-L^1-$ of formula (IX) is conjugated to -D through a thiourea linkage, i.e. $=X^1$ is $=S$ and $—X^2—$ is $—N(R^5)—$.

In certain embodiments $-L^1-$ of formula (IX) is conjugated to -D through a thioamide linkage, i.e. $=X^1$ is $=S$ and $—X^2—$ is $—C(R^6)(R^{6a})$.

In certain embodiments $-L^1-$ of formula (IX) is conjugated to -D through an amidine linkage, i.e. $=X^1$ is $=N(R^4)$ and $—X^2—$ is $—C(R^6)(R^{6a})—$.

In certain embodiments $-L^1-$ of formula (IX) is conjugated to -D through a guanidine linkage, i.e. $=X^1$ is $=N(R^4)$ and $—X^2—$ is $—N(R^5)—$.

In certain embodiments $-L^1-$ is of formula (IX'):

(IX')

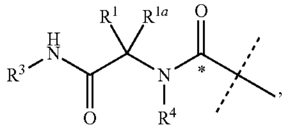

wherein the dashed line indicates the attachment to a π-electron-pair-donating heteroaromatic N of -D; and $—R^1$, $—R^{1a}$, $—R^3$ and $—R^4$ are used as defined in formula (IX).

In certain embodiments $—R^1$ and $—R^{1a}$ of formula (IX') are both —H.

In certain embodiments $—R^1$ of formula (IX') is —H and $—R^{1a}$ of formula (IX') is $C_{1-6}$ alkyl.

In certain embodiments $—R^3$ of formula (IX') is $C_{1-6}$ alkyl.

In certain embodiments $—R^4$ of formula (IX') is methyl.

In certain embodiments $—R^4$ of formula (IX') is ethyl.

In certain embodiments $-L^1-$ is of formula (X)

(X)

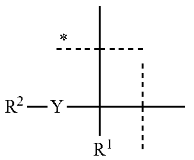

wherein the dashed line marked with an asterisk indicates the attachment to $—X^{0D}-L^2-$;

the unmarked dashed line indicates the attachment to a π-electron-pair-donating heteroaromatic N of -D;

—Y— is selected from the group consisting of $—N(R^3)—$, —O— and —S—;

$—R^1$, $—R^2$ and $—R^3$ are independently selected from the group consisting of —H, -T, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $—R^4$, which are the same or different; and wherein $C_{1-6}$ alkyl, $C_{2-6}$ alkenyl and $C_{2-6}$ alkynyl are optionally interrupted by one or more groups selected from the group consisting of -T-, —C(O)O—, —O—, —C(O)—, $—C(O)N(R^5)—$, $—S(O)_2N(R^5)—$, $—S(O)N(R^5)—$, $—S(O)_2—$, —S(O)—, $—N(R^5)S(O)_2N(R^{5a})—S—$, $—N(R^5)$, $—OC(OR^5)(R^{5a})—$, $—N(R^5)C(O)N(R^{5a})—$ and $—OC(O)N(R^5)—$;

each T is independently selected from the group consisting of phenyl, naphthyl, indenyl, indanyl, tetralinyl, $C_{3-10}$ cycloalkyl, 3- to 10-membered heterocyclyl and 8- to 11-membered heterobicyclyl, wherein each T is independently optionally substituted with one or more $—R^4$, which are the same or different;

wherein $—R^4$, $—R^5$ and $—R^{5a}$ are independently selected from the group consisting of —H and $C_{1-6}$ alkyl; wherein $C_{1-6}$ alkyl is optionally substituted with one or more halogen, which are the same or different; and wherein $-L^1-$ is substituted with $—X^{0D}-L^2-$ and wherein $-L^1-$ is optionally further substituted.

The optional further substituents of $-L^1-$ of formula (X) are as described elsewhere herein.

In certain embodiments $-L^1-$ of formula (X) is not further substituted.

In certain embodiments —Y— of formula (X) is $—N(R^3)—$.

In certain embodiments —Y— of formula (X) is —O—.

In certain embodiments —Y— of formula (X) is —S—.

In certain embodiments $—R^1$, $—R^2$ and $—R^3$ of formula (X) are independently selected from the group consisting of —H, -T, $C_{1-6}$ alkyl, $C_{2-6}$ alkenyl and $C_{2-6}$ alkynyl.

In certain embodiments $—R^1$ of formula (X) is independently selected from the group consisting of —H, -T, $C_{1-6}$ alkyl, $C_{2-6}$ alkenyl and $C_{2-6}$ alkynyl. In certain embodiments $—R^1$ of formula (X) is —H. In certain embodiments $—R^1$ of formula (X) is -T. In certain embodiments $—R^1$ of formula (X) is $C_{1-6}$ alkyl. In certain embodiments $—R^1$ of formula (X) is $C_{2-6}$ alkenyl. In certain embodiments $—R^1$ of formula (X) is $C_{2-6}$ alkynyl.

In certain embodiments $—R^2$ of formula (X) is independently selected from the group consisting of —H, -T, $C_{1-6}$ alkyl, $C_{2-6}$ alkenyl and $C_{2-6}$ alkynyl. In certain embodiments $—R^2$ of formula (X) is —H. In certain embodiments $—R^2$ of formula (X) is -T. In certain embodiments $—R^2$ of formula (X) is $C_{1-6}$ alkyl. In certain embodiments $—R^2$ of formula (X) is $C_{2-6}$ alkenyl. In certain embodiments $—R^2$ of formula (X) is $C_{2-6}$ alkynyl.

In certain embodiments $—R^3$ of formula (X) is independently selected from the group consisting of —H, -T, $C_{1-6}$ alkyl, $C_{2-6}$ alkenyl and $C_{2-6}$ alkynyl. In certain embodiments $—R^3$ of formula (X) is —H. In certain embodiments $—R^3$ of formula (X) is -T. In certain embodiments $—R^3$ of formula (X) is $C_{1-6}$ alkyl. In certain embodiments $—R^3$ of formula (X) is $C_{2-6}$ alkenyl. In certain embodiments $—R^3$ of formula (X) is $C_{2-6}$ alkynyl.

In certain embodiments T of formula (X) is selected from the group consisting of phenyl, naphthyl, indenyl, indanyl, tetralinyl, $C_{3-10}$ cycloalkyl, 3- to 10-membered heterocyclyl and 8- to 11-heterobicyclyl. In certain embodiments T of formula (X) is phenyl. In certain embodiments T of formula (X) is naphthyl. In certain embodiments T of formula (X) is indenyl. In certain embodiments T of formula (X) is indanyl. In certain embodiments T of formula (X) is tetralinyl. In certain embodiments T of formula (X) is $C_{3-10}$ cycloalkyl. In certain embodiments T of formula (X) is 3- to 10-membered heterocyclyl. In certain embodiments T of formula (X) is 8- to 11-heterobicyclyl.

In certain embodiments T of formula (X) is substituted with one or more $—R^4$.

In certain embodiments T of formula (X) is substituted with one $—R^4$.

In certain embodiments T of formula (X) is not substituted with $—R^4$.

In certain embodiments $—R^4$, $—R^5$ and $—R^{5a}$ of formula (X) are independently selected from the group consisting of —H and $C_{1-6}$ alkyl.

In certain embodiments —$R^4$ of formula (X) is selected from the group consisting of —H and $C_{1-6}$ alkyl. In certain embodiments —$R^4$ of formula (X) is —H. In certain embodiments —$R^4$ of formula (X) is $C_{1-6}$ alkyl.

In certain embodiments —$R^5$ of formula (X) is selected from the group consisting of —H and $C_{1-6}$ alkyl. In certain embodiments —$R^5$ of formula (X) is —H. In certain embodiments —$R^5$ of formula (X) is $C_{1-6}$ alkyl.

In certain embodiments —$R^{5a}$ of formula (X) is selected from the group consisting of —H and $C_{1-6}$ alkyl. In certain embodiments —$R^{5a}$ of formula (X) is —H. In certain embodiments —$R^{5a}$ of formula (X) is $C_{1-6}$ alkyl.

In certain embodiments -$L^1$- of formula (X) is connected to -D through a heminal linkage.

In certain embodiments -$L^1$- of formula (X) is connected to -D through an aminal linkage.

In certain embodiments -$L^1$- of formula (X) is connected to -D through a hemithioaminal linkage.

A moiety -$L^1$- suitable for drugs D that when bound to -$L^1$- comprise an electron-donating heteroaromatic $N^+$ moiety or a quaternary ammonium cation and becomes a moiety -$D^+$ upon linkage with -$L^1$- is of formula (XI)

(XI)

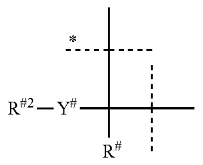

wherein the dashed line marked with an asterisk indicates the attachment to —$X^{0D}$-$L^2$-, the unmarked dashed line indicates the attachment to the $N^+$of -$D^+$;

—$Y^4$— is selected from the group consisting of —$N(R^{\#3})$—, —O— and —S—;

—$R^{\#1}$, —$R^{\#2}$ and —$R^{\#3}$ are independently selected from the group consisting of —H, -$T^\#$, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more —$R^{\#4}$ which are the same or different; and wherein $C_{1-6}$ alkyl, $C_{2-6}$ alkenyl and $C_{2-6}$ alkynyl are optionally interrupted by one or more groups selected from the group consisting of -$T^\#$-, —C(O)O—, —O—, —C(O)—, —$C(O)N(R^{\#5})$—, —$S(O)_2N(R^{\#5})$—, —$S(O)N(R^{\#5})$—, —$S(O)_2$—, —S(O)—, —$N(R^{\#5})S(O)_2N(R^{\#5a})$—, —S—, —$N(R^{\#5})$, —$OC(OR^{\#5})(R^{\#5a})$—, —$N(R^{\#5})C(O)N(R^{\#5a})$— and —$OC(O)N(R^{\#5})$—;

each $T^\#$is independently selected from the group consisting of phenyl, naphthyl, indenyl, indanyl, tetralinyl, $C_{3-10}$ cycloalkyl, 3- to 10-membered heterocyclyl and 8- to 11-membered heterobicyclyl, wherein each $T^\#$is independently optionally substituted with one or more —$R^{\#4}$, which are the same or different; and wherein —$R^{\#4}$, $R^{\#5}$ and —$R^{\#5a}$ are independently selected from the group consisting of —H and $C_{1-6}$ alkyl; wherein $C_{1-6}$ alkyl is optionally substituted with one or more halogen, which are the same or different; and each -$L^1$- is substituted with —$X^{0D}$-$L^2$- and optionally further substituted.

It is understood that in certain embodiments -$D^+$ may comprise both an electron-donating heteroaromatic $N^+$ and a quaternary ammonium cation and analogously the corresponding D may comprise both an electron-donating heteroaromatic N and a tertiary amine. It is also understood that if D is conjugated to -$L^1$-, then -$D^+$ and -$L^1$- form a quaternary ammonium cation, for which there may be a counter anion. Examples of counter anions include, but are not limited to, chloride, bromide, acetate, bicarbonate, sulfate, bisulfate, nitrate, carbonate, alkyl sulfonate, aryl sulfonate and phosphate.

Such drug moiety -$D^+$ comprises at least one, such as one, two, three, four, five, six, seven, eight, nine or ten electron-donating heteroaromatic $N^+$ or quaternary ammonium cations and analogously the corresponding released drug D comprises at least one, such as one, two, three, four, five, six, seven, eight, nine or ten electron-donating heteroaromatic N or tertiary amines. Examples of chemical structures including heteroaromatic nitrogens i.e. $N^+$ or N, that donate an electron to the aromatic if-system include, but are not limited to, pyridine, pyridazine, pyrimidine, quinoline, quinazoline, quinoxaline, pyrazole, imidazole, isoindazole, indazole, purine, tetrazole, triazole and triazine. For example, in the imidazole ring below the heteroaromatic nitrogen which donates one electron to the aromatic if-system is marked with "§ ":

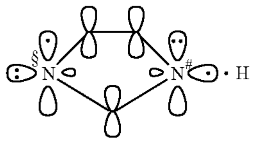

Such electron-donating heteroaromatic nitrogen atoms do not comprise heteroaromatic nitrogen atoms which donate one electron pair (i.e. not one electron) to the aromatic w-system, such as for example the nitrogen that is marked with "#" in the abovementioned imidazole ring structure. The drug D may exist in one or more tautomeric forms, such as with one hydrogen atom moving between at least two heteroaromatic nitrogen atoms. In all such cases, the linker moiety is covalently and reversibly attached at a heteroaromatic nitrogen that donates an electron to the aromatic if-system.

In certain embodiments —$Y^\#$— of formula (XI) is —$N(R^{\#3})$—. In certain embodiments —$Y^\#$— of formula (XI) is —O—. In certain embodiments —$Y^\#$— of formula (XI) is —S—.

In certain embodiments —$R^{\#1}$, —$R^{\#2}$ and —$R^{\#3}$ of formula (XI) are independently selected from the group consisting of —H, -$T^\#$, $C_{1-6}$ alkyl, $C_{2-6}$ alkenyl and $C_{2-6}$ alkynyl.

In certain embodiments —$R^{\#1}$ of formula (XI) is independently selected from the group consisting of —H, -$T^\#$, $C_{1-6}$ alkyl, $C_{2-6}$ alkenyl and $C_{2-6}$ alkynyl. In certain embodiments —$R^{\#1}$ of formula (XI) is —H. In certain embodiments —$R^{\#1}$ of formula (XI) is -$T^\#$. In certain embodiments —$R^{\#1}$ of formula (XI) is $C_{1-6}$ alkyl. In certain embodiments —$R^{\#1}$ of formula (XI) is $C_{2-6}$ alkenyl. In certain embodiments —$R^{\#1}$ of formula (XI) is $C_{2-6}$ alkynyl.

In certain embodiments —$R^{\#2}$ of formula (XI) is independently selected from the group consisting of —H, -$T^\#$, $C_{1-6}$ alkyl, $C_{2-6}$ alkenyl and $C_{2-6}$ alkynyl. In certain embodiments —$R^{\#2}$ of formula (XI) is —H. In certain embodiments —$R^2$ of formula (XI) is -$T^\#$. In certain embodiments —$R^{\#2}$ of formula (XI) is $C_{1-6}$ alkyl. In certain embodiments —$R^{\#2}$ of formula (XI) is $C_{2-6}$ alkenyl. In certain embodiments —$R^{\#2}$ of formula (XI) is $C_{2-6}$ alkynyl.

In certain embodiments, —$R^{\#3}$ of formula (XI) is independently selected from the group consisting of —H, -$T^{\#}$, $C_{1-6}$ alkyl, $C_{2-6}$ alkenyl and $C_{2-6}$ alkynyl. In certain embodiments —$R^{\#3}$ of formula (XI) is —H. In certain embodiments —$R^{\#3}$ of formula (XI) is -$T^{\#}$. In certain embodiments, —$R^{\#3}$ is $C_{1-6}$ alkyl. In certain embodiments —$R^{\#3}$ of formula (XI) is $C_{2-6}$ alkenyl. In certain embodiments —$R^{\#3}$ of formula (XI) is $C_{2-6}$ alkynyl.

In certain embodiments $T^{\#}$of formula (XI) is selected from the group consisting of phenyl, naphthyl, indenyl, indanyl, tetralinyl, $C_{3-10}$ cycloalkyl, 3- to 10-membered heterocyclyl and 8- to 11-heterobicyclyl. In certain embodiments $T^{\#}$of formula (XI) is phenyl. In certain embodiments $T^{\#}$of formula (XI) is naphthyl. In certain embodiments $T^{\#}$of formula (XI) is indenyl. In certain embodiments $T^{\#}$of formula (XI) is indanyl. In certain embodiments $T^{\#}$of formula (XI) is tetralinyl. In certain embodiments $T^{\#}$of formula (XI) is $C_{3-10}$ cycloalkyl. In certain embodiments $T^{\#}$of formula (XI) is 3- to 10-membered heterocyclyl. In certain embodiments $T^{\#}$of formula (XI) is 8- to 11-heterobicyclyl. In certain embodiments $T^{\#}$of formula (XI) is substituted with one or more —$R^4$.

In certain embodiments $T^{\#}$of formula (XI) is substituted with one —$R^4$.

In certain embodiments $T^{\#}$of formula (XI) is not substituted with —$R^4$.

In certain embodiments —$R^{\#4}$, —$R^{\#5}$ and —$R^{\#5a}$ of formula (XI) are independently selected from the group consisting of —H and $C_{1-6}$ alkyl.

In certain embodiments —$R^{\#4}$ of formula (XI) is selected from the group consisting of —H and $C_{1-6}$ alkyl. In certain embodiments —$R^{\#4}$ of formula (XI) is —H. In certain embodiments —$R^{\#4}$ of formula (XI) is $C_{1-6}$ alkyl.

In certain embodiments —$R^{\#5}$ of formula (XI) is selected from the group consisting of —H and $C_{1-6}$ alkyl. In certain embodiments —$R^5$ of formula (XI) is —H. In certain embodiments —$R^{\#5}$ of formula (XI) is $C_{1-6}$ alkyl.

In certain embodiments —$R^{\#5a}$ of formula (XI) is selected from the group consisting of —H and $C_{1-6}$ alkyl. In certain embodiments —$R^{\#5a}$ of formula (XI) is —H. In certain embodiments —$R^{\#5a}$ of formula (XI) is $C_{1-6}$ alkyl.

A moiety -$L^1$- suitable for drugs D that when bound to -$L^1$- comprise an electron-donating heteroaromatic $N^+$ moiety or a quaternary ammonium cation and becomes a moiety -$D^+$ upon linkage with -$L^1$- is of formula (XII)

(XII)

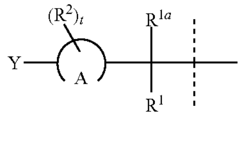

wherein the dashed line indicates the attachment to the $N^+$ of -$D^+$;

t is selected from the group consisting of 0, 1, 2, 3, 4, 5 and 6;

-A- is a ring selected from the group consisting of monocyclic or bicyclic aryl and heteroaryl, provided that -A- is connected to —Y and —$C(R^1)(R^{1a})$— via carbon atoms; wherein said monocyclic or bicyclic aryl and heteroaryl are optionally substituted with one or more —$R^2$, which are the same or different;

—$R^1$, —$R^{1a}$ and each —$R^2$ are independently selected from the group consisting of —H, —C(O)OH, -halogen, —$NO_2$, —CN, —OH, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more —$R^3$, which are the same or different; and wherein $C_{1-6}$ alkyl, $C_{2-6}$ alkenyl and $C_{2-6}$ alkynyl are optionally interrupted by one or more groups selected from the group consisting of -T-, —C(O)O—, —O—, —C(O)—, —C(O)N($R^4$)—, —$S(O)_2N(R^4)$—, —S(O)N($R^4$)—, —$S(O)_2$—, —S(O)—, —$N(R^4)S(O)_2N(R^{4a})$—, —S—, —N($R^4$)—, —$OC(OR^4)(R^{4a})$—, —$N(R^4)C(O)N(R^{4a})$— and —OC(O)N($R^4$)—;

each -T- is independently selected from the group consisting of phenyl, naphthyl, indenyl, indanyl, tetralinyl, $C_{3-10}$ cycloalkyl, 3- to 10-membered heterocyclyl and 8- to 11-membered heterobicyclyl, wherein each -T- is independently optionally substituted with one or more —$R^3$, which are the same or different;

wherein —$R^3$ is selected from the group consisting of —H, —$NO_2$, —$OCH_3$, —CN, —$N(R^4)(R^{4a})$, —OH, —C(O)OH and $C_{1-6}$ alkyl; wherein $C_{1-6}$ alkyl is optionally substituted with one or more halogen, which are the same or different;

wherein —$R^4$ and —$R^{4a}$ are independently selected from the group consisting of —H and $C_{1-6}$ alkyl; wherein $C_{1-6}$ alkyl is optionally substituted with one or more halogen, which are the same or different;

—Y is selected from the group consisting of:

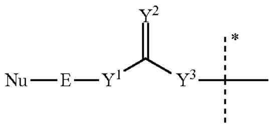,
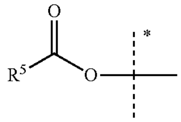,
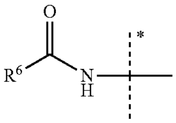,
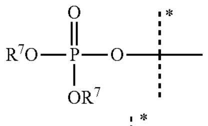,
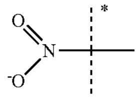,
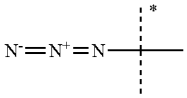,
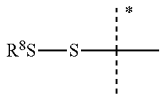,
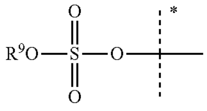,
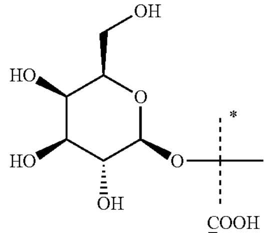,
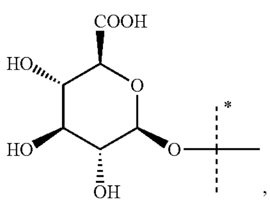,
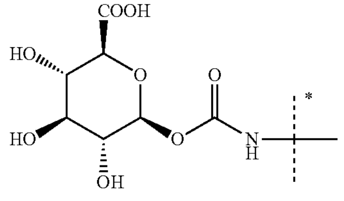

and a peptidyl moiety;

wherein the dashed line marked with an asterisk indicates the attachment to -A-;

-Nu is a nucleophile;

—$Y^1$— is selected from the group consisting of —O—, —$C(R^{10})(R^{10a})$—, —$N(R^{11})$— and —S—;

=$Y^2$ is selected from the group consisting of =O, =S and =$N(R^{12})$;

$Y^3$— is selected from the group consisting of —O—, —S— and —$N(R^{13})$;

-E- is selected from the group consisting of $C_{1-6}$ alkyl, $C_{2-6}$ alkenyl, $C_{2-6}$ alkynyl and -Q-; wherein $C_{1-6}$ alkyl, $C_{2-6}$ alkenyl, $C_{2-6}$ alkynyl are optionally substituted with one or more —$R^{14}$, which are the same or different;

—$R^5$, —$R^6$, each —$R^7$, —$R^8$, —$R^9$, —$R^{10}$, —$R^{10a}$, —$R^{11}$, —$R^{12}$ and —$R^{13}$ are independently selected from the group consisting of $C_{1-20}$ alkyl, $C_{2-20}$ alkenyl, $C_{2-20}$ alkynyl and -Q; wherein $C_{1-20}$ alkyl, $C_{2-20}$ alkenyl and $C_{2-20}$ alkynyl are optionally substituted with one or more —$R^{14}$, which are the same or different; and wherein $C_{1-10}$ alkyl, $C_{2-10}$ alkenyl and $C_{2-10}$ alkynyl are optionally interrupted by one or more groups selected from the group consisting of Q, —C(O)O—, —O—, —C(O)—, —$C(O)N(R^5)$—, —$S(O)_2N(R^{15})$, —S(O)N$(R^{15})$—, —$S(O)_2$—, —S(O)—, —$N(R^{15})S(O)_2N(R^{15a})$—, —S—, —$N(R^{15})$—, —$OC(OR^{15})R^{15a}$, —$N(R^{15})C(O)N(R^{15a})$— and —$OC(O)N(R^{15})$—;

each Q is independently selected from the group consisting of phenyl, naphthyl, indenyl, indanyl, tetralinyl, $C_{3-10}$ cycloalkyl, 3- to 10-membered heterocyclyl and 8- to 11-membered heterobicyclyl, wherein each Q is independently optionally substituted with one or more —$R^{14}$, which are the same or different;

wherein —$R^{14}$, —$R^{15}$ and —$R^{15a}$ are independently selected from the group consisting of —H and $C_{1-6}$ alkyl; wherein $C_{1-6}$ alkyl is optionally substituted with one or more halogen, which are the same or different; and each -$L^1$- is substituted with —$X^{0D}$-$L^2$- and optionally further substituted.

It is understood that in certain embodiments -$D^+$ may comprise both an electron-donating heteroaromatic $N^+$ and a quaternary ammonium cation and analogously the corresponding D may comprise both an electron-donating heteroaromatic N and a tertiary amine. It is also understood that if D is conjugated to -$L^1$-, then -$D^+$ and -$L^1$- form a quaternary ammonium cation, for which there may be a counter anion. Examples of counter anions include, but are not limited to, chloride, bromide, acetate, bicarbonate, sulfate, bisulfate, nitrate, carbonate, alkyl sulfonate, aryl sulfonate and phosphate.

The optional further substituents of -$L^1$- of formula (XII) are as described elsewhere herein.

In certain embodiments -$L^1$- of formula (XII) is not further substituted.

Such drug moiety -$D^+$ comprises at least one, such as one, two, three, four, five, six, seven, eight, nine or ten electron-donating heteroaromatic $N^+$ or quaternary ammonium cations and analogously the corresponding released drug D comprises at least one, such as one, two, three, four, five, six, seven, eight, nine or ten electron-donating heteroaromatic N or tertiary amines. Examples of chemical structures including heteroaromatic nitrogens i.e. $N^+$ or N, that donate an electron to the aromatic if-system include, but are not limited to, pyridine, pyridazine, pyrimidine, quinoline, quinazoline, quinoxaline, pyrazole, imidazole, isoindazole, indazole, purine, tetrazole, triazole and triazine. For example, in the imidazole ring below the heteroaromatic nitrogen which donates one electron to the aromatic if-system is marked with "§ ":

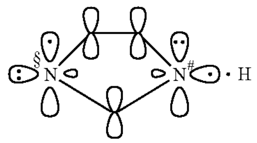

Such electron-donating heteroaromatic nitrogen atoms do not comprise heteroaromatic nitrogen atoms which donate one electron pair (i.e. not one electron) to the aromatic w-system, such as for example the nitrogen that is marked with "#" in the abovementioned imidazole ring structure. The drug D may exist in one or more tautomeric forms, such as with one hydrogen atom moving between at least two heteroaromatic nitrogen atoms. In all such cases, the linker moiety is covalently and reversibly attached at a heteroaromatic nitrogen that donates an electron to the aromatic if-system.

As used herein, the term "monocyclic or bicyclic aryl" means an aromatic hydrocarbon ring system which may be monocyclic or bicyclic, wherein the monocyclic aryl ring consists of at least 5 ring carbon atoms and may comprise up to 10 ring carbon atoms and wherein the bicylic aryl ring consists of at least 8 ring carbon atoms and may comprise up to 12 ring carbon atoms. Each hydrogen atom of a monocyclic or bicyclic aryl may be replaced by a substituent as defined below.

As used herein, the term "monocyclic or bicyclic heteroaryl" means a monocyclic aromatic ring system that may comprise 2 to 6 ring carbon atoms and 1 to 3 ring heteroatoms or a bicyclic aromatic ring system that may comprise 3 to 9 ring carbon atoms and 1 to 5 ring heteroatoms, such as nitrogen, oxygen and sulfur. Examples for monocyclic or bicyclic heteroaryl groups include, but are not limited to, benzofuranyl, benzothiophenyl, furanyl, imidazolyl, indolyl, azaindolyl, azabenzimidazolyl, benzoxazolyl, benzthiazolyl, benzthiadiazolyl, benzotriazolyl, tetrazinyl, tetrazolyl, isothiazolyl, oxazolyl, isoxazolyl, pyrazinyl, pyrazolyl, pyridazinyl, pyridinyl, pyrimidinyl, pyrrolyl, quinolinyl, quinazolinyl, quinoxalinyl, triazolyl, thiazolyl and thiophenyl. Each hydrogen atom of a monocyclic or bicyclic heteroaryl may be replaced by a substituent as defined below.

As used herein, the term "nucleophile" refers to a reagent or functional group that forms a bond to its reaction partner, i.e. the electrophile by donating both bonding electrons.

In certain embodiments t of formula (XII) is 0. In certain embodiments t of formula (XII) is 1.

In certain embodiments t of formula (XII) is 2. In certain embodiments t of formula (XII) is3.

In certain embodiments t of formula (XII) is 4. In certain embodiments t of formula (XII) is 5.

In certain embodiments t of formula (XII) is 6.

In certain embodiments -A- of formula (XII) is a ring selected from the group consisting of monocyclic or bicyclic aryl and heteroaryl. In certain embodiments -A- of formula (XII) is substituted with one or more —$R^2$ which are the same or different. In certain embodiments -A- of formula (XII) is not substituted with —$R^2$. In certain embodiments -A- of formula (XII) is selected from the group consisting of:

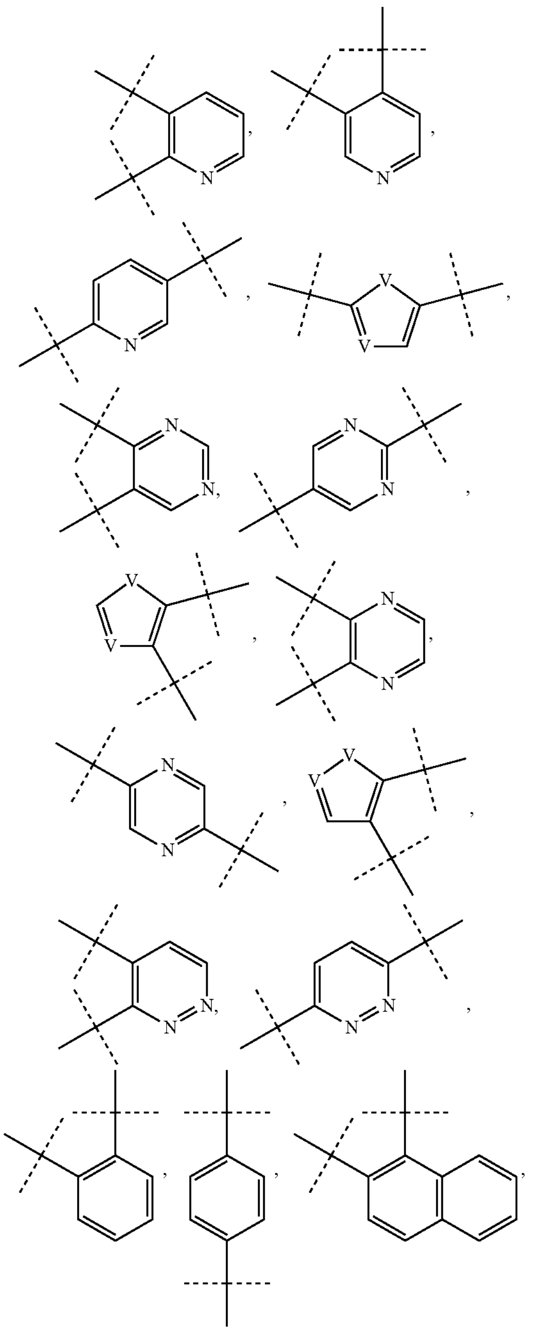

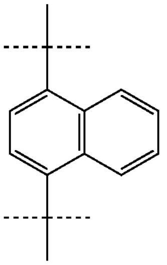

and

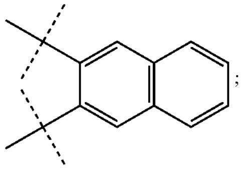

;

wherein each V is independently selected from the group consisting of O, S and N.

In certain embodiments —$R^1$, —$R^{1a}$ and each —$R^2$ of formula (XII) are independently selected from the group consisting of —H, —C(O)OH, -halogen, —CN, —$NO_2$, —OH, $C_{1-6}$ alkyl, $C_{2-6}$ alkenyl and $C_{2-6}$ alkynyl. In certain embodiments —$R^1$ of formula (XII) is —H. In certain embodiments —$R^1$ of formula (XII) is —C(O)OH. In certain embodiments —$R^1$ of formula (XII) is -halogen. In certain embodiments —$R^1$ of formula (XII) is —F. In certain embodiments —$R^1$ of formula (XII) is —CN. In certain embodiments —$R^1$ of formula (XII) is —$NO_2$. In certain embodiments —$R^1$ of formula (XII) is —OH. In certain embodiments —$R^1$ of formula (XII) is $C_{1-6}$ alkyl. In certain embodiments —$R^1$ of formula (XII) is $C_{2-6}$ alkenyl. In certain embodiments —$R^1$ is $C_{2-6}$ alkynyl. In certain embodiments —$R^{1a}$ of formula (XII) is —H. In certain embodiments —$R^{1a}$ of formula (XII) is —C(O)OH. In certain embodiments —$R^{1a}$ of formula (XII) is -halogen. In certain embodiments —$R^{1a}$ of formula (XII) is —F. In certain embodiments —$R^{1a}$ of formula (XII) is —CN. In certain embodiments —$R^{1a}$ of formula (XII) is —$NO_2$. In certain embodiments —$R^{1a}$ of formula (XII) is —OH. In certain embodiments —$R^{1a}$ of formula (XII) is $C_{1-6}$ alkyl. In certain embodiments —$R^{1a}$ of formula (XII) is $C_{2-6}$ alkenyl. In certain embodiments —$R^{1a}$ of formula (XII) is $C_{2-6}$ alkynyl.

In certain embodiments each of —$R^2$ of formula (XII) is independently selected from the group consisting of —H, —C(O)OH, -halogen, —CN, —$NO_2$, —OH, $C_{1-6}$ alkyl, $C_{2-6}$ alkenyl and $C_{2-6}$ alkynyl. In certain embodiments each of —$R^2$ of formula (XII) is —H. In certain embodiments each of —$R^2$ of formula (XII) is —C(O)OH. In certain embodiments each of —$R^2$ of formula (XII) is -halogen. In certain embodiments each of —$R^2$ of formula (XII) is —F. In certain embodiments each of —$R^2$ of formula (XII) is —CN. In certain embodiments each of —$R^2$ of formula (XII) is —$NO_2$. In certain embodiments each of —$R^2$ of formula (XII) is —OH. In certain embodiments each of —$R^2$ of formula (XII) is $C_{1-6}$ alkyl. In certain embodiments each of —$R^2$ of formula (XII) is $C_{2-6}$ alkenyl. In certain embodiments each of —$R^2$ of formula (XII) is $C_{2-6}$ alkynyl.

In certain embodiments T of formula (XII) is selected from the group consisting of phenyl, naphthyl, indenyl, indanyl, tetralinyl, $C_{3-10}$ cycloalkyl, 3- to 10-membered heterocyclyl and 8- to 11-membered heterobicyclyl. In certain embodiments T of formula (XII) is phenyl. In certain embodiments T of formula (XII) is naphthyl. In certain embodiments T of formula (XII) is indenyl. In certain embodiments T of formula (XII) is indanyl. In certain embodiments T of formula (XII) is tetralinyl. In certain embodiments T of formula (XII) is $C_{3-10}$ cycloalkyl. In certain embodiments T of formula (XII) is 3- to 10-membered heterocyclyl. In certain embodiments T of formula (XII) is 8- to 11-membered heterobicyclyl.

In certain embodiments T of formula (XII) is substituted with one or more —$R^3$, which are the same or different. In certain embodiments T of formula (XII) is substituted with one —$R^3$. In certain embodiments T of formula (XII) is not substituted with —$R^3$.

In certain embodiments —$R^3$ of formula (XII) is selected from the group consisting of —H, —$NO_2$, —$OCH_3$, —CN, —$N(R^4)(R^{4a})$, —OH, —C(O)OH and $C_{1-6}$ alkyl. In certain embodiments —$R^3$ of formula (XII) is —H. In certain embodiments —$R^3$ of formula (XII) is —$NO_2$. In certain embodiments —$R^3$ of formula (XII) is —$OCH_3$. In certain embodiments —$R^3$ of formula (XII) is —CN. In certain embodiments —$R^3$ of formula (XII) is —$N(R^4)(R^{4a})$. In certain embodiments —$R^3$ of formula (XII) is —OH. In certain embodiments —$R^3$ of formula (XII) is —C(O)OH. In certain embodiments —$R^3$ of formula (XII) is $C_{1-6}$ alkyl.

In certain embodiments —$R^4$ and —$R^{4a}$ of formula (XII) are independently selected from the group consisting of —H and $C_{1-6}$ alkyl. In certain embodiments —$R^4$ of formula (XII) is —H. In certain embodiments —$R^4$ is $C_{1-6}$ alkyl. In certain embodiments —$R^{4a}$ of formula (XII) is —H. In certain embodiments —$R^{4a}$ of formula (XII) is $C_{1-6}$ alkyl.

In certain embodiments —Y of formula (XII) is

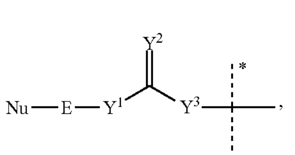

wherein -Nu, -E, —$Y^1$—, ═$Y^2$ and —$Y^3$— are as defined elsewhere herein and the dashed line marked with an asterisk indicates the attachment to -A- of formula (XII).

In certain embodiments -Nu of formula (XII) is a nucleophile selected from the group consisting of primary, secondary, tertiary amine and amide. In certain embodiments -Nu of formula (XII) is a primary amine. In certain embodiments -Nu of formula (XII) is a secondary amine. In certain embodiments -Nu of formula (XII) is a tertiary amine. In certain embodiments -Nu of formula (XII) is an amide.

In certain embodiments —$Y^1$— of formula (XII) is selected from the group consisting of —O—, —C($R^{10}$)($R^{10a}$)—, —N($R^{11}$)— and —S—. In certain embodiments —$Y^1$— of formula (XII) is —O—. In certain embodiments —$Y^1$— of formula (XII) is —C($R^{10}$)($R^{10a}$)— In certain embodiments —$Y^1$— of formula (XII) is —N($R^{11}$)—. In certain embodiments —$Y^1$— is —S—.

In certain embodiments ═$Y^2$ of formula (XII) is selected from the group consisting of ═O, ═S and ═N($R^{12}$). In certain embodiments ═$Y^2$ of formula (XII) is ═O. In certain embodiments ═$Y^2$ of formula (XII) is ═S. In certain embodiments ═$Y^2$ of formula (XII) is ═N($R^2$).

In certain embodiments —$Y^3$— of formula (XII) is selected from the group consisting of —O—, —S— and —N($R^{13}$). In certain embodiments —$Y^3$— of formula (XII) is —O—. In certain embodiments —$Y^3$— of formula (XII) is —S—. In certain embodiments —$Y^3$— of formula (XII) is —N($R^{13}$).

In certain embodiments —$Y^1$— of formula (XII) is —N($R^{11}$)—, ═$Y^2$ of formula (XII) is ═O and —$Y^3$— is —O—.

In certain embodiments —$Y^1$— of formula (XII) is —N($R^{11}$)—, ═$Y^2$ of formula (XII) is ═O, —$Y^3$— of formula (XII) is —O— and -Nu of formula (XII) is —$N(CH_3)_2$.

In certain embodiments -E- of formula (XII) is selected from the group consisting of $C_{1-6}$ alkyl, $C_{2-6}$ alkenyl, $C_{2-6}$ alkynyl and -Q-. In certain embodiments -E- of formula (XII) is $C_{1-6}$ alkyl. In certain embodiments -E- of formula (XII) is $C_{2-6}$ alkenyl. In certain embodiments -E- of formula (XII) is $C_{2-6}$ alkynyl. In certain embodiments -E- of formula (XII) is -Q-.

In certain embodiments Q of formula (XII) is selected from the group consisting of phenyl, naphthyl, indenyl, indanyl, tetralinyl, $C_{3-10}$ cycloalkyl, 3- to 10-membered heterocyclyl and 8- to 11-membered heterobicyclyl. In certain embodiments Q of formula (XII) is phenyl. In certain embodiments Q of formula (XII) is naphthyl. In certain embodiments Q of formula (XII) is indenyl. In certain embodiments Q of formula (XII) is indanyl. In certain embodiments Q of formula (XII) is tetralinyl. In certain embodiments Q of formula (XII) is $C_{3-10}$ cycloalkyl. In certain embodiments Q of formula (XII) is 3- to 10-membered heterocyclyl. In certain embodiments Q of formula (XII) is 8- to 11-membered heterobicyclyl. In certain embodiments Q of formula (XII) is substituted with one or more —$R^{14}$. In certain embodiments Q of formula (XII) is not substituted with —$R^{14}$.

In certain embodiments —$R^5$, —$R^6$, each —$R^7$, —$R^8$, —$R^9$, —$R^{10}$, —$R^{10a}$, —$R^{11}$, —$R^{12}$ and —$R^{13}$ of formula (XII) are independently selected from the group consisting of $C_{1-20}$ alkyl, $C_{2-20}$ alkenyl, $C_{2-20}$ alkynyl and -Q.

In certain embodiments —$R^5$ of formula (XII) is $C_{1-20}$ alkyl. In certain embodiments —$R^5$ of formula (XII) is $C_{2-20}$ alkenyl. In certain embodiments —$R^5$ of formula (XII) is $C_{2-20}$ alkynyl. In certain embodiments —$R^5$ of formula (XII) is -Q.

In certain embodiments —$R^6$ of formula (XII) is $C_{1-20}$ alkyl. In certain embodiments —$R^6$ of formula (XII) is $C_{2-20}$ alkenyl. In certain embodiments —$R^6$ of formula (XII) is $C_{2-20}$ alkynyl. In certain embodiments —$R^6$ is -Q.

In certain embodiments each of —$R^7$ of formula (XII) is independently selected from the group consisting of $C_{1-20}$ alkyl, $C_{2-20}$ alkenyl, $C_{2-20}$ alkynyl and -Q. In certain embodiments each of —$R^7$ of formula (XII) is $C_{1-20}$ alkyl. In certain embodiments each of —$R^7$ of formula (XII) is $C_{2-20}$ alkenyl. In certain embodiments each of —$R^7$ of formula (XII) is $C_{2-20}$ alkynyl. In certain embodiments each of —$R^7$ of formula (XII) is -Q.

In certain embodiments —$R^8$ of formula (XII) is $C_{1-20}$ alkyl. In certain embodiments —$R^8$ of formula (XII) is $C_{2-20}$ alkenyl. In certain embodiments —$R^8$ of formula (XII) is $C_{2-20}$ alkynyl. In certain embodiments —$R^8$ of formula (XII) is -Q.

In certain embodiments —$R^9$ of formula (XII) is $C_{1-20}$ alkyl. In certain embodiments —$R^9$ of formula (XII) is $C_{2-20}$ alkenyl. In certain embodiments —$R^9$ of formula (XII) is $C_{2-20}$ alkynyl. In certain embodiments —$R^9$ of formula (XII) is -Q.

In certain embodiments —$R^{10}$ of formula (XII) is $C_{1-20}$ alkyl. In certain embodiments —$R^{10}$ of formula (XII) is $C_{2-20}$ alkenyl. In certain embodiments —$R^{10}$ of formula (XII) is $C_{2-20}$ alkynyl. In certain embodiments —$R^{10}$ of formula (XII) is -Q.

In certain embodiments —$R^{10a}$ of formula (XII) is $C_{1-20}$ alkyl. In certain embodiments —$R^{10a}$ of formula (XII) is $C_{2-20}$ alkenyl. In certain embodiments —$R^{10a}$ of formula (XII) is $C_{2-20}$ alkynyl. In certain embodiments —$R^{10a}$ of formula (XII) is -Q.

In certain embodiments —$R^{11}$ of formula (XII) is $C_{1-20}$ alkyl. In certain embodiments —$R^{11}$ of formula (XII) is $C_{2-20}$ alkenyl. In certain embodiments —$R^{11}$ of formula (XII) is $C_{2-20}$ alkynyl. In certain embodiments —$R^{11}$ of formula (XII) is -Q.

In certain embodiments —$R^{12}$ of formula (XII) is $C_{1-20}$ alkyl. In certain embodiments —$R^{12}$ of formula (XII) is $C_{2-20}$ alkenyl. In certain embodiments —$R^{12}$ of formula (XII) is $C_{2-20}$ alkynyl. In certain embodiments —$R^{12}$ of formula (XII) is -Q.

In certain embodiments —$R^{13}$ of formula (XII) is $C_{1-20}$ alkyl. In certain embodiments —$R^{13}$ of formula (XII) is $C_{2-20}$ alkenyl. In certain embodiments —$R^{13}$ of formula (XII) is $C_{2-20}$ alkynyl. In certain embodiments —$R^{13}$ of formula (XII) is -Q.

In certain embodiments —$R^{14}$, —$R^{15}$ and —$R^{15a}$ of formula (XII) are selected from the group consisting of —H and $C_{1-6}$ alkyl.

In certain embodiments —$R^{14}$ of formula (XII) is —H. In certain embodiments —$R^{14}$ of formula (XII) is $C_{1-6}$ alkyl.

In certain embodiments —$R^{15}$ of formula (XII) is —H. In certain embodiments —$R^{15}$ of formula (XII) is $C_{1-6}$ alkyl.

In certain embodiments —$R^{15a}$ of formula (XII) is —H. In certain embodiments —$R^{15a}$ of formula (XII) is $C_{1-6}$ alkyl.

In certain embodiments —Y of formula (XII) is

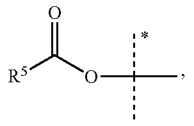

wherein —$R^5$ is as defined above and the dashed line marked with an asterisk indicates the attachment to -A-.

In certain embodiments —Y of formula (XII) is

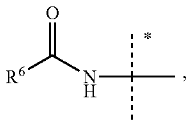

wherein —$R^6$ is as defined above and the dashed line marked with an asterisk indicates the attachment to -A-.

In certain embodiments —$R^6$ of formula (XII) is of formula (XIIa):

(XIIa)

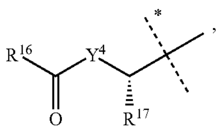

wherein —$Y^4$— is selected from the group consisting of $C_{3-10}$ cycloalkyl, 3- to 10-membered heterocyclyl and 8- to 11-membered heterobicyclyl, which are optionally substituted with one or more —$R^{18}$ which are the same or different;

—$R^{16}$ and —$R^{17}$ are independently selected from the group consisting of —H, $C_{1-10}$ alkyl, $C_{2-10}$ alkenyl and $C_{2-10}$ alkynyl; wherein $C_{1-10}$ alkyl, $C_{2-10}$ alkenyl and $C_{2-10}$ alkynyl are optionally substituted with one or more —$R^{18}$ which are the same or different; and wherein $C_{1-10}$ alkyl, $C_{2-10}$ alkenyl and $C_{2-10}$ alkynyl are optionally interrupted by one or more groups selected from the group consisting of -A'-, —C(O)O—, —O—, —C(O)—, —C(O)N($R^{19}$)—, —$S(O)_2N(R^{19})$, —S(O)N($R^{19}$)—, —$S(O)_2$—, —S(O)—, —$N(R^{19})S(O)_2N(R^{19})$—, —S—, —N($R^{19}$)—, —OC($OR^{19}$)$R^{10a}$—, —N($R^{19}$)C(O)N($R^{19a}$)—, —OC(O)N($R^{19}$)— and —N($R^{19}$)C(NH)N($R^{19a}$);

each A' is independently selected from the group consisting of phenyl, naphthyl, indenyl, indanyl, tetralinyl, $C_{3-10}$ cycloalkyl, 3- to 10-membered heterocyclyl and 8- to 11-membered heterobicyclyl, wherein each A' is independently optionally substituted with one or more —$R^{18}$ which are the same or different;

wherein —$R^{18}$, —$R^9$ and —$R^9$ are independently selected from the group consisting of —H and $C_{1-6}$ alkyl; wherein $C_{1-6}$ alkyl is optionally substituted with one or more halogen, which are the same or different; and wherein the dashed line marked with an asterisk indicates the attachment to the rest of —Y.

In certain embodiments —$Y^4$— of formula (XIIa) is selected from the group consisting of $C_{3-10}$ cycloalkyl, 3- to 10-membered heterocyclyl and 8- to 11-membered heterobicyclyl. In certain embodiments —$Y^4$— of formula (XIIa) is $C_{3-10}$ cycloalkyl. In certain embodiments —$Y^4$— of formula (XIIa) is 3- to 10-membered heterocyclyl. In certain embodiments —$Y^4$— of formula (XIIa) is 8- to 11-membered heterobicyclyl. In certain embodiments —$Y^4$— of formula (XIIa) is substituted with one or more —$R^{18}$ which are the same or different. In certain embodiments —$Y^4$— of formula (XIIa) is not substituted with —$R^{18}$.

In certain embodiments —$R^{16}$ and —$R^{17}$ of formula (XIIa) are selected from the group consisting of $C_{1-10}$ alkyl, $C_{2-10}$ alkenyl and $C_{2-10}$ alkynyl. In certain embodiments —$R^{16}$ of formula (XIIa) is $C_{1-10}$ alkyl. In certain embodiments —$R^{16}$ of formula (XIIa) is $C_{2-10}$ alkenyl. In certain embodiments —$R^{16}$ of formula (XIIa) is $C_{2-10}$ alkynyl. In certain embodiments —$R^{17}$ of formula (XIIa) is $C_{1-10}$ alkyl. In certain embodiments —$R^{17}$ of formula (XIIa) is $C_{2-10}$ alkenyl. In certain embodiments —$R^{17}$ of formula (XIIa) is $C_{2-10}$ alkynyl.

In certain embodiments A' of formula (XIIa) is selected from the group consisting of phenyl, naphthyl, indenyl, indanyl, tetralinyl, $C_{3-10}$ cycloalkyl, 3- to 10-membered heterocyclyl and 8- to 11-membered heterobicyclyl. In certain embodiments A' of formula (XIIa) is phenyl. In certain embodiments A' of formula (XIIa) is naphthyl. In certain embodiments A' of formula (XIIa) is indenyl. In certain embodiments A' of formula (XIIa) is indanyl. In certain embodiments A' of formula (XIIa) is tetralinyl. In certain embodiments A' of formula (XIIa) is $C_{3-10}$ cycloalkyl. In certain embodiments A' of formula (XIIa) is 3- to 10-membered heterocyclyl. In certain embodiments A' of formula (XIIa) is 8- to 11-membered heterobicyclyl.

In certain embodiments A' of formula (XIIa) is substituted with one or more —$R^{18}$, which are the same or different. In certain embodiments A' of formula (XIIa) is not substituted with —$R^{18}$.

In certain embodiments —$R^{18}$, —$R^{19}$ and —$R^{19a}$ of formula (XIIa) are selected from the group consisting of —H and $C_{1-6}$ alkyl.

In certain embodiments —$R^{18}$ of formula (XIIa) is —H. In certain embodiments —$R^{18}$ of formula (XIIa) is $C_{1-6}$ alkyl. In certain embodiments —$R^{19}$ of formula (XIIa) is —H. In certain embodiments —$R^{19}$ of formula (XIIa) is $C_{1-6}$ alkyl. In certain embodiments —$R^{19a}$ of formula (XIIa) is —H. In certain embodiments —$R^{9a}$ of formula (XIIa) is $C_{1-6}$ alkyl.

In certain embodiments —$R^6$ of formula (XII) is of formula (XIIb):

(XIIb)

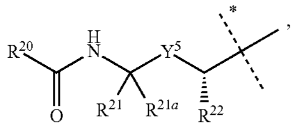

wherein —$Y^5$— is selected from the group consisting of -Q'-, $C_{1-10}$ alkyl, $C_{2-10}$ alkenyl and $C_{2-10}$ alkynyl; wherein $C_{1-10}$ alkyl, $C_{2-10}$ alkenyl and $C_{2-10}$ alkynyl are optionally substituted with one or more —$R^{23}$, which are the same or different; and wherein $C_{1-10}$ alkyl, $C_{2-10}$ alkenyl and $C_{2-10}$ alkynyl are optionally interrupted by one or more groups selected from the group consisting of -Q'-, —C(O)O—, —O—, —C(O)—, —C(O)N($R^{24}$)—, —$S(O)_2N(R^{24})$, —S(O)N($R^{24}$)—, —$S(O)_2$—, —S(O)—, —N($R^{24}$)$S(O)_2$N($R^{24a}$)—, —S—, —N($R^{24}$)—, —OC($OR^{24}$)$R^{24a}$—, —N($R^{24}$)C(O)N($R^{24a}$)—, —OC(O)N($R^{24}$)— and —N($R^{24}$)C(NH)N($R^{24a}$)—; —$R^{20}$, —$R^{21}$, —$R^{21a}$ and —$R^{22}$ are independently selected from the group consisting of —H, $C_{1-10}$ alkyl, $C_{2-10}$ alkenyl and $C_{2-10}$ alkynyl; wherein $C_{1-10}$ alkyl, $C_{2-10}$ alkenyl and $C_{2-10}$ alkynyl are optionally substituted with one or more —$R^{23}$ which are the same or different; and wherein $C_{1-10}$ alkyl, $C_{2-10}$ alkenyl and $C_{2-10}$ alkynyl are optionally interrupted by one or more groups selected from the group consisting of -Q'-, —C(O)O—O—, —C(O)—, —C(O)N($R^{24}$)—, —$S(O)_2N(R^{24})$, —S(O)N($R^{24}$)—, —$S(O)_2$—, —S(O)—, —N($R^{24}$)$S(O)_2$N($R^{24a}$)—, —S—, —N($R^{24}$)—, —OC($OR^{24}$)$R^{24a}$—, —N($R^{24}$)C(O)N($R^{24a}$)—, —OC(O)N($R^{24}$)— and —N($R^{24}$)C(NH)N($R^{24a}$)

each Q' is independently selected from the group consisting of phenyl, naphthyl, indenyl, indanyl, tetralinyl, $C_{3-10}$ cycloalkyl, 3- to 10-membered heterocyclyl and 8- to 11-membered heterobicyclyl, wherein each Q' is independently optionally substituted with one or more —$R^{23}$, which are the same or different;

wherein —$R^{23}$, —$R^{24}$ and —$R^{24a}$ are independently selected from the group consisting of —H and $C_{1-6}$ alkyl; wherein $C_{1-6}$ alkyl is optionally substituted with one or more halogen, which are the same or different;

optionally, the pair —$R^{21}$/—$R^{21a}$ is joined together with the atoms to which is attached to form a $C_{3-10}$ cycloalkyl, 3- to 10-membered heterocyclyl or an 8- to 11-membered heterobicyclyl; and wherein the dashed line marked with an asterisk indicates the attachment to the rest of —Y.

In certain embodiments —$Y^5$— of formula (XIIb) is selected from the group consisting of -Q'-, $C_{1-10}$ alkyl, $C_{2-10}$ alkenyl and $C_{2-10}$ alkynyl. In certain embodiments —$Y^5$— of formula (XIIb) is -Q'-. In certain embodiments —$Y^5$— of formula (XIIb) is $C_{1-10}$ alkyl. In certain embodiments —$Y^5$— of formula (XIIb) is $C_{2-10}$ alkenyl. In certain embodiments —$Y^5$— of formula (XIIb) is $C_{2-10}$ alkynyl.

In certain embodiments Q' of formula (XIIb) is selected from the group consisting of phenyl, naphthyl, indenyl, indanyl, tetralinyl, $C_{3-10}$ cycloalkyl, 3- to 10-membered heterocyclyl and 8- to 11-membered heterobicyclyl. In certain embodiments Q' of formula (XIIb) is phenyl. In certain embodiments Q' of formula (XIIb) is naphthyl. In certain embodiments Q' of formula (XIIb) is indenyl. In certain embodiments Q' of formula (XIIb) is indanyl. In certain embodiments Q' of formula (XIIb) is $C_{3-10}$ cycloalkyl. In certain embodiments Q' of formula (XIIb) is 3- to 10-membered heterocyclyl. In certain embodiments Q' of formula (XIIb) is 8- to 11-membered heterobicyclyl. In certain embodiments Q' of formula (XIIb) is substituted with one or more —$R^{23}$ which are the same or different. In certain embodiments Q' of formula (XIIb) is not substituted with —$R^{23}$.

In certain embodiments —$R^{20}$, —$R^{21}$, —$R^{21a}$ and —$R^{22}$ of formula (XIIb) are selected from the group consisting of —H, $C_{1-10}$ alkyl, $C_{2-10}$ alkenyl and $C_{2-10}$ alkynyl. In certain embodiments —$R^{20}$ of formula (XIIb) is —H. In certain embodiments —$R^{20}$ of formula (XIIb) is $C_{1-10}$ alkyl. In certain embodiments —$R^{20}$ of formula (XIIb) is $C_{2-10}$ alkenyl. In certain embodiments —$R^{20}$ of formula (XIIb) is $C_{2-10}$ alkynyl. In certain embodiments —$R^{21}$ of formula (XIIb) is —H. In certain embodiments —$R^{2}$ of formula (XIIb) is $C_{1-10}$ alkyl. In certain embodiments —$R^{21}$ of formula (XIIb) is $C_{2-10}$ alkenyl. In certain embodiments —$R^{21}$ of formula (XIIb) is $C_{2-10}$ alkynyl. In certain embodiments —$R^{21a}$ of formula (XIIb) is —H. In certain embodiments —$R^{21a}$ of formula (XIIb) is $C_{1-10}$ alkyl. In certain embodiments —$R^{21a}$ of formula (XIIb) is $C_{2-10}$ alkenyl. In certain embodiments —$R^{21a}$ of formula (XIIb) is $C_{2-10}$ alkynyl. In certain embodiments —$R^{22}$ of formula (XIIb) is —H. In certain embodiments —$R^{22}$ of formula (XIIb) is $C_{1-10}$ alkyl. In certain embodiments —$R^{22}$ of formula (XIIb) is $C_{2-10}$ alkenyl. In certain embodiments —$R^{22}$ of formula (XIIb) is $C_{2-10}$ alkynyl.

In certain embodiments —$R^{23}$, —$R^{24}$ and —$R^{24a}$ of formula (XIIb) are selected from the group consisting of —H and $C_{1-6}$ alkyl. In certain embodiments —$R^{23}$ of formula (XIIb) is —H. In certain embodiments —$R^{23}$ of formula (XIIb) is $C_{1-6}$ alkyl. In certain embodiments —$R^{24}$ of formula (XIIb) is —H. In certain embodiments —$R^{24}$ of formula (XIIb) is $C_{1-6}$ alkyl. In certain embodiments —$R^{24a}$ of formula (XIIb) is —H. In certain embodiments —$R^{24a}$ of formula (XIIb) is $C_{1-6}$ alkyl.

In certain embodiments the pair —$R^{21}$/—$R^{21a}$ of formula (XIIb) is joined together with the atoms to which is attached to form a $C_{3-10}$ cycloalkyl.

In certain embodiments —$R^6$ of formula (XIIb) is of formula (XIIc):

(XIIc)

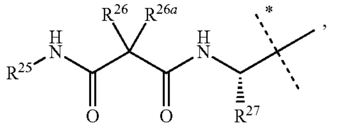

wherein

—$R^{25}$, —$R^{26}$, —$R^{26a}$ and —$R^{27}$ are independently selected from the group consisting of —H, $C_{1-10}$ alkyl, $C_{2-10}$ alkenyl and $C_{2-10}$ alkynyl; wherein $C_{1-10}$ alkyl, $C_{2-10}$ alkenyl and $C_{2-10}$ alkynyl are optionally substituted with one or more —$R^{28}$ which are the same or different; and wherein $C_{1-10}$ alkyl, $C_{2-10}$ alkenyl and $C_{2-10}$ alkynyl are optionally interrupted by one or more groups selected from the group consisting of -Q*-, —C(O)O—, —O—, —C(O)—, —C(O)N($R^{29}$)—, —$S(O)_2N(R^{29})$, —S(O)N($R^{29}$)—, —$S(O)_2$—, —S(O)—, —N($R^{29}$)$S(O)_2$N($R^{29a}$)—, —S—, —N($R^{29}$)—, —OC($OR^{29}$)$R^{29a}$—, —N($R^{29}$)C(O)N($R^{29a}$)—, —OC(O)N($R^{29}$)— and —N($R^{29}$)C(NH)N($R^{29a}$);

each Q* is independently selected from the group consisting of phenyl, naphthyl, indenyl, indanyl, tetralinyl, $C_{3-10}$ cycloalkyl, 3- to 10-membered heterocyclyl and 8- to 11-membered heterobicyclyl, wherein each Q* is independently optionally substituted with one or more —$R^{28}$, which are the same or different;

wherein —$R^{28}$, —$R^{29}$ and —$R^{29}$ are independently selected from the group consisting of —H and $C_{1-6}$ alkyl; wherein $C_{1-6}$ alkyl is optionally substituted with one or more halogen, which are the same or different;

optionally, the pair $—R^{26}/—R^{26a}$ is joined together with the atoms to which is attached to form a $C_{3-10}$ cycloalkyl, 3- to 10-membered heterocyclyl or an 8- to 11-membered heterobicyclyl; and wherein the dashed line marked with an asterisk indicates the attachment to the rest of —Y.

In certain embodiments $—R^{25}$, $—R^{26}$, $—R^{26a}$ and $—R^{27}$ of formula (XIIc) are selected from the group consisting of —H, $C_{1-10}$ alkyl, $C_{2-10}$ alkenyl and $C_{2-10}$ alkynyl. In certain embodiments $—R^{25}$ of formula (XIIc) is —H. In certain embodiments $—R^{25}$ of formula (XIIc) is $C_{1-10}$ alkyl. In certain embodiments $—R^{25}$ of formula (XIIc) is $C_{2-10}$ alkenyl. In certain embodiments $—R^{25}$ of formula (XIIc) is $C_{2-10}$ alkynyl. In certain embodiments $—R^{26}$ of formula (XIIc) is —H. In certain embodiments $—R^{26}$ of formula (XIIc) is $C_{1-10}$ alkyl. In certain embodiments $—R^{26}$ of formula (XIIc) is $C_{2-10}$ alkenyl. In certain embodiments $—R^{26}$ of formula (XIIc) is $C_{2-10}$ alkynyl. In certain embodiments $—R^{26a}$ of formula (XIIc) is —H. In certain embodiments $—R^{26a}$ of formula (XIIc) is $C_{1-10}$ alkyl. In certain embodiments $—R^{26a}$ of formula (XIIc) is $C_{2-10}$ alkenyl. In certain embodiments $—R^{26a}$ of formula (XIIc) is $C_{2-10}$ alkynyl. In certain embodiments $—R^{27}$ of formula (XIIc) is —H. In certain embodiments $—R^{27}$ of formula (XIIc) is $C_{1-10}$ alkyl. In certain embodiments $—R^{27}$ of formula (XIIc) is $C_{2-10}$ alkenyl. In certain embodiments $—R^{27}$ of formula (XIIc) is $C_{2-10}$ alkynyl.

In certain embodiments Q* of formula (XIIc) is selected from the group consisting of phenyl, naphthyl, indenyl, indanyl, tetralinyl, $C_{3-10}$ cycloalkyl, 3- to 10-membered heterocyclyl and 8- to 11-membered heterobicyclyl. In certain embodiments Q* of formula (XIIc) is phenyl. In certain embodiments Q* of formula (XIIc) is naphthyl. In certain embodiments Q* of formula (XIIc) is indenyl. In certain embodiments Q* of formula (XIIc) is indanyl. In certain embodiments Q* of formula (XIIc) is tetralinyl. In certain embodiments Q* of formula (XIIc) is $C_{3-10}$ cycloalkyl. In certain embodiments Q* of formula (XIIc) is 3- to 10-membered heterocyclyl. In certain embodiments Q* of formula (XIIc) is 8- to 11-membered heterobicyclyl. In certain embodiments Q* of formula (XIIc) is substituted with one or more $—R^{28}$, which are the same or different. In certain embodiments Q* of formula (XIIc) is not substituted with $—R^{28}$.

In certain embodiments $—R^{28}$, $—R^{29}$ and $—R^{29a}$ of formula (XIIc) are selected from the group consisting of —H and $C_{1-6}$ alkyl. In certain embodiments $—R^{28}$ of formula (XIIc) is —H. In certain embodiments $—R^{28}$ of formula (XIIc) is $C_{1-6}$ alkyl. In certain embodiments $—R^{29}$ of formula (XIIc) is —H. In certain embodiments $—R^{29}$ of formula (XIIc) is $C_{1-6}$ alkyl. In certain embodiments $—R^{29a}$ of formula (XIIc) is —H. In certain embodiments $—R^{29a}$ of formula (XIIc) is $C_{1-6}$ alkyl.

In certain embodiments the pair $—R^{26}/—R^{26a}$ of formula (XIIc) is joined together with the atoms to which is attached to form a $C_{3-10}$ cycloalkyl. In certain embodiments the pair $—R^{26}/—R^{26a}$ of formula (XIIc) is joined together with the atoms to which is attached to form a cyclobutyl.

In certain embodiments —Y of formula (XII) is

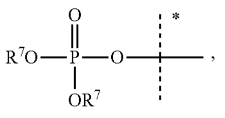

wherein each $—R^7$ is as defined above and the dashed line marked with an asterisk indicates the attachment to -A-. It is understood that in this instance the release of the drug D may be triggered by an enzyme, such as phosphatase.

In certain embodiments —Y of formula (XII) is

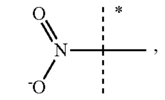

wherein the dashed line marked with an asterisk indicates the attachment to -A-.

In certain embodiments —Y of formula (XII) is

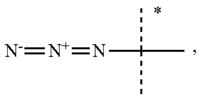

(wherein the dashed line marked with an asterisk indicates the attachment to -A-.

In certain embodiments —Y of formula (XII) is

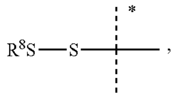

wherein $—R^8$ is as defined above and the dashed line marked with an asterisk indicates the attachment to -A-.

In certain embodiments —Y of formula (XII) is

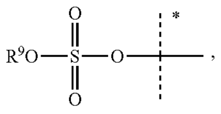

wherein $—R^9$ is as defined above and the dashed line marked with an asterisk indicates the attachment to -A-. It is understood that in this instance the release of the drug D may be triggered by an enzyme, such as sulfatase.

In certain embodiments —Y of formula (XII) is

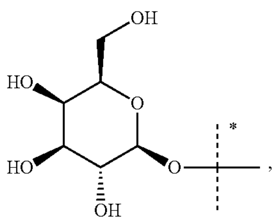

wherein the dashed line marked with an asterisk indicates the attachment to -A-. It is understood that in this instance the release of the drug D may be triggered by an enzyme, such as α-galactosidase.

In certain embodiments —Y of formula (XII) is

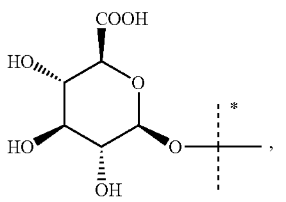

wherein the dashed line marked with an asterisk indicates the attachment to -A-. It is understood that in this instance the release of the drug D may be triggered by an enzyme, such as β-glucuronidase.

In certain embodiments —Y of formula (XII) is

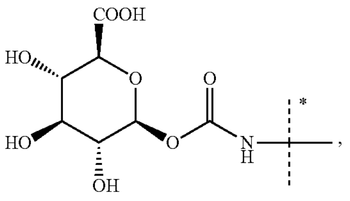

wherein the dashed line marked with an asterisk indicates the attachment to -A-. It is understood that in this instance the release of the drug D may be triggered by an enzyme, such as β-glucuronidase.

In certain embodiments —Y of formula (XII) is a peptidyl moiety.

It is understood that if —Y of formula (XII) is a peptidyl moiety, then the release of the drug D may be triggered by an enzyme, such as protease. In certain embodiments the protease is selected from the group consisting of cathepsin B and cathepsin K. In certain embodiments the protease is cathepsin B. In certain embodiments the protease is cathepsin K.

In certain embodiments —Y of formula (XII) is a peptidyl moiety, such as a dipeptidyl, tripeptidyl, tetrapeptidyl, pentapeptidyl or hexapeptidyl moiety. In certain embodiments —Y of formula (XII) is a dipeptidyl moiety. In certain embodiments —Y of formula (XII) is a tripeptidyl moiety. In certain embodiments —Y of formula (XII) is a tetrapeptidyl moiety. In certain embodiments —Y of formula (XII) is a pentapeptidyl moiety. In certain embodiments —Y of formula (XII) is a hexapeptidyl moiety.

In certain embodiments —Y of formula (XII) is a peptidyl moiety selected from the group consisting of:

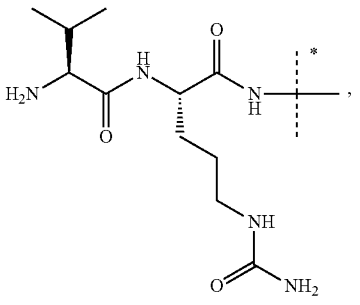

-continued

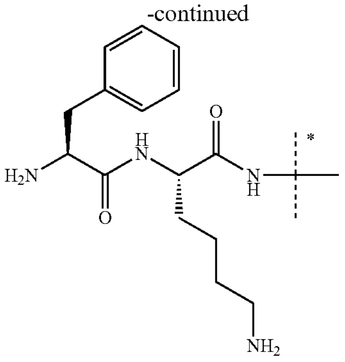

and

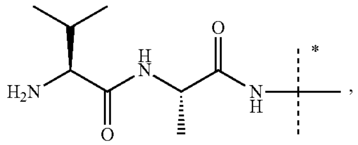

wherein the dashed line marked with an asterisk indicates the attachment to -A-.

In certain embodiments —Y of formula (XII) is

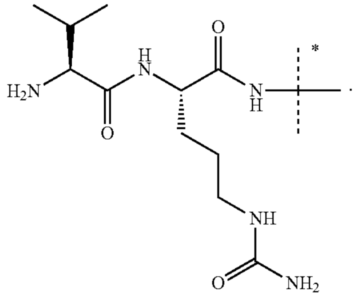

In certain embodiments —Y of formula (XII) is

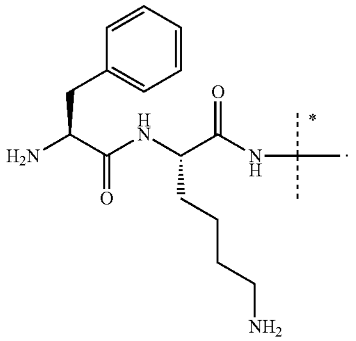

In certain embodiments —Y of formula (XII) is

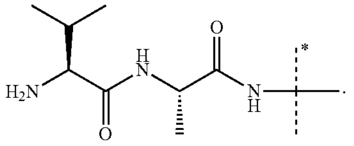

In certain embodiments one hydrogen given by $-R^{1a}$ of formula (XII) is replaced by $-X^{0D}-L^2-$ and $-L^1-$ is of formula (XII'):

(XII')

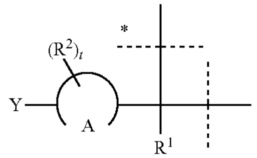

wherein the unmarked dashed line indicates the attachment to the $N^+$ of $-D^+$, the dashed line marked with an asterisk indicates the attachment to $-L^2-$; and $R^1$, —Ar—, —Y, $R^2$ and t are defined as in formula (XII).

In certain embodiments one hydrogen given by $—R^2$ of formula (XII) is replaced by $—X^{0D}-L^2-$ and $-L^1-$ is of formula (XII'):

(XII")

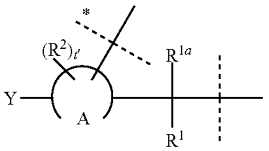

wherein the unmarked dashed line indicates the attachment to the $N^+$ of $-D^+$, the dashed line marked with an asterisk indicates the attachment to $—X^{0D}-L^2-$;

$—R^1$, —Ar—, —Y and $R^2$ are defined as in formula (XII); and t' is selected from the group consisting of 0, 1, 2, 3, 4 and 5.

In certain embodiments t' of formula (XII") is 0. In certain embodiments t' of formula (XII') is 1. In certain embodiments t' of formula (XII") is 2. In certain embodiments t' of formula (XII") is 3. In certain embodiments t' of formula (XII") is 4. In certain embodiments t' of formula (XII") is 5.

In certain embodiments all moieties $—X^{0D}—$ are identical. In certain embodiments a conjugate of the present invention comprises more than one type of $—X^{0D}—$, such as two, three or four different types of $—X^{0D}—$. In certain embodiment one hyaluronic acid strand comprises only one type of $—X^{0D}—$. In certain embodiments the conjugates comprise a first type of hyaluronic acid strands with a first type of $—X^{0D}—$ and a second type of hyaluronic acid strands with a second type of $—X^{0D}—$ and optionally a third type of hyaluronic acid strand with a third type of $—X^{0D}—$ and optionally a fourth type of hyaluronic acid strand with a fourth type of $—X^{0D}—$.

In certain embodiments $—X^{0D}—$ is a stable linkage, i.e $-L^1-$ and $—X^{0D}-L^2-$ are connected through a stable linkage.

In certain embodiments $—X^{0D}—$ is absent, in which case the moiety $-L^2-X^{0D}-L^1-$ is a moiety $-L^2-L^1-$, wherein the bond between $-L^2-$ and $-L^1-$ is a stable bond.

$-L^2-$ is absent or a spacer moiety.

In certain embodiments $-L^2-$ is absent.

In certain embodiments $-L^2-$ is a spacer moiety.

In certain embodiments $-L^2-$ does not comprise a degradable bond, i.e. all bonds of $-L^2-$ are stable bonds.

In certain embodiments $-L^2-$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$ $OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $—R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y4})—$, $—S(O)_2N(R^{y4})—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^{y4})(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

each $—R^{y2}$ is independently selected from the group consisting of halogen, —CN, oxo (=O), $—COOR^{y5}$, $—OR^{y5}$, $—C(O)R^{y5}$, $—C(O)N(R^{y5}R^{y5a})$, $—S(O)_2N(R^{y5}R^{y5a})$, $—S(O)N(R^{y5}R^{y5a})—$, $—S(O)_2R^{y5}$, $—S(O)R^{y5}$, $—N(R^{y5})S(O)_2N(R^{5a}R^{y5b})$, $—SR^5$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5a}R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^{y3}$, $—R^{y3a}$, $R^4$, $—R^{y4a}$, $—R^{y5}$, $—R^{y5a}$ and $—R^{y5b}$ is independently selected from the group consisting of —H, and $C_{1-6}$ alkyl, wherein $C_{1-6}$ alkyl is optionally substituted with one or more halogen, which are the same or different.

provided that $-L^2-$ is attached to $—X^{0C}—$ and $—X^{0D}—$ via a carbon atom of $-L^2-$.

In certain embodiments $-L^2-$ is a spacer moiety selected from the group consisting of -T-, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more $—R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, $—C(O)N(R^{y3})—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more $—R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —$S(O)_2N(R^{y4})$—, —S(O)N($R^{y4}$)—, —$S(O)_2$—, —S(O)—, —$N(R^{y4})S(O)_2N(R^{ya})$—, —S—, —N($R^{y4}$)—, —OC($OR^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (═O), —$COOR^{y5}$, —$OR^5$, —C(O)$R^{y5}$, —C(O)N($R^{y5}R^{y5a}$), —$S(O)_2N(R^{y5}R^{y5a})$, —S(O)N($R^{y5}R^{y5a}$)—, —$S(O)_2R^{y5}$, —S(O)$R^{y5}$, —N($R^{y5}$)$S(O)_2N(R^{y5a}R^{y5b})$, —$SR^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)$OR^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that -$L^2$- is attached to —$X^{0C}$— and —$X^{0D}$— via a carbon atom of -$L^2$-.

In certain embodiments -$L^2$- is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —$N(R^{y3})S(O)_2N(R^{ya})$—, —S—, —N($R^{y3}$)—OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen and $C_{1-6}$ alkyl; and each —$R^3$, —$R^{y3a}$, —$R^{y4}$, —$R^{y4a}$, —$R^5$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that -$L^2$- is attached to —$X^{0C}$— and —$X^{0D}$— via a carbon atom of -$L^2$-.

In certain embodiments -$L^2$- is a $C_{1-20}$ alkyl chain, which is optionally interrupted by one or more groups independently selected from —O—, -T-, —N($R^{y3}$)— and —C(O)N($R^{y1}$)—; and which $C_{1-20}$ alkyl chain is optionally substituted with one or more groups independently selected from —OH, -T, —N($R^{y3}$)— and —C(O)N($R^{y6}R^{y6a}$); wherein —$R^{y1}$, —$R^{y6}$, —$R^{y6a}$ are independently selected from the group consisting of H and $C_{1-4}$ alkyl, wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, provided that -$L^2$- is attached to —$X^{0C}$— and —$X^{0D}$— via a carbon atom of -$L^2$-.

In certain embodiments -$L^2$- has a molecular weight ranging from 14 g/mol to 750 g/mol.

In certain embodiments -$L^2$- has a chain length ranging from 1 to 20 atoms.

In certain embodiments -$L^2$- is a $C_{1-10}$ alkyl. In certain embodiments -$L^2$- is a $C_1$ alkyl. In certain embodiments -$L^2$- is a $C_2$ alkyl. In certain embodiments -$L^2$- is a $C_3$ alkyl. In certain embodiments -$L^2$- is a $C_4$ alkyl. In certain embodiments -$L^2$- is a $C_5$ alkyl. In certain embodiments -$L^2$- is a $C_6$ alkyl. In certain embodiments -$L^2$- is a $C_7$ alkyl. In certain embodiments -$L^2$- is a $C_8$ alkyl. In certain embodiments -$L^2$- is a $C_9$ alkyl. In certain embodiments -$L^2$- is a $C_{10}$ alkyl.

In certain embodiments all moieties —$X^{0C}$— are identical. In certain embodiments the conjugates comprise more than one type of —$X^{0C}$—, such as two, three or four different types of —$X^{0C}$—. In certain embodiment one hyaluronic acid strand comprises only one type of —$X^{0C}$—. In certain embodiments the conjugates comprise a first type of hyaluronic acid strands with a first type of —$X^{0C}$— and a second type of hyaluronic acid strands with a second type of —$X^{0C}$— and optionally a third type of hyaluronic acid strand with a third type of —$X^{0C}$— and optionally a fourth type of hyaluronic acid strand with a fourth type of —$X^{0C}$—

In certain embodiments —$X^{0C}$— is absent.

In certain embodiments —$X^{0C}$— is a stable linkage, i.e -$L^2$- and -$L^3$- are connected through a stable linkage.

In certain embodiments —$X^{0C}$— is a moiety selected from the group consisting of

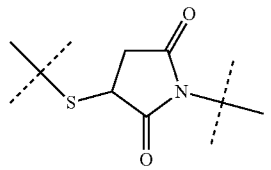

and

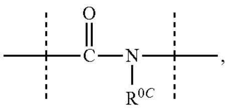

, wherein

—$R^{0C}$ selected from the group consisting of —H and $C_{1-6}$ alkyl.

In certain embodiments —$X^{0C}$— is

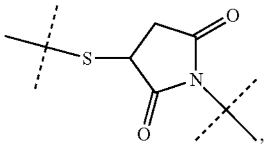

, wherein the dashed lines indicate attachment to -$L^2$- and -$L^3$-, respectively.

More specifically, in certain embodiments $—X^{0C}—$ is

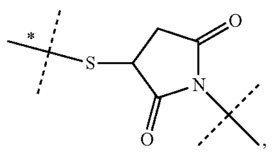

wherein the dashed line marked with the asterisk indicates attachment to $-L^2-$ and the unmarked dashed line indicates attachment to $-L^3-$.

$-L^3-$ is absent or a spacer moiety. In certain embodiments $-L^3-$ does not comprise a reversible linkage, i.e. all linkages in $-L^3-$ are stable linkages.

In certain embodiments $-L^3-$ is absent.

In certain embodiments $-L^3-$ is a spacer moiety.

In certain embodiments $-L^3-$ does not comprise a degradable bond, i.e. all bonds of $-L^3-$ are stable bonds.

In certain embodiments $-L^3-$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—OC(OR^3)(R^{y3a})—$, $—N(R^{y3})C(O)N(R^{y3a})—$, and $—OC(O)N(R^{y3})—$;

- $—R^{y1}$ and $—R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $—R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y4})—$, $—S(O)_2N(R^{y4})—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^4)(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

each $—R^{y2}$ is independently selected from the group consisting of halogen, —CN, oxo (=O), $—COOR^{y5}$, $—OR^5$, $—C(O)R^5$, $—C(O)N(R^{y5}R^{y5a})$, $—S(O)_2N(R^{y5}R^{y5a})$, $—S(O)N(R^{y5}R^{y5a})—$, $—S(O)_2R^{y5}$, $—S(O)R^{y5}$, $—N(R^{y5})S(O)_2N(R^{y5a}R^{y5b})$, $—SR^{y5}$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5a}R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^{y3}$, $—R^{y3a}$, $—R^4—R^{y4a}$, $—R^{y5}$, $—R^{y5a}$ and $—R^{y5}b$ is independently selected from the group consisting of —H, and $C_{1-6}$ alkyl, wherein $C_{1-6}$ alkyl is optionally substituted with one or more halogen, which are the same or different, provided that $-L^3-$ is attached to $—X_{0B}—$ and $—X^{0C}—$ via a carbon atom of $-L^3-$.

In certain embodiments $-L^3-$ is a spacer moiety selected from the group consisting of -T-, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more $—R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{ya})—$, —S—, $—N(R^{y3})—OC(OR^3)(R^{y3a})—$, $—N(R^{y3})C(O)N(R^{y3a})—$, and $—OC(O)N(R^{y3})—$;

- $—R^{y1}$ and $—R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more $—R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, $—C(O)N(R^{y4})—$, $—S(O)_2N(R^{y4})—$, $—S(O)N(R^{y4})—$, $—S(O)_2—$, —S(O)—, $—N(R^{Y4})S(O)_2N(R^{y4a})—$, —S—, $—N(R^{y4})—$, $—OC(OR^4)(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

$—R^{y2}$ is selected from the group consisting of halogen, —CN, oxo (=O), $—COOR^{y5}$, $—OR^5$, $—C(O)R^{y5}$, $—C(O)N(R^5R^{y5a})$, $—S(O)_2N(R^{y5}R^{y5a})$, $—S(O)N(R^{y5}R^{y5a})—$, $—S(O)_2R^{y5}$, $—S(O)R^{y5}$, $—N(R^{y5})S(O)_2N(R^{y5a}R^{y5b})$, $—SR^{y5}$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5}a\ R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^y$, $—R^{y3a}$, $—R^{y4}$, $—R^{y4a}$, $—R^{y5}$, $—R^{y5a}$ and $—R^{y5b}$ is independently of each other selected from the group consisting of —H, and $C_{1-6}$ alkyl; wherein $C_{1-6}$ alkyl is optionally substituted with one or more halogen, which are the same or different, provided that $-L^3-$ is attached to $—X^{0B}—$ and $—X^{0C}—$ via a carbon atom of $-L^3-$.

In certain embodiments $-L^3-$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{ya})—$, —S—, $—N(R^{y3})—OC(OR^{y3})(R^{y3a})—$, $—N(R^{y3})C(O)N(R^{y3a})—$, and $—OC(O)N(R^{y3})—$;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen and $C_{1-6}$ alkyl; and each —$R^3$, —$R^{y3a}$, $R^4$, —$R^{y4a}$, $R^5$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that -$L^3$- is attached to —$X^{0B}$— and —$X^{0C}$— via a carbon atom of -$L^3$-.

In certain embodiments -$L^3$- is a $C_{1-20}$ alkyl chain, which is optionally interrupted by one or more groups independently selected from —O—, -T-, —N($R^{y3}$)— and —C(O)N($R^{y1}$)—; and which $C_{1-20}$ alkyl chain is optionally substituted with one or more groups independently selected from —OH, -T, —N($R^{y3}$)— and —C(O)N($R^{y6}R^{y6a}$); wherein —$R^{y1}$, —$R^{y6}$, —$R^{y6a}$ are independently selected from the group consisting of H and $C_{1-4}$ alkyl, wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, provided that -$L^3$- is attached to —$X^{0B}$— and —$X^{0C}$— via a carbon atom of -$L^3$-.

In certain embodiments -$L^3$- has a molecular weight ranging from 14 g/mol to 750 g/mol.

In certain embodiments -$L^3$- has a chain length ranging from 1 to 20 atoms.

In certain embodiments -$L^3$- is a $C_{1-10}$ alkyl. In certain embodiments -$L^3$- is a $C_1$ alkyl. In certain embodiments -$L^3$- is a $C_2$ alkyl. In certain embodiments -$L^3$- is a $C_3$ alkyl. In certain embodiments -$L^3$- is a $C_4$ alkyl. In certain embodiments -$L^3$- is a $C_5$ alkyl. In certain embodiments -$L^3$- is a $C_6$ alkyl. In certain embodiments -$L^3$- is a $C_7$ alkyl. In certain embodiments -$L^3$- is a $C_8$ alkyl. In certain embodiments -$L^3$- is a $C_9$ alkyl. In certain embodiments -$L^3$- is a $C_{10}$ alkyl.

In certain embodiments all moieties —$X^{0B}$— are identical. In certain embodiments a conjugate or the present invention comprises more than one type of —$X^{0B}$—, such as two, three or four different types of —$X^{0B}$—. In certain embodiment one hyaluronic acid strand comprises only one type of —$X^{0B}$—. In certain embodiments the conjugates comprise a first type of hyaluronic acid strands with a first type of —$X^{0B}$— and a second type of hyaluronic acid strands with a second type of —$X^{0B}$— and optionally a third type of hyaluronic acid strand with a third type of —$X^{0B}$— and optionally a fourth type of hyaluronic acid strand with a fourth type of —$X^{0B}$—In certain embodiments —$X^{0B}$— is absent.

In certain embodiments —$X^{0B}$— is a stable linkage, i.e -$L^3$- and -$L^4$- are connected through a stable linkage.

In certain embodiments —$X^{0B}$— is a moiety selected from the group consisting of

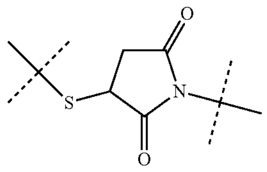 and 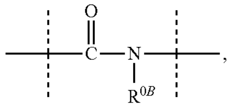, wherein

—$R^{0B}$ selected from the group consisting of —H and $C_{1-10}$ alkyl.

In certain embodiments —$R^{0B}$ is a —H. In certain embodiments —$R^{0B}$ is a $C_{1-10}$ alkyl. In certain embodiments —$R^{0B}$ is a $C_1$ alkyl. In certain embodiments —$R^{0B}$ is a 2 ak. In certain embodiments —$R^{0B}$ is a $C_3$ alkyl. In certain embodiments —$R^{0B}$ is a $C_4$ alkyl. In certain embodiments —$R^{0B}$ is a $C_5$ alkyl. In certain embodiments —$R^{0B}$ is a $C_6$ alkyl. In certain embodiments —$R^{0B}$ is a $C_7$ alkyl. In certain embodiments —$R^B$ is a $C_8$ alkyl. In certain embodiments —$R^{0B}$ is a $C_9$ alkyl. In certain embodiments —$R^B$ is a $C_1$ alkyl.

In certain embodiments $A^{0B}$- is

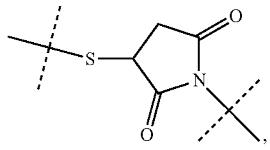, wherein the dashed lines indicate attachment to -$L^3$- and -$L^4$-, respectively.

In certain embodiments $A^{0B}$- is

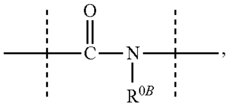, wherein the dashed lines indicate attachment to -$L^3$- and -$L^4$-, respectively.

In certain embodiments —$X^{0B}$— is

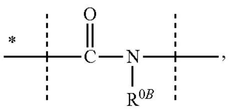, wherein the dashed line marked with the asterisk indicates attachment to -$L^3$- and the unmarked dashed line indicates attachment to -$L^4$-.

-$L^4$- is absent or a spacer moiety. In certain embodiments -$L^4$- does not comprise a reversible linkage, i.e. all linkages in -$L^4$- are stable linkages.

In certain embodiments -$L^4$- is absent.

In certain embodiments -$L^4$- is a spacer moiety.

In certain embodiments -$L^4$- does not comprise a degradable bond, i.e. all bonds of -$L^4$- are stable bonds.

In certain embodiments -$L^4$- is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —N($R^{y3}$)$S(O)_2N(R^{y3a})$—, —S—, —N($R^{y3}$)—OC($OR^{y3}$)($R^{y3a}$)—, —N($R^{y3}$)C(O)N($R^{y3a}$)—, and —OC(O)N($R^{y3}$)—;

—$R^1$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —$S(O)_2N(R^{y4})$—, —S(O)N($R^{y4}$)—, —$S(O)_2$—, —S(O)—, —N($R^{y4}$)$S(O)_2N(R^{y4a})$—, —S—, —N($R^{y4}$)—, —OC($OR^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (═O), —$COOR^{y5}$, —$OR^{y5}$, —C(O)$R^{y5}$, —C(O)N($R^{y5}R^{y5a}$), —$S(O)_2N(R^{y5}R^{y5a})$, —S(O)N($R^{y5}R^{y5a}$), —$S(O)_2R^{y5}$, —S(O)$R^{y5}$, —N($R^{y5}$)$S(O)_2N(R^{y5a}R^{y5b})$, —$SR^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)$OR^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$—$R^{y4}$—$R^{y4a}$, —$R^{y5}$, —$R^{y5a}$ and —$R^{y5}$b is independently selected from the group consisting of —H, and $C_{1-6}$ alkyl, wherein $C_{1-6}$ alkyl is optionally substituted with one or more halogen, which are the same or different, provided that -$L^4$- is attached to —$X^{0A}$— and —$X^{0B}$— via a carbon atom of -$L^4$-.

In certain embodiments -$L^4$- is a spacer moiety selected from the group consisting of -T-, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —N($R^{y3}$)$S(O)_2N(R^{ya})$—, —S—, —N($R^{y3}$)—OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —$S(O)_2N(R^{y4})$—, —S(O)N($R^{y4}$)—, —$S(O)_2$—, —S(O)—, —N($R^{y4}$)$S(O)_2N(R^{y4a})$—, —S—, —N($R^{y4}$)—, —OC($OR^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (═O), —$COOR^{y5}$, —$OR^{y5}$, —C(O)$R^{y5}$, —C(O)N($R^{y5}R^{y5a}$), —$S(O)_2N(R^{y5}R^{y5a})$, —S(O)N($R^{y5}R^{y5a}$), —$S(O)_2R^{y5}$, —S(O)$R^{y5}$, —N($R^{y5}$)$S(O)_2N(R^{y5a}R^{y5b})$, —$SR^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)$OR^{y5a}$, —N($R^{y5}$)C(O)N($R^{y5}$a $R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that -$L^4$- is attached to —$X^{0A}$— and —$X^{0B}$— via a carbon atom of -$L^4$-.

In certain embodiments -$L^4$- is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —N($R^{y3}$)$S(O)_2N(R^{y3a})$—, —S—, —N($R^{y3}$)—OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen and $C_{1-6}$ alkyl; and each —$R^3$, —$R^{y3a}$, —$R^{y4}$, —$R^{y4a}$, —$R^5$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that -$L^4$- is attached to —$X^{0A}$— and —$X^{0B}$— via a carbon atom of -$L^4$-.

In certain embodiments -$L^4$- is a $C_{1-20}$ alkyl chain, which is optionally interrupted by one or more groups independently selected from —O—, -T-, —N($R^{y3}$)— and —C(O)N($R^{y1}$)—; and which $C_{1-20}$ alkyl chain is optionally substituted with one or more groups independently selected from —OH, -T, —N($R^{y3}$)— and —C(O)N($R^{y6}R^{y6a}$); wherein —$R^{y1}$, —$R^{y6}$. —$R^{y6a}$ are independently selected from the group consisting of H and $C_{1-4}$ alkyl, wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, provided that $-L^4-$ is attached to $—X^{0A}—$ and $—X^{0B}—$ via a carbon atom of $-L^4-$.

In certain embodiments $-L^4-$ has a molecular weight ranging from 14 g/mol to 750 g/mol.

In certain embodiments $-L^4-$ has a chain length ranging from 1 to 20 atoms.

In certain embodiments $-L^4-$ is a $C_{1-10}$ alkyl. In certain embodiments $-L^4-$ is a $C_1$ alkyl. In certain embodiments $-L^4-$ is a $C_2$ alkyl. In certain embodiments $-L^4-$ is a $C_3$ alkyl. In certain embodiments $-L^4-$ is a $C_4$ alkyl. In certain embodiments $-L^4-$ is a $C_5$ alkyl. In certain embodiments $-L^4-$ is a $C_6$ alkyl. In certain embodiments $-L^4-$ is a $C_7$ alkyl. In certain embodiments $-L^4-$ is a $C_8$ alkyl. In certain embodiments $-L^4-$ is a $C_9$ alkyl. In certain embodiments $-L^4-$ is a $C_{10}$ alkyl.

In certain embodiments all moieties $—X^{0A}—$ are identical. In certain embodiments the conjugates comprise more than one type of $—X^{0A}—$, such as two, three or four different types of $—X^{0A}—$. In certain embodiment one hyaluronic acid strand comprises only one type of $—X^{0A}—$. In certain embodiments the conjugates comprise a first type of hyaluronic acid strands with a first type of $—X^{0A}—$ and a second type of hyaluronic acid strands with a second type of $—X^{0A}—$ and optionally a third type of hyaluronic acid strand with a third type of $X^{0A}—$ and optionally a fourth type of hyaluronic acid strand with a fourth type of $—X^{0A}—$In certain embodiments $—X^{0A}$ is absent.

In certain embodiments $X^{0A}—$ forms together with the carbonyl to which it is attached a stable linkage, i.e $-L^4-$ and the remainder of the unit $Z^2$ are connected through a stable linkage.

In certain embodiments $—X^{0A}-$ is

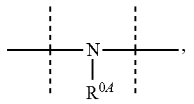

wherein the dashed lines indicate attachment to $-L^4-$ and to the remainder of $Z^2$, respectively; and $—R^{0A}$ selected from the group consisting of —H, methyl, ethyl, propyl, isobutyl, n-butyl, sec-butyl, isobutyl, tert-butyl, pentyl, 2-methylbutan-2-yl, 2,2-dimethylpropyl, 3-methylbutyl, pentan-2-yl, pentan-3-yl, 3-methylbutan-2-yl and 2-methylbutyl.

In certain embodiments $X^{0A}$ is

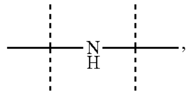

wherein the dashed lines indicate attachment to $-L^4-$ and to the remainder of $Z^2$, respectively.

In certain embodiments the only reversible bond in a moiety $—X^{0A}-L^4-X^{0B}-L^3-X^{0C}-L^2-X^{0D}-L^1-D$ is the bond that connects $-L^1-$ and -D, which leads to the drug being released in its free form.

In certain embodiments the moiety $—X^{0A}-L^4-X^{0B}-L^3-X^{0C}-L^2-X^{0D}—$ is of formula (i)

(i)

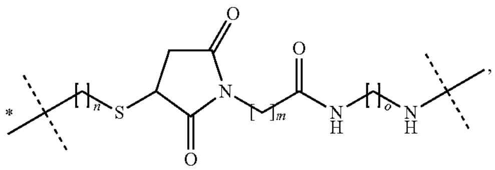

wherein the dashed line marked with the asterisk indicates attachment to $-L^1-$;

the unmarked dashed line indicates attachment to the remainder of $Z^2$ n is selected from the group consisting of 0, 1, 2, 3, 4, 5, 6, 7, 8, 9, 10, 11, 12, 13, 14, 15, 16, 17 and 18;

m is selected from the group consisting of 1, 2, 3, 4, 5, 6, 7, 8, 9, 10, 11, 12, 13, 14, 15, 16, 17 and 18;

o is selected from the group consisting of 1, 2, 3, 4, 5, 6, 7, 8, 9, 10, 11, 12, 13, 14, 15, 16, 17 and 18; and wherein the moiety of formula (i) is optionally further substituted.

It is understood that in formula (i) $—X^{0D}—$ is absent.

In certain embodiments n of formula (i) is selected from the group consisting of 3, 4, 5, 6, 7, 8, and 9. In certain embodiments n of formula (i) is 3, 4, 5, 6, or 7. In certain embodiments n of formula (i) is 3. In certain embodiments n of formula (i) is 4. In certain embodiments n of formula (i) is 5. In certain embodiments n of formula (i) is 6.

In certain embodiments m of formula (i) is selected from the group consisting of 1, 2, 3, 4, 5, 6 or 7. In certain embodiments m of formula (i) is 1, 2, 3, 4 or 5. In certain embodiments m of formula (i) is 1. In certain embodiments m of formula (i) is 2. In certain embodiments m of formula (i) is 3. In certain embodiments m of formula (i) is 4.

In certain embodiments o of formula (i) is selected from the group consisting of 1, 2, 3, 4, 5, 6 or 7. In certain embodiments o of formula (i) is 1, 2, 3, 4 or 5. In certain embodiments o of formula (i) is 1. In certain embodiments o of formula (i) is 2. In certain embodiments o of formula (i) is 3. In certain embodiments o of formula (i) is 4.

In certain embodiments the moiety $—X^{0A}-L^4-X^{0B}-L^3-X^{0C}-L^2-X^{0D}-L^1-$ is selected from the group consisting of (Ia-i)

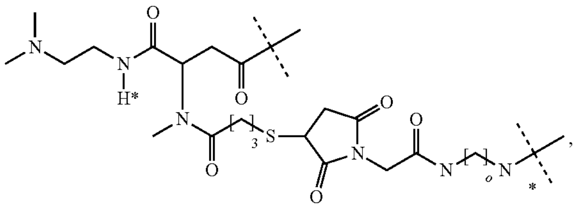

(Ia-ii)

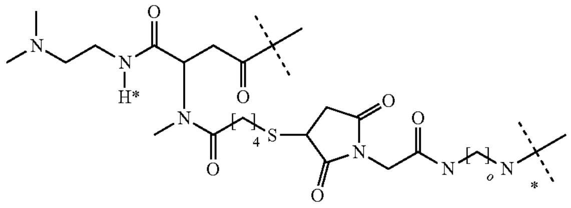

-continued
(Ia-iii)
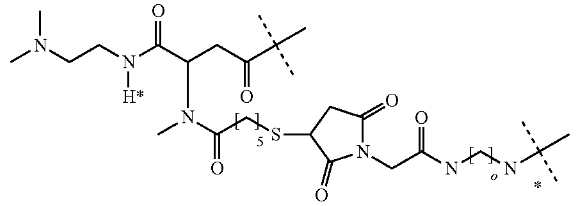
(Ia-iv)
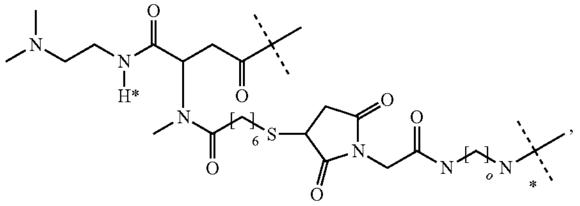,
(Ib-i)
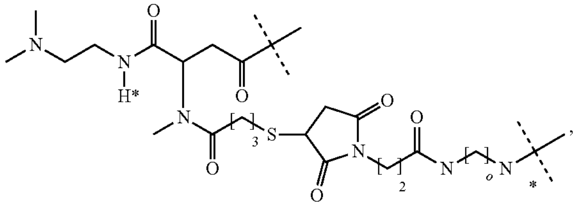,
(Ib-ii)
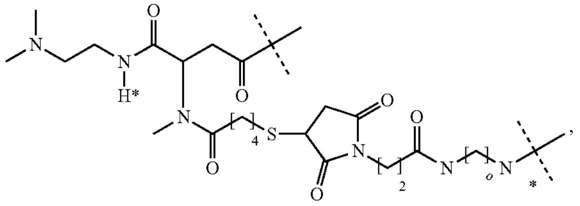,
(Ib-iii)
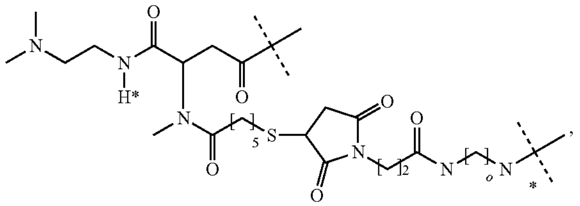,
(Ib-iv)
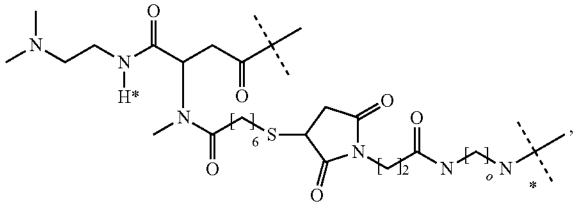,
(Ic-i)
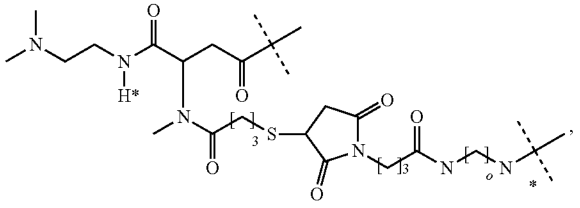,
-continued
(Ic-ii)
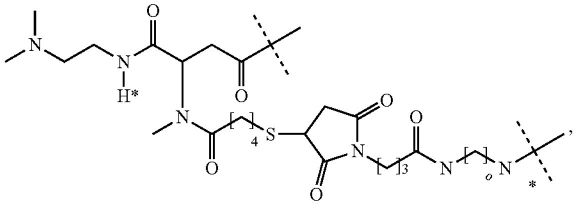,
(Ic-iii)
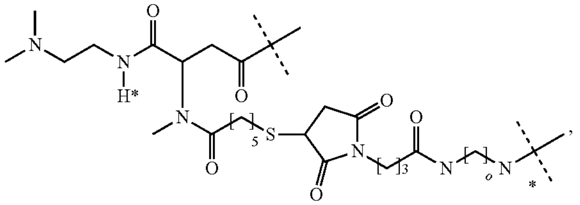,
(Ic-iv)
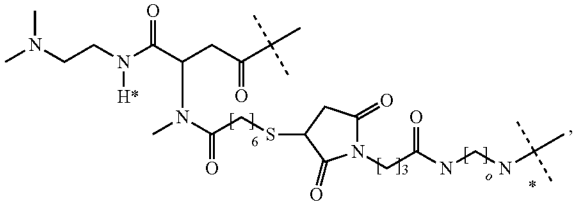,
(Id-i)
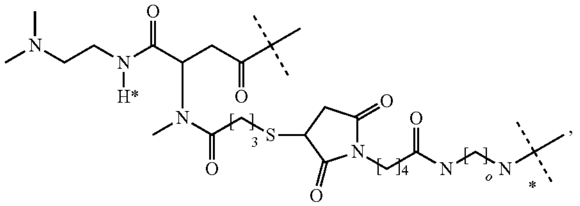,
(Id-ii)
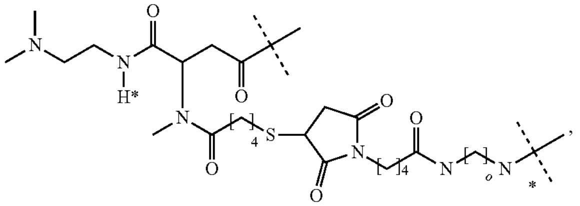,
(Id-iii)
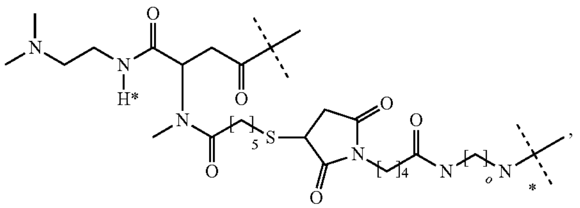, -continued (Id-iv)

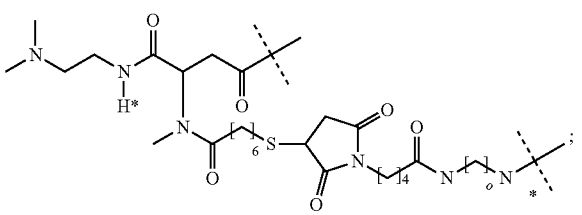

wherein the unmarked dashed line indicates the attachment to a nitrogen of -D by forming an amide bond;

o is selected from the group consisting of 1, 2, 3 and 4; and the dashed line marked with the asterisk indicates attachment to the remainder of $Z^2$.

In certain embodiments the moiety —$X^{0A}$-$L^4$-$X^{0B}$-$L^3$-$X^{0C}$-$L^2$-$X^{0D}$-$L^1$- is of formula (Ia-i) with o being 1. In certain embodiments the moiety —$X^{0A}$-$L^4$-$X^{0B}$-$L^3$-$X^{0C}$-$L^2$-$X^{0D}$-$L^1$- is of formula (Ia-i) with o being 2. In certain embodiments the moiety —$X^{0A}$-$L^4$-$X^{0B}$-$L^3$-$X^{0C}$-$L^2$-$X^{0D}$-$L^1$- is of formula (Ia-i) with o being 3. In certain embodiments the moiety —$X^{0A}$-$L^4$-$X^{0B}$-$L^3$-$X^{0C}$-$L^2$-$X^{0D}$-$L^1$- is of formula (Ia-i) with o being 4.

In certain embodiments the moiety —$X^{0A}$-$L^4$-$X^{0B}$-$L^3$-$X^{0C}$-$L^2$-$X^{0D}$-$L^1$- is of formula (Ia-ii) with o being 1. In certain embodiments the moiety —$X^{0A}$-$L^4$-$X^{0B}$-$L^3$-$X^{0C}$-$L^2$-$X^{0D}$-$L^1$- is of formula (Ia-ii) with o being 2. In certain embodiments the moiety —$X^{0A}$-$L^4$-$X^{0B}$-$L^3$-$X^{0C}$-$L^2$-$X^{0D}$-$L^1$- is of formula (Ia-ii) with o being 3. In certain embodiments the moiety —$X^{0A}$-$L^4$-$X^{0B}$-$L^3$-$X^{0C}$-$L^2$-$X^{0D}$-$L^1$- is of formula (Ia-ii) with o being 4.

In certain embodiments the moiety —$X^{0A}$-$L^4$-$X^{0B}$-$L^3$-$X^{0C}$-$L^2$-$X^{0D}$-$L^1$- is of formula (Ia-iii) with o being 1. In certain embodiments the moiety —$X^{0A}$-$L^4$-$X^{0B}$-$L^3$-$X^{0C}$-$L^2$-$X^{0D}$-$L^1$- is of formula (Ia-iii) with o being 2. In certain embodiments the moiety —$X^{0A}$-$L^4$-$X^{0B}$-$L^3$-$X^{0C}$-$L^2$-$X^{0D}$-$L^1$- is of formula (Ia-iii) with o being 3. In certain embodiments the moiety —$X^{0A}$-$L^4$-$X^{0B}$-$L^3$-$X^{0C}$-$L^2$-$X^{0D}$-$L^1$- is of formula (Ia-iii) with o being 4.

In certain embodiments the moiety —$X^{0A}$-$L^4$-$X^{0B}$-$L^3$-$X^{0C}$-$L^2$-$X^{0D}$-$L^1$- is of formula (Ia-iv) with o being 1. In certain embodiments the moiety —$X^{0A}$-$L^4$-$X^{0B}$-$L^3$-$X^{0C}$-$L^2$-$X^{0D}$-$L^1$- is of formula (Ia-iv) with o being 2. In certain embodiments the moiety —$X^{0A}$-$L^4$-$X^{0B}$-$L^3$-$X^{0C}$-$L^2$-$X^{0D}$-$L^1$- is of formula (Ia-iv) with o being 3. In certain embodiments the moiety —$X^{0A}$-$L^4$-$X^{0B}$-$L^3$-$X^{0C}$-$L^2$-$X^{0D}$-$L^1$- is of formula (Ia-iv) with o being 4.

In certain embodiments the moiety —$X^{0A}$-$L^4$-$X^{0B}$-$L^3$-$X^{0C}$-$L^2$-$X^{0D}$-$L^1$- is of formula (Ib-i) with o being 1. In certain embodiments the moiety —$X^{0A}$-$L^4$-$X^{0B}$-$L^3$-$X^{0C}$-$L^2$-$X^{0D}$-$L^1$- is of formula (Ib-i) with o being 2. In certain embodiments the moiety —$X^{0A}$-$L^4$-$X^{0B}$-$L^3$-$X^{0C}$-$L^2$-$X^{0D}$-$L^1$- is of formula (Ib-i) with o being 3 In certain embodiments the moiety —$X^{0A}$-$L^4$-$X^{0B}$-$L^3$-$X^{0C}$-$L^2$-$X^{0D}$-$L^1$- is of formula (Ib-i) with o being 4.

In certain embodiments the moiety —$X^{0A}$-$L^4$-$X^{0B}$-$L^3$-$X^{0C}$-$L^2$-$X^{0D}$-$L^1$- is of formula (Ib-ii) with o being 1. In certain embodiments the moiety —$X^{0A}$-$L^4$-$X^{0B}$-$L^3$-$X^{0C}$-$L^2$-$X^{0D}$-$L^1$- is of formula (Ib-ii) with o being 2. In certain embodiments the moiety —$X^{0A}$-$L^4$-$X^{0B}$-$L^3$-$X^{0C}$-$L^2$-$X^{0D}$-$L^1$- is of formula (Ib-ii) with o being 3. In certain embodiments the moiety —$X^{0A}$-$L^4$-$X^{0B}$-$L^3$-$X^{0C}$-$L^2$-$X^{0D}$-$L^1$- is of formula (Ib-ii) with o being 4.

In certain embodiments the moiety —$X^{0A}$-$L^4$-$X^{0B}$-$L^3$-$X^{0C}$-$L^2$-$X^{0D}$-$L^1$- is of formula (Ib-iii) with o being 1. In certain embodiments the moiety —$X^{0A}$-$L^4$-$X^{0B}$-$L^3$-$X^{0C}$-$L^2$-$X^{0D}$-$L^1$- is of formula (Ib-iii) with o being 2. In certain embodiments the moiety —$X^{0A}$-$L^4$-$X^{0B}$-$L^3$-$X^{0C}$-$L^2$-$X^{0D}$-$L^1$- is of formula (Ib-iii) with o being 3. In certain embodiments the moiety —$X^{0A}$-$L^4$-$X^{0B}$-$L^3$-$X^{0C}$-$L^2$-$X^{0D}$-$L^1$- is of formula (Ib-iii) with o being 4.

In certain embodiments the moiety —$X^{0A}$-$L^4$-$X^{0B}$-$L^3$-$X^{0C}$-$L^2$-$X^{0D}$-$L^1$- is of formula (Ib-iv) with o being 1. In certain embodiments the moiety —$X^{0A}$-$L^4$-$X^{0B}$-$L^3$-$X^{0C}$-$L^2$-$X^{0D}$-$L^1$- is of formula (Ib-iv) with o being 2. In certain embodiments the moiety —$X^{0A}$-$L^4$-$X^{0B}$-$L^3$-$X^{0C}$-$L^2$-$X^{0D}$-$L^1$- is of formula (Ib-iv) with o being 3. In certain embodiments the moiety —$X^{0A}$-$L^4$-$X^{0B}$-$L^3$-$X^{0C}$-$L^2$-$X^{0D}$-$L^1$- is of formula (Ib-iv) with o being 4.

In certain embodiments the moiety —$X^{0A}$-$L^4$-$X^{0B}$-$L^3$-$X^{0C}$-$L^2$-$X^{0D}$-$L^1$- is of formula (Ic-i) with o being 1. In certain embodiments the moiety —$X^{0A}$-$L^4$-$X^{0B}$-$L^3$-$X^{0C}$-$L^2$-$X^{0D}$-$L^1$- is of formula (Ic-i) with o being 2. In certain embodiments the moiety —$X^{0A}$-$L^4$-$X^{0B}$-$L^3$-$X^{0C}$-$L^2$-$X^{0D}$-$L^1$- is of formula (Ic-i) with o being 3. In certain embodiments the moiety —$X^{0A}$-$L^4$-$X^{0B}$-$L^3$-$X^{0C}$-$L^2$-$X^{0D}$-$L^1$- is of formula (Ic-i) with o being 4.

In certain embodiments the moiety —$X^{0A}$-$L^4$-$X^{0B}$-$L^3$-$X^{0C}$-$L^2$-$X^{0D}$-$L^1$- is of formula (Ic-ii) with o being 1. In certain embodiments the moiety —$X^{0A}$-$L^4$-$X^{0B}$-$L^3$-$X^{0C}$-$L^2$-$X^{0D}$-$L^1$- is of formula (Ic-ii) with o being 2. In certain embodiments the moiety —$X^{0A}$-$L^4$-$X^{0B}$-$L^3$-$X^{0C}$-$L^2$-$X^{0D}$-$L^1$- is of formula (Ic-ii) with o being 3. In certain embodiments the moiety —$X^{0A}$-$L^4$-$X^{0B}$-$L^3$-$X^{0C}$-$L^2$-$X^{0D}$-$L^1$- is of formula (Ic-ii) with o being 4.

In certain embodiments the moiety —$X^{0A}$-$L^4$-$X^{0B}$-$L^3$-$X^{0C}$-$L^2$-$X^{0D}$-$L^1$- is of formula (Ic-iii) with o being 1. In certain embodiments the moiety —$X^{0A}$-$L^4$-$X^{0B}$-$L^3$-$X^{0C}$-$L^2$-$X^{0D}$-$L^1$- is of formula (Ic-iii) with o being 2. In certain embodiments the moiety —$X^{0A}$-$L^4$-$X^{0B}$-$L^3$-$X^{0C}$-$L^2$-$X^{0D}$-$L^1$- is of formula (Ic-iii) with o being 3. In certain embodiments the moiety —$X^{0A}$-$L^4$-$X^{0B}$-$L^3$-$X^{0C}$-$L^2$-$X^{0D}$-$L^1$- is of formula (Ic-iii) with o being 4.

In certain embodiments the moiety —$X^{0A}$-$L^4$-$X^{0B}$-$L^3$-$X^{0C}$-$L^2$-$X^{0D}$-$L^1$- is of formula (Ic-iv) with o being 1. In certain embodiments the moiety —$X^{0A}$-$L^4$-$X^{0B}$-$L^3$-$X^{0C}$-$L^2$-$X^{0D}$-$L^1$- is of formula (Ic-iv) with o being 2. In certain embodiments the moiety —$X^{0A}$-$L^4$-$X^{0B}$-$L^3$-$X^{0C}$-$L^2$-$X^{0D}$-$L^1$- is of formula (Ic-iv) with o being 3. In certain embodiments the moiety —$X^{0A}$-$L^4$-$X^{0B}$-$L^3$-$X^{0C}$-$L^2$-$X^{0D}$-$L^1$- is of formula (Ic-iv) with o being 4.

In certain embodiments the moiety —$X^{0A}$-$L^4$-$X^{0B}$-$L^3$-$X^{0C}$-$L^2$-$X^{0D}$-$L^1$- is of formula (Id-i) with o being 1. In certain embodiments the moiety —$X^{0A}$-$L^4$-$X^{0B}$-$L^3$-$X^{0C}$-$L^2$-$X^{0D}$-$L^1$- is of formula (Id-i) with o being 2. In certain embodiments the moiety —$X^{0A}$-$L^4$-$X^{0B}$-$L^3$-$X^{0C}$-$L^2$-$X^{0D}$-$L^1$- is of formula (Id-i) with o being 3. In certain embodiments the moiety —$X^{0A}$-$L^4$-$X^{0B}$-$L^3$-$X^{0C}$-$L^2$-$X^{0D}$-$L^1$- is of formula (Id-i) with o being 4.

In certain embodiments the moiety —$X^{0A}$-$L^4$-$X^{0B}$-$L^3$-$X^{0C}$-$L^2$-$X^{0D}$-$L^1$- is of formula (Id-ii) with o being 1. In certain embodiments the moiety —$X^{0A}$-$L^4$-$X^{0B}$-$L^3$-$X^{0C}$-$L^2$-$X^{0D}$-$L^1$- is of formula (Id-ii) with o being 2. In certain embodiments the moiety —$X^{0A}$-$L^4$-$X^{0B}$-$L^3$-$X^{0C}$-$L^2$-$X^{0D}$-$L^1$- is of formula (Id-ii) with o being 3. In certain embodiments the moiety —$X^{0A}$-$L^4$-$X^{0B}$-$L^3$-$X^{0C}$-$L^2$-$X^{0D}$-$L^1$- is of formula (Id-ii) with o being 4.

In certain embodiments the moiety —$X^{0A}$-$L^4$-$X^{0B}$-$L^3$-$X^{0C}$-$L^2$-$X^{0D}$-$L^1$- is of formula (Id-iii) with o being 1. In certain embodiments the moiety —$X^{0A}$-$L^4$-$X^{0B}$-$L^3$-$X^{0C}$-$L^2$-

$X^{0D}$-$L^1$- is of formula (Id-iii) with o being 2. In certain embodiments the moiety —$X^{0A}$-$L^4$-$X^{0B}$-$L^3$-$X^{0C}$-$L^2$-$X^{0D}$-$L^1$- is of formula (Id-iii) with o being 1. In certain embodiments the moiety —$X^{0A}$-$L^4$-$X^{0B}$-$L^3$-$X^{0C}$-$L^2$-$X^{0D}$-$L^1$- is of formula (Id-iii) with o being 4.

In certain embodiments the moiety —$X^{0A}$-$L^4$-$X^{0B}$-$L^3$-$X^{0C}$-$L^2$-$X^{0D}$-$L^1$- is of formula (Id-iv) with o being 1. In certain embodiments the moiety —$X^{0A}$-$L^4$-$X^{0B}$-$L^3$-$X^{0C}$-$L^2$-$X^{0D}$-$L^1$- is of formula (Id-iv) with o being 2. In certain embodiments the moiety —$X^{0A}$-$L^4$-$X^{0B}$-$L^3$-$X^{0C}$-$L^2$-$X^{0D}$-$L^1$- is of formula (Id-iv) with o being 3. In certain embodiments the moiety —$X^{0A}$-$L^4$-$X^{0B}$-$L^3$-$X^{0C}$-$L^2$-$X^{0D}$-$L^1$- is of formula (Id-iv) with o being 4.

In certain embodiments the moiety —$X^{0A}$-$L^4$-$X^{0B}$-$L^3$-$X^{0C}$-$L^2$-$X^{0D}$-$L^1$- is of formula (le-i):

(Ie-i)

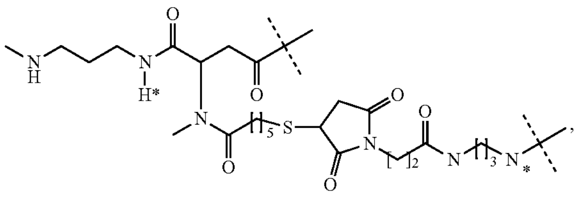

wherein the unmarked dashed line indicates the attachment to a nitrogen of -D by forming an amide bond; and the dashed line marked with the asterisk indicates attachment to the remainder of $Z^2$.

In certain embodiments all moieties —$X^{0F}$— are identical. In certain embodiments the conjugates comprise more than one type of —$X^{0F}$—, such as two, three or four different types of —$X^{0F}$—. In certain embodiment one hyaluronic acid strand comprises only one type of —$X^{0F}$—. In certain embodiments the conjugates comprise a first type of hyaluronic acid strands with a first type of —$X^{0F}$— and a second type of hyaluronic acid strands with a second type of —$X^{0F}$— and optionally a third type of hyaluronic acid strand with a third type of —$X^{0F}$— and optionally a fourth type of hyaluronic acid strand with a fourth type of —$X^{0F}$—.

In certain embodiments —$X^{0F}$— is absent.

In certain embodiments —$X^{0F}$— is a stable linkage, i.e —SP— is connected to —CL- through a stable linkage.

In certain embodiments —$X^{0F}$— is an amide bond, in particular an amide of formula (F)

(F)

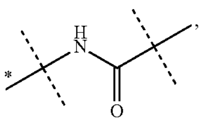

wherein the dashed line marked with the asterisk indicates attachment to —SP— and the unmarked dashed line indicates attachment to —CL-.

In certain embodiments the conjugate comprises a first type of hyaluronic acid strand in which —$X^{0F}$— is an amide bond, in particular an amide bond of formula (F), and a second type of hyaluronic acid strand in which —$X^{0F}$— is of formula (F-i)

(F-i)

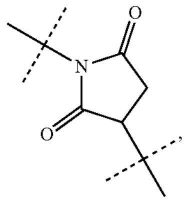

wherein dashed lines indicate attachment to —SP— and —CL-.

In particular, in the second type of hyaluronic acid strand $X^{0F}$— is of formula (F-ii)

(F-ii)

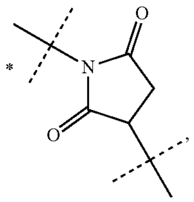

wherein the dashed line marked with the asterisk indicates attachment to —SP— and the unmarked dashed line indicates attachment to —CL-.

—SP— is absent or a spacer moiety. In certain embodiments —SP— does not comprise a reversible linkage, i.e. all linkages in —SP— are stable linkages.

In certain embodiments —SP— is absent.

In certain embodiments —SP— is a spacer moiety.

In certain embodiments —SP— does not comprise a degradable bond, i.e. all bonds of —SP— are stable bonds. In certain embodiments at least one of the at least one degradable bond in the direct connection between two carbon atoms marked with the * connected by a moiety —CL- is provided by —SP—.

In certain embodiments —SP— is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—OC(O$R^3$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

each $—R^{y2}$ is independently selected from the group consisting of halogen, —CN, oxo (=O), $—COOR^{y5}$, $—OR^5$, $—C(O)R^{y5}$, $—C(O)N(R^{y5}R^{y5a})$, $—S(O)_2N(R^{y5}R^{y5a})$, $—S(O)N(R^{y5}R^{y5a})—$, $—S(O)_2R^{y5}$, $—S(O)R^{y5}$, $—N(R^{y5})S(O)_2N(R^{y5a}R^{y5b})$, $—SR^{y5}$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{5a}R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^{y3}$, $—R^{y3a}—R^{y4}—R^{y4a}$, $—R^{y5}$, $—R^{y5a}$ and $—R^{y5}$b is independently selected from the group consisting of —H, and $C_{1-6}$ alkyl, wherein $C_{1-6}$ alkyl is optionally substituted with one or more halogen, which are the same or different, provided that —SP— is attached to $—X^{0E}—$ and $—X^{0F}—$ via a carbon atom of —SP—.

In certain embodiments —SP— is a spacer moiety selected from the group consisting of -T-, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more $—R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more $—R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, $—C(O)N(R^{y4})—$, $—S(O)_2N(R^{y4})—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^{y4})(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

$—R^{y2}$ is selected from the group consisting of halogen, —CN, oxo (=O), $—COOR^{y5}$, $—OR^{y5}$, $—C(O)R^{y5}$, $—C(O)N(R^{y5}R^{y5a})$, $—S(O)_2N(R^{y5}R^{y5a})$, $—S(O)N(R^{y5}R^{y5a})$, $—S(O)_2R^{y5}$, $—S(O)R^{y5}$, $—N(R^{y5})S(O)_2N(R^{y5a}R^{y5b})$, $—SR^{y5}$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5}a\ R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^{y3}$, $—R^{y3a}$, $—R^{y4}$, $—R^{y4a}$, $—R^{y5}$, $—R^{y5a}$ and $—R^{y5b}$ is independently of each other selected from the group consisting of —H, and $C_{1-6}$ alkyl; wherein $C_{1-6}$ alkyl is optionally substituted with one or more halogen, which are the same or different, provided that —SP— is attached to $—X^{0E}—$ and $—X^{0F}—$ via a carbon atom of —SP—.

In certain embodiments —SP— is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{Y3})—$, $—S(O)_2N(R^{y3})—$, $—S(O)N(R^{Y3})—$, $—S(O)_2—$, —S(O)—, $—N(R^{y3})S(O)_2N(R^{ya})—$, —S—, $—N(R^{y3})—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each $—R^{y2}$ is independently selected from the group consisting of halogen and $C_{1-6}$ alkyl; and each $—R^{y3}$, $—R^{y3a}$, $R^{y4}$, $—R^{y4a}$, $R^{y5}$, $—R^{y5a}$ and $—R^{y5b}$ is independently of each other selected from the group consisting of —H, and $C_{1-6}$ alkyl; wherein $C_{1-6}$ alkyl is optionally substituted with one or more halogen, which are the same or different, provided that —SP— is attached to $—X^{0E}—$ and $X^{0F}—$ via a carbon atom of —SP—.

In certain embodiments —SP— is a $C_{1-20}$ alkyl chain, which is optionally interrupted by one or more groups independently selected from —O—, -T-, $—N(R^{y3})—$ and $—C(O)N(R^{y1})—$; and which $C_{1-20}$ alkyl chain is optionally substituted with one or more groups independently selected from —OH, -T, $—N(R^{y3})—$ and $—C(O)N(R^{y6}R^{y6a})$; wherein $—R^{y1}$, $—R^{y6}$, $—R^{y6a}$ are independently selected from the group consisting of H and $C_{1-4}$ alkyl, wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, provided that —SP— is attached to $—X^{0E}—$ and $—X^{0F}—$ via a carbon atom of —SP—.

In certain embodiments —SP— has a molecular weight ranging from 14 g/mol to 750 g/mol.

In certain embodiments —SP— has a chain length ranging from 1 to 20 atoms.

In certain embodiments all moieties —SP— of a conjugate are identical.

In certain embodiments —SP— is a $C_{1-10}$ alkyl. In certain embodiments —SP— is a $C_1$ alkyl. In certain embodiments —SP— is a $C_2$ alkyl. In certain embodiments —SP— is a $C_3$ alkyl. In certain embodiments —SP— is a $C_4$ alkyl. In certain embodiments —SP— is a $C_5$ alkyl. In certain embodiments —SP— is a $C_6$ alkyl. In certain embodiments —SP— is a $C_7$ alkyl. In certain embodiments —SP— is a $C_8$ alkyl. In certain embodiments —SP— is a $C_9$ alkyl. In certain embodiments —SP— is a $C_{10}$ alkyl.

In certain embodiments —SP— is a moiety of formula (E)

(E)

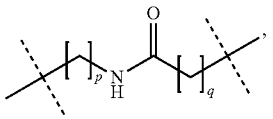

wherein dashed lines indicate attachment to $—X^{0E}—$ and $—X^{0F}—$;

p is an integer selected from the group consisting of 1, 2, 3, 4, 5, 6, 7, 8, 9, 10, 11, 12, 13, 14 and 15; and q is an integer selected from the group consisting of 1, 2, 3, 4, 5, 6, 7, 8, 9, 10, 11, 12, 13, 14 and 15.

In certain embodiments —SP— is a moiety of formula (E-i)

(E-i)

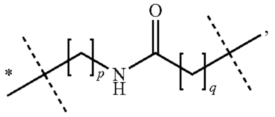

wherein dashed the dashed line indicate attachment to $—X^{0E}—$ and the unmarked dashed line indicates attachment to $—X^{0F}—$;

p is an integer selected from the group consisting of 1, 2, 3, 4, 5, 6, 7, 8, 9, 10, 11, 12, 13, 14 and 15; and q is an integer selected from the group consisting of 1, 2, 3, 4, 5, 6, 7, 8, 9, 10, 11, 12, 13, 14 and 15.

In certain embodiments a conjugate comprises more than one type of —SP—, such as two, three or four different types of —SP—. In certain embodiment one hyaluronic acid strand comprises only one type of —SP—. In certain embodiments a conjugate comprise a first type of hyaluronic acid strands with a first type of —SP— and a second type of hyaluronic acid strands with a second type of —SP— and optionally a third type of hyaluronic acid strand with a third type of —SP— and optionally a fourth type of hyaluronic acid strand with a fourth type of —SP—.

In certain embodiments the conjugate comprises a first type of hyaluronic acid strand in which —SP— is $C_{1-10}$ alkyl, such as a methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl or 3,3-dimethylpropyl. In particular —SP— of the first type of hyaluronic acid is n-propyl. In certain embodiments such conjugate comprises a second type of hyaluronic acid strand in which —SP— is of formula (E), in particular of formula (E-i) and in particular of formula (E-i) in which p is 3 and q is 2.

In certain embodiments all moieties $—X^{0E}—$ are identical. In certain embodiments the conjugates comprise more than one type of $—X^{0E}—$, such as two, three or four different types of $—X^{0E}—$. In certain embodiment one hyaluronic acid strand comprises only one type of $—X^{0E}—$. In certain embodiments the conjugates comprise a first type of hyaluronic acid strands with a first type of $—X^{0E}—$ and a second type of hyaluronic acid strands with a second type of $—X^{0E}—$ and optionally a third type of hyaluronic acid strand with a third type of $—X^{0E}—$ and optionally a fourth type of hyaluronic acid strand with a fourth type of $—X^{0E}$.

In certain embodiments $—X^{0E}—$ is a stable linkage, i.e —SP— is connected to the remainder of a unit $Z^3$ through a stable linkage.

In certain embodiments a moiety $—X^{0E}—SP—X^{0F}—CL-X^{0F}—SP—X^{0E}—$ has the structure of formula (G-i)

(G-i)

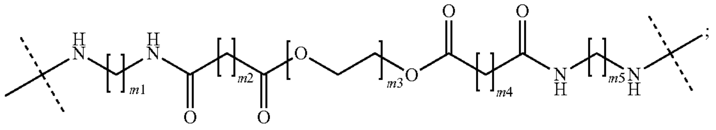

In certain embodiments p of formula (E) or (E-i) is selected from the group consisting of 1, 2, 3, 4, 5, 6, 7 and 8. In certain embodiments p of formula (E) or (E-i) is selected from the group consisting of 2, 3, 4, 5, and 6. In certain embodiments p of formula (E) or (E-i) is 2. In certain embodiments p of formula (E) or (E-i) is 3. In certain embodiments p of formula (E) or (E-i) is 4. In certain embodiments p of formula (E) or (E-i) is 5.

In certain embodiments q of formula (E) or (E-i) is selected from the group consisting of 1, 2, 3, 4, 5, 6, 7 and 8. In certain embodiments q of formula (E) or (E-i) is selected from the group consisting of 1, 2, 3, 4 and 5. In certain embodiments q of formula (E) or (E-i) is 1. In certain embodiments q of formula (E) or (E-i) is 2. In certain embodiments q of formula (E) or (E-i) is 3. In certain embodiments q of formula (E) or (E-i) is 4. In certain embodiments q of formula (E) or (E-i) is 5.

In certain embodiments p of formula (E) or (E-i) is 3 and q of formula (E) or (E-i) is 2.

wherein dashed lines indicate attachment to the carbonyl of the hyaluronic acid; and each m1, m2, m3, m4 and m5 is independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments each m1 of formula (G-i) is individually selected from the group consisting of 1, 2, 3, 4, 5, 6, 7 and 8. In certain embodiments each m1 of formula (G-i) is individually selected from the group consisting of 1, 2, 3, 4 and 5. In certain embodiments m1 of formula (G-i) is 1. In certain embodiments m1 of formula (G-i) is 2. In certain embodiments m1 of formula (G-i) is 3. In certain embodiments m1 of formula (G-i) is 4. In certain embodiments m1 of formula (G-i) is 5.

In certain embodiments each m2 of formula (G-i) is individually selected from the group consisting of 1, 2, 3, 4, 5, 6, 7 and 8. In certain embodiments each m2 of formula (G-i) is individually selected from the group consisting of 1, 2, 3, 4 and 5. In certain embodiments m2 of formula (G-i) is 1. In certain embodiments m2 of formula (G-i) is 2. In certain embodiments m2 of formula (G-i) is 3. In certain embodiments m2 of formula (G-i) is 4. In certain embodiments m2 of formula (G-i) is 5.

In certain embodiments each m3 of formula (G-i) is individually selected from the group consisting of 0, 1, 2, 3, 4, 5, 6, 7 and 8. In certain embodiments each m3 of formula (G-i) is individually selected from the group consisting of 0, 1, 2, 3, 4 and 5. In certain embodiments m3 of formula (G-i) is 0. In certain embodiments m3 of formula (G-i) is 1. In certain embodiments m3 of formula (G-i) is 2. In certain embodiments m3 of formula (G-i) is 3. In certain embodiments m3 of formula (G-i) is 4. In certain embodiments m3 of formula (G-i) is 5.

In certain embodiments each m4 of formula (G-i) is individually selected from the group consisting of 0, 1, 2, 3, 4, 5, 6, 7 and 8. In certain embodiments each m4 of formula (G-i) is individually selected from the group consisting of 0, 1, 2, 3, 4 and 5. In certain embodiments m4 of formula (G-i) is 0. In certain embodiments m4 of formula (G-i) is 1. In certain embodiments m4 of formula (G-i) is 2. In certain embodiments m4 of formula (G-i) is 3. In certain embodiments m4 of formula (G-i) is 4. In certain embodiments m4 of formula (G-i) is 5.

In certain embodiments each m5 of formula (G-i) is individually selected from the group consisting of 0, 1, 2, 3, 4, 5, 6, 7 and 8. In certain embodiments m5 of formula (G-i) is selected from the group consisting of 0, 1, 2, 3, 4 and 5. In certain embodiments m5 of formula (G-i) is 0. In certain embodiments m5 of formula (G-i) is 1. In certain embodiments m5 of formula (G-i) is 2. In certain embodiments m5 of formula (G-i) is 3. In certain embodiments m5 of formula (G-i) is 4. In certain embodiments m5 of formula (G-i) is 5.

In certain embodiments m1, m2, m3, m4 and m5 are 3.

In certain embodiments a moiety —$X^{0E}$—SP—$X^{0F}$—CL-$X^{0F}$—SP—$X^{0E}$— has the structure of formula (G-ii)

In certain embodiments each m2 of formula (G-ii) is individually selected from the group consisting of 1, 2, 3, 4, 5, 6, 7 and 8. In certain embodiments each m2 of formula (G-ii) is individually selected from the group consisting of 1, 2, 3, 4 and 5. In certain embodiments m2 of formula (G-ii) is 1. In certain embodiments m2 of formula (G-ii) is 2. In certain embodiments m2 of formula (G-ii) is 3. In certain embodiments m2 of formula (G-ii) is 4. In certain embodiments m2 of formula (G-ii) is 5.

In certain embodiments each m3 of formula (G-ii) is individually selected from the group consisting of 1, 2, 3, 4, 5, 6, 7 and 8. In certain embodiments each m3 of formula (G-ii) is individually selected from the group consisting of 1, 2, 3, 4 and 5. In certain embodiments m3 of formula (G-ii) is 1. In certain embodiments m3 of formula (G-ii) is 2. In certain embodiments m3 of formula (G-ii) is 3. In certain embodiments m3 of formula (G-ii) is 4. In certain embodiments m3 of formula (G-ii) is 5.

In certain embodiments each m4 of formula (G-ii) is individually selected from the group consisting of 1, 2, 3, 4, 5, 6, 7 and 8. In certain embodiments each m4 of formula (G-ii) is individually selected from the group consisting of 1, 2, 3, 4 and 5. In certain embodiments m4 of formula (G-ii) is 1. In certain embodiments m4 of formula (G-ii) is 2. In certain embodiments m4 of formula (G-ii) is 3. In certain embodiments m4 of formula (G-ii) is 4. In certain embodiments m4 of formula (G-ii) is 5.

In certain embodiments each m5 of formula (G-ii) is individually selected from the group consisting of 1, 2, 3, 4, 5, 6, 7, 8, 9, 10, 11, 12, 13 and 14. In certain embodiments each m5 of formula (G-ii) is individually selected from the group consisting of 1, 2, 3, 4, 5, 6, 7, 8, 9 and 10. In certain embodiments m5 of formula (G-ii) is 3. In certain embodiments m5 of formula (G-ii) is 4. In certain embodiments m5 of formula (G-ii) is 5. In certain embodiments m5 of formula (G-ii) is 6. In certain embodiments m5 of formula (G-ii) is (G-ii)

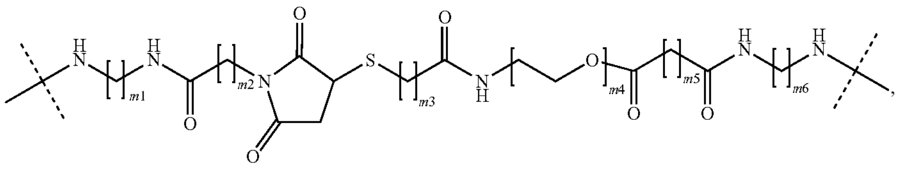

wherein dashed lines indicate attachment to the carbonyl of the hyaluronic acid; and each m1, m2, m3, m4, m5 and m6 is independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments each m1 of formula (G-ii) is individually selected from the group consisting of 1, 2, 3, 4, 5, 6, 7 and 8. In certain embodiments each m1 of formula (G-ii) is individually selected from the group consisting of 1, 2, 3, 4 and 5. In certain embodiments m1 of formula (G-ii) is 1. In certain embodiments m1 of formula (G-ii) is 2. In certain embodiments m1 of formula (G-ii) is 3. In certain embodiments m1 of formula (G-ii) is 4. In certain embodiments m1 of formula (G-ii) is 5.

7. In certain embodiments m5 of formula (G-ii) is 8. In certain embodiments m5 of formula (G-ii) is 9. In certain embodiments m5 of formula (G-ii) is 10.

In certain embodiments each m6 of formula (G-ii) is individually selected from the group consisting of 1, 2, 3, 4, 5, 6, 7 and 8. In certain embodiments each m6 of formula (G-ii) is individually selected from the group consisting of 1, 2, 3, 4 and 5. In certain embodiments m6 of formula (G-ii) is 1. In certain embodiments m6 of formula (G-ii) is 2. In certain embodiments m6 of formula (G-ii) is 3. In certain embodiments m6 of formula (G-ii) is 4. In certain embodiments m6 of formula (G-ii) is 5.

In certain embodiments m1 and m6 of formula (G-ii) are 3, m2, m3 and m4 of formula (G-ii) are 2 and m5 is 7.

In certain embodiments a moiety —$X^{0A}$-$L^4$-$X^{0B}$-$L^3$-$X^{0C}$-$L^2$-$X^{0D}$-$L^1$-D is of formula (H-i)

(H-i)

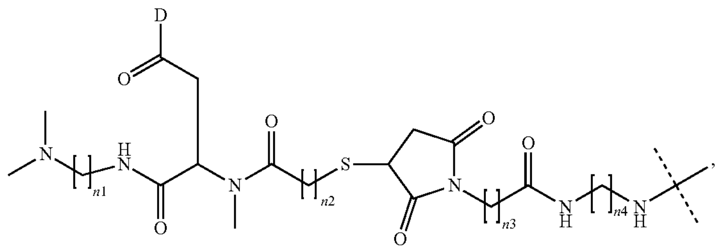

wherein the dashed line indicates attachment to the carbonyl of the hyaluronic acid;

-D is used as defined above;

In certain embodiments -D of formula (H-i) is an antibiotic moiety as defined above.

In certain embodiments a moiety $—X^{0A}$-$L^4$-$X^{0B}$-$L^3$-$X^{0C}$-$L^2$-$X^{0D}$-$L^1$-D is of formula (H-ii)

(H-ii)

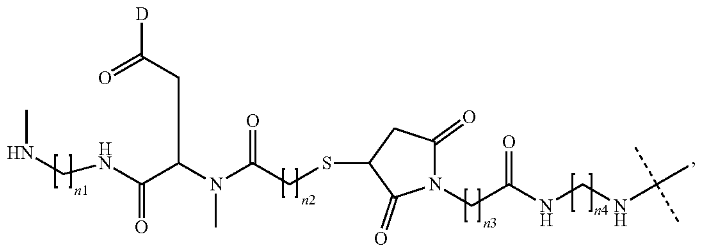

each n1 is independently an integer selected from the group consisting of 2 or 3; and n2, n3 and n4 is independently an integer selected from the group consisting of 1, 2, 3, 4, 5, 6, 7, 8, 9, 10, 11, 12, 13, 14, 15 and 16.

In certain embodiments n1 of formula (H-i) is 2. In certain embodiments n1 of formula (H-i) is 3.

In certain embodiments n2 of formula (H-i) is an integer selected from the group consisting of 1, 2, 3, 4, 5, 6, 7 and 8. In certain embodiments n2 of formula (H-i) is an integer selected from the group consisting of 2, 3, 4, 5, and 6. In certain embodiments n2 of formula (H-i) is 2. In certain embodiments n2 of formula (H-i) is 3. In certain embodiments n2 of formula (H-i) is 4. In certain embodiments n2 of formula (H-i) is 5.

In certain embodiments n3 of formula (H-i) is an integer selected from the group consisting of 1, 2, 3, 4, 5, 6, 7, 8, 9 and 10. In certain embodiments n3 of formula (H-i) is an integer selected from the group consisting of 1, 2, 3, 4, 5 and 6. In certain embodiments n3 of formula (H-i) is 1. In certain embodiments n3 of formula (H-i) is 2. In certain embodiments n3 of formula (H-i) is 3. In certain embodiments n3 of formula (H-i) is 4. In certain embodiments n3 of formula (H-i) is 5. In certain embodiments n3 of formula (H-i) is 6.

In certain embodiments n4 of formula (H-i) is an integer selected from the group consisting of 1, 2, 3, 4, 5, 6, 7, 8, 9 and 10. In certain embodiments n4 of formula (H-i) is an integer selected from the group consisting of 1, 2, 3, 4, 5 and 6. In certain embodiments n4 of formula (H-i) is 1. In certain embodiments n4 of formula (H-i) is 2. In certain embodiments n4 of formula (H-i) is 3. In certain embodiments n4 of formula (H-i) is 4. In certain embodiments n4 of formula (H-i) is 5. In certain embodiments n4 of formula (H-i) is 6.

In certain embodiments n1 and n3 of formula (H-i) are 2, n2 of formula (H-i) is 5 and n4 of formula (H-i) is 3.

wherein the dashed line indicates attachment to the carbonyl of the hyaluronic acid;

-D is used as defined above;

each n1 is independently an integer selected from the group consisting of 2 or 3; and n2, n3 and n4 is independently an integer selected from the group consisting of 1, 2, 3, 4, 5, 6, 7, 8, 9, 10, 11, 12, 13, 14, 15 and 16.

In certain embodiments n1 of formula (H-ii) is 2. In certain embodiments n1 of formula (H-ii) is 3.

In certain embodiments n2 of formula (H-ii) is an integer selected from the group consisting of 1, 2, 3, 4, 5, 6, 7 and 8. In certain embodiments n2 of formula (H-ii) is an integer selected from the group consisting of 2, 3, 4, 5, and 6. In certain embodiments n2 of formula (H-ii) is 2. In certain embodiments n2 of formula (H-ii) is 3. In certain embodiments n2 of formula (H-ii) is 4. In certain embodiments n2 of formula (H-ii) is 5.

In certain embodiments n3 of formula (H-ii) is an integer selected from the group consisting of 1, 2, 3, 4, 5, 6, 7, 8, 9 and 10. In certain embodiments n3 of formula (H-ii) is an integer selected from the group consisting of 1, 2, 3, 4, 5 and 6. In certain embodiments n3 of formula (H-ii) is 1. In certain embodiments n3 of formula (H-ii) is 2. In certain embodiments n3 of formula (H-ii) is 3. In certain embodiments n3 of formula (H-ii) is 4. In certain embodiments n3 of formula (H-ii) is 5. In certain embodiments n3 of formula (H-ii) is 6.

In certain embodiments n4 of formula (H-ii) is an integer selected from the group consisting of 1, 2, 3, 4, 5, 6, 7, 8, 9 and 10. In certain embodiments n4 of formula (H-ii) is an integer selected from the group consisting of 1, 2, 3, 4, 5 and 6. In certain embodiments n4 of formula (H-ii) is 1. In certain embodiments n4 of formula (H-ii) is 2. In certain embodiments n4 of formula (H-ii) is 3. In certain embodiments n4 of formula (H-ii) is 4. In certain embodiments n4 of formula (H-ii) is 5. In certain embodiments n4 of formula (H-ii) is 6.

In certain embodiments n1 and n4 of formula (H-ii) are 3, n2 of formula (H-ii) is 5 and n3 of formula (H-ii) is 2.

In certain embodiments -D of formula (H-ii) is an antibody moiety as defined above.

A conjugates release one or more type of drug over an extended period of time, i.e. they are sustained-release conjugates. In certain embodiments the release occurs with a release half-life ranging between 1 day and 1 month. In certain embodiments the release occurs with a release half-life ranging between 1 day and 20 days. In certain embodiments the release occurs with a release half-life between 1 day and 15 days. In certain embodiments the release half-life may also range from 2 to 20 days or from 4 to 15 days. If the drug is an antibiotic such continuous release is advantageous for the eradication of biofilms and thus the treatment of infections, such as infections in body compartments, such as for example joint infections, compared to one or more bolus injections of the respective antibiotic.

In another aspect the present invention relates to a pharmaceutical composition comprising at least one conjugate and at least one excipient. In certain embodiments the pharmaceutical composition comprises one conjugate. In certain embodiments the pharmaceutical composition comprises two conjugates. In certain embodiments the pharmaceutical composition comprises three conjugates. In certain embodiments the pharmaceutical composition comprises more than three conjugates.

Such pharmaceutical composition may have a pH ranging from pH 3 to pH 8, such as ranging from pH 4 to pH 6 or ranging from pH 4 to pH 5. In certain embodiments the pH of the pharmaceutical composition is about 4. In certain embodiments the pH of the pharmaceutical composition is about 4.5. In certain embodiments the pH of the pharmaceutical composition is about 5.

In one embodiment such pharmaceutical composition is a suspension formulation.

In certain embodiments such pharmaceutical is a dry composition. It is understood that such dry composition may be obtained by drying, such as lyophilizing, a suspension composition.

If the pharmaceutical composition is a parenteral composition, suitable excipients may be categorized as, for example, buffering agents, isotonicity modifiers, preservatives, stabilizers, anti-adsorption agents, oxidation protection agents, viscosifiers/viscosity enhancing agents, anti-agglomeration agents or other auxiliary agents. However, in some cases, one excipient may have dual or triple functions. Excipient may be selected from the group consisting of (i) Buffering agents: physiologically tolerated buffers to maintain pH in a desired range, such as sodium phosphate, bicarbonate, succinate, histidine, citrate and acetate, sulphate, nitrate, chloride, pyruvate; antacids such as $Mg(OH)_2$ or $ZnCO_3$ may be also used;

(ii) Isotonicity modifiers: to minimize pain that can result from cell damage due to osmotic pressure differences at the injection depot; glycerin and sodium chloride are examples; effective concentrations can be determined by osmometry using an assumed osmolality of 285-315 mOsmol/kg for serum;

(iii) Preservatives and/or antimicrobials: multidose parenteral formulations require the addition of preservatives at a sufficient concentration to minimize risk of patients becoming infected upon injection and corresponding regulatory requirements have been established; typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride;

(iv) Stabilizers: Stabilisation is achieved by strengthening of the protein-stabilising forces, by destabilisation of the denatured state, or by direct binding of excipients to the protein; stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives; in addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the formulation's container; e.g., poloxamer (Pluronic F-68), PEG dodecyl ether (Brij 35), polysorbate 20 and 80, dextran, polyethylene glycol, PEG-polyhistidine, BSA and HSA and gelatins; chosen concentration and type of excipient depends on the effect to be avoided but typically a monolayer of surfactant is formed at the interface just above the CMC value;

(vi) Oxidation protection agents: antioxidants such as ascorbic acid, ectoine, methionine, glutathione, monothioglycerol, morin, polyethylenimine (PEI), propyl gallate, and vitamin E; chelating agents such as citric acid, EDTA, hexaphosphate, and thioglycolic acid may also be used;

(vii) Viscosifiers or viscosity enhancers: retard settling of the particles in the vial and syringe and are used in order to facilitate mixing and resuspension of the particles and to make the suspension easier to inject (i.e., low force on the syringe plunger); suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly (glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone; such block copolymers as well as the abovementioned poloxamers may exhibit reverse thermal gelation behavior (fluid state at room temperature to facilitate administration and gel state above sol-gel transition temperature at body temperature after injection);

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue; a spreading agent such as but not limited to hyaluronidase temporarily decreases the viscosity of the extracellular matrix and promotes diffusion of injected drugs;

(ix) Anti-agglomeration agents, such as propylene glycol; and (x) Other auxiliary agents: such as wetting agents, viscosity modifiers, antibiotics, hyaluronidase; acids and bases such as hydrochloric acid and sodium hydroxide are auxiliary agents necessary for pH adjustment during manufacture.

Another aspect is the conjugate of the present invention or a pharmaceutical composition comprising such conjugate for use in a method of treating a disease that can be treated with D-H or D-OH. If -D is an antibiotic moiety the conjugate is for use in a method of preventing or treating an infection.

In certain embodiments the infection is in a body compartment. Such body compartment may be selected from the group consisting body cavities, body spaces, brain or parts thereof, ear or parts thereof, nose, throat, sinuses, lung or parts thereof, abdomen, bone, skin, muscle, abscess, small intestine, large intestine, cyst, uterus, amniotic sac and joint.

In certain embodiments such body compartment may be any cavity of the human body, such as the oral cavity, cranial cavity, spinal cavity, dorsal cavity, thoracic cavity, pericardial cavity, abdominal cavity, ventral cavity, retroperitoneal space, abdominopelvic cavity, pelvic cavity and its enclosed organs.

In certain embodiments the body compartment is selected from the group consisting of the retropharyngeal space, retropalatial space, mediastinal space, retrosternal space, pleural space, retroperitoneal space, prevesical space, paravesical space, vesicocervical space, rectovaginal space, pararectal space, presacral space, subphrenic space, subhepatic space, supramesocolic space and inframesocolic space.

In certain embodiments the body compartment is the brain or one or more parts of it.

In certain embodiments the body compartment is the ear or one or more parts of it, such as the middle ear.

In certain embodiments the body compartment is the nose, throat, and sinuses.

In certain embodiments the body compartment is the lung or parts of it.

In certain embodiments the body compartment is the abdomen.

In certain embodiments the body compartment is bone, such as the pelvis.

In certain embodiments the body compartment is the skin.

In certain embodiments the body compartment is muscles.

In certain embodiments the body compartment is an abscess.

In certain embodiments the body compartment is the small intestine, such as the duodenum, ileum and jejunum.

In certain embodiments the body compartment is the large intestine, such as the colon, appendix and rectum.

In certain embodiments the body compartment is a cyst.

In certain embodiments the body compartment is the uterus.

In certain embodiments the body compartment is the amniotic sac.

In certain embodiments the body compartment is a joint.

If the infection is in a joint, the conjugate of the present invention may be administered via intraarticular injection.

In certain embodiments a single injection into the intra-articular compartment of at least one conjugate of the present invention provides a concentration of at least 1 μg antibiotic/ml synovial fluid for at least 3 days, such as for 3 days, 4 days or 5 days.

In certain embodiments a single injection into the intra-articular compartment of at least one conjugate of the present invention provides a concentration of at least 5 μg antibiotic/ml synovial fluid for at least 3 days, such as for 3 days, 4 days or 5 days.

In certain embodiments a single injection into the intra-articular compartment of at least one conjugate of the present invention provides a concentration of at least 25 μg antibiotic/ml synovial fluid for at least 3 days, such as for 3 days, 4 days or 5 days.

In certain embodiments a single injection into the intra-articular compartment of at least one conjugate of the present invention provides a concentration of at least 50 μg antibiotic/ml synovial fluid for at least 3 days, such as for 3 days, 4 days or 5 days.

In certain embodiments a single injection into the intra-articular compartment of at least one conjugate of the present invention provides a concentration of at least 75 μg antibiotic/ml synovial fluid for at least 3 days, such as for 3 days, 4 days or 5 days.

In certain embodiments a single injection into the intra-articular compartment of at least one conjugate of the present invention provides a concentration of at least 100 μg antibiotic/ml synovial fluid for at least 3 days, such as for 3 days, 4 days or 5 days.

In certain embodiments a single injection into the intra-articular compartment of at least one conjugate of the present invention provides a concentration of at least 150 μg antibiotic/ml synovial fluid for at least 3 days, such as for 3 days, 4 days or 5 days.

In certain embodiments a single injection into the intra-articular compartment of at least one conjugate of the present invention provides a concentration of at least 200 μg antibiotic/ml synovial fluid for at least 3 days, such as for 3 days, 4 days or 5 days.

In certain embodiments a single injection into the intra-articular compartment of at least one conjugate of the present invention provides a concentration of at least 250 μg antibiotic/ml synovial fluid for at least 3 days, such as for 3 days, 4 days or 5 days.

In certain embodiments a single injection into the intra-articular compartment of at least one conjugate of the present invention provides a concentration of at least 300 μg antibiotic/ml synovial fluid for at least 3 days, such as for 3 days, 4 days or 5 days.

In certain embodiments a single injection into the intra-articular compartment of at least one conjugate of the present invention provides a concentration of at least 400 μg antibiotic/ml synovial fluid for at least 3 days, such as for 3 days, 4 days or 5 days.

In certain embodiments a single injection into the intra-articular compartment of at least one conjugate of the present invention provides a concentration of at least 500 μg antibiotic/ml synovial fluid for at least 3 days, such as for 3 days, 4 days or 5 days.

In certain embodiments the antibiotic moieties released from the conjugate after a single intra-articular injection provide a concentration of said antibiotic in the intra-articular compartment that is at least 1.1-fold above the minimal biofilm eradicating concentration of the respective antibiotic for at least 3 days, such as for at least 4 days, at least 5 days, at least 6 days or at least 7 days.

In certain embodiments the antibiotic moieties released from the conjugate after a single intra-articular injection provide a concentration of said antibiotic in the intra-articular compartment that is at least 1.2-fold above the minimal biofilm eradicating concentration of the respective antibiotic for at least 3 days, such as for at least 4 days, at least 5 days, at least 6 days or at least 7 days.

In certain embodiments the antibiotic moieties released from the conjugate after a single intra-articular injection provide a concentration of said antibiotic in the intra-articular compartment that is at least 1.3-fold above the minimal biofilm eradicating concentration of the respective antibiotic for at least 3 days, such as for at least 4 days, at least 5 days, at least 6 days or at least 7 days.

In certain embodiments the antibiotic moieties released from the conjugate after a single intra-articular injection provide a concentration of said antibiotic in the intra-articular compartment that is at least 1.4-fold above the minimal biofilm eradicating concentration of the respective antibiotic for at least 3 days, such as for at least 4 days, at least 5 days, at least 6 days or at least 7 days.

In certain embodiments the antibiotic moieties released from the conjugate after a single intra-articular injection provide a concentration of said antibiotic in the intra-articular compartment that is at least 1.5-fold above the minimal biofilm eradicating concentration of the respective antibiotic for at least 3 days, such as for at least 4 days, at least 5 days, at least 6 days or at least 7 days.

In certain embodiments the antibiotic moieties released from the conjugate after a single intra-articular injection provide a concentration of said antibiotic in the intra-articular compartment that is at least 1.6-fold above the minimal biofilm eradicating concentration of the respective antibiotic for at least 3 days, such as for at least 4 days, at least 5 days, at least 6 days or at least 7 days.

In certain embodiments the antibiotic moieties released from the conjugate after a single intra-articular injection provide a concentration of said antibiotic in the intra-articular compartment that is at least 1.7-fold above the minimal biofilm eradicating concentration of the respective antibiotic for at least 3 days, such as for at least 4 days, at least 5 days, at least 6 days or at least 7 days.

In certain embodiments the volume of an intraarticular injection is no more than 12 ml, such as no more than 11 ml, such as no more than 10 ml or such as no more than 9 ml such as no more than 8 ml.

If the infection is in a joint, such infected joint may be a synovial joint. Such synovial joint may be selected from the group consisting of hinge joints and ball and socket joints. In certain embodiments the joint is a hinge joint. In certain embodiments the joint is a ball and socket joint.

Such synovial joints may be selected from the group consisting of joints of the knee, hip, shoulder, elbow, foot, hand, sternoclavicular joint and vertebral articulations.

Examples for a joint of the knee are tibiofemoral joint and patellofemoral joint.

Examples for a joint of the shoulder are glenohumeral joint and acromioclavicular joint.

Examples for a joint of the elbow are humero-ulnar joint, humero-radial joint and radio-ulnar joint.

It is understood that the term "joints of the foot" also covers joints of the toes. Examples for a joint of the foot are ankle, subtalar and talocalcaneal joint.

It is understood that the term "joints of the hand" also covers joints of the fingers. Example for a joint of the hand are wrist, intercarpal joint, midcarpal joint, carpometacarpal joint and metacarpophalangeal joint.

Examples for a vertebral articulation are zygapophyseal joints, temporomandibular joints and sacroiliac joints.

In certain embodiments the joint is selected from the group consisting of knee, hip, shoulder, elbow and ankle. In certain embodiments the joint is a knee. In certain embodiments the joint is a hip. In certain embodiments the joint is a shoulder.

In certain embodiments the infection, such as an infection in a body compartment, such as in a joint, is related to a surgical implant.

Examples for such surgical implant are pins, rods, screws, artificial joints, mesh, clips, sutures, wires, tubes, catheters, pumps, filters, prostheses, plates, fasteners, washers, bolts, seeds, beads, staples, nails, shunts, cuffs, buttons, ports, cement, fixators, stents, fillers, wax, wraps, weights, stimulators, anchors, expanders, guidewires, fillers, polymers, film, fixators, drains, lines and cones.

In certain embodiments the surgical implant is an artificial joint. In certain embodiments the surgical implant is a prosthesis.

In certain embodiments surgical implants are at least partially made from one or more material selected from the group consisting of metals, ceramics, natural polymers, artificial polymers, bone cement, foreign organic material, artificial tissue and natural tissue. Such natural tissue may be selected from the group consisting of ligament, skin, muscle and bone. In certain embodiments the natural tissue is bone.

In certain embodiments the conjugate is for use in a method of preventing a joint infection, in particular a surgical implant-related joint infection. In such case the conjugate of the present invention may be administered to the joint prior, during or after the implantation of the surgical implant. In certain embodiments it is administered prior to the implantation a surgical implant. In certain embodiments it is administered during the implantation of a surgical implant. In certain embodiments it is administered after the implantation of a surgical implant, such as for example no more than 1 hour after the implantation, no later than 2 hours after the implantation, no later than 5 hours after the implantation, no later than 10 hours after the implantation, no later than 24 hours after the implantation, no later than 48 hours after the implantation or no later than 72 hours after the implantation, no later than 96 hours after the implantation, no later than a week after the implantation, no later than two weeks after the implantation, no later than three weeks after the implantation, no later than four weeks after the implantation, no later than six weeks after the implantation or no later than eight weeks after the implantation. In certain embodiments it may be administered later than two months after the implantation.

In certain embodiments the infection, such as an infection in a body compartment, in particular in a joint, such as a joint infection related to a surgical implant, comprises the presence of a biofilm, in particular a biofilm on at least one surface of the surgical implant. Such biofilm may comprise organisms selected from the group consisting of bacteria, mycobacteria and fungi. Accordingly, in certain embodiments the method of preventing or treating an infection, such as an infection in a body compartment, in particular an infection in a joint, such as an infection related to a surgical implant, comprises the step of preventing the formation of a biofilm or eradicating an existing biofilm.

In certain embodiments such biofilm comprises bacteria. Such bacteria may be gram-positive or gram-negative. They may be aerobic or anaerobic bacteria. In certain embodiments the biofilm comprises multiple different species. In certain embodiments the biofilm comprises one predominant species, to which at least 80%, such as at least 85%, at least 90%, at least 92%, at least 95%, at least 96%, at least 97%, at least 98% or at least 99%, of all bacteria present in the biofilm belong.

Examples for gram-positive bacteria are *Staphylococcus, Streptococcus, Enterococcus, Clostridium, Bacillus, Listeria* and lactic acid bacteria, such as *Staphylococcus aureus, Staphylococcus epidermidis, Staphylococcus saprophyticus, Streptococcus pneumoniae, Streptococcus pyogenes, Streptococcus agalactiae, Streptococcus dysgalactiae, Streptococcus viridans, Enterococcus faecalis, Enterococcus faecium, Clostridium tetani, Clostridium botulinum, Clostridium perfringes, Clostridium difficile, Bacillus anthracis, Listeria monocytogenes* and *Propionibacterium acnes.*

Examples for gram-negative bacteria are Enterobacteriaceae, Vibrionaceae, Pseudomonadaceae, Bacteroidaceae, *Actinomyces, Neisseria, Hemophilus, Bordetella, Legionella, Treponema, Borrelia, Chlamydia, Rickettsia, Ehrlichia, Mycoplasma* and *Burkholderia*, such as *Salmonella* species, *Shigella dysenteriae, Klebsiella pneumoniae, Escherichia coli, Escherichia faecalis, Vibrio cholera, Campylobacter jejuni, Pseudomonas aeruginosa, Bacteroides fragilis, Neisseria meningitidis, Neisseria gonorrhoeae, Haemophilus influenza, Actinomyces isrealli, Mycoplasma pneumoniae, Acinetobacter baumanii, Citrobacter, Achromobacter* and *Stenotrophomonas.*

In certain embodiments the biofilm comprises mycobacteria.

In certain embodiments the biofilm comprises fungi. Such fungi may be molds or yeasts.

Examples for fungi are *Candida, Aspergillus, Cryptococcus, Trichosporon, Coccidioides*, and *Pneumocystis*, such as *Candida albicans, Candida parapsilosis, Candida tropicalis, Candida parapsilosis, Candida glabrata; Aspergillus fumigatus, Coccioides immitis, Coccioides neoformans, Trichosporon asahii*, and *Pneumocystis carinii.*

In a further aspect the present invention relates to the use of the conjugates of the present invention or the pharmaceutical compositions comprising said conjugates as a medicament.

If -D is an antibiotic moiety said medicament is an antibiotic for the prevention or treatment of an infection, such as an infection in a body compartment, In a further aspect the present invention relates to a method of preventing a disease or treating a patient suffering from a disease that can be prevented or treated with D-H or D-OH comprising administering an effective amount of the conjugate of the present invention or the pharmaceutical compositions comprising said conjugates to the patient.

If D-H or D-OH is an antibiotic the disease that can be prevented or treated is preferably an infection, such as a joint infection, such as a joint infection related to surgical implants, as described above.

Any of the antibody conjugates (e.g., anti-VEGF antibodies), i.e. conjugates in which -D is an antibody moiety, provided herein may be used in therapeutic methods.

In one aspect, such antibody conjugate for use as a medicament is provided. In another aspect, the invention provides an antibody conjugate for use in treating a disorder associated with pathological angiogenesis. In some embodiments, the disorder associated with pathological angiogenesis is an ocular disorder or a cell proliferative disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma. In another aspect, an anti-VEGF antibody conjugate for use in treating a disorder associated with undesirable vascular permeability is provided. In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases.

In another aspect, an antibody conjugate for use in a method of treatment is provided. The invention also provides an antibody conjugate for use in a method of treating a subject having a disorder associated with pathological angiogenesis comprising administering to the individual an effective amount of the antibody conjugate. In certain instances, the invention provides an anti-VEGF antibody (e.g., an anti-VEGF antibody) conjugate for use in a method of treating a subject having a disorder associated with pathological angiogenesis comprising administering to the individual an effective amount of the anti-VEGF antibody conjugate. In some instances, the disorder associated with pathological angiogenesis is an ocular disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g, allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma.

The conjugates of the present invention may be synthesized by different methods.

In certain embodiments in a first step, hyaluronic acid strands mainly comprising units $Z^1$ and $Z^6$ are prepared from unmodified hyaluronic acid strands consisting of units $Z^1$ by reacting the unmodified hyaluronic acid strands with an activation reagent and optionally an additive agent to form hyaluronic acid strands comprising units $Z^1$ and $Z^{10}$ and by adding a reagent $Y^{0C}$-$L^4$-$Y^{0I}$, wherein the functional groups —$Y^{0I}$ are reactive with functional groups —$Y^{0H}$ by using methods known in the field. In certain embodiments hyaluronic acid strands comprising units $Z^1$ and $Z^{10}$ are isolated before adding $Y^{0C}$-$L^4$-$Y^{0I}$. Optionally, functional groups —$Y^{0C}$ may be protected with a protecting group known to the skilled person in the field. In a second step, hyaluronic acid strands mainly comprising units $Z^1$, $Z^5$, and $Z^7$ units are prepared by reacting the hyaluronic acid strands mainly comprising units $Z^1$ and $Z^6$ with a reagent $Y^{0D}$-$L^3$-$Y^{0J}$, wherein functional groups —$Y^{0J}$ are reactive with functional groups —$Y^{0C}$ by using methods known to the skilled person in the field. Optionally, functional groups —$Y^{0D}$ may be protected with a protecting group. In such an embodiment —SP— and -$L^4$-$X^{0B}$-$L^3$, and —$X^{0A}$— and —$X^{0E}$, and —$Y^{0B}$ and —$Y^{0D}$ are the same, respectively. In a third step, a crosslinker reagent $Y^{0A}$—CL-$Y^{0A}$ with functional groups —$Y^{0A}$ being reactive with functional groups —$Y^{0D}$ and —$Y^{0B}$ present in units $Z^7$ and $Z^5$ units, respectively, is prepared. In a fourth step, a monoconjugate reagent D-$L^1$-$X^{0D}$-$L^2$-$Y^{0G}$ is prepared, wherein said functional group —$Y^{0G}$ is reactive with functional group —$Y^{0D}$ of unit $Z^7$.

Next, the crosslinker reagent $Y^{0A}$—CL-$Y^{0A}$, the monoconjugate reagent D-$L^1$-$X^{0D}$-$L^2$-$Y^{0G}$ and the hyaluronic acid strands mainly comprising units $Z^1$, $Z^5$, and $Z^7$ may be conjugated at the same time, i.e. by mixing all reagents together in one step, to obtain a conjugate of the present invention.

Alternatively, the hyaluronic acid strands mainly comprising units $Z^1$, $Z^5$, and $Z^7$ and the monoconjugate reagent D-$L^1$-$X^{0D}$-$L^2$-$Y^{0G}$ may be mixed first and reacted to generate hyaluronic acid strands mainly comprising units $Z^1$, $Z^2$, and $Z^5$, followed by addition of the crosslinker reagent $Y^{0A}$—CL-$Y^{0A}$ to form a conjugate of the present invention.

Alternatively, the hyaluronic acid strands mainly comprising units $Z^1$, $Z^5$, and $Z^7$ and the crosslinker reagent $Y^{0A}$—CL-$Y^{0A}$ may be mixed first and reacted to generate crosslinked hyaluronic acid strands mainly comprising units $Z^1$, $Z^3$, and $Z^7$ crosslinked via a moiety —CL-, followed by addition and reaction of the monoconjugate reagent D-$L^1$-$X^{0D}$-$L^2$-$Y^{0G}$ to form a conjugate of the present invention. In order to allow the monoconjugate reagent to react with the crosslinked hyaluronic acid strands, it may be necessary to first crush the crosslinked hyaluronic acid strands to form smaller particles or to perform the crosslinking step in a fashion which generates small particles or microparticles.

Alternatively, hyaluronic acid strands mainly comprising units $Z^1$, $Z^6$, and $Z^5$ are prepared by reacting unmodified hyaluronic acid strands consisting of units $Z^1$ with an activation reagent and optionally an additive agent to form hyaluronic acid strands comprising units $Z^1$ and $Z^{10}$ and by subsequently adding a reagent $Y^{0C}$-$L^4$-$Y^{0I}$, wherein functional groups —$Y^{0'}$ are reactive with functional groups —$Y^{0H}$ by using methods known in the field.

Alternatively, hyaluronic acid strands comprising units $Z^1$ and $Z^{10}$ are isolated before adding reagent $Y^{0C}$-$L^4$-$Y^{0I}$. Optionally, functional groups —$Y^{0C}$ may be protected with a protecting group known to the skilled person in the field. In such an embodiment —SP— and -$L^4$-, and —$X^{0A}$— and $X^{0E}$ and $Y^{0B}$ and —$Y^{0C}$ are the same, respectively. In a second step, a crosslinker reagent $Y^{0A}$—CL-$Y^{0A}$ with functional groups —$Y^{0A}$ reactive with functional groups —Y and —$Y^{0B}$ is prepared according to procedures described elsewhere herein or according to standard procedures. In a third step, the functionalized hyaluronic acid strands mainly comprising units $Z^1$, $Z^6$, and $Z^5$ are mixed and reacted with the crosslinker reagent $Y^{0A}$—CL-$Y^{0A}$ to give a crosslinked hyaluronic acid mainly comprising units $Z^1$, $Z^3$, and $Z^6$ crosslinked with a moiety —CL- and with units $Z^6$ still carrying functional groups —$Y^{0C}$. The third step may comprise sterile filtration and/or crushing of the resulting crosslinked hyaluronic acid gel or the reaction is performed in a way to generate small particles or microparticles. In a fourth step, the functional groups —Y of units $Z^6$ are reacted with a reagent $Y^{0D}$-$L^3$-$Y^{0J}$, wherein functional groups —Y are reactive with functional groups —$Y^{0C}$ by using known methods, to provide crosslinked hyaluronic acid strands comprising mainly units $Z^1$, units $Z^3$ crosslinked by —CL- and $Z^7$. Optionally, functional groups —$Y^{0D}$ may be protected with a protecting group. In a fifth step, a monoconjugate D-$L^1$-$X^{0D}$-$L^2$-$Y^{0G}$ with the functional group $Y^{0G}$ being reactive with the functional group —$Y^{0D}$ of units $Z^7$ is prepared according to methods described elsewhere herein or according to standard procedures, which in a sixth step is reacted with the crosslinked hyaluronic acid strands of the fourth step.

In certain embodiments functionalized hyaluronic acid strands mainly comprising units $Z^1$, $Z^5$, and $Z^7$ are prepared as described above. In this embodiment —SP— and -$L^4$-$X^{0B}$-$L^3$-, and —$X^{0A}$— and —$X^{0E}$—, and $Y^{0B}$ and —$Y^{0D}$ are the same, respectively. In a second step, a monoconjugate reagent D-$L^1$-$X^{0D}$-$L^2$-$Y^{0G}$ and a bisconjugate reagent $Y^{0G}$-$L^2$-$X^{0D}$-$L^1$-D-$L^1$-$X^{0D}$-$L^2$-$Y^{0G}$ wherein a functional group —$Y^{0G}$ is reactive with a functional group —$Y^{0D}$ of a unit $Z^7$, are prepared according to methods described elsewhere herein or according to standard procedures. In a third step, a conjugate of the present invention is formed by mixing and reacting the functionalized hyaluronic acid strands, the monoconjugate reagent, and the bisconjugate reagent.

In one embodiment all three components are mixed and reacted all at the same time. In a second embodiment the functionalized hyaluronic acid strands and the monoconjugate reaent are mixed and reacted followed by addition of the bisconjugate reagent. Step three may comprise sterile filtration of the different components directly into a pre-fill syringe device in which the cross-linking is carried out.

In the methods described above $—Y^{0J}$ is used as defined for $—Y^{0A}$, $—Y^{0B}$, $—Y^{0C}$ and $—Y^{0D}$ and $—Y^{0I}$ is selected from the group consisting of (x'-1)

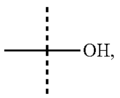

(x'-2)

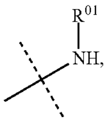

(x'-3)

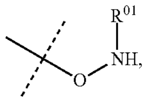

(x'-4)

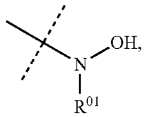

(x'-5)

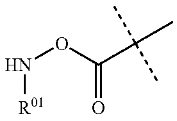

, (x'-6)

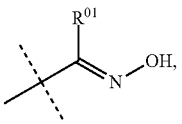

(x'-7)

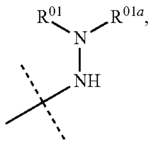

(x'-8)

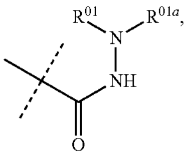

(x'-9)

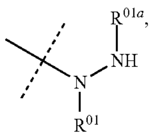

(x'-10)

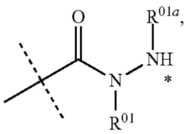

-continued (x'-11)

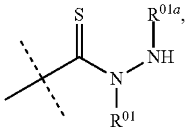

(x'-12)

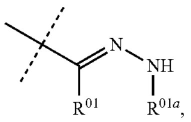

(x'-13)

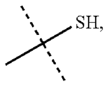

(x'-14)

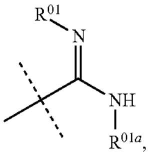

(x'-15)

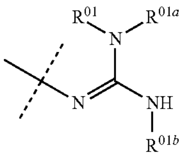

and (x'-16)

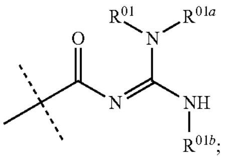

wherein dashed lines indicate attachment to remainder of the molecule.

In another aspect the present invention relates to a method of preparing a pharmaceutical formulation comprising a conjugate comprising crosslinked hyaluronic acid strands to which a plurality of drug moieties are covalently conjugated, wherein the method comprises the steps of (a) providing said conjugate;

(b) subjecting the conjugate of step (a) to a solution comprising a buffering agent, a surfactant and a salt comprising multivalent ions, to which a swelling agent is added after addition of said solution;

(c) homogenizing the admixture of step (b);

(d) deswelling the conjugate of step (c) in a deswelling solution comprising at least a deswelling agent;

(e) isolating the conjugate from the admixture of step (d);

(f) subjecting the conjugate of step (e) to a solution comprising a buffering agent, a surfactant, a salt comprising multivalent ions, a hydrophilic polymer of a molecular weight higher than 10 kDa, a density-modifying agent and a polarity-modifying agent, to which a swelling agent is added after addition of said solution;

(g) homogenizing the admixture of step (f);

(h) deswelling the conjugate of step (g) in a deswelling solution comprising at least a deswelling agent;

(i) isolating the conjugate from the admixture of step (h); and wherein, there may be optional washing steps between steps (c) and (d), (f) and (g), and (g) and (h).

It was surprisingly found that this method allows for the formulation of such conjugates, in particular of the conjugates as described elsewhere herein. It is understood however that this method can also be applied to other conjugates comprising crosslinked hyaluronic acid strands to which a plurality of drug moieties are covalently conjugated.

It is understood that in step (b) the solution that comprises a buffering agent, a surfactant and a salt comprising multivalent ions may provide swelling to the conjugate, before the addition of the swelling agent.

It is also understood that in step (f) the solution that comprises a buffering agent, a surfactant, a salt comprising multivalent ions, a hydrophilic polymer of a molecular weight higher than 10 kDa, a density-modifying agent and a polarity-modifying agent may provide swelling to the conjugate of step (e), before the addition of the swelling agent.

As used herein, the term "buffer" or "buffering agent" refers to a chemical compound that maintains the pH in a desired range. Physiologically tolerated buffers are, for example acetate, adipate, alanine, ammonium, arginine, ascorbate, aspartate, benzoate, bicarbonate, carbonate, citrate, diethanolamine, edetate, ethylenediamine, fumarate, gluconate, glutamate, glycine, guanidine, histidine, lactate, lysine, malate, metaphosphate, pentetate, phosphate, pyruvate, sorbate, succinate, tartrate, tromethamine and a-ketoglutarate. Antacids such as $CaCO_3$, $Mg(OH)_2$ or $ZnCO_3$ may be also used.

As used herein, the term "surfactant" or "surfactant agent" refers to a chemical compound that reduces the surface tension of a liquid to which it is added.

As used herein, the term "density-modifying agent" refers to a chemical compound that modifies the density of a liquid to which it is added. The density-modifying agent may also serve as a polarity-modifying agent.

As used herein, the term "polarity-modifying agent" refers to a chemical compound that modifies the polarity of a liquid to which it is added. The polarity-modifying agent may also serve as a density-modifying agent.

As used herein, the term "swelling agent" refers to a fluid used to swell a gel, network or solid so that the gel, network or solid may increase their volume after swelling such as by at least 1.1, 1.5, 2, 5, 10, 50, 100 or 1000 times their volume in the non-swollen state.

As used herein, the term "deswelling agent" refers to a fluid used to reduce the swelling of a gel, network or solid so that the gel, network or solid may decrease their volume after deswelling such as by at least 1.1, 1.5, 2, 5, 10, 50, 100 or 1000 times their volume in the swollen state.

As used herein, the term "polar protic solvent" refers to a solvent which comprises bonds between atoms with different electronegativities, has large dipole moments and has at least one hydrogen atom directly bound to an electronegative atom such as an oxygen, nitrogen or sulfur atom.

As used herein, the term "polar aprotic solvent" refers to a solvent which comprises bonds between atoms with different electronegativities, has large dipole moments and has at least one hydrogen atom directly bound to an electronegative atom such as an oxygen, nitrogen or sulfur atom.

As used herein, the term "homogenization" refers to any process that is used to make a mixture of two mutually non-miscible compounds the same throughout.

As used herein, the term "formulation", "pharmaceutical formulation", "admixture" or "composition" refers to a formulation containing one or more active ingredients and one or more excipients, as well as any product which results, directly or indirectly, from combination, complexation or aggregation of any two or more of the ingredients of the formulation, or from dissociation of one or more of the ingredients, or from other types of reactions or interactions of one or more of the ingredients. It is understood that said active ingredients may also be present in the form of inactive conjugates or compounds, from which the active ingredient is released.

As used herein, the term "reconstitution" means the addition of a liquid to a dry pharmaceutical formulation in order to bring back the original form of a formulation, such as a solution or suspension.

As used herein, the term "reconstituted formulation" refers to the formulation obtained upon reconstitution of a dry pharmaceutical formulation by addition of a reconstitution solution.

As used herein, the term "reconstitution solution" refers to the liquid used to reconstitute the dry pharmaceutical formulation prior to administration to a patient in need thereof.

The conjugate is subjected to a solution comprising a buffering agent. Exemplary buffering agents may be selected from the group consisting of histidine, 1,3-diaminopropane, 1,4-diaminopropane, 1,4-piperazinediethanesulfonic acid (PIPES), 2-(cyclohexylamino)ethanesulfonic acid (CHES), 2-(N-morpholino)ethanesulfonic acid (MES), 2-[bis(2-hydroxyethyl)amino]-2-(hydroxymethyl)propane-1,3-diol [(BTM), 2-amino-2-methylpropan-1-ol (AMP), 2-bis(2-hydroxyethyl)amino-2-(hydroxymethyl)-1,3-propanediol (BIS-TRIS), 2-hydroxy-3-[tris(hydroxymethyl)methylamino]-1-propanesulfonic acid (TAPSO), 3-(cyclohexylamino)-1-propanesulfonic acid (CAPS), 3-(N,N-bis[2-hydroxyethyl]amino)-2-hydroxypropanesulfonic acid (DIPSO), 3-(N-morpholino)propanesulfonic acid (MOPS), 3-[4-(2-hydroxyethyl)piperazin-1-yl]propane-1-sulfonic acid (HEPPS), 3-{[1,3-dihydroxy-2-(hydroxymethyl)propan-2-yl]amino}propane-1-sulfonic acid (TAPS), acetamidoglycine, acetic acid, aconitic acid, adipic acid, alanine, ammonia, arginine, ascorbic acid, aspartic acid, benzoic acid, besylic acid, boric acid, butyric acid, carbonic acid, cholamine, citraconic acid, citric acid, diethanolamine, ethanolamine, ethylenediamine, ethylenediaminetetraacetic acid (EDTA), formic acid, fumaric acid, gluconic acid, glutamic acid, glutaric acid, glycine, glycinamide, glycylglycine, guanidine, histamine, imidazole, isobutyric acid, lactic acid, lysine, maleic acid, malic acid, malonic acid, metaphosphoric acid, N-(2-acetamido)-2-aminoethanesulfonic acid (ACES), N-(2-acetamido)-iminodiacetic acid (ADA), N-(2-hydroxy-1,1-bis(hydroxymethyl)ethyl)glycine (TRICINE), N-(2-Hydroxyethyl)piperazine-N-(4-butanesulfonic acid) (HEPBS), N-(2-hydroxyethyl)piperazine-N'-(2-ethanesulfonic acid) (HEPES), N-[tris(hydroxymethyl)methyl]-2-aminoethanesulfonic acid (TES), nitrilotriacetic acid (NTA), oxalic acid, pentetic acid (DTPA), phosphoric acid, piperazine, piperidine, pivalic acid, propionic acid, pyridine, pyrrolidine, pyruvic acid, quinoline, sorbic acid, spermidine, spermine, squaric acid, succinic acid, tartronic acid, tetramic acid, tetronic acid, tosylic acid, triethanolamine (TEA), trimethylamine, tromethamine (TRIS), tryptamine, tryptophan, tyramine, tyrosine, a-ketoglutaric acid, $-hydroxy-4-morpholinepropanesulfonic acid (MOPSO) and mixtures thereof.

It is clear to the person skilled in the art that the corresponding conjugate acids, bases or salts of the buffering agents and mixtures thereof are also included.

In certain embodiments, the buffering agent is selected from the group consisting of histidine, 1,3-diaminopropane, 2-(N-morpholino)ethanesulfonic acid (MES), 2-bis(2-hydroxyethyl)amino-2-(hydroxymethyl)-1,3-propanediol (BIS-TRIS), acetic acid, adipic acid, ammonia, arginine, boric acid, carbonic acid, citric acid, diethanolamine, ethanolamine, ethylenediamine, formic acid, gluconic acid, glutaric acid, glycine, glycinamide, guanidine, histamine, imidazole, lysine, malic acid, N-(2-hydroxy-1,1-bis (hydroxymethyl)ethyl)glycine (TRICINE), N-(2-hydroxyethyl)piperazine-N'-(2-ethanesulfonic acid) (HEPES), N-[tris(hydroxymethyl)methyl]-2-aminoethanesulfonic acid (TES), phosphoric acid, piperazine, propionic acid, pyruvic acid, spermidine, spermine, succinic acid, tartronic acid, triethanolamine (TEA), tromethamine (TRIS), tyrosine and mixtures thereof.

In certain embodiments, the buffering agent is selected from the group consisting of histidine, acetic acid, ammonia, arginine, citric acid, diethanolamine, ethylenediamine, gluconic acid, glycine, guanidine, imidazole, lysine, N-(2-hydroxyethyl)piperazine-N'-(2-ethanesulfonic acid) (HEPES), phosphoric acid, piperazine, spermidine, spermine, succinic acid, tartronic acid, triethanolamine (TEA), tromethamine (TRIS) and mixtures thereof.

In certain embodiments, the buffering agent is selected from the group consisting of histidine, arginine, diethanolamine, guanidine, spermidine and tromethamine (TRIS).

In certain embodiments, the buffering agent is selected from the group consisting of histidine, arginine and tromethamine (TRIS).

In certain embodiments, the buffering agent is histidine.

As defined herein, the term "histidine" is intended to encompass both D-histidine and L-histidine and mixtures thereof. In certain embodiments, the term "histidine" refers to L-histidine. In certain embodiments, the term "histidine" refers to D-histidine. In certain embodiments, the term "histidine" refers to a mixture of L-histidine and D-histidine.

In certain embodiments, the buffering agent is L-histidine.

The buffering agent maintains the pH of a solution within a desired range. In certain embodiments, the pH of the solutions of steps (b) and (f) is not higher than 9. In certain embodiments, the pH of the solutions of steps (b) and (f) is from about pH 3 to about pH 9. In certain embodiments, the pH of the solutions of steps (b) and (f) is from about pH 4 to about pH 8. In certain embodiments, the pH of the solutions of steps (b) and (f) is from about pH 5 to about pH 7. In certain embodiments, the pH of the solutions of steps (b) and (f) is about 6.

In certain embodiments, the pH of the solutions of steps (b) and (f) is 6.0.

The buffering agent may be added in an amount of about 0.01 mM to about 500 mM. In certain embodiments, the buffering agent has a concentration ranging from about 0.5 mM to about 350 mM. In certain embodiments, the buffering agent has a concentration ranging from about 1 mM to about 250 mM. In certain embodiments, the buffering agent has a concentration ranging from about 5 mM to 100 mM. In certain embodiments, the buffering agent has a concentration ranging from about 10 mM to 50 mM. In certain embodiments, the buffering agent has a concentration of about 20 mM. In certain embodiments, the buffering agent has a concentration of 20 mM.

The conjugate is subjected to a solution comprising a surfactant. Exemplary surfactants may be selected from the group consisting polyoxyethylenesorbitan monooleate (Polysorbate 80, Tween$^9$ 80 and Tween$^9$ 80R); alcohols such as propanol, butanol, pentanol, hexanol, heptanol or octanol; alkyl and aryl amine salts such as primary amine salts, quaternary amine salts, secondary amine salts or tertiary amine salts; alkyl dimethyl betaines; alkyl ethoxylate sulfates; alkyl phenyl polyoxyethylene ethers such as Octoxynol 9, Triton X-100, Igepal™ or Nonidet P40; alkyl phosphates such as monoalkylphosphates or dialkylphosphates; alkyl polyoxyethylene ethers such as Laureth-4, Laureth-9, Laureth-23, Ceteth-2, Ceteth-10, Ceteth-20, Ceteareth-6, Ceteareth-20, Ceteareth-25, Steareth-2, Steareth-10, Steareth-20, Oleth-2, Oleth-10, Oleth-20, Deceth-10 or Trideceth-10; alkyl sulfates such as sodium dodecylsulfate (SDS); alkyl xanthates; bile acid salts such as cholic acid sodium salt or deoxycholic acid sodium salt; cationic lipids such as cetyl trimethylammonium bromide, cetyl trimethylammonium chloride, dioctadecyl dimethyl ammonium bromide, dioctadecyl dimethyl ammonium chloride, 1,2-diacyl-3-trimethylammonium propane, 1,2-diacyl-3-dimethyl ammonium propane, [2,3-bis(oleoyl)propyl] trimethyl ammonium chloride or [N—(N-dimethylaminoethane)-carbamoyl]cholesterol, dioleoyl); dialkyl sulfosuccinate salts such as Aerosol OT; Ethylenediamine tetrakis(ethoxylate-block-propoxylate) tetrols such as Tetronic 304, Tetronic 904, Tetronic 90R$^4$ or Tetronic 1304; fatty acids such as palmitic acid, oleic acid, lauric acid, myristic acid, stearic acid, arachidic acid, behenic acid, lignoceric acid, palmitoleic acid, linoleic acid, linolenic acid or arachidonic acid and salts thereof such as sodium or potassium salts; glycosides such as octyl glucoside or dodecyl maltoside; linear and branched alkylbenzene sulfonates; poly(ethylene glycol)-block-poly(propylene glycol)-block-poly(ethylene glycol)s such as Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188 (Pluronic® F68), Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 benzoate or Poloxamer 182 dibenzoate; polyoxyethylenesorbitan esters such as polyethyleneoxy(40)-sorbitol hexaoleate ester, polyoxyethylenesorbitan monolaurate (Polysorbate 20, Tween® 20 and Tween® 21), polyoxyethylenesorbitan monopalmitate (Polysorbate 40, Tween® 40), polyoxyethylenesorbitan monostearate (Polysorbate 60, Tween® 60 and Tween® 61), polyoxyethylenesorbitan trioleate (Polysorbate 85, Tween® 85) or polyoxyethylenesorbitan tristearate (Polysorbate 65, Tween® 65); polyvinyl alcohol; polyvinylpyrrolidone; sorbitan esters such as sorbitan monolaurate (Span® 20), sorbitan monooleate (Span® 80), sorbitan monopalmitate (Span® 40), sorbitan monostearate (Span® 60), sorbitan sequioleate (Span® 83), sorbitan trioleate (Span® 85) or sorbitan tristearate (Span® 65); starch and their derivatives and mixtures thereof.

In certain embodiments, the surfactant is selected from the group consisting of polyoxyethylenesorbitan monooleate (Polysorbate 80, Tween® 80 and Tween® 80R), alkyl phenyl polyoxyethylene ethers such as Octoxynol 9, Triton X-100, Igepal™ or Nonidet P40; alkyl polyoxyethylene ethers such as Laureth-9, Ceteth-10, Ceteareth-20, Steareth-10, Oleth-10, Deceth-10 or Trideceth-10; alkyl sulfates such as sodium dodecylsulfate (SDS); bile acid salts such as cholic acid sodium salt or deoxycholic acid sodium salt; cationic lipids such as cetyl trimethylammonium chloride, dioctadecyl dimethyl ammonium chloride, 1,2-diacyl-3-trimethylammonium propane, 1,2-diacyl-3-dimethyl ammonium propane or [2,3-bis(oleoyl)propyl] trimethyl ammonium chloride; Ethylenediamine tetrakis(ethoxylate-block-propoxylate) tetrols such as Tetronic 90R$^4$; glycosides such as octyl glucoside or dodecyl maltoside; poly(ethylene glycol)-block-poly(propylene glycol)-block-poly(ethylene glycol)s such as Poloxamer 101, Poloxamer 188 (Pluronic® F68) or Poloxamer 288; polyoxyethylenesorbitan esters such as polyethyleneoxy(40)-sorbitol hexaoleate ester, polyoxyethylenesorbitan monolaurate (Polysorbate 20, Tween® 20 and Tween® 21); polyvinyl alcohol; polyvinylpyrrolidone; sorbitan esters such as sorbitan monolaurate (Span® 20) or sorbitan monooleate (Span® 80) and mixtures thereof.

In certain embodiments, the surfactant is selected from the group consisting of polyoxyethylenesorbitan monooleate (Polysorbate 80, Tween® 80 and Tween® 80R), alkyl phenyl polyoxyethylene ethers such as Triton X-100; alkyl polyoxyethylene ethers such as Laureth-9 and Ceteth-10; alkyl sulfates such as sodium dodecylsulfate (SDS); bile acid salts such as cholic acid sodium salt; cationic lipids such as cetyl trimethylammonium chloride; Ethylenediamine tetrakis(ethoxylate-block-propoxylate) tetrols such as Tetronic $90R^4$; glycosides such as octyl glucoside; poly (ethylene glycol)-block-poly(propylene glycol)-block-poly (ethylene glycol)s such as Poloxamer 188 (Pluronic® F68); polyoxyethylenesorbitan esters such as polyoxyethylenesorbitan monolaurate (Polysorbate 20, Tween® 20 and Tween® 21) and mixtures thereof.

In certain embodiments, the surfactant is selected from the group consisting of polyoxyethylenesorbitan monooleate (Polysorbate 80, Tween® 80 and Tween® 80R) poly(ethylene glycol)-block-poly(propylene glycol)-block-poly(ethylene glycol)s such as Poloxamer 188 (Pluronic® F68) and polyoxyethylenesorbitan esters such as polyoxyethylenesorbitan monolaurate (Polysorbate 20, Tween® 20 and Tween® 21) and mixtures thereof.

In certain embodiments, the surfactant is a polyoxyethylenesorbitan monooleate, such as polysorbate 80.

The surfactant may be added in an amount of about 0.01% (w/w) to about 10% (w/w). In certain embodiments, the surfactant is added in an amount of about 0.1% (w/w) to about 7% (w/w). In certain embodiments, the surfactant is added in an amount of about 1% (w/w) to about 5% (w/w). In certain embodiments, the surfactant is added in an amount of about 1.5% (w/w) to about 3.0% (w/w). In certain embodiments, the surfactant is added in an amount of about 2% (w/w). In certain embodiments, the surfactant is added in an amount of 2% (w/w).

The conjugate is subjected to a solution comprising a salt comprising multivalent ions. Exemplary salts may be selected from the group consisting of calcium salts and complexes such as calcium chloride, calcium acetate, calcium ascorbate, calcium bromide, calcium carbonate, calcium citrate, calcium dihydrogen phosphate, calcium disulfate, calcium fluoride, calcium formate, calcium fumarate, calcium gluconate, calcium hydrogen carbonate, calcium hydrogenphosphate, calcium hydrogen sulfate, calcium hydroxide, calcium iodide, calcium lactate, calcium levulinate, calcium malate, calcium malonate, calcium nitrate, calcium oxalate, calcium phosphate, calcium propionate or calcium sulfate; aluminium salts and complexes such as aluminium acetate, aluminium ascorbate, aluminium bromide, aluminium carbonate, aluminium chloride, aluminium citrate, aluminium dihydrogen phosphate, aluminium disulfate, aluminium fluoride, aluminium formate, aluminium fumarate, aluminium gluconate, aluminium hydrogen carbonate, aluminium hydrogenphosphate, aluminium hydrogen sulfate, aluminium hydroxide, aluminium iodide, aluminium lactate, aluminium levulinate, aluminium malate, aluminium malonate, aluminium nitrate, aluminium oxalate, aluminium phosphate, aluminium propionate or aluminium sulfate; barium salts and complexes such as barium acetate, barium ascorbate, barium bromide, barium carbonate, barium chloride, barium citrate, barium dihydrogen phosphate, barium disulfate, barium fluoride, barium formate, barium fumarate, barium gluconate, barium hydrogen carbonate, barium hydrogenphosphate, barium hydrogen sulfate, barium hydroxide, barium iodide, barium lactate, barium levulinate, barium malate, barium malonate, barium nitrate, barium oxalate, barium phosphate, barium propionate or barium sulfate; copper(II) salts and complexes such as copper(II) acetate, copper(II) ascorbate, copper(II) bromide, copper(II) carbonate, copper(II) chloride, copper(II) citrate, copper(II) dihydrogen phosphate, copper(II) disulfate, copper(II) fluoride, copper(II) formate, copper(II) fumarate, copper(II) gluconate, copper(II) hydrogen carbonate, copper(II) hydrogenphosphate, copper(II) hydrogen sulfate, copper(II) hydroxide, copper(II) iodide, copper(II) lactate, copper(II) levulinate, copper(II) malate, copper(II) malonate, copper(II) nitrate, copper(II) oxalate, copper(II) phosphate, copper(II) propionate or copper(II) sulfate; iron (II) salts and complexes such as iron(II) acetate, iron(II) ascorbate, iron(II) bromide, iron(II) carbonate, iron(II) chloride, iron(II) citrate, iron(II) dihydrogen phosphate, iron(II) disulfate, iron(II) fluoride, iron(II) formate, iron(II) fumarate, iron(II) gluconate, iron(II) hydrogen carbonate, iron(II) hydrogenphosphate, iron(II) hydrogen sulfate, iron (II) hydroxide, iron(II) iodide, iron(II) lactate, iron(II) levulinate, iron(II) malate, iron(II) malonate, iron(II) nitrate, iron(II) oxalate, iron(II) phosphate, iron(II) propionate or iron(II) sulfate; iron(III) salts and complexes such as iron (III) acetate, iron(III) ascorbate, iron(III) bromide, iron(III) carbonate, iron(III) chloride, iron(III) citrate, iron(III) dihydrogen phosphate, iron(III) disulfate, iron(III) fluoride, iron (III) formate, iron(III) fumarate, iron(III) gluconate, iron(III) hydrogen carbonate, iron(III) hydrogenphosphate, iron(III) hydrogen sulfate, iron(III) hydroxide, iron(III) iodide, iron (III) lactate, iron(ITT) levulinate, iron(ITT) malate, iron (ITT) malonate, iron(ITT) nitrate, iron(III) oxalate, iron(III) phosphate, iron(III) propionate and iron(III) sulfate; lanthanum salts and complexes such as lanthanum acetate, lanthanum ascorbate, lanthanum bromide, lanthanum carbonate, lanthanum chloride, lanthanum citrate, lanthanum dihydrogen phosphate, lanthanum disulfate, lanthanum fluoride, lanthanum formate, lanthanum fumarate, lanthanum gluconate, lanthanum hydrogen carbonate, lanthanum hydrogenphosphate, lanthanum hydrogen sulfate, lanthanum hydroxide, lanthanum iodide, lanthanum lactate, lanthanum levulinate, lanthanum malate, lanthanum malonate, lanthanum nitrate, lanthanum oxalate, lanthanum phosphate, lanthanum propionate or lanthanum sulfate; magnesium salts and complexes such as magnesium acetate, magnesium ascorbate, magnesium bromide, magnesium carbonate, magnesium chloride, magnesium citrate, magnesium dihydrogen phosphate, magnesium disulfate, magnesium fluoride, magnesium formate, magnesium fumarate, magnesium gluconate, magnesium hydrogen carbonate, magnesium hydrogenphosphate, magnesium hydrogen sulfate, magnesium hydroxide, magnesium iodide, magnesium lactate, magnesium levulinate, magnesium malate, magnesium malonate, magnesium nitrate, magnesium oxalate, magnesium phosphate, magnesium propionate or magnesium sulfate; manganese(II) salts and complexes such as manganese (II) acetate, manganese(II) ascorbate, manganese(II) bromide, manganese(II) carbonate, manganese(II) chloride, manganese(II) citrate, manganese(II) dihydrogen phosphate, manganese(II) disulfate, manganese(II) fluoride, manganese (II) formate, manganese(II) fumarate, manganese(II) gluconate, manganese(II) hydrogen carbonate, manganese(II) hydrogenphosphate, manganese(II) hydrogen sulfate, manganese(II) hydroxide, manganese(II) iodide, manganese(II) lactate, manganese(II) levulinate, manganese(II) malate, manganese(II) malonate, manganese(II) nitrate, manganese (II) oxalate, manganese(II) phosphate, manganese(II) propionate or manganese(II) sulfate; scandium salts and complexes such as scandium acetate, scandium ascorbate, scandium bromide, scandium carbonate, scandium chloride, scandium citrate, scandium dihydrogen phosphate, scandium disulfate, scandium fluoride, scandium formate, scandium fumarate, scandium gluconate, scandium hydrogen carbonate, scandium hydrogenphosphate, scandium hydrogen sulfate, scandium hydroxide, scandium iodide, scandium lactate, scandium levulinate, scandium malate, scandium malonate, scandium nitrate, scandium oxalate, scandium phosphate, scandium propionate and scandium sulfate; strontium salts and complexes such as strontium acetate, strontium ascorbate, strontium bromide, strontium carbonate, strontium chloride, strontium citrate, strontium dihydrogen phosphate, strontium disulfate, strontium fluoride, strontium formate, strontium fumarate, strontium gluconate, strontium hydrogen carbonate, strontium hydrogenphosphate, strontium hydrogen sulfate, strontium hydroxide, strontium iodide, strontium lactate, strontium levulinate, strontium malate, strontium malonate, strontium nitrate, strontium oxalate, strontium phosphate, strontium propionate or strontium sulfate; zinc salts and complexes such as zinc acetate, zinc ascorbate, zinc bromide, zinc carbonate, zinc chloride, zinc citrate, zinc dihydrogen phosphate, zinc disulfate, zinc fluoride, zinc formate, zinc fumarate, zinc gluconate, zinc hydrogen carbonate, zinc hydrogenphosphate, zinc hydrogen sulfate, zinc hydroxide, zinc iodide, zinc lactate, zinc levulinate, zinc malate, zinc malonate, zinc nitrate, zinc oxalate, zinc phosphate, zinc propionate, zinc sulfate and mixtures thereof.

In certain embodiments, the salt is selected from the group consisting of calcium salts and complexes such as calcium chloride, calcium acetate, calcium ascorbate, calcium bromide, calcium carbonate, calcium citrate, calcium dihydrogen phosphate, calcium disulfate, calcium fluoride, calcium formate, calcium fumarate, calcium gluconate, calcium hydrogen carbonate, calcium hydrogenphosphate, calcium hydrogen sulfate, calcium hydroxide, calcium iodide, calcium lactate, calcium levulinate, calcium malate, calcium malonate, calcium nitrate, calcium oxalate, calcium phosphate, calcium propionate or calcium sulfate; iron(II) salts and complexes such as iron(II) acetate, iron(II) ascorbate, iron(II) bromide, iron(II) carbonate, iron(II) chloride, iron (II) citrate, iron(II) dihydrogen phosphate, iron(II) disulfate, iron(II) fluoride, iron(II) formate, iron(II) fumarate, iron(II) gluconate, iron(II) hydrogen carbonate, iron(II) hydrogenphosphate, iron(II) hydrogen sulfate, iron(II) hydroxide, iron(II) iodide, iron(II) lactate, iron(II) levulinate, iron(II) malate, iron(II) malonate, iron(II) nitrate, iron(II) oxalate, iron(II) phosphate, iron(II) propionate or iron(II) sulfate; lanthanum salts and complexes such as lanthanum acetate, lanthanum ascorbate, lanthanum bromide, lanthanum carbonate, lanthanum chloride, lanthanum citrate, lanthanum dihydrogen phosphate, lanthanum disulfate, lanthanum fluoride, lanthanum formate, lanthanum fumarate, lanthanum gluconate, lanthanum hydrogen carbonate, lanthanum hydrogenphosphate, lanthanum hydrogen sulfate, lanthanum hydroxide, lanthanum iodide, lanthanum lactate, lanthanum levulinate, lanthanum malate, lanthanum malonate, lanthanum nitrate, lanthanum oxalate, lanthanum phosphate, lanthanum propionate or lanthanum sulfate; magnesium salts and complexes such as magnesium acetate, magnesium ascorbate, magnesium bromide, magnesium carbonate, magnesium chloride, magnesium citrate, magnesium dihydrogen phosphate, magnesium disulfate, magnesium fluoride, magnesium formate, magnesium fumarate, magnesium gluconate, magnesium hydrogen carbonate, magnesium hydrogenphosphate, magnesium hydrogen sulfate, magnesium hydroxide, magnesium iodide, magnesium lactate, magnesium levulinate, magnesium malate, magnesium malonate, magnesium nitrate, magnesium oxalate, magnesium phosphate, magnesium propionate or magnesium sulfate; zinc salts and complexes such as zinc acetate, zinc ascorbate, zinc bromide, zinc carbonate, zinc chloride, zinc citrate, zinc dihydrogen phosphate, zinc disulfate, zinc fluoride, zinc formate, zinc fumarate, zinc gluconate, zinc hydrogen carbonate, zinc hydrogenphosphate, zinc hydrogen sulfate, zinc hydroxide, zinc iodide, zinc lactate, zinc levulinate, zinc malate, zinc malonate, zinc nitrate, zinc oxalate, zinc phosphate, zinc propionate, zinc sulfate and mixtures thereof.

In certain embodiments, the salt is selected from the group consisting of calcium salts and complexes such as calcium chloride, calcium acetate, calcium ascorbate, calcium bromide, calcium carbonate, calcium citrate, calcium dihydrogen phosphate, calcium disulfate, calcium fluoride, calcium formate, calcium fumarate, calcium gluconate, calcium hydrogen carbonate, calcium hydrogenphosphate, calcium hydrogen sulfate, calcium hydroxide, calcium iodide, calcium lactate, calcium levulinate, calcium malate, calcium malonate, calcium nitrate, calcium oxalate, calcium phosphate, calcium propionate or calcium sulfate; magnesium salts and complexes such as magnesium acetate, magnesium ascorbate, magnesium bromide, magnesium carbonate, magnesium chloride, magnesium citrate, magnesium dihydrogen phosphate, magnesium disulfate, magnesium fluoride, magnesium formate, magnesium fumarate, magnesium gluconate, magnesium hydrogen carbonate, magnesium hydrogenphosphate, magnesium hydrogen sulfate, magnesium hydroxide, magnesium iodide, magnesium lactate, magnesium levulinate, magnesium malate, magnesium malonate, magnesium nitrate, magnesium oxalate, magnesium phosphate, magnesium propionate, magnesium sulfate and mixtures thereof.

In certain embodiments, the salt is selected from the group consisting of calcium salts and complexes such as calcium chloride, calcium acetate, calcium ascorbate, calcium bromide, calcium carbonate, calcium citrate, calcium dihydrogen phosphate, calcium disulfate, calcium fluoride, calcium formate, calcium fumarate, calcium gluconate, calcium hydrogen carbonate, calcium hydrogenphosphate, calcium hydrogen sulfate, calcium hydroxide, calcium iodide, calcium lactate, calcium levulinate, calcium malate, calcium malonate, calcium nitrate, calcium oxalate, calcium phosphate, calcium propionate and calcium sulfate.

In certain embodiments, the salt is selected from the group consisting of calcium salts and complexes such as calcium chloride, calcium acetate, calcium ascorbate, calcium citrate, calcium gluconate, calcium lactate, calcium levulinate, calcium malate and calcium malonate.

In certain embodiments, the salt is calcium chloride.

The salt may be added in an amount of about 0.01 mM to about 500 mM. In certain embodiments, the salt has a concentration ranging from about 0.1 mM to about 350 mM. In certain embodiments, the salt has a concentration ranging from about 1 mM to about 250 mM. In certain embodiments, the salt has a concentration ranging from about 5 mM to 100 mM. In certain embodiments, the salt has a concentration ranging from about 10 mM to 75 mM. In certain embodiments, the salt has a concentration of about 50 mM. In certain embodiments, the salt has a concentration of 50 mM.

A swelling agent is added to the conjugate after addition of a solution comprising a buffering agent, a surfactant and a salt comprising multivalent ions.

In certain embodiments, the swelling agent is a polar aprotic solvent. Exemplary swelling agents may be selected from the group consisting of dimethyl sulfoxide, 1,2-dimethoxyether, 1,3-dimethyl-2-imidazolidinone, 1,3-dioxolane, 1,4-dioxane, 2,5-dimethyltetrahydrofuran, 2-methyltetrahydrofuran, 4-acetyl morpholine, 4-propionyl morpholine, acetone, acetonitrile, diethyl carbonate, diethyl ether, dimethyl carbonate, ethyl acetate, ethyl formate, ethyl lactate, ethylene carbonate, gamma-butyrolactone, gamma-valerolactone, hexamethylphosphoramide, methyl acetate, methyl carbonate, monomethyl ether acetate, N,N-dimethylpropyleneurea, N,N-dimethylacetamide, N,N-dimethylformamide, N-formyl morpholine, N-methyl-2-pyrrolidone, propylene carbonate, sulfolane, tetrahydrofuran, tetrahydropyran, tripyrrolidinophosphoric acid triamide and mixtures thereof.

In certain embodiments, the swelling agent may be selected from the group consisting of dimethyl sulfoxide, 1,3-dimethyl-2-imidazolidinone, 4-acetyl morpholine, 4-propionyl morpholine, hexamethylphosphoramide, N,N-dimethylpropyleneurea, N,N-dimethylacetamide, N,N-dimethylformamide, N-formyl morpholine, N-methyl-2-pyrrolidone, sulfolane, tripyrrolidinophosphoric acid triamide and mixtures thereof.

In certain embodiments, the swelling agent may be selected from the group consisting of dimethyl sulfoxide, N,N-dimethylacetamide, N,N-dimethylformamide, N-methyl-2-pyrrolidone and sulfolane.

In certain embodiments, the swelling agent is dimethyl sulfoxide.

The swelling agent may be added in an amount of about 10% (v/v) to about 99% (v/v). In certain embodiments, the swelling agent is added in an amount of about 30% (v/v) to about 97% (v/v). In certain embodiments, the swelling agent is added in an amount of about 50% (v/v) to about 95% (v/v). In certain embodiments, the swelling agent is added in an amount of about 80% (v/v) to about 90% (v/v). In certain embodiments, the swelling agent is added in an amount of about 87% (v/v). In certain embodiments, the swelling agent is added in an amount of about 85% (v/v). In certain embodiments, the swelling agent is added in an amount of about 83% (v/v). In certain embodiments, the swelling agent is added in an amount of 87% (v/v). In certain embodiments, the swelling agent is added in an amount of 85% (v/v). In certain embodiments, the swelling agent is added in an amount of 83% (v/v).

The conjugate is subjected to a deswelling solution comprising at least a deswelling agent.

In certain embodiments, a deswelling agent is a polar protic solvent.

Exemplary deswelling agents may be selected from the group consisting of ethanol, 1,4-butanediol, acetic acid, cyclohexanol, diethylene glycol, diethylene glycol monoethyl ether, diethylene glycol monomethyl ether, ethylene diamine, ethylene glycol, ethylene glycol monoethyl ether, ethylene glycol monomethyl ether, formamide, formic acid, glycerine, isobutanol, isopropanol, methanesulfonic acid, methanol, n-butanol, n-hexanol, n-pentanol, n-propanol, propionic acid, propylene diamine, propylene glycol, propylene glycol monoethyl ether, propylene glycol monomethyl ether, sec-butanol, t-butanol, triethylene glycol monoethyl ether, triethylene glycol monomethyl ether, triethylene glycol, trifluoroacetic acid, water and mixtures thereof.

In certain embodiments, the deswelling agent may be selected from the group consisting of ethanol, 1,4-butanediol, diethylene glycol, ethylene glycol, formamide, glycerine, isobutanol, isopropanol, methanol, n-butanol, n-hexanol, n-pentanol, n-propanol, propylene glycol, sec-butanol, t-butanol and mixtures thereof.

In certain embodiments, the deswelling agent may be selected from the group consisting of ethanol, isopropanol, methanol and n-propanol.

In certain embodiments, the deswelling agent is ethanol.

The deswelling agent may be added in an amount of about 10% (v/v) to about 99% (v/v). In certain embodiments, the deswelling agent is added in an amount of about 30% (v/v) to about 97% (v/v). In certain embodiments, the deswelling agent is added in an amount of about 50% (v/v) to about 95% (v/v). In certain embodiments, the deswelling agent is added in an amount of about 70% (v/v) to about 90% (v/v). In certain embodiments, the deswelling agent is added in an amount of about 87% (v/v). In certain embodiments, the deswelling agent is added in an amount of about 80% (v/v). In certain embodiments, the deswelling agent is added in an amount of about 74% (v/v). In certain embodiments, the deswelling agent is added in an amount of 87.5% (v/v). In certain embodiments, the deswelling agent is added in an amount of 80% (v/v). In certain embodiments, the deswelling agent is added in an amount of 74% (v/v).

In certain embodiments, the conjguate is subjected to a solution comprising a hydrophilic polymer of a molecular weight higher than 10 kDa. Exemplary hydrophilic polymers may be selected from the group consisting of hyaluronic acids and derivatives, functionalized hyaluronic acids, 2-methacryloyl-oxyethyl phosphoryl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carboxymethyl celluloses, hydroxypropyl methylcelluloses, chitins, chitosans, dextrans, dextrins, gelatins, gellans, pullulans, mannans, pectins, rhamnogalacturonans, starches, hydroxyalkyl starches, hydroxyethyl starches and other carbohydrate-based polymers, xylans, copolymers and mixtures thereof.

In certain embodiments, the hydrophilic polymer may be selected from the group consisting of hyaluronic acids and derivatives, functionalized hyaluronic acids, poly(acrylic acids), poly(ethylene glycol), poly(glycolic acids), poly(lactic acids), poly(lactic-co-glycolic acids), poly(propylene glycols), poly(vinyl alcohols), poly(vinylpyrrolidones), carboxymethyl celluloses, hydroxypropyl methylcelluloses, chitosans, dextrans, dextrins, pullulans, hydroxyalkyl starches, hydroxyethyl starches and other carbohydrate-based polymers, xylans, copolymers and mixtures thereof.

In certain embodiments, the hydrophilic polymer may be selected from the group consisting of hyaluronic acids, carboxymethyl celluloses, hydroxypropyl methylcelluloses, chitosans, dextrans, pullulans, hydroxyethyl starches and mixtures thereof.

In certain embodiments, the hydrophilic polymer is hyaluronic acid.

The hydrophilic polymer may be added in an amount of about 0.01 g/l to about 100 g/l. In certain embodiments, the hydrophilic polymer has a concentration ranging from about 0.1 g/l to about 50 g/l. In certain embodiments, the hydrophilic polymer has a concentration ranging from about 0.5 g/l to about 10 g/l. In certain embodiments, the hydrophilic polymer has a concentration ranging from about 1 g/l to about 5 g/l. In certain embodiments, the hydrophilic polymer has a concentration of about 2 g/l. In certain embodiments, the hydrophilic polymer has a concentration of 2 g/l.

In certain embodiments, the conjugate may be subjected to a solution comprising a density-modifying agent.

Exemplary density-modifying agents may be selected from the group consisting of trehalose, arabitol, cellobiose, dextrose, erythritol, fructose, fucitol, fucose, galactitol, gentiobiose, iditol, inositol, isomalt, isomaltose, isomaltulose, lactitol, lactose, lactulose, laminaribiose, maltitol, maltose, maltotetraitol, maltotriitol, maltulose, mannitol, mannose, melibiose, neohesperidose, neotrehalose, nigerose, polyglycitol, potassium chloride, potassium sulfate, raffinose, ribitol, rutinose, sambubiose, sodium chloride, sodium sulfate, sophorose, sorbitol, sucrose, threitol, volemitol, xylitol and mixtures thereof.

In certain embodiments, the density-modifying agent may be selected from the group consisting of trehalose, erythritol, inositol, isomaltose, lactose, maltitol, mannitol, sodium chloride, sodium sulfate, sorbitol, sucrose, xylitol and mixtures thereof.

In certain embodiments, the density-modifying agent may be selected from the group consisting of trehalose, lactose, mannitol, sorbitol, sucrose and mixtures thereof.

In certain embodiments, the density-modifying agent is trehalose.

As defined herein, the term "trehalose" is intended to encompass all salts and hydration states of trehalose, such as trehalose anhydrous or trehalose dihydrate. In certain embodiments, the term "trehalose" refers to trehalose anhydrous.

In certain embodiments, the term "trehalose" refers to trehalose dihydrate.

The density-modifying agent may be added in an amount of about 0.1% (w/w) to about 25% (w/w). In certain embodiments, the density-modifying agent is added in an amount of about 1% (w/w) to about 20% (w/w). In certain embodiments, the density-modifying agent is added in an amount of about 2% (w/w) to about 10% (w/w). In certain embodiments, the density-modifying agent is added in an amount of about 5% (w/w). In certain embodiments, the density-modifying agent is added in an amount of 5% (w/w).

In certain embodiments, the conjugate may be subjected to a solution comprising a polarity-modifying agent.

In certain embodiments, the polarity-modifying agent is selected from the group consisting of polar protic and polar aprotic solvents.

Exemplary polarity-modifying agents may be selected from the group consisting of propylene glycol, acetonitrile, dimethyl sulfoxide, ethanol, ethylene glycol, ethylene glycol monomethyl ether, glycerol, isopropanol, methanol, N,N-dimethylformamide, n-propanol and mixtures thereof.

In certain embodiments, the polarity-modifying agent may be selected from the group consisting of propylene glycol, dimethyl sulfoxide, ethanol, ethylene glycol, glycerol and mixtures thereof.

In certain embodiments, the polarity-modifying agent may be selected from the group consisting of propylene glycol, ethanol, glycerol and mixtures thereof.

In certain embodiments, the polarity-modifying agent is propylene glycol.

As defined herein, the term "propylene glycol" is intended to encompass (R)-1,2-dihydroxypropane, (S)-1,2-dihydroxypropane, (RS)-1,2-dihydroxypropane and mixtures thereof. In certain embodiments, the term "propylene glycol" refers to (R)-1,2-dihydroxypropane. In certain embodiments, the term "propylene glycol" refers to (S)-1,2-dihydroxypropane. In certain embodiments, the term "propylene glycol" refers to (RS)-1,2-dihydroxypropane.

In certain embodiments, the polarity-modifying agent is (RS)-1,2-dihydroxypropane.

The polarity-modifying agent may be added in an amount of about 0.1% (w/w) to about 75% (w/w). In certain embodiments, the polarity-modifying agent is added in an amount of about 1% (w/w) to about 50% (w/w). In certain embodiments, the polarity-modifying agent is added in an amount of about 2% (w/w) to about 35% (w/w). In certain embodiments, the polarity-modifying agent is added in an amount of about 5% (w/w) to about 20% (w/w). In certain embodiments, the polarity-modifying agent is added in an amount of about 10% (w/w). In certain embodiments, the polarity-modifying agent is added in an amount of 10% (w/w).

In certain embodiments, homogenization may be achieved by mechanical methods such as extrusion, injection, atomization, shearing, molding or emulsion-templating, sonication, vortexing, manual grinding or combined procedures thereof.

In certain embodiments, isolation of the conjugate may be achieved by evaporation of a liquid solution comprising the conjugate, lyophilization, filtration, centrifugation or combined procedures thereof.

In certain embodiments, the method of preparing a pharmaceutical formulation comprises the steps of (a) providing said conjugate;

(b) subjecting the conjugate of step (a) to a solution comprising L-histidine, polysorbate 80 and $CaCl_2$ to which dimethyl sulfoxide is added after addition of said solution;

(c) homogenizing the admixture of step (b);

(d) deswelling the conjugate of step (c) in ethanol, acetic acid and polysorbate 80; (e) isolating the conjugate from the admixture of step (d);

(f) subjecting the conjugate of step (e) to a solution comprising L-histidine, polysorbate 80, $CaCl_2$, hyaluronic acid of a molecular weight higher than 10 kDa, trehalose dihydrate and (RS)-1,2-dihydroxypropane, to which dimethyl sulfoxide is added after addition of said solution;

(g) homogenizing the admixture of step (f);

(h) deswelling the conjugate of step (g) in ethanol;

(i) isolating the conjugate from the admixture of step (h); and wherein, there may be optional washing steps between steps (c) and (d), (f) and (g), and (g) and (h).

In certain embodiments the pharmaceutical formulation obtained by the process is dried, such as by lyophilization or by treating the conjugate in a high vacuum.

Prior to applying such dry pharmaceutical formulation to a patient in need thereof, the dry pharmaceutical formulation is reconstituted. Reconstitution of the dry pharmaceutical formulation into a reconstituted formulation is done by adding a predefined amount of reconstitution solution to the dry pharmaceutical formulation. Therefore, a further aspect of the present invention is a method of reconstituting the dry pharmaceutical formulation, wherein the method comprises the step of (a) contacting the dry pharmaceutical formulation of the present invention with a reconstitution solution.

Another aspect of the present invention is a reconstituted pharmaceutical formulation obtainable from the method of reconstituting the dry pharmaceutical formulation of the present invention.

Reconstitution may take place in the container in which the dry pharmaceutical formulation comprising the conjugate is provided, such as in a vial; syringe, such as a dual-chamber syringe; ampoule; cartridge, such as a dual-chamber cartridge; or the dry pharmaceutical formulation may be transferred to a different container and is then reconstituted.

In certain embodiments, the container in which the reconstitution of the dry pharmaceutical formulation takes place is a vial.

In certain embodiments, the container in which the reconstitution of the dry pharmaceutical formulation takes place is a syringe.

In certain embodiments, the container in which the reconstitution of the dry pharmaceutical formulation takes place is a dual-chamber syringe.

In certain embodiments, the container in which the reconstitution of the dry pharmaceutical formulation takes place is a cartridge.

In certain embodiments, the container in which the reconstitution of the dry pharmaceutical formulation takes place is a dual-chamber cartridge.

In certain embodiments, the dry pharmaceutical formulation according to the present invention is provided in a first chamber of the dual-chamber syringe and the reconstitution solution is provided in a second chamber of the dual-chamber syringe.

In certain embodiments, the dry pharmaceutical formulation according to the present invention is provided in a first chamber of the dual-chamber cartridge and the reconstitution solution is provided in a second chamber of the dual-chamber cartridge.

Another aspect of the present invention refers to a container comprising the dry pharmaceutical formulation or the reconstituted formulation of the present invention.

The reconstitution solution is a sterile liquid, such as water or buffer, which may comprise further additives, such as preservatives and/or antimicrobials.

In certain embodiments, the reconstituted solution comprises one or more preservative and/or antimicrobial.

In certain embodiments, the reconstituted solution comprises one or more excipient.

In certain embodiments, the reconstitution solution is sterile water.

In certain embodiments, the reconstitution solution is sterile water comprising 0.7-1.1% benzylalcohol.

In certain embodiments, the reconstitution solution is sterile water comprising 0.9% benzylalcohol.

The buffering agent maintains the pH of the reconstituted formulation within a desired range.

In certain embodiments, the pH of the reconstituted formulation is not higher than 9. In certain embodiments, the pH of the reconstituted formulation is from about pH 3 to about pH 9. In certain embodiments, the pH of the reconstituted formulation is from about pH 4 to about pH 6. In certain embodiments, the pH of the reconstituted formulation is from about pH 4.5 to about pH 5.5.

In certain embodiments, the buffering agent has a concentration ranging from 1 to 50 mM in the reconstituted formulation. In certain embodiments, the buffering agent has a concentration ranging from 2 to 30 mM in the reconstituted formulation. In certain embodiments, the buffering agent has a concentration ranging from 5 to 20 mM in the reconstituted formulation.

In certain embodiments, the buffering agent has a concentration of about 10 mM in the reconstituted formulation.

1. A method of preparing a pharmaceutical formulation comprising a conjugate comprising crosslinked hyaluronic acid strands to which a plurality of drug moieties are covalently conjugated, wherein the method comprises the steps of (a) providing said conjugate;

(b) subjecting the conjugate of step (a) to a solution comprising a buffering agent, a surfactant and a salt comprising multivalent ions to which a swelling agent is added after addition of said solution;

(c) homogenizing the admixture of step (b);

(d) deswelling the conjugate of step (c) in a deswelling solution comprising at least a deswelling agent;

(e) isolating the conjugate from the admixture of step (d);

(f) subjecting the conjugate of step (e) to a solution comprising a buffering agent, a surfactant, a salt comprising multivalent ions, a hydrophilic polymer of a molecular weight higher than 10 kDa, a density-modifying agent and a polarity-modifying agent, to which a swelling agent is added after addition of said solution;

(g) homogenizing the admixture of step (f);

(h) deswelling the conjugate of step (g) in a deswelling solution comprising at least a deswelling agent;

(i) isolating the conjugate from the admixture of step (h); and wherein, there may be optional washing steps between steps (c) and (d), (f) and (g), and (g) and (h).

2. The method of claim 1, wherein the buffering agent is selected from the group consisting of may be selected from the group consisting of histidine, 1,3-diaminopropane, 1,4-diaminopropane, 1,4-piperazinediethanesulfonic acid (PIPES), 2-(cyclohexylamino)ethanesulfonic acid (CHES), 2-(N-morpholino) ethanesulfonic acid (MES), 2-[bis(2-hydroxyethyl) amino]-2-(hydroxymethyl)propane-1,3-diol[(BTM), 2-amino-2-methylpropan-1-ol (AMP), 2-bis(2-hydroxyethyl)amino-2-(hydroxymethyl)-1,3-propanediol (BIS-TRIS), 2-hydroxy-3-[tris(hydroxymethyl)methylamino]-1-propanesulfonic acid (TAPSO), 3-(cyclohexylamino)-1-propanesulfonic acid (CAPS), 3-(N,N-bis[2-hydroxyethyl]amino)-2-hydroxypropanesulfonic acid (DIPSO), 3-(N-morpholino)propanesulfonic acid (MOPS), 3-[4-(2-hydroxyethyl)piperazin-1-yl]propane-1-sulfonic acid (HEPPS), 3-{[1,3-dihydroxy-2-(hydroxymethyl)propan-2-yl]amino}propane-1-sulfonic acid (TAPS), acetamidoglycine, acetic acid, aconitic acid, adipic acid, alanine, ammonia, arginine, ascorbic acid, aspartic acid, benzoic acid, besylic acid, boric acid, butyric acid, carbonic acid, cholamine, citraconic acid, citric acid, diethanolamine, ethanolamine, ethylenediamine, ethylenediaminetetraacetic acid (EDTA), formic acid, fumaric acid, gluconic acid, glutamic acid, glutaric acid, glycine, glycinamide, glycylglycine, guanidine, histamine, imidazole, isobutyric acid, lactic acid, lysine, maleic acid, malic acid, malonic acid, metaphosphoric acid, N-(2-acetamido)-2-aminoethanesulfonic acid (ACES), N-(2-acetamido)-iminodiacetic acid (ADA), N-(2-hydroxy-1,1-bis(hydroxymethyl)ethyl)glycine (TRICINE), N-(2-Hydroxyethyl)piperazine-N-(4-butanesulfonic acid) (HEPBS), N-(2-hydroxyethyl)piperazine-N'-(2-ethanesulfonic acid) (HEPES), N-[tris(hydroxymethyl) methyl]-2-aminoethanesulfonic acid (TES), nitrilotriacetic acid (NTA), oxalic acid, pentetic acid (DTPA), phosphoric acid, piperazine, piperidine, pivalic acid, propionic acid, pyridine, pyrrolidine, pyruvic acid, quinoline, sorbic acid, spermidine, spermine, squaric acid, succinic acid, tartronic acid, tetramic acid, tetronic acid, tosylic acid, triethanolamine (TEA), trimethylamine, tromethamine (TRIS), tryptamine, tryptophan, tyramine, tyrosine, a-ketoglutaric acid, P-hydroxy-4-morpholinepropanesulfonic acid (MOPSO) and mixtures thereof.

3. The method of claim 1 or 2, wherein the buffering agent is selected from the group consisting of histidine, arginine, diethanolamine, guanidine, spermidine and tromethamine.

4. The method of any one of claims 1 to 3, wherein the swelling agent is a polar aprotic solvent.

5. The method of any one of claims 1 to 4, wherein the swelling agent is selected from the group consisting of dimethyl sulfoxide, 1,2-dimethoxyether, 1,3-dimethyl-2-imidazolidinone, 1,3-dioxolane, 1,4-dioxane, 2,5-dimethyltetrahydrofuran, 2-methyltetrahydrofuran, 4-acetyl morpholine, 4-propionyl morpholine, acetone, acetonitrile, diethyl carbonate, diethyl ether, dimethyl carbonate, ethyl acetate, ethyl formate, ethyl lactate, ethylene carbonate, gamma-butyrolactone, gamma-valerolactone, hexamethylphosphoramide, methyl acetate, methyl carbonate, monomethyl ether acetate, N,N'-dimethylpropyleneurea, N,N-dimethylacetamide, N,N-dimethylformamide, N-formyl morpholine, N-methyl-2-pyrrolidone, propylene carbonate, sulfolane, tetrahydrofuran, tetrahydropyran, tripyrrolidinophosphoric acid triamide and mixtures thereof.

6. The method of any one of claims 1 to 5, wherein the swelling agent is dimethyl sulfoxide.

7. The method of any one of claims 1 to 6, wherein the deswelling agent is selected from the group consisting of ethanol, 1,4-butanediol, acetic acid, cyclohexanol, diethylene glycol, diethylene glycol monoethyl ether, diethylene glycol monomethyl ether, ethylene diamine, ethylene glycol, ethylene glycol monoethyl ether, ethylene glycol monomethyl ether, formamide, formic acid, glycerine, isobutanol, isopropanol, methanesulfonic acid, methanol, n-butanol, n-hexanol, n-pentanol, n-propanol, propionic acid, propylene diamine, propylene glycol, propylene glycol monoethyl ether, propylene glycol monomethyl ether, sec-butanol, t-butanol, triethylene glycol monoethyl ether, triethylene glycol monomethyl ether, triethylene glycol, trifluoroacetic acid, water and mixtures thereof.

8. The method of any one of claims 1 to 7, wherein the hydrophilic polymer is selected from the group consisting of consisting of hyaluronic acids and derivatives, functionalized hyaluronic acids, 2-methacryloyloxyethyl phosphoryl cholins, poly(acrylic acids), poly (acrylates), poly(acrylamides), poly(alkyloxy) polymers, poly(amides), poly(amidoamines), poly (amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly (esters), poly(ethylenes), poly(ethyleneglycols), poly (ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly (lactic acids), poly(lactic-co-glycolic acids), poly (methacrylamides), poly(methacrylates), poly (methyloxazolines), poly(organophosphazenes), poly (ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carboxymethyl celluloses, hydroxypropyl methylcelluloses, chitins, chitosans, dextrans, dextrins, gelatins, gellans, pullulans, mannans, pectins, rhamnogalacturonans, starches, hydroxyalkyl starches, hydroxyethyl starches and other carbohydrate-based polymers, xylans, copolymers and mixtures thereof.

9. The method of any one of claims 1 to 8, wherein the density-modifying agent is selected from the group consisting of from the group consisting of trehalose, arabitol, cellobiose, dextrose, erythritol, fructose, fucitol, fucose, galactitol, gentiobiose, iditol, inositol, isomalt, isomaltose, isomaltulose, lactitol, lactose, lactulose, laminaribiose, maltitol, maltose, maltotetraitol, maltotriitol, maltulose, mannitol, mannose, melibiose, neohesperidose, neotrehalose, nigerose, polyglycitol, potassium chloride, potassium sulfate, raffinose, ribitol, rutinose, sambubiose, sodium chloride, sodium sulfate, sophorose, sorbitol, sucrose, threitol, volemitol, xylitol and mixtures thereof.

10. The method of any one of claims 1 to 9, wherein the method comprises the steps of (a) providing said conjugate;

(b) subjecting the conjugate of step (a) to a solution comprising L-histidine, polysorbate 80 and $CaCl_2$ to which dimethyl sulfoxide is added after addition of said solution;

(c) homogenizing the admixture of step (b);

(d) deswelling the conjugate of step (c) in ethanol, acetic acid and polysorbate 80;

(e) isolating the conjugate from the admixture of step (d);

(f) subjecting the conjugate of step (e) to a solution comprising L-histidine, polysorbate 80, $CaCl_2$, hyaluronic acid of a molecular weight higher than 10 kDa, trehalose dihydrate and (RS)-1,2-dihydroxypropane, to which dimethyl sulfoxide is added after addition of said solution;

(g) homogenizing the admixture of step (f);

(h) deswelling the conjugate of step (g) in ethanol;

(i) isolating the conjugate from the admixture of step (h); and wherein, there may be optional washing steps between steps (c) and (d), (f) and (g), and (g) and (h).

EXAMPLES

Materials and Methods

All materials were commercially available except where stated otherwise.

RP-HPLC Purification:

For preparative RP-HPLC a Waters 600 controller and a 2487 Dual Absorbance Detector was used, equipped with the following column: Waters XBridge™ BEH300 Prep C18 10 µm, 150 ×30 mm, flow rate 40 mL/min. Gradients of solvent system A (water containing 0.1% TFA v/v) and solvent system B (acetonitrile containing 0.1% TFA v/v) were used. Products were detected at 215 nm. HPLC fractions containing product were pooled and lyophilized if not stated otherwise.

Flash Chromatography:

Flash chromatography purifications were performed on an Isolera One system or an Isolera Four system from Biotage AB, Sweden, using Biotage KP-Sil silica cartridges and $CH_2Cl_2$/MeOH, $CH_2Cl_2$/ACN, $CH_2Cl_2$/THF, n-heptane/ethyl acetate or n-heptane/methyl acetate as eluents. Products were detected at 215 nm, 254 nm or 280 nm.

RP-LPLC Purification:

Low pressure RP chromatography purifications were performed on an Isolera One system or an Isolera Four system from Biotage AB, Sweden, using Biotage SNAP C18 cartridges. Gradients of solvent system A (water containing 0.1% TFA v/v) and solvent system B (acetonitrile containing 0.1% TFA v/v) were used. Products were detected at 215 nm. LPLC fractions containing product were pooled and lyophilized if not stated otherwise.

Analytical Methods

UPLC-MS Analysis:

Analytical ultra-performance LC (UPLC)-MS was performed on a Waters Acquity system or an Agilent 1290 Infinity II equipped with a Waters BEH300 C18 column (2.1×50 mm, 1.7 µm particle size or 2.1×100 mm, 1.7 µm particle size; solvent A: water containing 0.04% TFA (v/v), solvent B: acetonitrile containing 0.05% TFA (v/v) or solvent A: water containing 0.1% FA (v/v), solvent B: acetonitrile containing 0.1% FA (v/v)) coupled to an LTQ Orbitrap Discovery mass spectrometer from Thermo Scientific or coupled to a Waters Micromass ZQ or coupled to Single Quad MS System from Agilent or coupled to an Agilent Triple Quad 6460 system.

SEC Analysis:

Size-exclusion chromatography (SEC) was performed on an Agilent 1260 system, equipped with a Sepax Zenix SEC-150 column (150 Å, 7.8×300 mm; isocratic: 60:40 v/v mixture of water containing 0.05% TFA and acetonitrile containing 0.04% TFA) with detection at 215 nm and 280 nm.

Fluorescamine Assay for Amine Content Determination:

Amine content of the amine-HA was determined by reacting the free amino groups with fluorescamine under alkaline conditions and fluorescence quantification of the formed fluorophores, as methodically described in M. C. Miedel, J. D. Hulmes, Y. C. Pan (1989), Journal of Biochemical and Biophysical Methods 18: 37-52.

OPA Assay for Amine Content Determination:

Amine content of the amine-HA was determined by reacting the free amino groups with o-phthalaldehyde (OPA) and N-acetylcysteine under alkaline conditions and photometric quantification of the formed chromophores, as methodically described by Molnar-Perl (Ed.) (2015), Journal of Chromatography Library 70: 405-444.

Ellman Assay:

Thiol content of a thiolated compound, which can either be soluble or insoluble in aqueous systems is determined by reaction of the free compound thiol groups with DTNB reagent in neutral pH and photometric determination of the released 5-thio-2-nitrobenzoic acid (TNB) as methodically described in G. L. Ellman (1959), Archives of Biochemistry and Biophysics 82: 70-77.

Injection Force Measurement:

The injection force was determined with a Multitest 1-d device from Mecmesin Ltd., UK. Hydrogels were present in 1 mL LL syringes (BD) to which 27G ½" needles (BD) were attached. The samples were injected with a velocity of 344 mm/min, which was equal to 10 s/mL for the used syringes.

Quantitative Amino Acid Analysis (QAAA):

Quantitative amino acid analysis was performed to determine the amount of daptomycin in a sample matrix with unknown content. For the content determination, a material sample containing daptomycin was hydrolysed using a TFA/HCl mixture and microwave irradiation. The resulting single amino acids was dye labelled and analysed chromatographically. The contents of aspartic acid, alanine and omithine were calculated using calibration curves of the respective amino acid standards. The amount of daptomycin was calculated using the averaged content values of aspartic acid, alanine and ornithine.

Daptomycin Content by UV Measurement:

For determination of the daptomycin content of a transient daptomycin-linker HA-hydrogel conjugate, the sample is completely hydrolyzed under strongly alkaline conditions and the UV absorption of the resulting sample at 360 nm is used to calculate the daptomycin content.

Hydrogel Degradation Kinetics:

A hydrogel sample was incubated with degradation buffer of the desired pH in a water bath at the desired temperature. For each sampling time-point, the reaction mixture was homogenized, centrifuged, supernatant was withdrawn, filtered through a syringe filter and transferred into a sterile Eppendorf tube. Samples were further incubated at the same temperature. At the end of the incubation time, all samples were quenched with acetic acid, and analysed chromatographically. The obtained peak areas of the individual samples were used to calculate degradation kinetics.

Example 1

Synthesis of Azelaic Acid Monobenzyl Ester a1

Azelaic acid monobenzyl ester a1 was synthesized according to the following scheme:

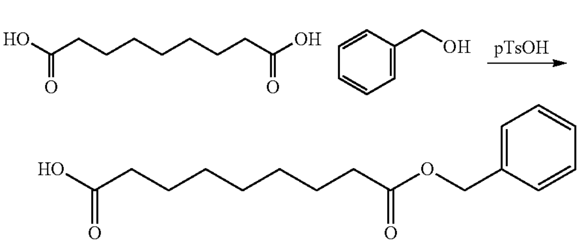

a1

A mixture of azelaic acid (37.6 g, 200 mmol), benzyl alcohol (21.7 g, 200 mmol), p-toluenesulfonic acid (0.80 g, 4.2 mmol) in toluene (240 mL) was refluxed for 7 h in a Dean-Stark apparatus. After cooling down, the solvent was evaporated and sat. aqueous $NaHCO_3$ solution (300 mL) was added. The mixture was extracted with MTBE (3×200 mL) and the combined organic phases were dried over $MgSO_4$. After evaporation of the solvent, the residue was purified by flash chromatography to yield pure a1.

Yield: 23.2 g (83.4 mmol, 42%)

MS: m/z 279.16=$[M+H]^+$, (calculated monoisotopic mass: [M]=278.15.)

Example 2
Synthesis of Enzymatically Cleavable Purification Tag b8
The enzymatically cleavable purification tag b8 was synthesized according to the following scheme:
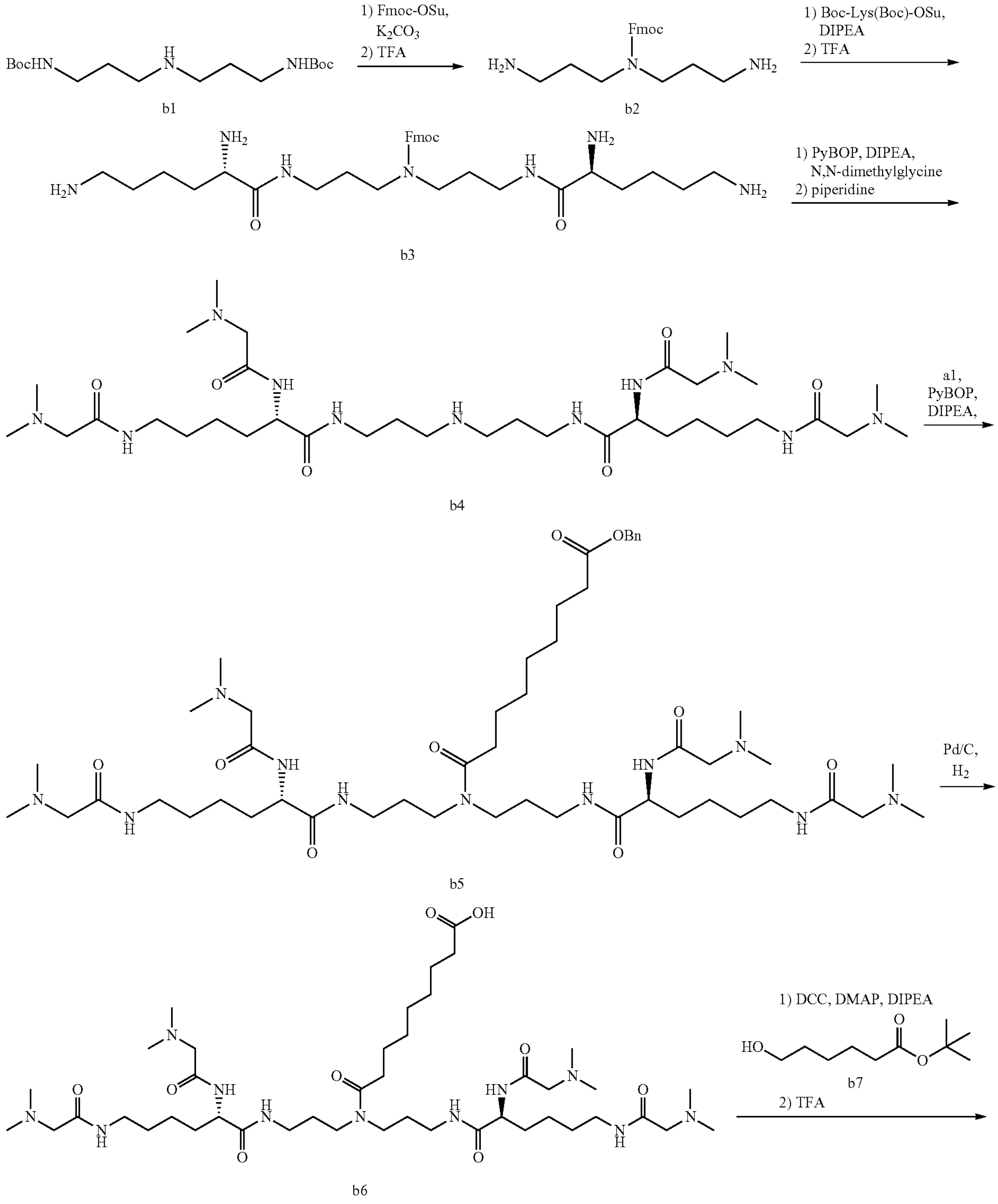

-continued

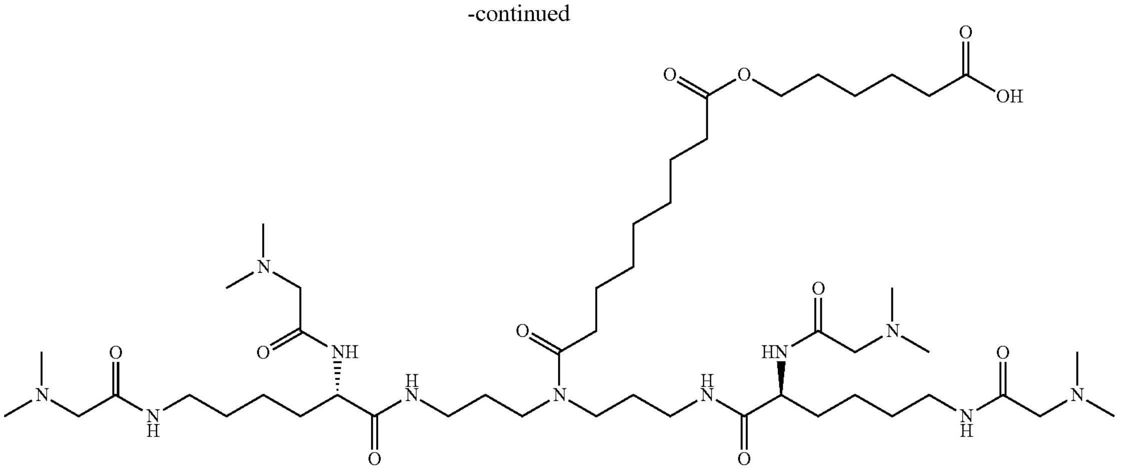

b8

Fmoc-OSu (9.77 g; 28.96 mmol) was added to a solution of 1,9-bis-Boc-1,5,9-triazanonane b1 (8.00 g; 24.14 mmol) in THF (80 mL). To this mixture a solution of $K_2CO_3$ (5.00 g; 36.20 mmol) in water (80 mL) was added dropwise over 10 minutes at room temperature and the mixture was stirred for additional 50 min at this temperature after complete addition. The mixture was diluted with ethyl acetate (600 mL) and was washed with hydrochloric acid (0.16 M, 3×200 mL), saturated $NaHCO_3$ solution (200 mL) and brine (100 mL). The organic layer was dried over $MgSO_4$, filtered and all volatiles were removed in vacuo. The crude residue was purified by flash chromatography to yield the Fmoc-protected intermediate (not shown in the reaction scheme) as a colorless, glassy solid, which was dissolved in TFA (30.0 mL; 389.4 mmol) at room temperature. The solution was stirred at room temperature for 35 min before the product was precipitated by addition of diethyl ether (40 mL diethylether for 2 mL reaction solution) in 50 mL Falcon tubes. The precipitate was collected by centrifugation, the ether supernatant was discarded and the residue was dissolved in methanol (1 mL methanol per tube). The combined methanolic solutions were added to diethyl ether (200 mL) and all tubes were washed with methanol (total ~150 mL). The washing solutions were added to the ether/mehanol mixture, whereupon a colorless, clear solution formed. This solution was concentrated and the oily residue was dried in high vacuum overnight to give crude, Fmoc-protected triamine b2 as 2× TFA salt, which was used in the next step without further purification.

Yield: 13.68 g (23.5 mmol, 97% over two steps)

MS: m/z 354.22=$[M+H]^+$, (calculated monoisotopic mass: [M]=353.21.)

DIPEA (20.44 mL; 117.20 mmol) was added to a solution of compound b2 (13.63 g; 23.44 mmol) and Boc-Lys(Boc)-OSu (24.95 g; 56.25 mmol) in DMF (250 mL) and the mixture was stirred at room temperature for 45 min. The reaction mixture was diluted with ethyl acetate (1200 mL) and the organic layer was washed with hydrochloric acid (0.1 M, 4×500 mL), saturated $NaHCO_3$ solution (3×250 mL) and brine (200 mL). After drying over $MgSO_4$ and filtration, all volatiles were removed and the crude residue was purified by flash column chromatography. The pure intermediate (not shown in the reaction scheme) was dissolved in TFA (40 mL; 519.19 mmol and the solution was stirred at room temperature for 2 hours. The reaction mixture was added to diethyl ether (2 mL reaction solution in 40 mL ether in 50 mL Falcon tubes). The precipitates were collected by centrifugation. After discarding the supernatants, all precipitates were washed with diethyl ether. After pre-drying on the rotavap to the combined residues were dried in high vacuum overnight to yield pure, Fmoc-protected pentaamine b3 as 4× TFA salt.

Yield: 19.52 g (18.3 mmol, 78% over two steps)

MS: m/z 610.42=$[M+H]^+$, (calculated monoisotopic mass: [M]=609.40.)

DIPEA (18.02 mL; 103.29 mmol) was added to a suspension of N,N-dimethylglycine (8.88 g; 86.08 mmol) and PyBOP (44.79 g; 86.08 mmol) in DMF (180 mL). The mixture was stirred for 15 minutes at room temperature. This solution was added in one portion to a stirring solution of compound b3 (18.35 g; 17.22 mmol) and DIPEA (15.01 mL; 86.08 mmol) in DMF (180 mL). The reaction mixture was stirred at room temperature for 35 min. TFA (22.02 mL; 285.82 mmol) was added and the solution was concentrated to yield a yellow oil. The intermediate (not shown in the reaction scheme) was precipitated twice from a methanolic solution by addition diethyl ether. After washing the precipitate with diethyl ether, the product slurry was concentrated and the material was dried in vacuo for 72 hours before it was dissolved in DMF (69.00 mL) and piperidine (17.50 mL; 0.18 mol) was added in one portion. The resulting mixture was stirred at room temperature for 35 min. The reaction mixture was concentrated and TFA (200 mL) was added to the residue. The slurry was filtered through a PE frit and the product was precipitated from the filtrate by addition of diethyl ether. After washing the residue with diethyl ether, it was dried in vacuo overnight to yield pentaamine b4 as 5× TFA salt.

Yield: 19.82 g (15.3 mmol, 89% over two steps)

MS: m/z 728.56=$[M+H]^+$, (calculated monoisotopic mass: [M]=727.54.)

Azelaic acid monobenzyl ester a1 (804.1 mg, 2.89 mmol) and PyBOP (1.50 g, 2.89 mmol) were dissolved in acetonitrile (10 mL). DIPEA (1.21 mL, 6.93 mmol) was added and the solution was mixed intensively and incubated for 3 min at ambient temperature. Subsequently, the mixture was added to a solution of b4 (3.00 g, 2.31 mmol) and DIPEA (3.02 mL, 17.33 mmol) in acetonitrile (30 mL). The reaction mixture was stirred at ambient temperature for 40 minutes. The volatiles of the reaction mixture were removed and TFA (10 mL) was added to give approx. 15 mL overall volume. The product was collected through precipitation by addition of diethylether to the solution and centrifugation. After discarding the supernatant, the residue was purified by precipitation from a methanolic solution by addition of diethylether and centrifugation. After drying the residue in high vacuum overnight, benzyl ester b5 was obtained as 4×TFA salt.

Yield: 3.09 g (2.14 mmol, 93%)

MS: m/z 988.69=$[M+H]^+$, (calculated monoisotopic mass: [M]=987.68.)

Benzyl ester b5 (3.09 g, 2.14 mmol) was dissolved in methanol (100 mL). Palladium on activated charcoal (10% Pd basis; 425.00 mg, 0.40 mmol) was added and the mixture was stirred at room temperature under a hydrogen atmosphere for 1 hour. The suspension was filtered through a pad of Celite, which was subsequently flushed with methanol. The combined filtrates were concentrated to approx. 25 mL volume in vacuo. The product was collected through precipitation by addition of diethylether and centrifugation. The residue was washed with diethylether and dried in high vacuum overnight to yield acid intermediate b6 (2.46 g; 84.94%) as 4×TFA salt.

Yield: 2.46 g (1.82 mmol, 85%)

MS: m/z 898.65=$[M+H]^+$, (calculated monoisotopic mass: [M]=897.63.)

To a solution of intermediate b6 (2.00 g, 1.48 mmol) and DIPEA (1.29 mL, 7.38 mmol) in a mixture of acetonitrile (10 mL) and DMF (1 mL), DMAP (180.4 mg, 1.48 mmol), tert-butyl 6-hydroxyhexanoate b7 (1.72 mL, 8.86 mmol) and DCC (914.1 mg, 4.43 mmol) were added subsequently under stirring. The mixture was stirred at ambient temperature overnight followed by quenching by addition of TFA (796.4 μL, 10.34 mmol). Volatiles were removed under reduced pressure and the crude residue was treated with 0.1% TFA (15 mL) and 10% TFA (5 mL). The formed precipitate was removed from the product solution by filtration. The reaction vessel was washed with 0.1% TFA (3×5 mL) and the washing fractions were used to flush the filter residue of the first filtration. The combined filtrates were purified by preparative HPLC to yield the tert-butyl ester intermediate (not shown in the reaction scheme) as a white foam. This intermediate was dissolved in TFA (6 mL) and the reaction mixture was stirred at ambient temperature before it was diluted with additional TFA to a total volume of approximately 8 mL. The product was collected by precipitation from diethylether and centrifugation. After washing with diethylether, the pellets were dried in high vacuum overnight to yield the enzymatically cleavable purification tag b8 as 4×TFA salt.

Yield: 988 mg (0.67 mmol, 45% over two steps)

MS: m/z 1012.72=$[M+H]^+$, (calculated monoisotopic mass: [M]=1011.70.)

Example 3

Synthesis of a Permanent Linker with an Enzymatically Cleavable Bond c9

The enzymatically cleavable linker c9 was synthesized according to the following scheme:

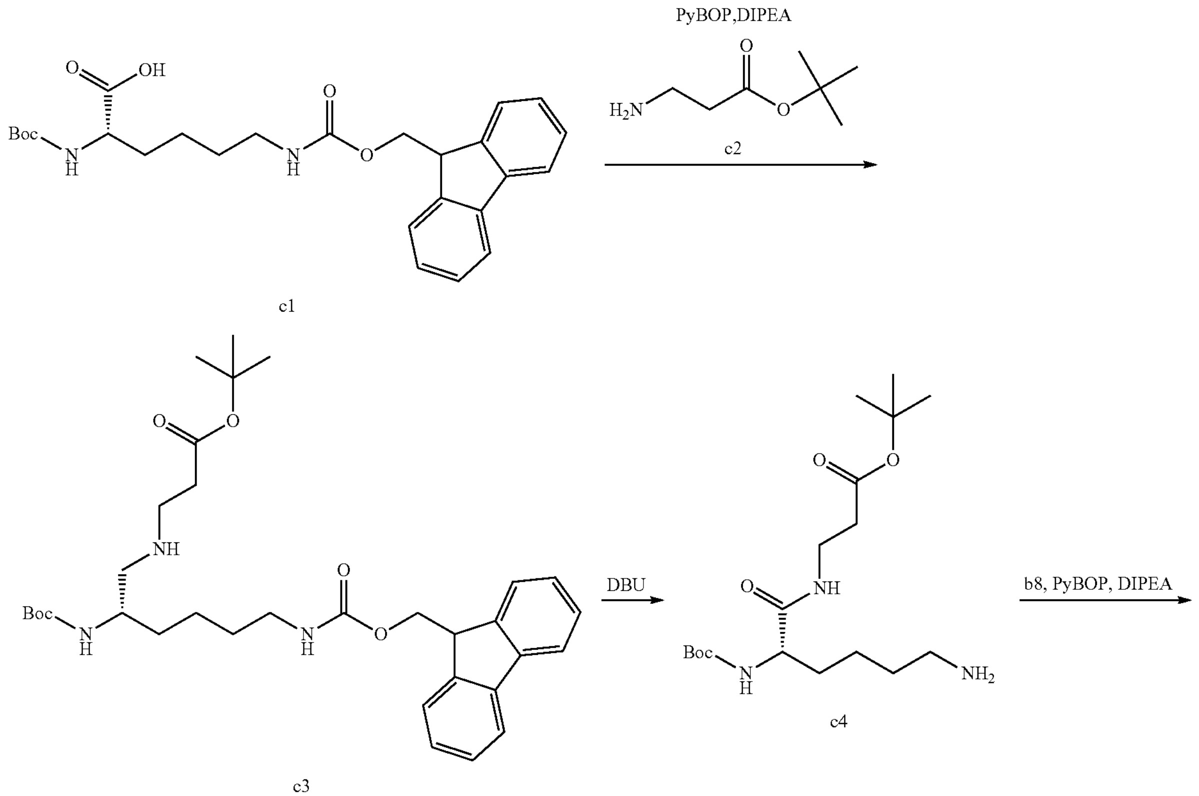

c1 c3 c4

-continued
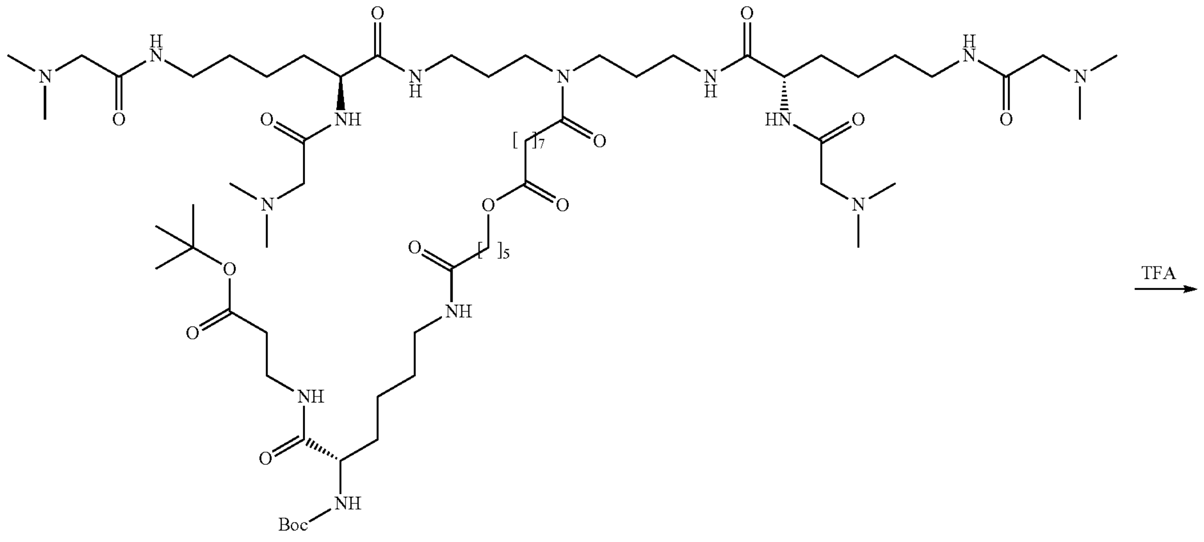
c5
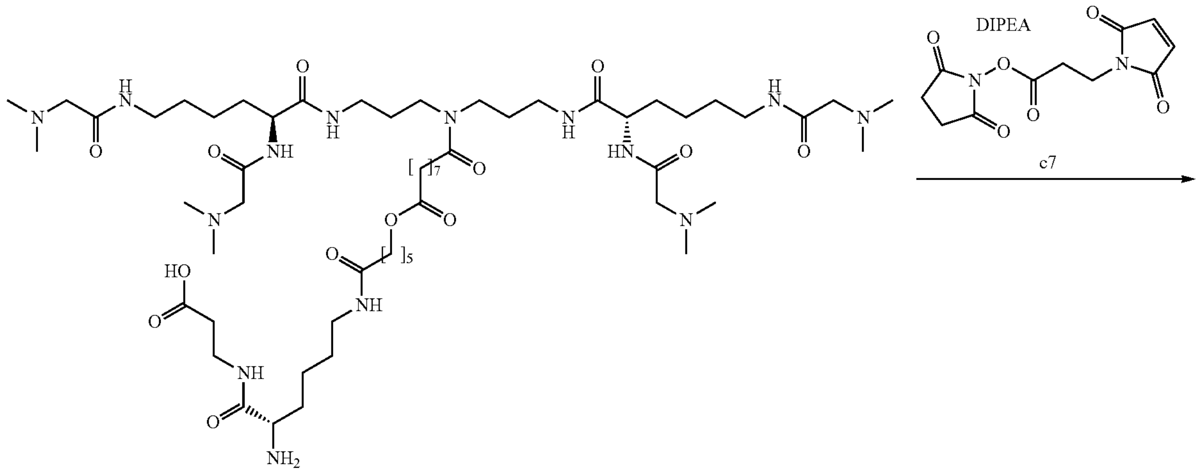
c6

-continued
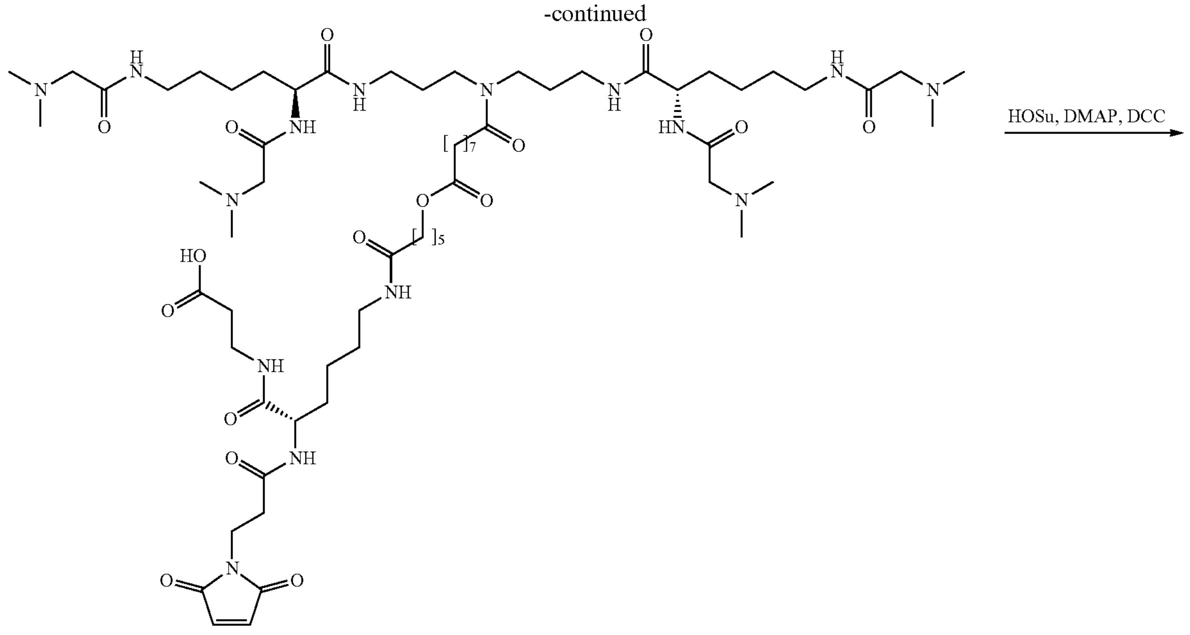
c8
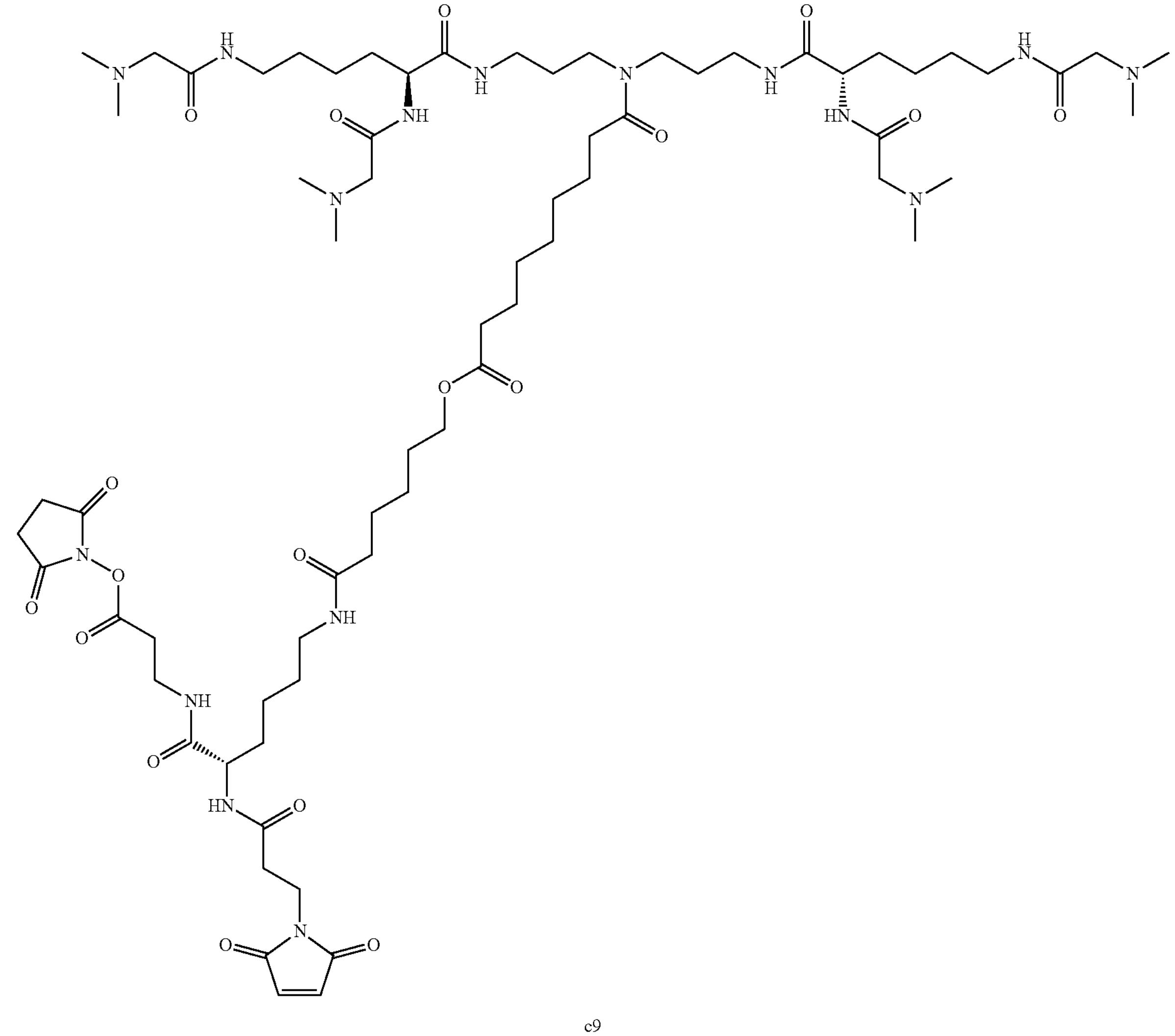 [SMILES: CN(C)CC(=O)NCCCC[C@H](NC(=O)CN(C)C)C(=O)NCCCN(CCCNC(=O)[C@H](CCCCNC(=O)CN(C)C)NC(=O)CN(C)C)C(=O)CCCCCCCC(=O)OCCCCCC(=O)NCCCC[C@H](NC(=O)CCN1C(=O)C=CC1=O)C(=O)NCCC(=O)ON1C(=O)CCC1=O]
c9

Boc-Lys(Fmoc)-OH c1 (2.06 g, 4.40 mmol) and PyBOP (2.29 g, 4.40 mmol) were suspended in acetonitrile (40 mL). DIPEA (2.30 mL, 13.21 mmol) was added and the mixture was stirred at room temperature for 2 minutes before a freshly prepared solution of P-alanine t-butyl ester hydrochloride c2 (800.0 mg, 4.40 mmol) and DIPEA (1.54 mL, 8.81 mmol) in acetonitrile (10 mL) were added. The mixture was stirred at ambient temperature for 40 min before it was diluted with 250 mL ethyl acetate. The solution was washed with 0.1 M HCl (5×200 mL), saturated $NaHCO_3$ solution (3×100 mL) and brine (50 mL). After drying over $MgSO_4$ and filtration, all volatiles were removed in vacuo. The residue was dissolved in ethyl acetate (35 mL) and the solution was filtered through a 0.22 μm RC syringe filter. All volatiles were removed in vacuo and the residue was dried in high vacuum overnight to give crude compound c3.

Yield: 2.81 g

MS: m/z 596.33=$[M+H]^+$, (calculated monoisotopic mass: [M]=595.33.)

To a solution of crude intermediate c3 (2.80 g) in tetrahydrofuran (20 mL) DBU (0.75 mL, 5.03 mmol) was added and the solution was stirred at ambient temperature for 15 min before acetic acid (1.15 mL, 20.12 mmol) was added to the reaction mixture. The solution was concentrated in vacuo (approximately 7.5 mL), diluted with addition of acetonitrile (9 mL) and water (7 mL) and purified by preparative HPLC to yield intermediate c4 as TFA salt.

Yield: 1.87 g (3.84 mmol, 87%)

MS: m/z 374.27=$[M+H]^+$, (calculated monoisotopic mass: [M]=373.26.)

To a solution of b8 (988.0 mg, 0.67 mmol) and PyBOP (367.6 mg, 0.71 mmol) acetonitrile (10 mL), DIPEA (880.2 μL, 5.05 mmol) was added and the mixture was stirred at ambient temperature for approx. 5 min. A freshly prepared solution of c4 (360.8 mg, 0.74 mmol) and DIPEA (293.4 μL, 1.68 mmol) in acetonitrile (5 mL) was added and the reaction mixture was stirred at ambient temperature for 25 min. The solution was cooled to 0° C. and quenched by addition of TFA (550.0 μL, 7.14 mmol) and the product was collected by precipitation diethylether and centrifugation. The residue was dissolved in acetonitrile again precipitated from of diethylether. After centrifugation, the residue was dissolved in acetonitrile. After removal of all volatiles in vacuo, the residue was dried in high vacuum overnight to yield compound c5 as 4×TFA salt.

Yield: 1.16 g (0.63 mmol, 94%)

MS: m/z 684.48=$[M+2H]^{2+}$, (calculated monoisotopic mass: [M]=1366.95.)

A solution of compound c5 (1.16 g, 0.64 mmol) in TFA (12.00 mL, 155.76 mmol) was stirred at room temperature for 30 min before the product was collected by precipitation from diethylether and centrifugation. The residue was washed with diethylether and dried in high vacuum overnight to yield intermediate c6 as 5×TFA salt.

Yield: 1.09 g (0.61 mmol, 97%)

MS: m/z 606.43=$[M+2H]^{2+}$, (calculated monoisotopic mass: [M]=1210.84.)

To a solution of compound c6 (1.09 g, 0.61 mmol) and 3-maleimidopropionic acid N-hydroxysuccinimide ester c7 (203.8 mg, 0.77 mmol) in acetonitrile (15 mL), DIPEA (801.0 μL, 4.59 mmol) was added and the mixture was stirred at ambient temperature for one hour. The reaction was quenched by addition of TFA (471.8 μL, 6.12 mmol) and all volatiles were removed under reduced pressure. The residue was purified by preparative HPLC to yield intermediate c8 as 4×TFA salt.

Yield: 1.04 g (0.57 mmol, 92%)

MS: m/z 681.94=$[M+2H]^{2+}$, (calculated monoisotopic mass: [M]=1361.86.)

To a solution of compound c8 (203.0 mg, 111.61 μmol) in acetonitrile (6.1 mL), DMAP (1.4 mg, 11.16 μmol), HOSu (128.5 mg; 1.12 mmol) and DCC (230.3 mg; 1.12 mmol) were added and the mixture was stirred at ambient temperature for 4.5 hours. Acetonitrile was removed from the suspension under reduced pressure and aqueous TFA (0.1% v/v; approx. 15 mL) was added to the white residue that remained in the flask. The aqueous suspension was filtered through a 0.22 μm PES syringe filter and the filtrate was immediately cooled to 0° C. The solution was purified by preparative HPLC to yield the enzymatically cleavable linker c9 as 4× TFA salt.

Yield: 156 mg (81.4 gmol, 73%)

MS: m/z 730.45=$[M+2H]^{2+}$, (calculated monoisotopic mass: [M]=1458.88.)

Example 4

Preparation of Immobilized Lipase B d1

100 mg of Lipase B from *Candida antarctica* were dissolved in 5 mL water. The solution was filtered via 0.22 μm syringe filter to give a solution of 4.97 mL volume.

7 mL of NHS activated agarose slurry (approx. 3.5 mL of resin) were transferred into a syringe equipped with a frit. The resin was washed five times with each time 10 mL water, the wash solution was each time expelled and discarded. The resin was washed five times with each time 10 mL PBS, the wash solution was each time expelled and discarded.

The Lipase B solution was diluted with PBS to an overall volume of 16 mL. The solution was drawn into the syringe and the resulting suspension was incubated for 1.5 h at ambient temperature under gentle agitation. The solution was expelled and the resin was washed two times with each time 5 mL PBS, the wash solutions were each time discarded. The resin was washed two times with each time 5 mL of 0.5 M ethanolamine, 0.5 M NaCl, pH 8.4 solution, the solution was each time expelled and discarded. 5 mL of 0.5 M ethanolamine, 0.5 M NaCl, pH 8.4 solution were drawn up into the syringe and the resulting suspension was incubated for 30 min at ambient temperature. The solvent was expelled and the resin was washed ten times with PBS, the solvent was each time discarded. A solution of 45 mM hydroxylamine in PBS pH 7.4 was drawn into the syringe and the resulting suspension was incubated for 16 h at ambient temperature. The solution was expelled and the resin was washed ten times with each time 5 mL PBS, 5 mM EDTA, pH 6.5, the solvent was each time discarded. Fresh solution was drawn into the syringe and the resulting suspension was transferred into a Falcon tube to give immobilized Lipase B dl in an overall suspension volume of 11.6 mL.

Example 5

Preparation of Ranibizumab Conjugates e4 and e5

The ranibizumab conjugates e4 and e5 were synthesized according to the following scheme:

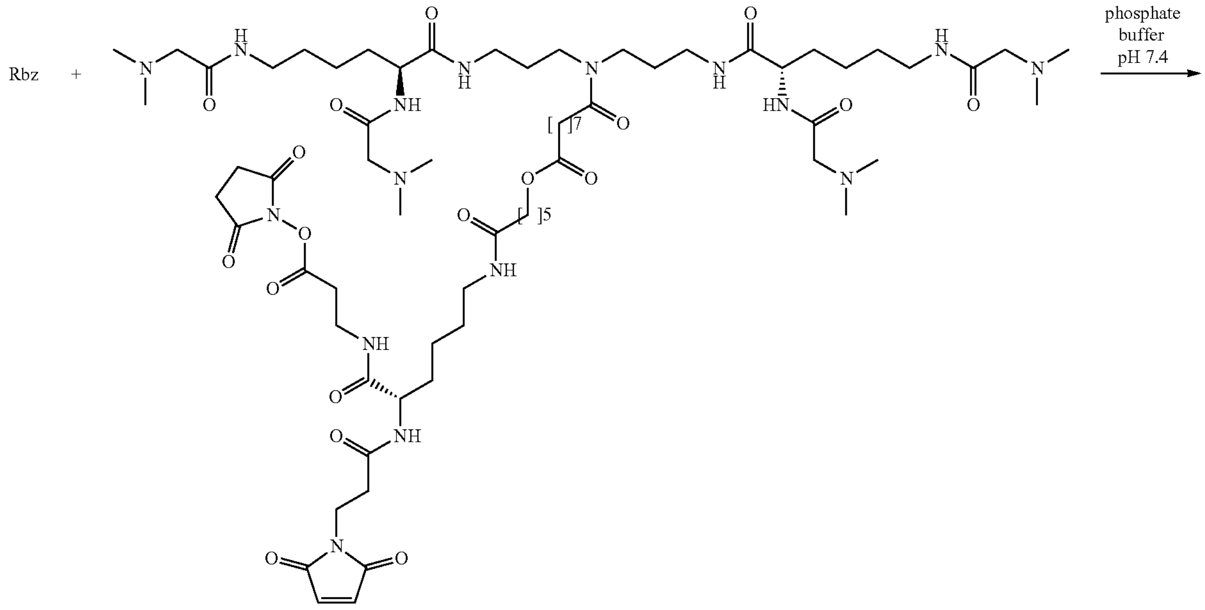

c9

-continued
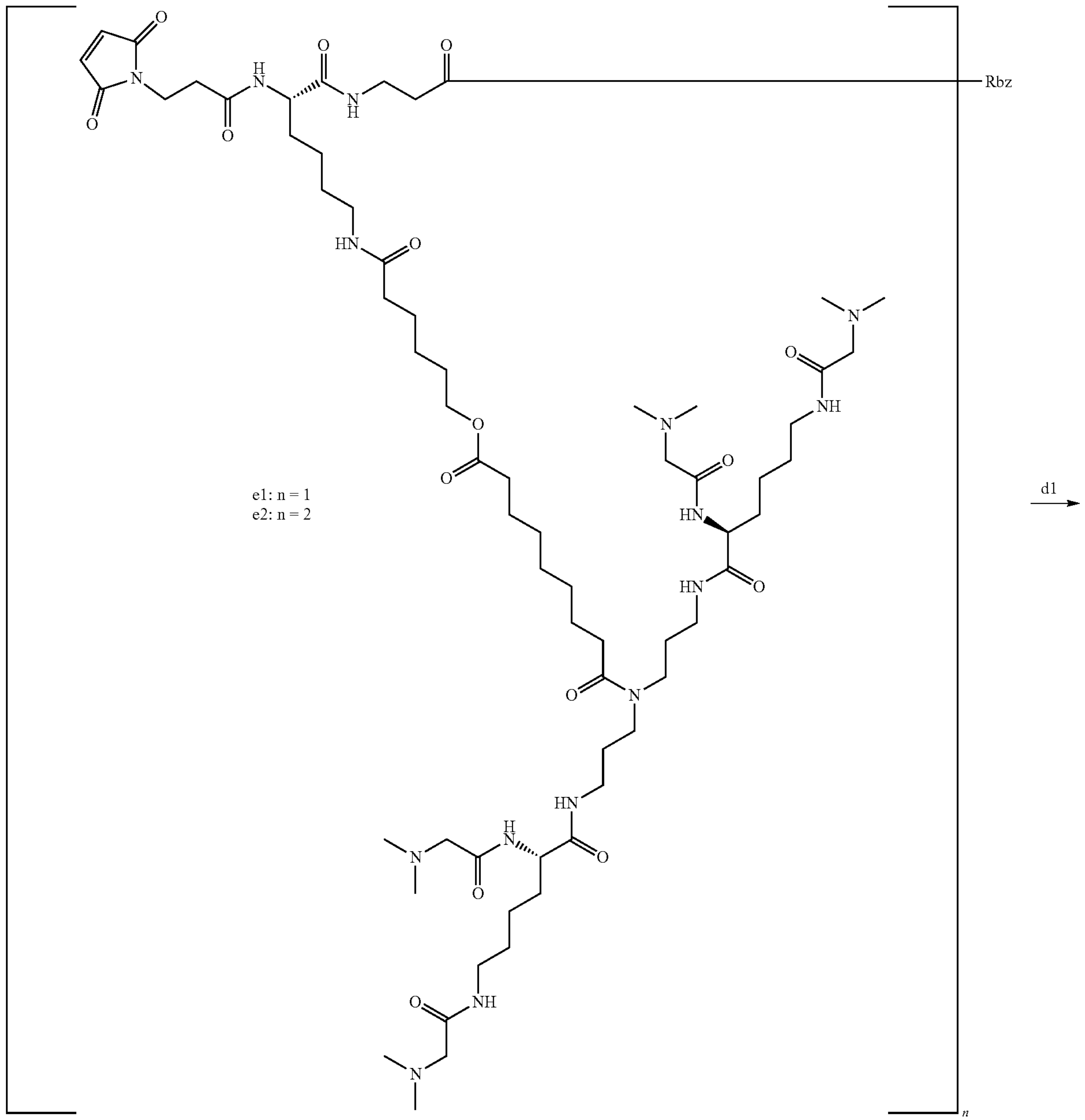

-continued

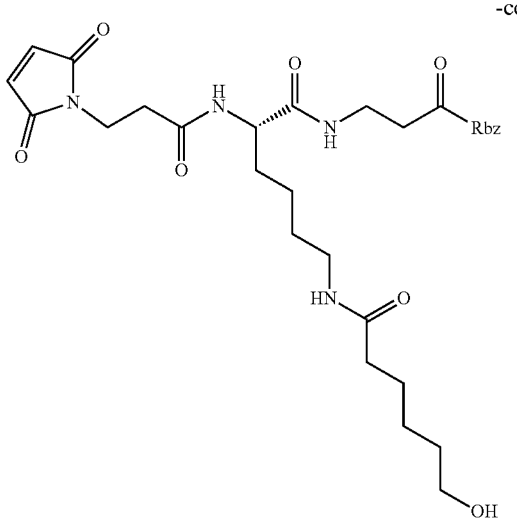

e3

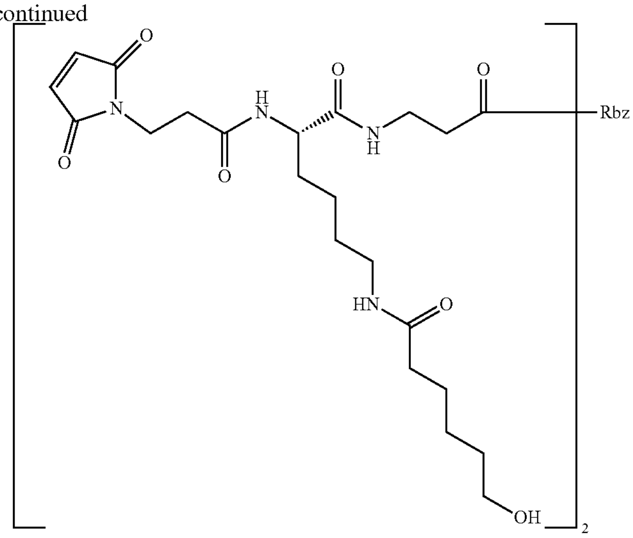

e4

Buffer exchange and concentration may be performed with either a HiPrep column followed by concentration via centrifugal filters (small scale) or by using a tangential flow filtration (TFF) system (larger scale).

Approx. 5 mL Rbz at 40 mg/mL formulated in 10 mM histidine, 10 wt % α,α-D-trehalose, 0.01% Tween 20, pH 5.5 was used in this example. After buffer exchange to 30 mM phosphate pH 7.4, the Rbz solution was concentrated using centrifugal filters to give a final volume of 4.94 mL with a concentration of 40.6 mg/mL.

200.5 mg Rbz (4.94 mL at 40.6 mg/mL) in 30 mM sodium phosphate, pH 7.4 was mixed with 1.75 eq. (47.2 μL) of compound c9 (corrected with respect to NHS content, 100 mM stock solution in DMSO) were added, and the solution was shaken carefully (no stirrer was used). The solution was incubated for 12 min followed by a dilution to 50 mL overall volume by addition of 20 mM succinic acid pH 4.0 solution.

The monoconjugate and bisconjugate species e1 and e2 were isolated from the conjugation mixture by cation exchange chromatography. A GE Healthcare Source S column (6 mL volume) was used with the following buffers: 20 mM succinic acid, pH 4.0 (buffer A); and 20 mM succinic acid, 1 M NaCl, pH 4.0 (buffer B). The gradient was linear, 10%-45% B, 28 CV (6 mL/min flow rate). The load was approximately 100 mg. The conjugate mixture was analyzed by MS prior to CIEC and in the deconvoluted MS spectrum, a 48382 m/z peak (native Rbz), a 49726 peak (monoconjugate e1), a 51073 peak (bisconjugate e2), and a 52417 peak (trisconjugate) were indicated. CIEC fraction 1 predominantly contained native Rbz (m/z peak of 48382), CIEC fraction 2 predominantly contained the monoconjugate e1 (m/z peak of 49728) and CIEC fraction 3 predominantly contained the bisconjugate e2 (m/z peak of 51073).

After the isolation of the conjugates, the respective protein solutions were concentrated using centrifugal filters to give 7.9 mL of e1 at a concentration of 8.1 mg/mL and 3.6 mL of e2 at a concentration of 9.1 mg/mL.

7.94 mL of protein solution e1 were mixed with 331 μL of Lipase B loaded agarose gel suspension dl. The resulting suspension was incubated for 18 h at 4° C. under gentle agitation. Quantitative cleavage of the ester bond between the ranibizumab linker conjugate and the purification tag was confirmed via MS (m/z peak of 48853). The samples were centrifuged for 5 min at 3000 RPM followed by filtration of the supernatant via a 0.22 μm syringe filter to give 8 mL of filtrate. Buffer exchange to 10 mM histidine, 150 mM NaCl, 0.01% Tween20, pH 5.5 was achieved via a HiPrep column connected to an Akta system. The resulting protein solution was concentrated via centrifugal filters to give e3 with a final volume of 1.4 mL and a protein content of 41.5 mg/mL.

3.61 mL of protein solution e2 were mixed with 150 μL of Lipase B loaded agarose gel suspension d1. The resulting suspension was incubated for 18 h at 4° C. under gentle agitation. Quantitative cleavage of the ester bond between the ranibizumab linker conjugate and the purification tag was confirmed via MS (m/z peak of 49318). The samples were centrifuged for 5 min at 3000 RPM followed by filtration of the supernatant via a 0.22 μm syringe filter to give 5 mL of filtrate. Buffer exchange to 10 mM histidine, 150 mM NaCl, 0.01% Tween20, pH 5.5 was achieved via a HiPrep column connected to an Akta system. The resulting protein solution was concentrated via centrifugal filters to give e4 with a final volume of 0.6 mL and a protein content of 49.3 mg/mL.

Example 6

Preparation of Thiol Functionalized HAs f2 and f4

Hyaluronic acid sodium salt (50-90 kDa, 500 mg, 1.25 mmol COOH eqv.) was dissolved in 100 mM MES 400 mM 1,3-diaminopropane buffer pH 5.5 (62.5 mL) under vigorous stirring. HOBt (572.8 mg; 3.74 mmol) and EDC·HCl (239.0 mg; 1.25 mmol) were added. The suspension was stirred at ambient temperature overnight. Sodium acetate trihydrate (8.48 g) was added, whereupon the suspension turned into a solution. The crude amine-modified HA was precipitated by addition of absolute ethanol, washed with 80% (v/v) ethanol and absolute ethanol and dried under high vacuum overnight. The pellets were dissolved in water (40 mL) to form a clear solution. 4 M NaOH (13.50 mL) was added and the solution was stirred at ambient temperature for two hours before of acetic acid (3.09 mL) was added. The product was precipitated by addition of absolute ethanol, washed with 80% (v/v) ethanol and absolute ethanol and dried under high vacuum to give amine-functionalized HA f1 as acetate salt. The amine content of the material was determined by fluorescence measurement after chemical derivatization (fluorescamine assay).

Yield: 467 mg (acetate salt, amine-content: 0.352 mmol/g, 14.6% DS)

Amine-functionalized HA f1 (400 mg, 1.41 mmol amines) was dissolved in 100 mM HEPES buffer pH 8.40 (35.0 mL). A freshly prepared solution of SPDP (88.0 mg; 0.28 mmol) in acetonitrile (5 mL) was added to the mixture while stirring. The mixture was stirred at ambient temperature for 120 minutes before a freshly prepared solution of TCEP (161.4 mg; 0.56 mmol) and 4 N NaOH (0.56 mL) in water (4.44 mL) were added to the reaction mixture. The solution was stirred for one hour at ambient temperature. Sodium acetate trihydrate (6.12 g) was added to the reaction mixture and the dissolved product was collected by addition of absolute ethanol and centrifugation. After washing with 80% (v/v) ethanol, absolute ethanol and drying in high vacuum for three hours crude thiol-HA was obtained as white solid. The crude material was dissolved in 1% acetic acid (40 mL) by vigorous stirring under an argon atmosphere. Sodium acetate trihydrate (6.12 g) was added to the solution and the resulting mixture was filtered through a 0.22 μm PES syringe filter. The product was precipitated from the filtrate by addition of absolute ethanol and centrifugation. After washing with 80% (v/v) ethanol and absolute ethanol, the material was dried under high vacuum for four hours to give thiol-functionalized HA f2 as white pellets. Thiol content was determined via Ellman assay.

Yield: 373.9 mg (thiol-content: 0.234 mmol/g)

Another thiol-functionalized HA f4 was prepared analogously to the procedures described above, starting from a larger size hyaluronic acid sodium salt (90-130 kDa, 500 mg) via amine-functionalized HA f3.

Yield f3: 440 mg (amine-content: 0.289 mmol/g)

Yield f4: 378 mg (thiol-content: 0.222 mmol/g)

Example 7

Preparation of Protein-Linker Bisconjugate Cross-Linked, Protein Loaded HA Gels p1 and p2

Solution A was prepared by dissolving thiol functionalized HA f2 (9.5 mg) in 10 mM histidine, 150 mM NaCl, 0.01% Tween20 buffer, pH 5.5 (475 μL). Solution A (62.6 μL) was mixed with ranibizumab linker monoconjugate solution e3 (149.9 μL), ranibizumab linker bisconjugate solution e4 (68.5 μL) and 10 mM histidine, 150 mM NaCl, 0.01% Tween20 buffer, pH 5.5 (19 μL). The mixture was drawn into a 1 mL syringe and incubated for 18 hours at ambient temperature to yield protein-linker bisconjugate cross-linked protein loaded HA gel p1. Injection force of the material was determined with a force gauge test stand.

Yield: 300 μL transparent gel (injection force: 16 N)

Solution B was prepared by dissolving thiol functionalized HA f4 (9.4 mg) in 10 mM histidine, 150 mM NaCl, 0.01% Tween20 buffer, pH 5.5 (470 μL). Solution B (61.6 μL) was mixed with ranibizumab linker monoconjugate solution e3 (149.9 μL), ranibizumab linker bisconjugate solution e4 (68.5 μL) and 10 mM histidine, 150 mM NaCl, 0.01% Tween20 buffer, pH 5.5 (20 μL). The mixture was drawn into a 1 mL syringe and incubated for 18 hours at ambient temperature to yield protein-linker bisconjugate cross-linked protein loaded HA gel p2. Injection force of the material was determined with a force gauge test stand.

Yield: 300 μL transparent gel (injection force: 23 N)

Example 8

Preparation of Degradable Crosslinker g3

Degradable crosslinker g3 was synthesized according to the following scheme. Theoretical calculations of the Mw of the polydisperse PEG conjugates were exemplarily performed for a PEG 1000 with 23 ethylene glycol units that has a Mw of 1031.22 g/mol (exact mass: 1030.61 g/mol):

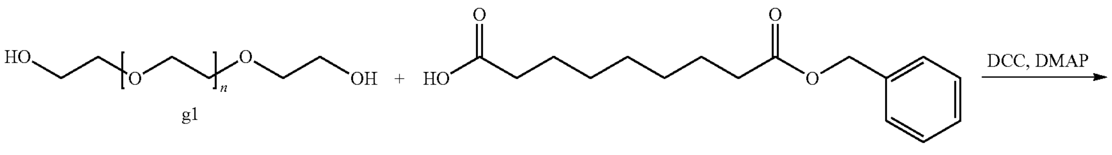

g1 a1

-continued

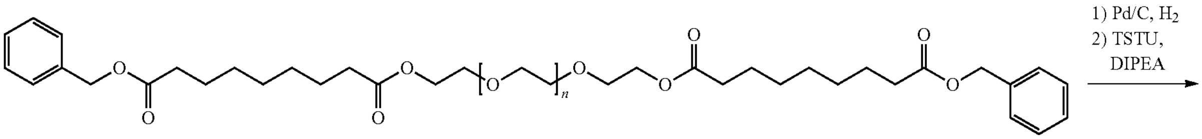

g2

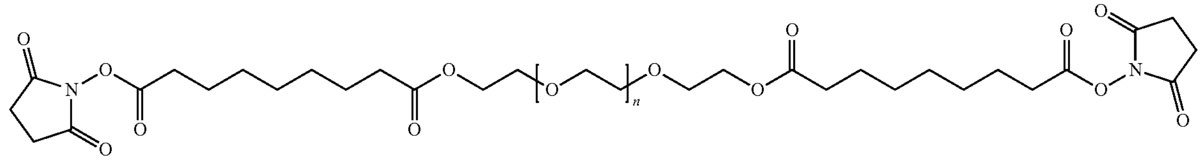

g3

Poly(ethylene glycol) g1 (1 kDa, 20.0 g) and azelaic acid monobenzylester a1 (13.92 g, 50.00 mmol) were dissolved in DCM (90 mL). The solution was cooled to 0° C. and a solution of DCC (10.32 g, 50.00 mmol) and DMAP (0.05 g, 0.40 mmol) in DCM (10 mL) was added. After stirring at 0° C. for 30 minutes, the reaction mixture was allowed to warm to room temperature. After an overall reaction time of 2.5 h, reaction mixture was cooled to 10° C. and afterwards filtered. The filter residue was washed with DCM (200 mL), the washing solution combined with the first filtrate and all volatiles were removed under reduced pressure. The residue was dissolved in DCM (40 mL), followed by addition of MTBE (800 mL). The resulting solution was cooled to −20° C. overnight for precipitation of the product. The supernatant was decanted and the suspension was filtered. The filter residue was washed with −20° C. cold MTBE (200 mL) and was afterwards dried in high vacuum for 16 hours to yield intermediate g2.

Yield: 24.62 g (15.9 mmol, 79%)

MS: m/z 776.45=$[M+2H]^{2+}$, (calculated monoisotopic mass: [M]=1550.90.)

Compound g2 (24.50 g, 15.79 mmol) was dissolved in anhydrous tetrahydrofuran (73.5 mL) and palladium on activated charcoal (10% Pd basis, 0.34 g, 3.16 mmol) was added. The reaction mixture was stirred at ambient temperature under a hydrogen atmosphere for 1 h at 45° C. The reaction mixture was filtered through a pad of celite 503, which was washed with additional tetrahydrofuran (50 mL). To the combined filtrates, TSTU (14.26 g, 47.36 mmol) and DIPEA (8.25 mL, 47.36 mmol) were added and the reaction mixture was stirred at ambient temperature overnight. The reaction mixture was filtered and the filter residue was washed with additional THF (50 mL). The combined filtrates were washed with a mixture of 0.5 M phosphate buffer pH 7.5 and saturated NaCl solution (2:1, 2×150 mL). The organic phase was washed with saturated NaCl solution (50 mL). After drying over $MgSO_4$ and filtration, all volatiles were removed under reduced pressure to give 24 g of crude cross-linker. 12 g of the crude material were dissolved in dichloromethane (140 mL), followed by addition of MTBE (500 mL). The mixture was stored at −24° C. overnight and the supernatant was decanted. The remaining product slurry was filtered. The filter residue was washed with -18° C. cold MTBE (200 mL) and was afterwards dried in high vacuum to yield degradable cross-linker g3.

Yield: 7.69 g (4.91 mmol, 310%)

MS: m/z 783.42=$[M+2H]^{2+}$, (calculated monoisotopic mass: [M]=1564.83.)

Example 9

Preparation of Crosslinked, Degradable and Thiol Functionalized HA h4

Hyaluronic acid sodium salt (130-300 kDa, 1.00 g, 2.49 mmol COOH eqv.) was dissolved in 100 mM MES 400 mM 1,3-diaminopropane buffer pH 5.5 (125 mL) under vigorous stirring. HOBt (1.15 g; 7.48 mmol) and EDC·HCl (1.43 g; 7.48 mmol) were added. The mixture was stirred at ambient temperature overnight. Sodium acetate trihydrate (17.0 g) was added and the crude amine-modified HA was precipitated by addition of absolute ethanol, washed with 80% (v/v) ethanol and absolute ethanol and dried under high vacuum overnight. The pellets were dissolved in water (80 mL) to form a clear solution. 4 M NaOH (27 mL) was added and the solution was stirred at ambient temperature for two hours before of acetic acid (6.08 mL) was added. The product was precipitated by addition of absolute ethanol, washed with 80% (v/v) ethanol, absolute ethanol and dried in high vacuum. The residue was dissolved in a mixture of water (80 mL) and acetic acid (10 mL). The amino-functionalized HA was precipitated by addition of absolute ethanol, washed with 80% (v/v) ethanol, absolute ethanol and dried under high vacuum to give a white solid. The material was dissolved in water (80 mL) and sodium acetate trihydrate (10.88 g) was added. The resulting solution was filtered through a 0.22 μM filter. The product was precipitated by addition of absolute ethanol. The material was washed with 80% (v/v) ethanol, absolute ethanol and was dried in high vacuum to give amine-functionalized HA hi (561.5 mg; 49%) as acetate salt. The amine content of the material was determined by fluorescence measurement after chemical derivatization (fluorescamine assay).

Yield: 561.5 mg (acetate salt, amine-content: 1.372 mmol/g, 63% DS)

Amine-functionalized HA hi (150 mg, 0.206 mmol amines) was dissolved in 10 mM succinate buffer pH 4.0 (2.5 mL) and filtered via a 0.22 μm PES syringe filter and a female/female Luer-Lock adapter into a 2 mL-Luer Lock syringe to provide 2 mL of filtrate containing 120 mg hi (0.165 mmol amines) in the new syringe. Solution C was prepared by dissolving degradable crosslinker g3 (400 mg) in acetonitrile (2 mL). Solution C (284 μL, equals 56.8 mg or 0.04 mmol g3) was transferred into an empty syringe. The syringe was connected to the syringe with the filtered HA solution via a line of a female/female Luer Lock adapter, a male/female Luer-Lock adapter with a 150 μm stainless steel mesh (4 mm diameter), a 4×3 mm PTFE tubing (1.9 mm length) and a second male/female Luer-Lock adapter. Both liquids were extensively mixed in the syringes by successive transfer from one syringe to the other. A white emulsion was formed. After obtaining a stable emulsion, one of the syringes was expelled completely and the whole mixture was collected in the other syringe without an air layer. The empty syringe was disconnected from the device, keeping the adapters with the steel mesh connected to the emulsion containing syringe. Into a new 2 mL-Luer Lock syringe 1 M HEPES buffer pH 8.4 (0.12 mL) was pipetted. The syringe was connected to the female/female-Luer Lock adapter of the mixing device. Both liquids were extensively mixed in the syringes by successive transfer from one syringe to the other. Gelling instantly occured upon mixing. The material was successively transferred from one syringe to the other—every time passing the gelatinous material through the steel mesh. After 5 minutes transferring the particular material from one syringe to the other, the material was kept in one of the syringes and the whole device was incubated at ambient temperature overnight. The material was again successively transferred from one syringe to the other. After approx. 20 runs, the material was collected in one of the syringes. The empty syringe and the female/female-Luer Lock adapter were removed and the gel particles were transferred into a syringe equipped with a frit. The material was successively washed with 10 mM succinate buffer pH 4.0 (3×10 mL), 100 mM HEPES buffer pH 8.4 (3×10 mL), water (3×10 mL) and absolute ethanol (5×8 mL). Afterwards, the material was dried in high vacuum to give h2.

Yield: 90.5 mg (calculated amine content: 0.548 mmol/g)

Cross-linked amine-HA h2 (25 mg, approx. 13.7 μmol amine) was transferred into a 5 mL syringe equipped with a frit. The material was swollen in water (4 mL) for 5 min. The solvent was discarded and the material was washed with 100 mM HEPES buffer pH 8.4 (2×4 mL) by discarding the solvent after each washing step. A solution of SPDP (10.7 mg, 34.3 gmol) in a mixture of acetonitrile (0.5 mL) and 100 mM HEPES buffer pH 8.40 (1.0 mL) was prepared and drawn into the syringe to the pre-swollen, cross-linked amine-HA. The resulting suspension was incubated at ambient temperature for 90 minutes under gentle agitation. The solvent was expelled and the gel was successively washed with $H_2O$/ACN (1:1, 5×4 mL) and absolute ethanol (5×4 mL) by discarding the solvent after each washing step. The solid residue was dried in high vacuum for 72 hours to yield cross-linked HA crosslinked, degradable and protected thiol functionalized HA h3. The protected intermediate cross-linked HA h3 was swollen in water (2×4 mL, 5 min each) and was afterwards washed with 100 mM succinate buffer pH 4.0 (5×4 mL). The solvents were each time discarded. A freshly prepared solution of 50 mM TCEP in 100 mM succinate buffer pH 4.0 (4 mL) were drawn to the material and the syringe was incubated at ambient temperature under gentle agitation for two hours. The solvent was discarded and the residue was washed with 100 mM succinate buffer pH 4.0 (7×3.5 mL) and absolute ethanol (5×3.5 mL). The residue was dried in high vacuum overnight to give cross-linked, degradable and thiol functionalized HA h4. The thiol content of the material was determined via Ellman assay.

Yield: 25.9 mg (thiol content: 0.261 mmol/g)

Example 10

Preparation of Ranibizumab Loaded, Crosslinked and Degradable HA Gel i1

Thiol functionalized, crosslinked, degradable HA h5 (4.7 mg, 1.23 μmol thiol) were transferred into a 5 mL syringe equipped with a frit. The HA was swollen in water (2 mL) for 10 min. The solvent was discarded and the HA was washed with water (2 mL) and the solvent was discarded. The HA was washed with 20 mM succinate, 50 mM EDTA, 0.1% Tween 20 buffer pH 5.5 (3×1 mL), by discarding the solvent after each washing step. Ranibizumab monoconjugate e3 (17.5 mg, 0.36 μmol) in 20 mM succinic acid buffer pH 5.0 (1.71 g) were mixed with 0.5 M succinate buffer pH 6.5 (80 μL). 1.78 g of solution were drawn into the syringe containing the swollen HA gel h4 and incubated for three days under gentle agitation at ambient temperature. The solvent was expelled and the HA gel was washed twice with 20 mM succinate pH 5.0 buffer. The solvent was each time discarded. The HA was washed with 10 mM histidine, 10 wt % α,α-D-trehalose, 0.01% Tween 20 buffer pH 5.5 (5×2 mL), the solvent was each time discarded. Fresh buffer was drawn into the syringe and the resulting suspension was transferred into an Eppendorf tube. The HA gel was allowed to settle and the supernatant was discarded to give ranibizumab loaded, crosslinked and degradable HA gel i1 as a dense, protein loaded HA suspension. The ranibizumab content of the suspension was determined by QAAA.

Yield: 249 mg (ranibizumab content: 25.8 mg/g)

Example 11

Synthesis of Linker Reagent 1f

Linker reagent 1f was synthesized according to the following scheme:

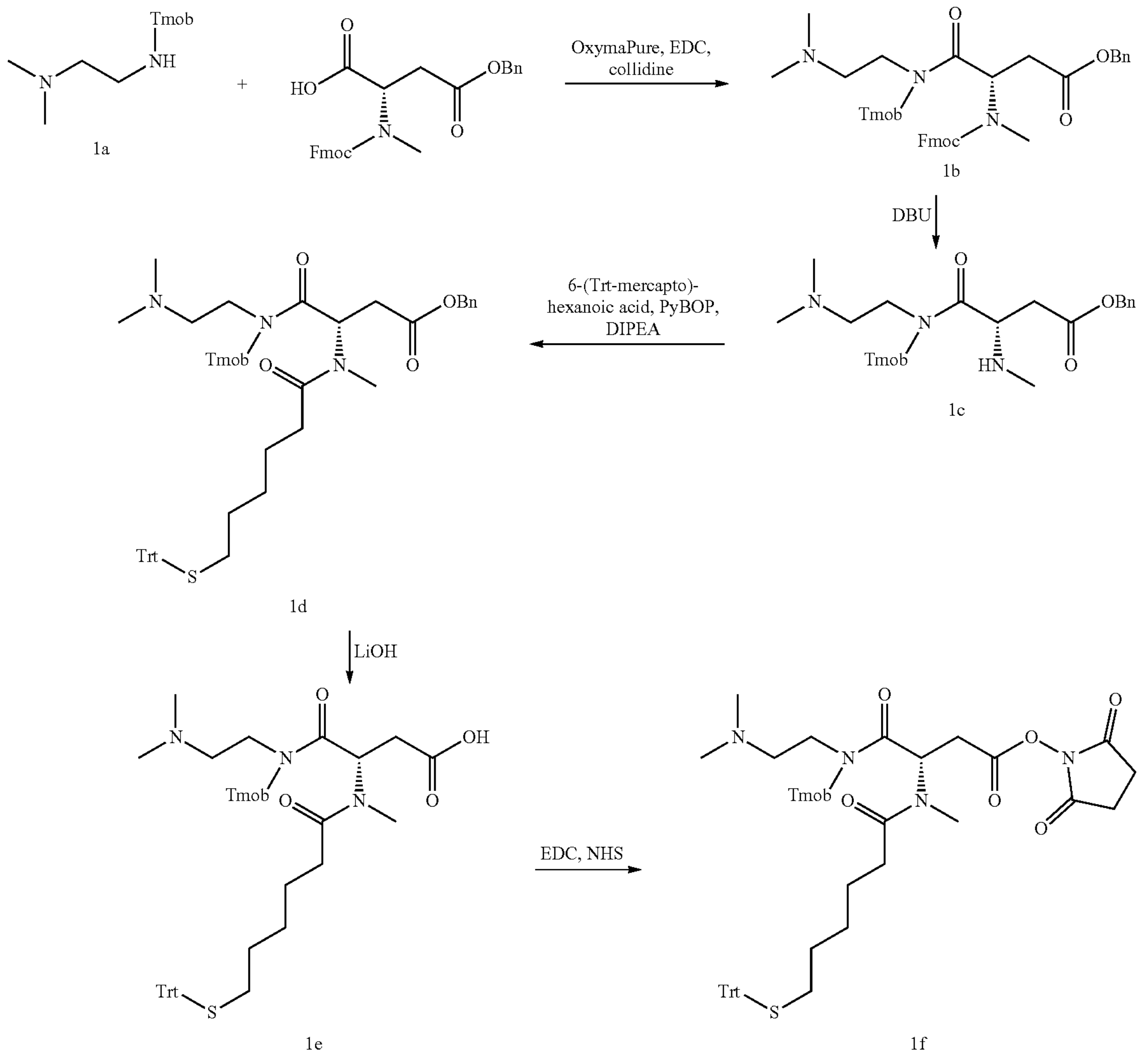

To a solution of N,N-dimethylethylenediamine (2.00 g, 22.69 mmol) and $NaCNBH_3$ (1.35 g, 21.55 mmol) in MeOH (40 mL) was added 2,4,6-trimethoxybenzaldehyde (4.23 g, 21.55 mmol) over two hours. After complete addition, the mixture was stirred at r.t. for 1 hour, acidified with 1 M HCl (60 mL) and stirred for further 30 min. To the reaction mixture saturated $NaHCO_3$ solution (70 mL) was added and the solution was extracted with $CH_2Cl_2$ (5×150 mL). The combined organic phases were dried over $Na_2SO_4$, filtered and the solvents were evaporated in vacuo. The resulting N,N-dimethyl-N'-Tmob-ethylenediamine 1a was dried in high vacuum and used in the next reaction step without further purification.

To a solution of Fmoc-N-Me-Asp(OBn)-OH (4.63 g, 10.07 mmol) in $CH_2Cl_2$ (108 mL) EDC (2.51 g, 13.09 mmol), OxymaPure® (2.00 g, 14.09 mmol) and 2,4,6-collidine (2.53 mL, 2.32 g, 19.13 mmol) were added and the mixture was stirred for 5 min. A solution of crude 1a (3.00 g, max. 11.18 mmol) in $CH_2Cl_2$ (27 mL) was added and the solution was stirred at r.t. for 1 hour. The reaction was quenched by addition of 0.1 M HCl (300 mL) and the acidified mixture was extracted with $CH_2Cl_2$ (5×40 mL). The combined organic layers were washed with saturated $NaHCO_3$ solution (2×90 mL). The organic phase was dried over $Na_2SO_4$, filtered and the solvent was evaporated in vacuo. Crude 1b was purified by flash chromatography.

Yield: 5.31 g (7.48 mmol, 74% over two steps)

MS: m/z 710.23=$[M+H]^+$, (calculated monoisotopic mass: [M]=709.34.)

To a solution of 1b (5.31 g, 7.48 mmol) in THF (53 mL) DBU (1.31 mL, 1.33 g, 8.75 mmol) was added and the solution was stirred at r.t. for 12 min. The reaction mixture was submitted to flash chromatography and 1c was isolated from the product fractions by evaporation of the solvents in vacuo.

Yield: 3.16 g (6.48 mmol, 87%)

MS: m/z 488.13=$[M+H]^+$, (calculated monoisotopic mass: [M]=487.27.)

To a solution of 1c (3.16 g, 6.48 mmol), PyBOP (4.05 g, 7.78 mmol) and DIPEA (3.39 mL, 2.51 g, 19.44 mmol) in $CH_2Cl_2$ (32 mL), a solution of 6-tritylmercaptohexanoic acid (3.04 g, 7.78 mmol) in $CH_2Cl_2$ (32 mL) was added and the mixture was stirred for 24 hours. Additional 6-tritylmercaptohexanoic acid (633 mg, 1.62 mmol) and PyBOP (843 mg, 1.62 mmol) were added and the mixture was stirred for additional 5 hours. After dilution with $CH_2Cl_2$ (600 mL), the organic layer was washed with 0.1 M HCl (3x300 mL) and brine (300 mL), dried over $Na_2SO_4$, filtered and the solvent was evaporated in vacuo. Crude id was purified by flash chromatography.

Yield: 5.06 g (5.88 mmol, 91%)

MS: m/z 860.45=$[M+H]^+$, (calculated monoisotopic mass: [M]=859.42.)

To a solution of 1d in a mixture of THF (61 mL) and water (61 mL) LiOH (423 mg, 17.66 mmol) was added and the solution was stirred at r.t. for six hours. After dilution with $CH_2Cl_2$ (500 mL), the organic layer was washed with a mixture of 0.1 M HCl/brine (1:1 v/v, 3x300 mL). The aqueous layers were re-extracted with $CH_2Cl_2$ (5x100 mL). The combined organic layers were washed with brine (200 mL), dried over $Na_2SO_4$, filtered and the solvents were evaporated in vacuo. Crude 1e was dried in high vacuum and used without further purification in the next step.

To a solution of crude 1e (5.05 g, max. 6.56 mmol) in $CH_2Cl_2$ (60 mL), NHS (1.13 g, 9.85 mmol) and EDC (1.89 g, 9.85 mmol) were added and the mixture was stirred at r.t. for 130 min. After evaporation of the solvent in vacuo, the residue was dissolved in a mixture of MeCN/water/TFA (8:2:0.002 v/v, 10 mL) and the resulting solution was purified by automated RP-LPLC to yield pure if after lyophilization.

Yield: 4.15 g (4.52 mmol, 76%, 96% purity by UV215)

MS: m/z 867.44=$[M+H]^+$, (calculated monoisotopic mass: [M]=866.39.)

Example 12

Synthesis of Cross-Linker Reagent 2b

Cross-linker reagent 2b was synthesized according to the following scheme:

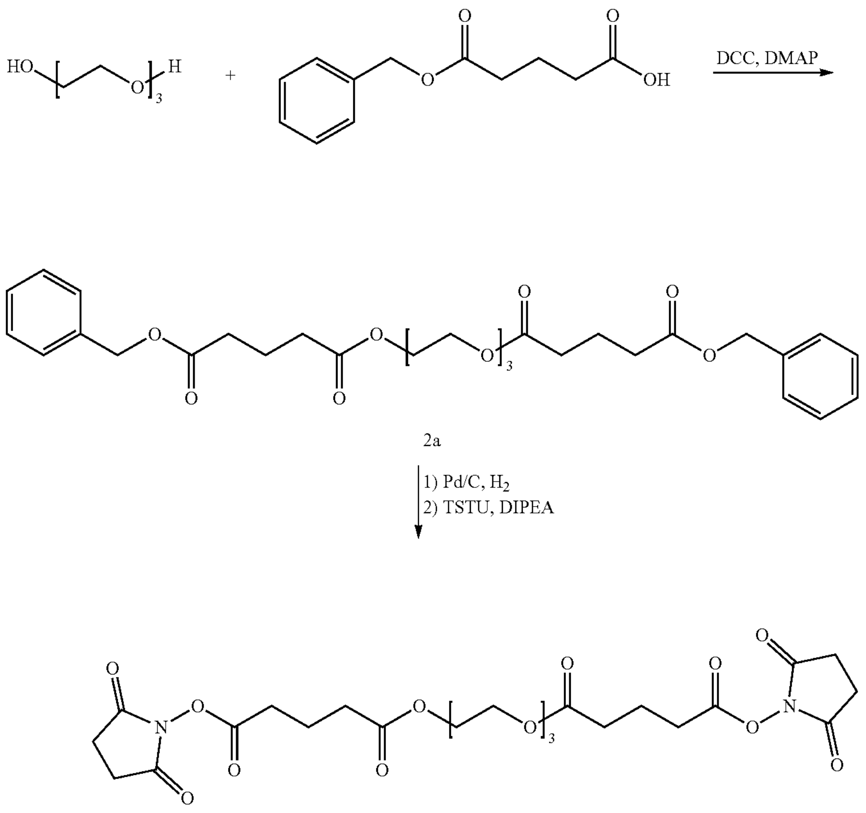

2a

2b

To a cooled solution of triethylene glycol (5.00 g, 33.29 mmol), glutaric acid monobenzyl ester (22.20 g, 99.88 mmol) and DMAP (0.20 g, 1.66 mmol) in $CH_2Cl_2$ (100 mL) DCC (20.61 g, 99.88 mmol) was added and the mixture was stirred at 0° C. for 5 min, then at r.t. for additional 30 min. After filtration, the filtrate was diluted with $CH_2Cl_2$ (500 mL) and the organic layer was washed with a mixture of saturated $NaHCO_3$ solution/water (1:1 v/v, 2x500 mL) and brine (250 mL). The organic phase was dried over $MgSO_4$, filtrated and all volatiles were evaporated in vacuo. Crude 2a was purified by flash chromatography.

Yield: 13.64 g (24.42 mmol, 73%)

MS: m/z 559.08=$[M+H]^+$, (calculated monoisotopic mass: [M]=558.25.)

To a solution of 2a (13.64 g, 24.42 mmol) in THF (55 mL) palladium on charcoal (10% Pd, 1.04 g) was added and the mixture was stirred under a hydrogen gas atmosphere at 50° C. for two hours. The reaction mixture was filtered through a pad of Celite 503, which was flushed with additional THF (50 mL). The combined filtrates were split in half and to each solution TSTU (14.70 g, 48.84 mmol) and DIPEA (8.51 mL, 6.31 g, 48.84 mmol) were added and both reaction mixtures were stirred at r.t. for 16 hours. Both reaction mixtures were combined and filtered through a glass filter funnel, which was flushed with additional THF (50 mL). After removal of all volatiles from the combined organic layers, the residue was dissolved in $CH_2Cl_2$ (500 mL). The solution was washed with 0.5 M phosphate buffer pH 7.4 (2×500 mL), 0.5 M HCl (3×250 mL) and brine (2×250 mL). The organic phase was dried over $MgSO_4$, filtered and all volatiles were evaporated in vacuo. Crude 2b was purified by flash chromatography.

Yield: 10.79 g (18.84 mmol, 77%, 98% purity by UV215)

MS: m/z 573.00=$[M+H]^+$, (calculated monoisotopic mass: [M]=572.19.)

Example 13

Synthesis of Amine-HAs 3, 3' and 3"

Synthesis of Compound 3 in 1 g Scale

To a solution of hyaluronic acid sodium salt (90-130 kDa, 1.00 g, 2.49 mmol COOH eqv.) in 100 mM MES 400 mM 1,3-diaminopropane buffer pH 5.5 (125 mL) $HOBt{\times}H_2O$ (1.15 g, 7.48 mmol) was added. EDC (2.87 g, 14.96 mmol) was added to the mixture and it was stirred at r.t. overnight. Sodium acetate trihydrate (16.97 g) was added to the reaction mixture and the solution was partitioned between twelve 50 mL Falcon tubes. To each tube absolute EtOH (ad 50 mL) was added, the tubes were shaken and centrifuged. The supernatants were decanted, and the pellets were washed with 80% v/v EtOH (40 mL each tube) and absolute EtOH (40 mL each tube). The residues were dried in high vacuum for 50 min. The crude material was dissolved in water (80 mL) and 4 M NaOH (26.67 mL) was added. The resulting mixture was stirred at r.t. for two hours before AcOH (6.10 mL) was added while stirring. The solution was partitioned between ten 50 mL Falcon tubes. To each tube absolute EtOH (ad 50 mL) was added, the tubes were shaken and centrifuged. The supernatants were decanted, and the pellets were washed with 80% v/v EtOH (40 mL each tube) and absolute EtOH (40 mL each tube). The residues were dried in high vacuum overnight. The obtained material was dissolved in 10% TFA (w/w) in water (50 mL). The solution was partitioned between ten 50 mL Falcon tubes. To each tube isopropanol (ad 50 mL) was added, the tubes were shaken and centrifuged. The supernatants were decanted, and the pellets were washed with isopropanol (40 mL each tube) and dried in high vacuum overnight to yield amine-HA 3 as white solid. The amine content of the material was determined by photometric measurement after chemical derivatization (OPA-assay).

Yield: 1.09 g (TFA salt, 87%, amine-content: 1.422 mmol/g, 71% DS)

Synthesis of Compound 3' in 2 g Scale

To a solution of hyaluronic acid sodium salt (90-130 kDa, 2.00 g, 4.99 mmol COOH eqv.) in 100 mM MES 400 mM 1,3-diaminopropane buffer pH 5.5 (250 mL) $HOBt{\times}H_2O$ (2.29 g, 14.96 mmol) was added. EDC (5.74 g, 29.93 mmol) was added to the mixture and it was stirred at r.t. overnight. Sodium acetate trihydrate (33.94 g) was added to the reaction mixture and the solution was partitioned between twenty-eight 50 mL Falcon tubes. To each tube absolute EtOH (ad 50 mL) was added, the tubes were shaken and centrifuged. The supernatants were decanted, and the pellets were washed with 80% v/v EtOH (40 mL each tube) and absolute EtOH (40 mL each tube). The residues were dried in high vacuum for 60 min. The crude material was dissolved in water (160 mL) and 4 M NaOH (53.34 mL) was added. The resulting mixture was stirred at r.t. for two hours before AcOH (12.20 mL) was added while stirring. The solution was partitioned between twenty-two 50 mL Falcon tubes. To each tube absolute EtOH (ad 50 mL) was added, the tubes were shaken and centrifuged. The supernatants were decanted, and the pellets were washed with 80% v/v EtOH (40 mL each tube) and absolute EtOH (40 mL each tube). The residues were dried in high vacuum overnight. 1.92 g of the obtained material were dissolved in 10% TFA (w/w) in water (96.6 mL). The solution was partitioned between eighteen 50 mL Falcon tubes. To each tube isopropanol (ad 50 mL) was added, the tubes were shaken and centrifuged. The supernatants were decanted, and the pellets were washed with isopropanol (40 mL each tube) and dried in high vacuum for 65 hours to yield amine-HA 3". The amine content of the material was determined by photometric measurement after chemical derivatization (OPA-assay).

Yield: 2.13 g (TFA salt, 86, amine-content: 1.400 mmol/g, 70% DS)

Synthesis of Compound 3" in 2 g Scale

The synthesis of amine-HA 3" was carried out as described for compound 3' to yield compound 3" as white solid. The amine content of the material was determined by photometric measurement after chemical derivatization (OPA-assay).

Yield: 2.06 g (TFA salt, 83, amine-content: 1.413 mmol/g, 71% DS)

Example 14

Synthesis of Daptomycin Linker Thiol 4b

Daptomycin Linker Thiol 4b was Synthesized According to the Following Scheme:

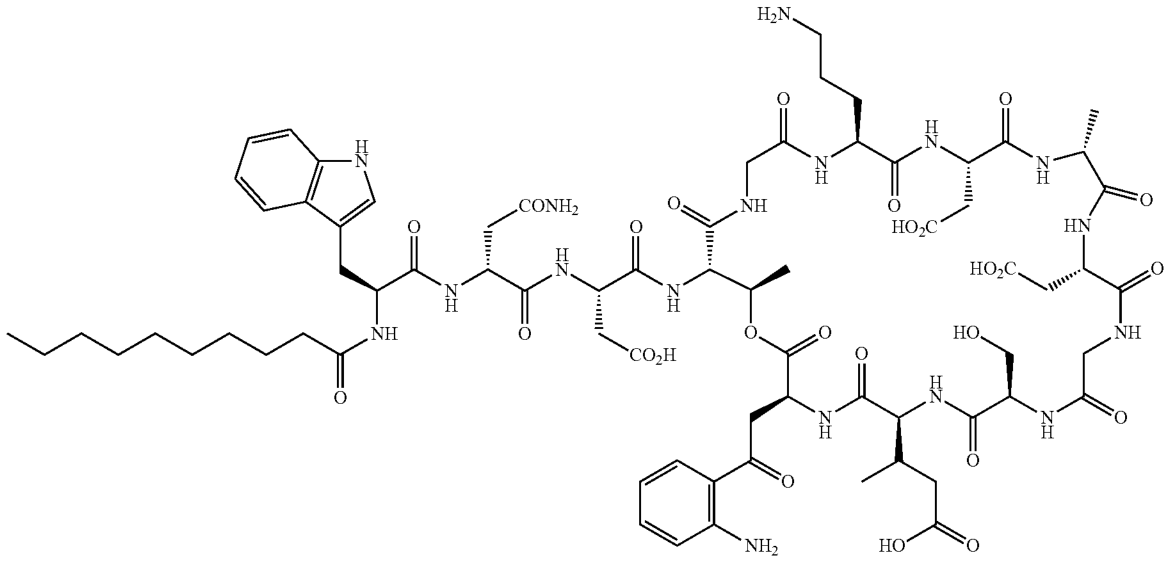
1f, DIPEA
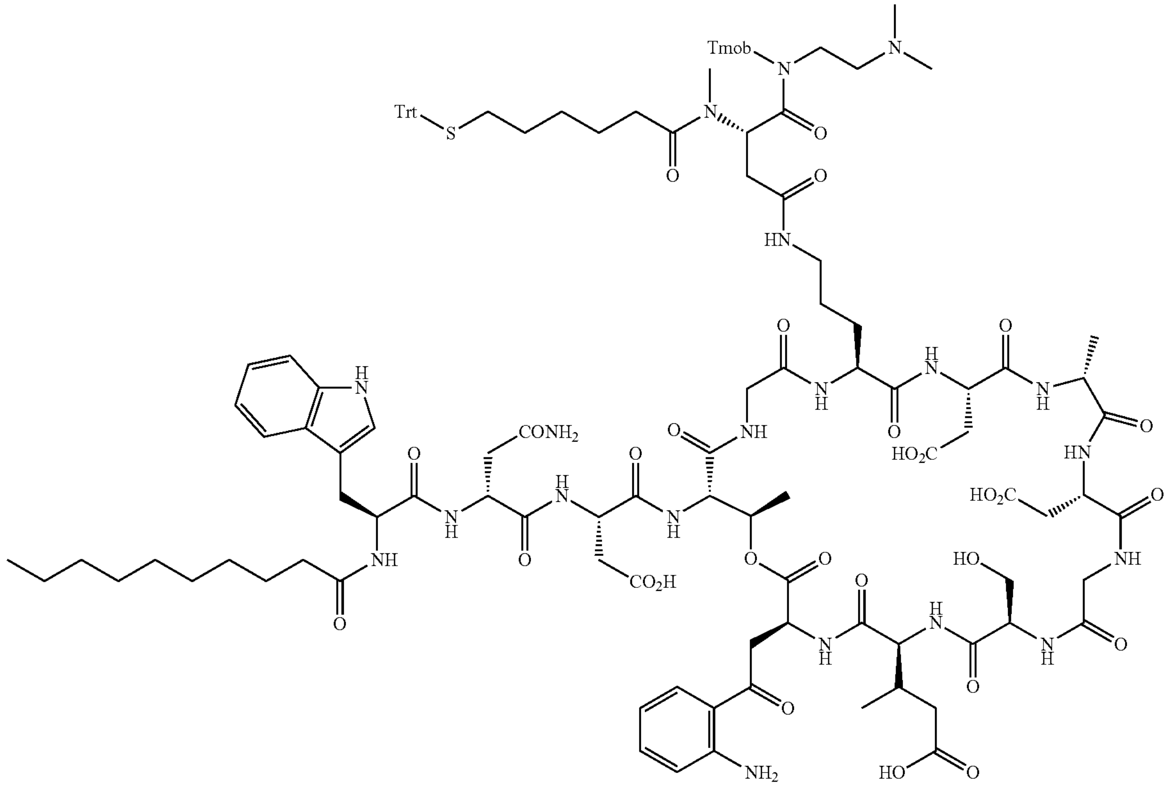
4a
HFIP, TES, TFA

-continued

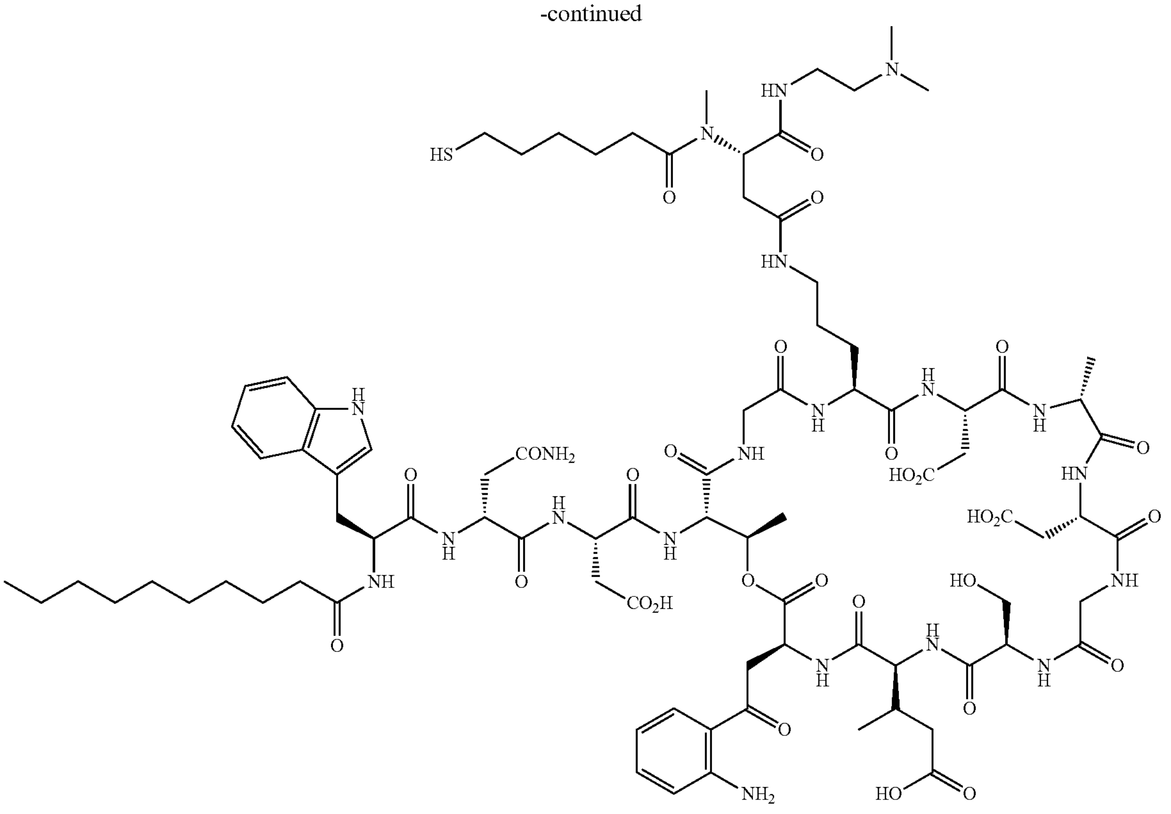

4b

To a mixture of daptomycin (1.08 g, approx. 0.63 mmol) and if (0.99 g, 1.01 mmol) in DMSO (38 mL) DIPEA (0.97 mL, 0.72 g, 5.69 mmol) was added and it was stirred for 380 min. After quenching with TFA (0.44 mL, 0.66 g, 5.69 mmol), the mixture was added to MTBE in 50 mL Falcon tubes (1 mL solution and 40 mL MTBE per tube) to precipitate the conjugate. The tubes were shaken and centrifuged. After decanting the supernatants, the residues were combined and dried in high vacuum overnight. Crude 4a was used for the next step without further purification.

Crude 4a (2.50 g, max. 0.63 mmol) was dissolved in a mixture of HFIP/TES (39:1 v/v, 57 mL) and the solution was stirred at r.t. for 5 min. TFA (4.01 mL) was added and the reaction mixture was stirred at r.t. for two hours. All volatiles were removed in vacuo and the residue was dissolved in a mixture of DCM/TFA (98:2 v/v, 3.0 mL). The solution was added to MTBE in 50 mL Falcon tubes (1 mL solution and 40 mL MTBE per tube) to precipitate the material. The tubes were shaken and centrifuged. After decanting the supernatants, the combined residues were dried in high vacuum overnight. Crude 4b was purified by RP-LPLC to afford pure and mixed product fractions. Pure product fractions were lyophilized to afford a first crop of pure linker thiol. The mixed fractions were additionally purified by preparative RP-HPLC to afford a second crop of pure linker thiol. Both product batches were combined to afford pure 4b.

Yield: 1.00 g (0.46 mmol, 72%, 99% purity at 215 nm)

MS: m/z 975.92=$[M+2H]^{2+}$, (calculated monoisotopic mass: [M]=1948.89.)

Example 15

Synthesis of Transient Daptomycin-Linker HA-Hydrogel Conjugates 5, 5', 5a, 5b, 5c and 5d

Synthesis of 5 (Molar Ratio of Amines/Maleimides/Thiols/Cross-Linker=1.3:1:1:0.3)

All reagent solutions in DMSO were separately filtered through sterile 0.22 μm PTFE syringe filters before the actual hydrogel conjugate synthesis.

A solution of 3" in DMSO (50 mg/mL, 13.00 mL) was mixed with a solution of 4b in DMSO (200 mg/mL, 7.70 mL), a solution of N-succinimidyl 3-maleimidopropionate in DMSO (50 mg/mL, 3.76 mL) and a solution of 2b in DMSO (50 mg/mL, 1.21 mL) in a 50 mL Falcon tube. The yellow solution was drawn into a 30 mL Luer Lock syringe. DIPEA (1.20 mL) was added to the mixture in the 30 mL syringe through the syringe tip, the syringe was closed with a sterile screw cap and vigorously shaken for 30 seconds. An 18G blunt cannula was mounted onto the syringe and the solidifying reaction mixture was transferred into three 10 mL Luer Lock syringes. Due to the increasing viscosity of the mixture, the 18G blunt cannula was exchanged for a 14G cannula after filling the first syringe. The three 10 mL Luer Lock syringes were closed with sterile caps and stored at r.t., in the dark overnight. The gel portions in the syringes were shred into particles by passing them through two stainless steel mesh plates (144 μm mesh size, 3.7 mm diameter) in row, which were fixed with PTFE O-rings in three LL connectors that were mounted on the syringes. The particulate gel portions were directly injected into three portions of EtOH/AcOH (98:2 v/v, 3×35 mL) in 50 mL Falcon tubes. The tubes were vigorously shaken until free-floating particle suspension were obtained. After a short settling time, the slightly turbid supernatants were removed from the dense particle suspensions. The solid conjugate was collected in two 20 mL syringe reactors and was washed with EtOH/AcOH (98:2 v/v, 5×10 mL each) and absolute EtOH (5×10 mL each). After expelling the liquids completely from the suspensions, two sterile 0.22 μm PTFE syringe filters were attached and the materials were dried in high vacuum at r.t. overnight to yield 1642 mg intermediate 1 as yellow powder.

Intermediate 1 (1642 mg) was briefly soaked in 20 mM histidine, 100 mM $CaCl_2$, 2% Tween® 80 buffer pH 6.0 (39.4 mL) in a sterile plastic bottle by gentle swirling. To the pre-swollen suspension, DMSO (200 mL) was added. After complete addition, the bottle was vigorously shaken, and the gel suspension was transferred into six Falcon tubes. After gentle centrifugation, the clear supernatants were removed. To each tube DMSO (20 mL per tube) was added, the tubes were shaken and centrifuged again gently. After removal of the clear supernatants, DMSO (4 mL per tube) was added and the tubes were gently agitated to afford homogeneous suspensions. The combined suspensions were injected in six portions though a 25G nanoneedle (Japan Bio Products Co., Ltd.) into 2% v/v AcOH and 1% v/v Tween® 80 in absolute EtOH (6×35 mL) in six 50 mL Falcon tubes. The injected suspensions were distributed between twelve 50 mL Falcon tubes in 25 mL portions. To the tubes 2% v/v AcOH and 1% v/v Tween® 80 in absolute EtOH (25 mL per tube) was added. The tubes were vigorously shaken and left standing shortly. The slightly turbid supernatants were removed from the dense suspensions and the latter were combined in two 20 mL syringe reactors. The solids were washed with 2% v/v AcOH and 1% v/v Tween® 80 in absolute EtOH (5×10 mL per syringe) and 2% v/v AcOH in absolute EtOH (5×10 mL per syringe). After expelling the liquids completely from the suspensions without pressing the particles together, two sterile 0.22 μm PTFE syringe filters were attached to the syringe reactors and the materials were dried in high vacuum at r.t. overnight to yield 1626 mg intermediate 2 as yellow granules.

Intermediate 2 (1626 mg) was soaked in 20 mM histidine, 10% α,α-trehalose, 0.2% 1 MDa native hyaluronic acid, 10% propylene glycol, 2% Tween® 80 pH 6.0 (13.17 mL) in two equal portions in 50 mL Falcon tubes for 15 minutes. DMSO (40 mL per tube) was added and the tubes were shaken vigorously for approximately four hours. After dilution with additional DMSO (20 mL), the combined suspensions were subsequently injected through a 14 G and a 25G nanoneedle (Japan Bio Products Co., Ltd.) into absolute EtOH (10×35 mL) in equal portions in ten 50 mL Falcon tubes. The tubes with the injected suspensions were vigorously shaken and left standing for sedimentation. The clear supernatants were removed from the dense suspensions and the latter were combined in a 20 mL syringe reactor. The solid was washed with absolute EtOH (10×10 mL). After expelling the liquid completely from the suspension without pressing the particles together, a sterile 0.22 μm PTFE syringe filter was attached to the syringe reactor and the material was dried in high vacuum at r.t. overnight to yield 1174 mg conjugate 5 as fine, yellow powder. The daptomycin content of 5 was determined by QAAA.

Yield: 1174 mg (51%, daptomycin content: 459 mg/g)

Synthesis of 5' (Molar Ratio of Amines/Maleimides/Thiols/Cross-Linker=1.3:1:1:0.3)

The synthesis of 5' was carried out as described for compound 5, using a solution of 3' in DMSO (50 mg/mL, 13.00 mL), a solution of 4b in DMSO (200 mg/mL, 7.62 mL), a solution of N-succinimidyl 3-maleimidopropionate in DMSO (50 mg/mL, 3.73 mL), a solution of 2b in DMSO (50 mg/mL, 1.20 mL) and DIPEA (1.21 mL) to give compound 5' as fine, yellow powder. The daptomycin content of 5' was determined by UV measurement after total hydrolysis.

Yield: 1262 mg (55%, daptomycin content: 483 mg/g)

Synthesis of 5a (Molar Ratio of Amines/Maleimides/Thiols/Cross-Linker=1.3:1:1:0.3)

A solution of 3 in DMSO (50 mg/mL, 2499 μL) was mixed with a solution of 4b in DMSO (200 mg/mL, 1490 μL), a solution of N-succinimidyl 3-maleimidopropionate in DMSO (50 mg/mL, 728 μL) and a solution of 2b in DMSO (50 mg/mL, 235 μL) in a 50 mL Falcon tube. To test the mixture for filterability, an aliquot of approx. 1.2 mL was passed through a sterile 0.22 μm PTFE syringe filter. The filtrate was combined with the remaining portion of the solution and the mixture was drawn into a 10 mL syringe. DIPEA (240 μL) was added to the solution, the syringe was closed and vigorously shaken for 30 seconds. The syringe with the reaction mixture was stored at r.t. in the dark overnight. The gel in the syringe was shred into particles by passing it through two stainless steel mesh plates (144 μm mesh size, 3.7 mm diameter) in row, which were fixed with PTFE O-rings in three LL connectors that were mounted on the syringe. The particulate gel was directly injected into a portion of EtOH/AcOH (98:2 v/v, 40 mL) in a 50 mL Falcon tube. The syringe and the shredding line were flushed with a small portion of EtOH/AcOH (98:2 v/v, 4 mL) and the washing liquid was combined with the suspension in the Falcon tube. The tube was vigorously shaken until a free-floating particle suspension was obtained. The suspension was transferred into a 10 mL syringe reactor with PP frit in portions until the whole material was present in the syringe reactor. The particles were washed with EtOH/AcOH (98:2 v/v, 15×8 mL). After expelling all liquids, hydrogel 5a was dried in high vacuum for 8 hours. The daptomycin content of 5a was determined by QAAA.

Yield: 301 mg (68%, daptomycin content: 489 mg/g)

Synthesis of 5b (Molar Ratio of Amines/Maleimides/Thiols/Cross-Linker=1.02:1:1:0.02)

A solution of 3 in DMSO (50 mg/mL, 240 μL) was mixed with a solution of 4b in DMSO (200 mg/mL, 182 μL), a solution of N-succinimidyl 3-maleimidopropionate in DMSO (50 mg/mL, 89.1 μL) and a solution of 2b in DMSO (50 mg/mL, 1.9 μL) in a 2 mL Eppendorf tube. DIPEA (26.4 μL) was added to the solution, the tube was shaken, centrifuged and left standing at r.t. in the dark for gelation overnight. The gel was transferred into a 2 mL LL syringe and passed through two stainless steel mesh plates (144 μm mesh size, 3.7 mm diameter) in row, which were fixed with PTFE O-rings in three LL connectors that were mounted on the syringe. The particulate gel was directly injected into a portion of EtOH/AcOH (98:2 v/v, 10 mL) in a 15 mL Falcon tube. The syringe and the shredding line were flushed with a small portion of EtOH/AcOH (98:2 v/v, 2 mL) and the washing liquid was combined with the suspension in the Falcon tube. The tube was vigorously shaken until a free-floating particle suspension was obtained, then centrifuged. After decanting the supernatant, the particles were suspended in EtOH/AcOH (98:2 v/v, 10 mL) and transferred into a 10 mL syringe reactor with PP frit in portions until the whole material was present in the syringe reactor. The particles were washed with EtOH/AcOH (98:2 v/v, 5×8 mL). After expelling all liquids, hydrogel 5b was dried in high vacuum overnight. The daptomycin content of 5b was determined by QAAA.

Yield: 40 mg (810%, daptomycin content: 570 mg/g)

Synthesis of 5c (Molar Ratio of Amines/Maleimides/Thiols/Cross-Linker=1.05:1:1:0.05)

A solution of 3 in DMSO (50 mg/mL, 240 μL) was mixed with a solution of 4b in DMSO (200 mg/mL, 177 μL), a solution of N-succinimidyl 3-maleimidopropionate in DMSO (50 mg/mL, 86.5 μL) and a solution of 2b in DMSO (50 mg/mL, 4.7 μL) in a 2 mL Eppendorf tube. DIPEA (25.9 μL) was added to the solution, the tube was shaken, centrifuged and left standing at r.t. in the dark for gelation overnight. Work-up was carried out as described for compound 5b. The daptomycin content of 5c was determined by QAAA.

Yield: 40 mg (83%, daptomycin content: 564 mg/g)

Synthesis of 5d (Molar Ratio of Ratio Amines/Maleimides/Thiols/Cross-Linker=1.1:1:1:0.1)

A solution of 3 in DMSO (50 mg/mL, 240 μL) was mixed with a solution of 4b in DMSO (200 mg/mL, 168.9 μL), a solution of N-succinimidyl 3-maleimidopropionate in DMSO (50 mg/mL, 82.6 μL) and a solution of 2b in DMSO (50 mg/mL, 8.9 μL) in a 2 mL Eppendorf tube. DIPEA (25.2 μL) was added to the solution, the tube was shaken, centrifuged and left standing at r.t. in the dark for gelation overnight. Work-up was carried out as described for compound 5b. The daptomycin content of 5d was determined by QAAA.

Yield: 37 mg (80%, daptomycin content: 476 mg/g)

Example 16

Degradation Study of Transient Daptomycin-Linker Hydrogel Conjugates

The transient daptomycin-linker hydrogel conjugates were analyzed regarding carrier degradation. For that purpose, transient daptomycin-linker HA-conjugates 5, 5b, 5c, and 5d were incubated at pH 7.4 and 37° C. The samples were visually checked for the presence of the solid carrier particles daily. As soon as no particles could be detected in the sample anymore, the material was deemed to be fully degraded to soluble products. It was found that the transient daptomycin-linker HA-hydrogel conjugate 5 was fully degraded after about 55 days. The less cross-linked, transient daptomycin-linker HA-conjugates 5b and 5c were fully degraded after about 36 days and conjugate 5d needed more than 49 days for full degradation.

Abbreviations

ACN Acetonitrile
AcOH Acetic Acid
Asp Aspartic Acid
Bn Benzyl
Boc tert-Butyloxycarbonyl
CIEC Cation-Exchange Chromatography
CV Column Volumes
DBU 1,8-Diazabicyclo[5.4.0]undec-7-ene
DCC Dicyclohexylcarbodiimide
DCM Dichloromethane
DIPEA N,N-Diisopropylethylamine
DMAP 4-(Dimethylamino)pyridine
DMF N,N-Dimethylformamide
DMSO Dimethyl Sulfoxide
DS Degree of Substitution
DTNB 5,5'-Dithiobis(2-nitrobenzoic Acid)
EDC N-(3-Dimethylaminopropyl)-N'-ethylcarbodiimide Hydrochloride
EDTA Ethylenediaminetetraacetic Acid
eqv. Equivalents
EtOH Ethanol
FA Formic Acid
Fmoc Fluorenylmethyloxycarbonyl
HA Hyaluronic Acid
HEPES (4-(2-Hydroxyethyl)-1-piperazineethanesulfonic acid)
HFIP 1,1,1,3,3,3-Hexafluoro-2-propanol HOBt 1-Hydroxybenzotriazole
HOSu N-hydroxysuccinimide
HPLC High-Performance Liquid Chromatography
LC Liquid Chromatography
LL Luer Lock
LPLC Low Pressure Liquid Chromatography
MeCN Acetonitrile
MeOH Methanol
MES 2-(N-Morpholino)ethanesulfonic acid
MS Mass Spectrometry
MTBE tert-Butyl Methyl Ether
Mw Molecular Weight
NHS N-Hydroxysuccinimide
OPA o-Phthalaldehyde
OxymaPure® Ethyl cyano(hydroxyimino)acetate
PBS Phosphate-buffered Saline
PE Polyethylene
PEG Poly(ethylene glycol)
PES Polyethersulfone
PTFE Polytetrafluoroethylene
pTsOH p-Toluenesulfonic Acid
PyBOP Benzotriazol-1-yl-oxytripyrrolidinophosphonium Hexafluorophosphate
QAAA Quantitative Amino Acid Analysis
Rbz Ranibizumab
RP Reversed Phase
RP-HPLC Reversed Phase High-Performance Liquid Chromatography
RP-LPLC Reversed Phase Low Pressure Liquid Chromatography
RPM Revolutions Per Minute
r.t. Room Temperature
SEC Size-exclusion chromatography
SPDP 3-(2-Pyridyldithio)propionic Acid N-hydroxysuccinimide Ester
Su Succinimidyl
TCEP Tris(2-carboxyethyl)phosphine
TES Triethylsilane
TFA Trifluoroacetic Acid
TFF Tangetial Flow Filtration
THF Tetrahydrofurane
Tmob 2,4,6-Trimethoxybenzyl
TNB 5-Thio-2-nitrobenzoic Acid
TSTU N,N,N',N'-Tetramethyl-O—(N-succinimidyl)uronium Tetrafluorborate
Tween® 20 Polyethylene Glycol Sorbitan Monolaurate
Tween® 80 Polyethylene Glycol Sorbitan Monooleate
UPLC-MS Mass Spectrometry Coupled Ultra Performance Liquid Chromatography
UV Ultraviolet

The invention claimed is:

1. A conjugate comprising crosslinked hyaluronic acid strands to which a plurality of drug moieties are covalently and reversibly conjugated, wherein the conjugate comprises a plurality of connected units selected from the group consisting of

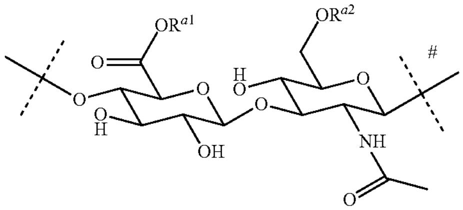

$Z^1$

,

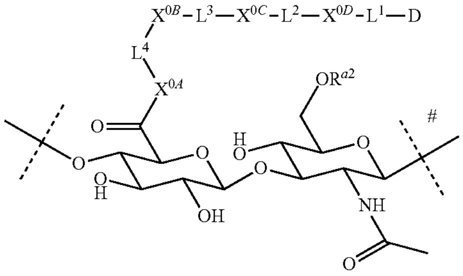

$Z^2$ and

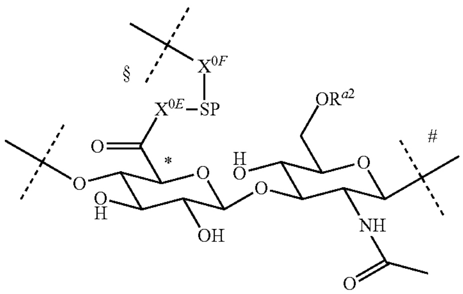

$Z^3$

, wherein an unmarked dashed line indicates a point of attachment to an adjacent unit at a dashed line marked with #or to a hydrogen;

a dashed line marked with #indicates a point of attachment to an adjacent unit at an unmarked dashed line or to a hydroxyl;

a dashed line marked with § indicates a point of connection between at least two units $Z^3$ via a moiety -CL-;

each -D is independently a drug moiety;

each $-L^1-$ is independently a linker moiety to which -D is covalently and reversibly conjugated; wherein the bond between $-L^1-$ and -D is cleaved in aqueous buffer at pH 7.4 and 37° C. with a half-life ranging from 12 hours to three months and -D is released non-enzymatically in its unmodified, pharmacologically active form;

each $-L^2-$, $-L^3-$ and $-L^4-$ is independently either absent or a spacer moiety;

each —CL- is independently a moiety connecting at least two units $Z^3$ and wherein there is at least one degradable bond in the direct connection between any two carbon atoms marked with the * connected by a moiety —CL-;

each —SP— is independently absent or a spacer moiety;

each $—R^{a1}$ is independently selected from the group consisting of —H, $C_{1-4}$ alkyl, an ammonium ion, a tetrabutylammonium ion, a cetyl methylammonium ion, an alkali metal ion and an alkaline earth metal ion;

each $—R^{a2}$ is independently selected from the group consisting of —H and $C_{1-10}$ alkyl;

each $—X^{0A}—$, $—X^{0B}—$, $—X^{0C}$ and $—X^{0D}$ is independently either absent or a linkage;

each $—X^{0E}—$ is (x-2)

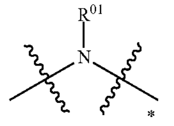

wherein the unmarked dashed line indicate attachment to —SP— and the dashed line marked with an asterisk indicate attachment to the carbonyl of the hyaluronic acid, wherein $R^{01}$ is independently selected from the group consisting of halogen, —H, —CN, $-T^0$, $C_{1-50}$ alkyl, $C_{2-50}$ alkenyl, and $C_{2-50}$ alkynyl: wherein $-T^0$, $C_{1-50}$ alkyl, $C_{2-50}$ alkenyl, and $C_{2-50}$ alkynyl are optionally substituted with one or more $—R^{02}$, which are the same or different, and wherein $C_{1-50}$ alkyl, $C_{2-50}$ alkenyl, and $C_{2-50}$ alkynyl are optionally interrupted by one or more groups selected from the group consisting of $-T^0$, —C(O)O—, —O—, C(O)—, $—C(O)N(R^{03})—$, $—S(O)_2N(R^{03})—$, $—S(O)N(R^{03})—$, $—S(O)_2—$, —S(O)—, $N(R^{03})S(O)_2N(R^{03a})—$, —S—, $—N(R^{03})—$, $—OC(OR^{03})(R^{03a})$, $—N(R^{03})C(O)N(R^{03a})—$, and $—OC(O)N(R^{03})$ wherein each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more $R^{02}$, which are the same or different; and wherein each $—R^{02}$, $—R^{03}$ and $—R^{03a}$ is independently selected from the group consisting of H and $C_{1-6}$ alkyl: wherein $C_{1-6}$ alkyl is optionally substituted with one or more halogen, which are the same or different;

each $—X^{0F}$- is (x-21)

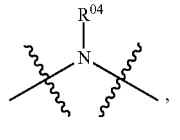

wherein $R^{04}$ is independently selected from the group consisting of halogen, —H, CN, $T^0$, $C_{1-50}$ alkyl, $C_{2-50}$ alkenyl, and $C_{2-50}$ alkynyl: wherein $T^0$, $C_{1-50}$ alkyl, $C_{2-50}$ alkenyl, and $C_{2-50}$ alkynyl are optionally substituted with one or more $R^{06}$, which are the same or different, and wherein $C_{1-50}$ alkyl, $C_{2-50}$ alkenyl, and $C_{2-50}$ alkynyl are optionally interrupted by one or more groups selected from the group consisting of $T^0$, —C(O)O—, —O—, —C(O)—, $—C(O)N(R^{07})—$, $—S(O)_2N(R^{07})—$, $—S(O)N(R^{07})—$, $—S(O)_2—$, —S(O)—, $—N(R^{07})S(O)_2N(R^{07a})—$, —S—, $N(R^{07})—$, $—OC(OR^{07})(R^{07a})$, $—N(R^{07})C(O)N(R^{07a})—$, and $—OC(O)N(R^{07})$; wherein each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl;

wherein each $T^0$ is independently optionally substituted with one or more $R^{06}$, which are the same or different; and wherein each $R^{06}$, $R^{07}$ and $R^{07a}$ is independently selected from the group consisting of H and $C_{1-6}$ alkyl; wherein $C_{1-6}$ alkyl is optionally substituted with one or more halogen, which are the same or different;

optionally $—X^{0A}—$ and/or $—X^{0B}$- form together with $-L^4$- or parts of $-L^4$- one or more ring structure selected from the group consisting of 4- to 7-membered heterocyclyl, 8- to 11-membered heterobicyclyl and adamantyl;

optionally $—X^{0B}—$ and/or $—X^{0C}—$ form together with $-L^3$- or parts of $-L^3$- one or more ring structure selected from the group consisting of 4- to 7-membered heterocyclyl, 8- to 11-membered heterobicyclyl and adamantyl;

optionally, $—X^{0C}—$ and/or $—X^{0D}—$ form together with $-L^2$- or parts of $-L^2$- one or more ring structure selected from the group consisting of 4- to 7-membered heterocyclyl, 8- to 11-membered heterobicyclyl and adamantyl;

optionally $—X^{0E}—$ and/or $—X^{0F}—$ form together with —SP— or parts of —SP— one or more ring structure selected from the group consisting of 4- to 7-membered heterocyclyl, 8- to 11-membered heterobicyclyl and adamantyl;

wherein all units $Z^1$ present in the conjugate may be the same or different;

all units $Z^2$ present in the conjugate may be the same or different;

all units $Z^3$ present in the conjugate may be the same or different;

at least one unit $Z^3$ is present per hyaluronic acid strand which is connected to at least one unit $Z^3$ on a different hyaluronic acid strand; and the conjugate comprises at least one unit $Z^2$;

wherein —CL- is a moiety of formula (D)

(D)

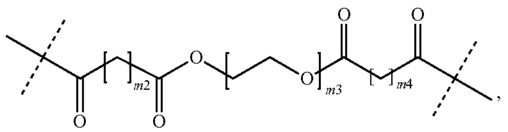

wherein the dashed lines indicate attachment to a moiety $—X^{0F}—$; and m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25;

and wherein $-L^1-$ is of formula (I):

(I)

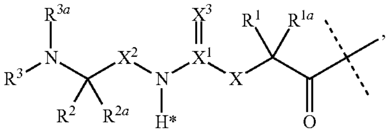

wherein the dashed line indicates the attachment to a nitrogen, hydroxyl or thiol of -D;

—X— is selected from the group consisting of $—C(R^4R^{4a})—$, $—N(R^4)—$, —O—, $—C(R^4R^{4a})—C(R^5R^{5a})—$, $—C(R^5R^{5a})—C(R^4R^{4a})—$, $—C(R^4R^{4a})—N(R^6)—$, $—N(R^6)—C(R^4R^{4a})—$, $—C(R^4R^{4a})—O—$, $—O—C(R^4R^{4a})—$, and $—C(R^7R^{7a})—$, $X^1$ is selected from the group consisting of C and S(O);

$—X^2—$ is selected from the group consisting of $—C(R^8R^{8a})—$ and $—C(R^8R^{8a})—C(R^9R^{9a})—$;

$=X^3$ is selected from the group consisting of =O, =S, and =N—CN;

$—R^1$, $—R^{1a}$, $—R^2$, $—R^{2a}$, $—R^4$, $—R^{4a}$, $—R^5$, $—R^{5a}$, $—R^6$, $—R^8$, $—R^{8a}$, $—R^9$ and $—R^{9a}$ are independently selected from the group consisting of —H and $C_{1-6}$ alkyl;

$—R^3$ and $—R^{3a}$ are independently selected from the group consisting of —H and $C_{1-6}$ alkyl, provided that in case one of $—R^3$ and $—R^{3a}$ or both are other than —H they are connected to N to which they are attached through an $sp^3$-hybridized carbon atom;

$—R^7$ is selected from the group consisting of $—N(R^{10}R^{10a})$ and $—NR^{10}—(C=O)—R^{11}$;

$—R^{7a}$, $—R^{10}$, $—R^{10a}$ and $—R^{11}$ are independently selected from the group consisting of —H and $C_{1-6}$ alkyl;

alternatively, one or more of the pairs $—R^{1a}/—R^{4a}$, $—R^{1a}/—R^{5a}$, $—R^{1a}/—R^{7a}$, $—R^{4a}/—R^{5a}$ and $—R^{8a}/—R^{9a}$ form a chemical bond;

alternatively, one or more of the pairs $—R^1/—R^{1a}$, $—R^2/—R^{2a}$, $—R^4/—R^{4a}$, $—R^5/—R^{5a}$, $—R^8/—R^{8a}$ and $—R^9/—R^{9a}$ are joined together with the atom to which they are attached to form a $C_{3-10}$ cycloalkyl or 3- to 10-membered heterocyclyl;

alternatively, one or more of the pairs $—R^1/—R^4$, $—R^1/—R^5$, $—R^1/—R^6$, $—R^1/—R^{7a}$, $—R^4/—R^5$, $—R^4/—R^6$, $—R^8/—R^9$ and $—R^2/—R^3$ are joined together with the atoms to which they are attached to form a ring A;

alternatively, $—R^3/—R^{3a}$ are joined together with the nitrogen atom to which they are attached to form a 3- to 10-membered heterocycle;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein $-L^1-$ is substituted with $—X^{0D}-L^2-$ and wherein $-L^1-$ is optionally further substituted, provided that the hydrogen marked with the asterisk in formula (I) is not replaced by $—X^{0D}-L^2-$ or a substituent.

2. The conjugate of claim 1, wherein the conjugate comprises crosslinked hyaluronic acid strands to which a plurality of drug moieties are covalently and reversibly conjugated, wherein the conjugate comprises a plurality of connected units selected from the group consisting of $Z^1$

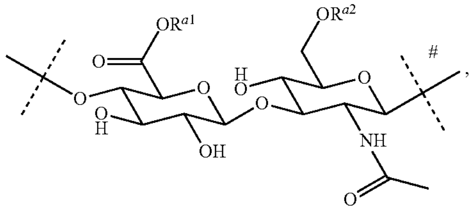

$Z^2$

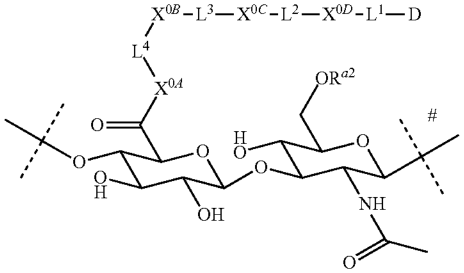

and $Z^3$

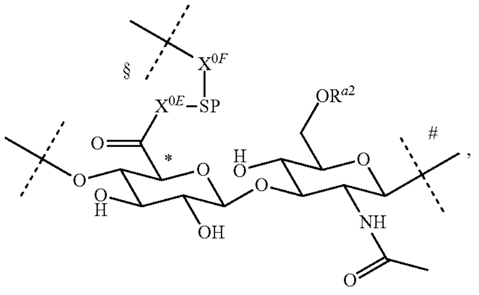

wherein an unmarked dashed line indicates a point of attachment to an adjacent unit at a dashed line marked with #or to a hydrogen;

a dashed line marked with #indicates a point of attachment to an adjacent unit at an unmarked dashed line or to a hydroxyl;

a dashed line marked with § indicates a point of connection between at least two units $Z^3$ via a moiety —CL-;

-D, $-L^1-$, $-L^2-$, $-L^3-$, $-L^4-$, —SP—, —CL-, $—X^{0A}—$, $—X^{0B}—$, $—X^{0C}—$, $—X^{0D}—$, $—X^{0E}—$, $—X^{0F}—$, $—R^{a1}$ and $—R^{a2}$ are used as in claim 1;

wherein all units $Z^1$ present in the conjugate may be the same or different;

all units $Z^2$ present in the conjugate may be the same or different;

all units $Z^3$ present in the conjugate may be the same or different;

the number of $Z^1$ units ranges from 1% to 98% of the total number of units present in the conjugate;

the number of $Z^2$ units ranges from 1% to 98% of the total number of units present in the conjugate, provided at least one unit $Z^2$ is present in the conjugate;

the number of $Z^3$ units ranges from 1% to 97% of the total number of units present in the conjugate, provided that at least one unit $Z^3$ is present per strand; and wherein at least 70% of all hyaluronic acid strands comprise at least one moiety $Z^2$ and at least one moiety $Z^3$.

3. The conjugate of claim 2, wherein the number of units $Z^2$ ranges from 1% to 70% of all units present in the conjugate.

4. The conjugate of claim 2, wherein the number of units $Z^3$ ranges from 1% to 30%.

5. The conjugate of claim 2, wherein the number of units $Z^1$ ranges from 10% to 97%.

6. The conjugate of claim 1, wherein -D is an antibiotic moiety.

7. The conjugate of claim 1, wherein -D is an anti VEGF antibody moiety or fragment thereof.

8. A pharmaceutical composition comprising at least one conjugate of claim 1 and at least one excipient.

9. A method of treating a patient suffering from a disease b that can be treated with D-H or D-OH, comprising administering an effective amount of the conjugate of claim 1 to the patient.

10. A method of preparing a pharmaceutical formulation comprising a conjugate of claim 1, wherein the method comprises the steps of (a) providing said conjugate;

(b) subjecting the conjugate of step (a) to a solution comprising a buffering agent, a surfactant and a salt comprising multivalent ions to which a swelling agent is added after addition of said solution;

(c) homogenizing the admixture of step (b);

(d) deswelling the conjugate of step (c) in a deswelling solution comprising at least a deswelling agent;

(e) isolating the conjugate from the admixture of step (d);

(f) subjecting the conjugate of step (e) to a solution comprising a buffering agent, a surfactant, a salt comprising bivalent ions, a hydrophilic polymer of a molecular weight higher than 10 kDa, a density-modifying agent and a polarity-modifying agent, to which a swelling agent is added after addition of said solution;

(g) homogenizing the admixture of step (f);

(h) deswelling the conjugate of step (g) in a deswelling solution comprising at least a deswelling agent;

(i) isolating the conjugate from the admixture of step (h); and wherein, there may be optional washing steps between steps (c) and (d), (f) and (g), and (g) and (h).

* * * * *